US010954534B2

United States Patent
Poulos et al.

(10) Patent No.: US 10,954,534 B2
(45) Date of Patent: Mar. 23, 2021

(54) PRODUCTION OF CANNABIGEROLIC ACID IN YEAST

(71) Applicant: Librede Inc., Sherman Oaks, CA (US)

(72) Inventors: Jason L. Poulos, Los Angeles, CA (US); Anthony N. Farina, Pasadena, CA (US)

(73) Assignee: Librede Inc., Sherman Oaks, CA (US)

( * ) Notice: Subject to any disclaimer, the term of this patent is extended or adjusted under 35 U.S.C. 154(b) by 0 days.

(21) Appl. No.: 16/539,436

(22) Filed: Aug. 13, 2019

(65) Prior Publication Data

US 2020/0017889 A1    Jan. 16, 2020

Related U.S. Application Data

(63) Continuation-in-part of application No. 16/122,702, filed on Sep. 5, 2018, now Pat. No. 10,392,635, which is a continuation of application No. 15/815,651, filed on Nov. 16, 2017, now Pat. No. 10,093,949, which is a continuation of application No. 14/795,816, filed on Jul. 9, 2015, now Pat. No. 9,822,384.

(60) Provisional application No. 62/024,099, filed on Jul. 14, 2014.

(51) Int. Cl.
*C12P 7/42*         (2006.01)
*C12N 9/00*         (2006.01)
*C12N 9/88*         (2006.01)
*C12N 9/10*         (2006.01)
*C12N 1/20*         (2006.01)
*C12N 15/00*        (2006.01)
*C12N 1/14*         (2006.01)
*C12N 15/81*        (2006.01)

(52) U.S. Cl.
CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search
CPC ...... C12N 9/1029; C12N 9/88; C12N 9/1085; C12N 9/93; C12P 7/42
See application file for complete search history.

(56) References Cited

PUBLICATIONS

"Office Action," Canada Patent Application No. 2990071, dated Nov. 25, 2019, 4 pages.

*Primary Examiner* — Yong D Pak
(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

5 Claims, 8 Drawing Sheets

Specification includes a Sequence Listing.

PRODUCTION OF CANNABIGEROLIC ACID IN YEAST

CROSS-REFERENCE TO RELATED APPLICATIONS

This patent application is a continuation-in-part of U.S. Non-Provisional patent application Ser. No. 16/122,702, filed Sep. 5, 2018, titled "Production of Tetrahydrocannabinolic Acid in Yeast," now U.S. Pat. No. 10,392,635, issued on Aug. 27, 2019, which is a continuation of U.S. Non-Provisional patent application Ser. No. 15/815,651, filed Nov. 16, 2017, titled "Production of Cannabidiolic Acid in Yeast," now U.S. Pat. No. 10,093,949, issued on Oct. 9, 2018, which is a continuation of U.S. Non-Provisional patent application Ser. No. 14/795,816, filed Jul. 9, 2015, titled "Production of Cannabinoids in Yeast," now U.S. Pat. No. 9,822,384, issued on Nov. 21, 2017, which in turn claims the benefit and priority of U.S. Provisional Patent Application Ser. No. 62/024,099, filed Jul. 14, 2014, titled "Terpenophenolic Production in Microorganisms." All of the aforementioned disclosures are hereby incorporated by reference herein in their entireties including all references and appendices cited therein.

REFERENCE TO SEQUENCE LISTINGS

The present application is filed with sequence listing(s) attached hereto and incorporated by reference, including Appendix 1A titled "Additional Examples," Appendix 1B titled "Sequence IDs" and Appendix 1C titled "Additional Sequence IDs".

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
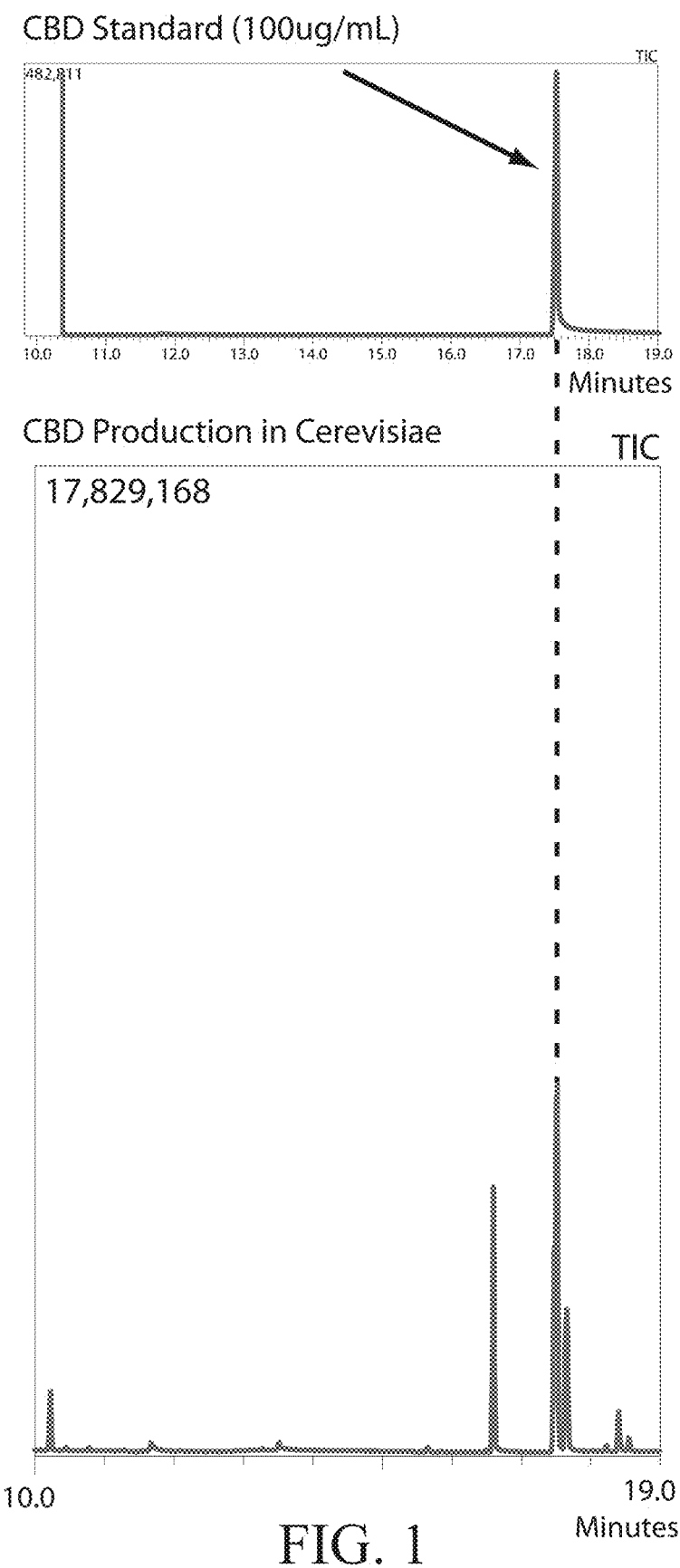
FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, $CO_2$ extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

FIG. 1 shows gas chromatography-mass spectrometry of cannabidiol (CBD) produced in *S. cerevisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
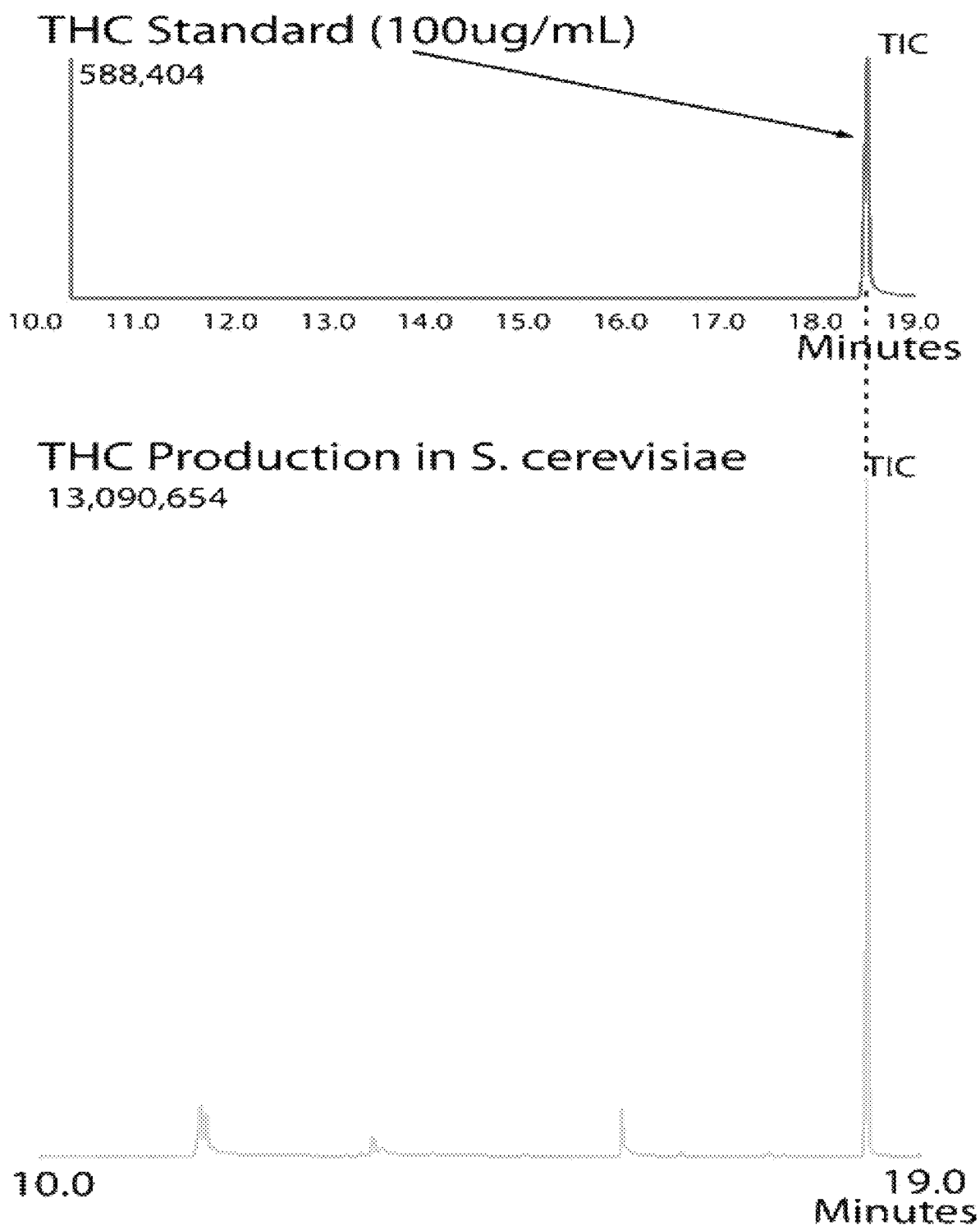
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows gas chromatography-mass spectrometry of tetrahydrocannabinol (THC) produced in *S. cerevisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
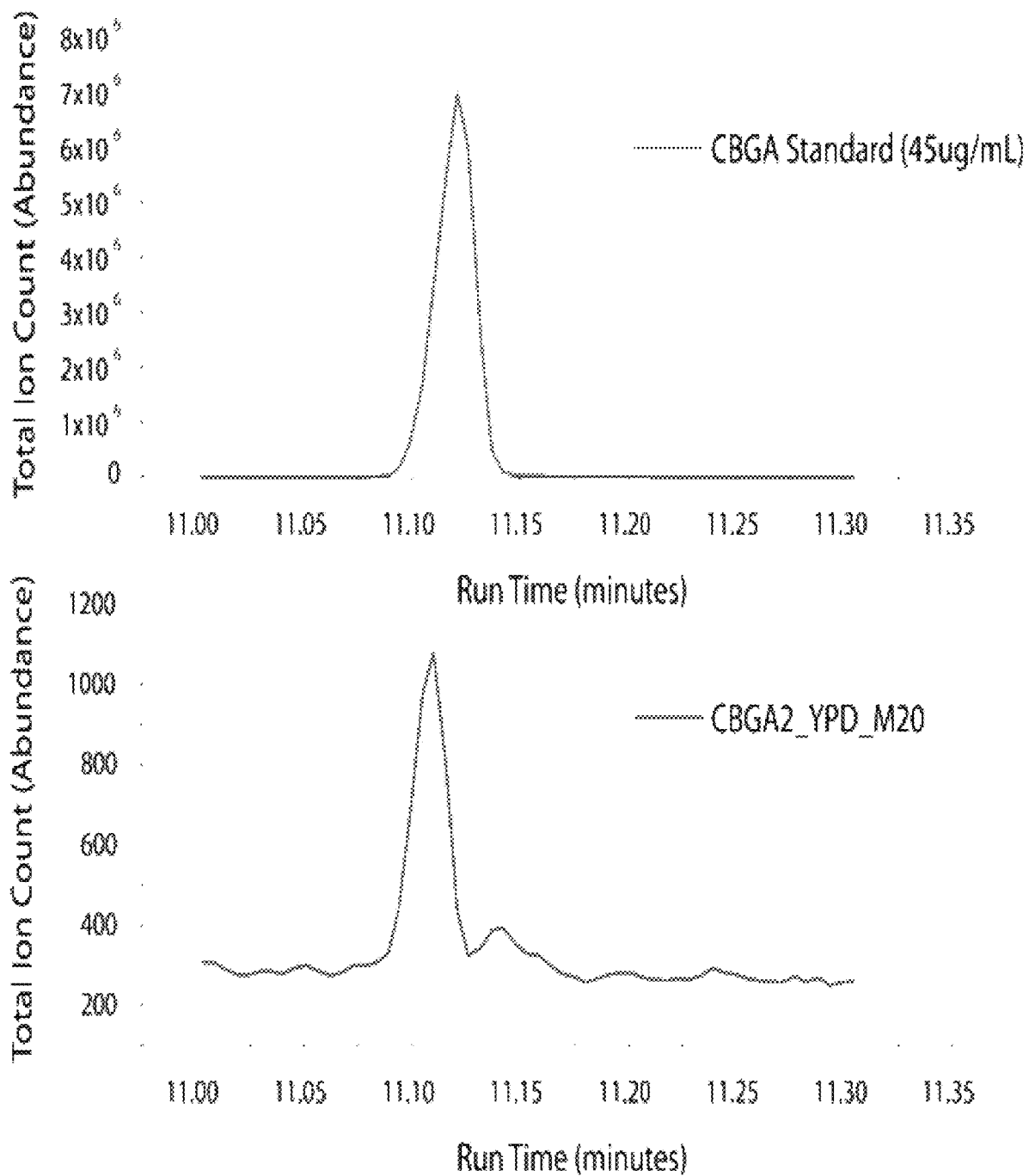
FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows gas chromatography-mass spectrometry of cannabigerolic acid (CBGA) produced in *S. cerevisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
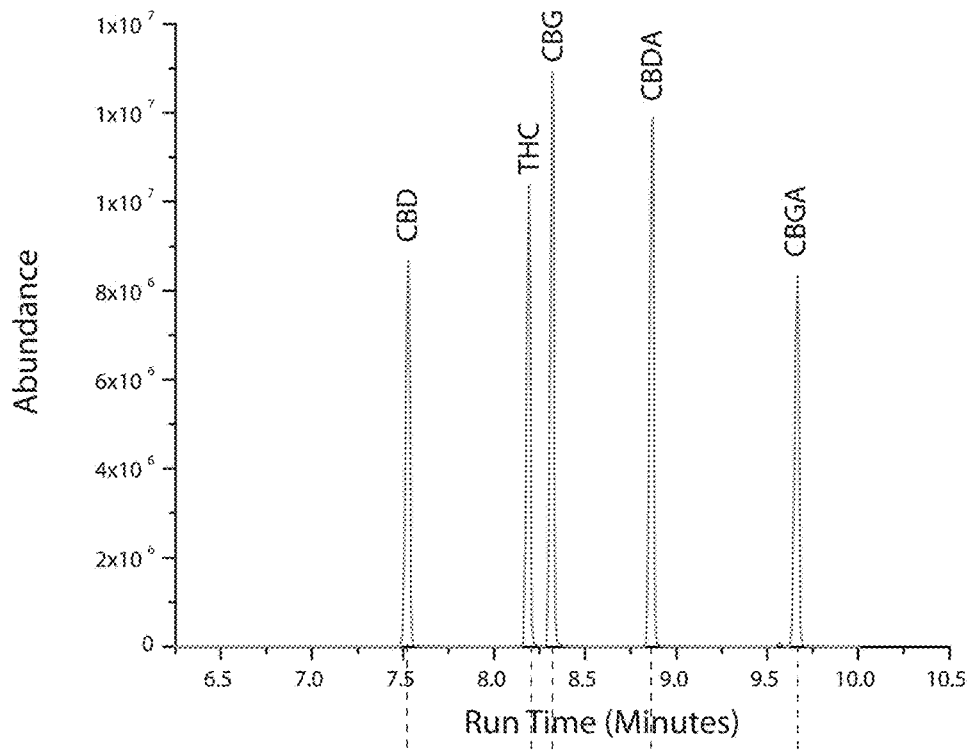
FIG. 4 shows exemplary experimental data achieved in connection with Example 4 of Appendix 1A titled "Additional Examples" for CBGA, CBDA, CBD, CBG and THC production in *K. marxianus*.
Figure 4:
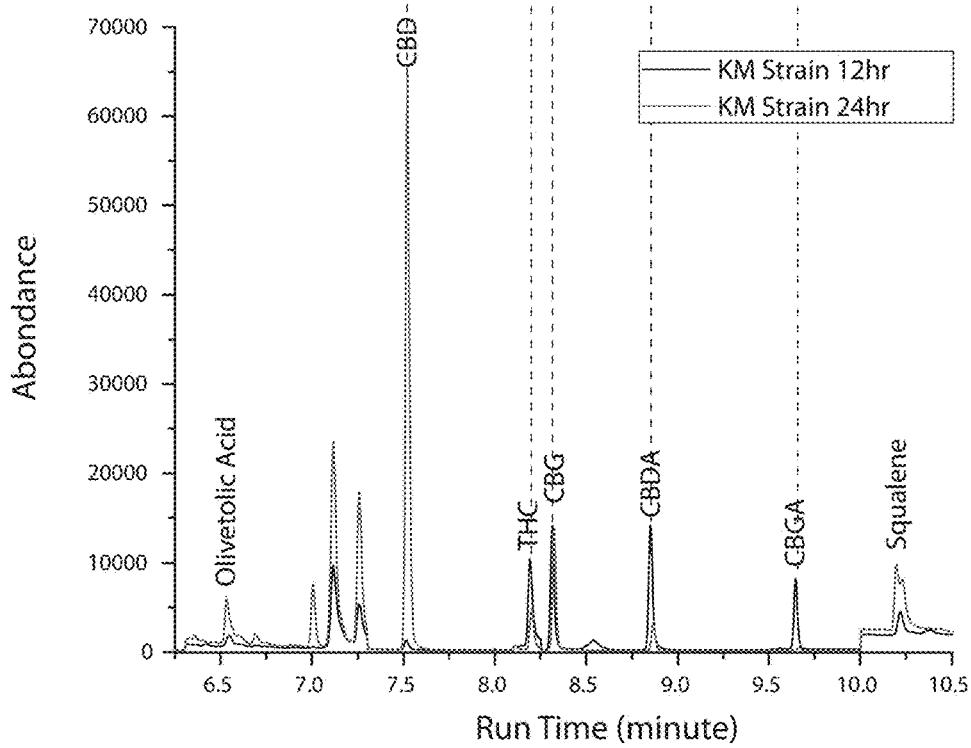

FIG. 4 shows exemplary experimental data achieved in connection with Example 4 of Appendix 1A titled "Additional Examples" for CBGA, CBDA, CBD, CBG and THC production in *K. marxianus*.

FIG. 4 shows gas chromatography-mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
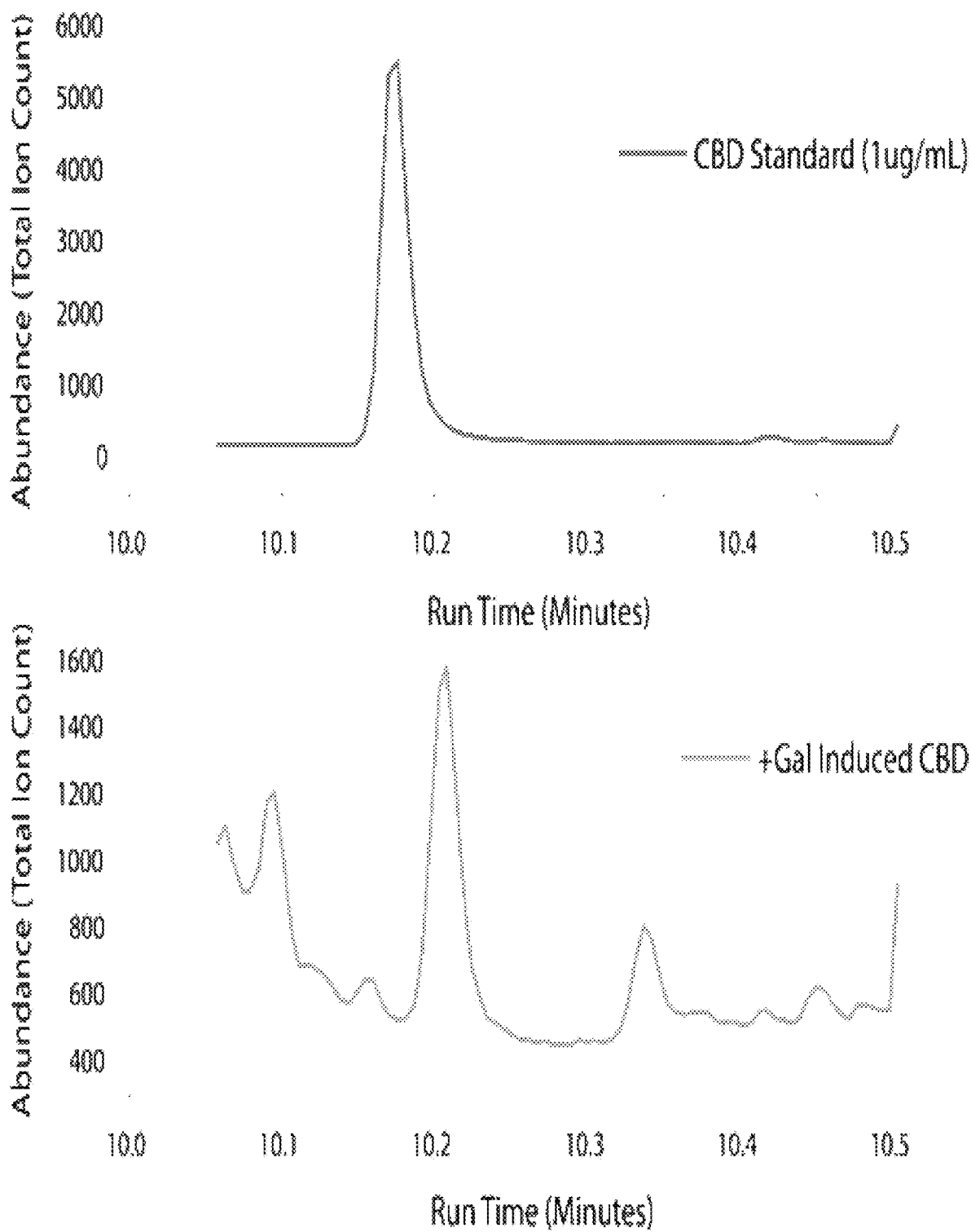
FIG. 5 show exemplary experimental data achieved in connection with Example 5 of Appendix 1A titled "Additional Examples" for galactose induced CBD production in *S. cerevisiae*.

FIG. 5 show exemplary experimental data achieved in connection with Example 5 of Appendix 1A titled "Additional Examples" for galactose induced CBD production in S. cerevisiae.

FIG. 5 shows gas chromatography—mass spectrometry of induced cannabidiol (CBD) production in S. cerevisiae. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
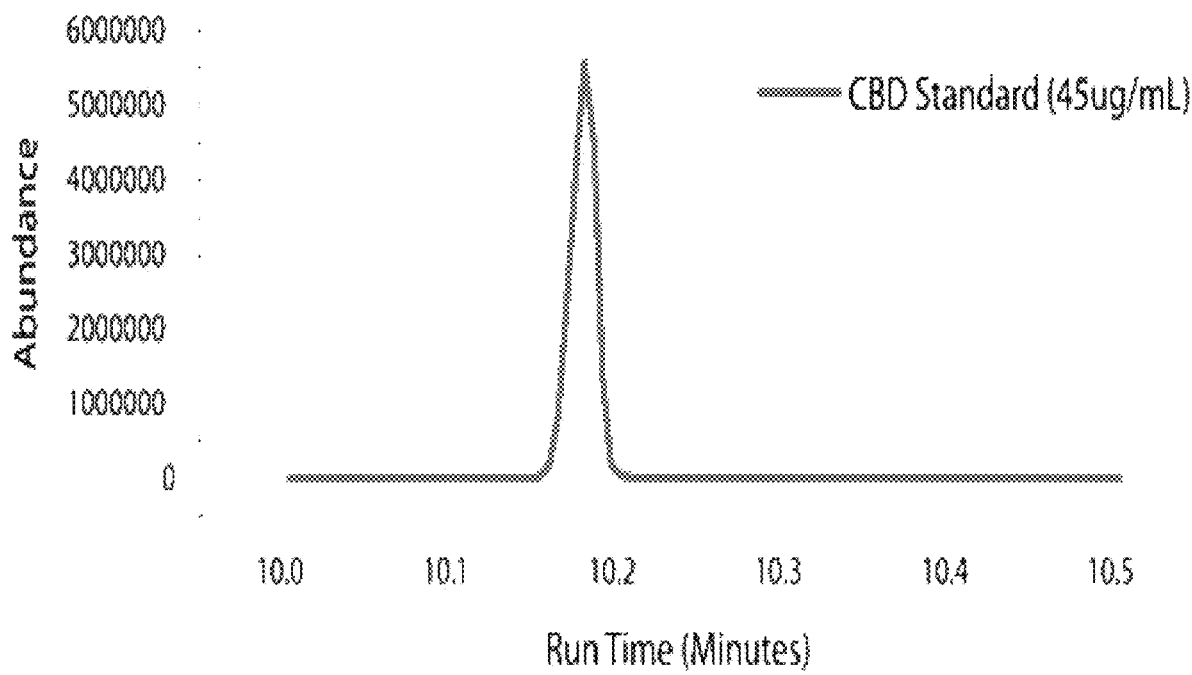
FIG. 6 shows exemplary experimental data achieved in connection with Example 6 of Appendix 1A titled "Additional Examples" for secretion of CBD into media by *S. cerevisiae*.
Figure 6:
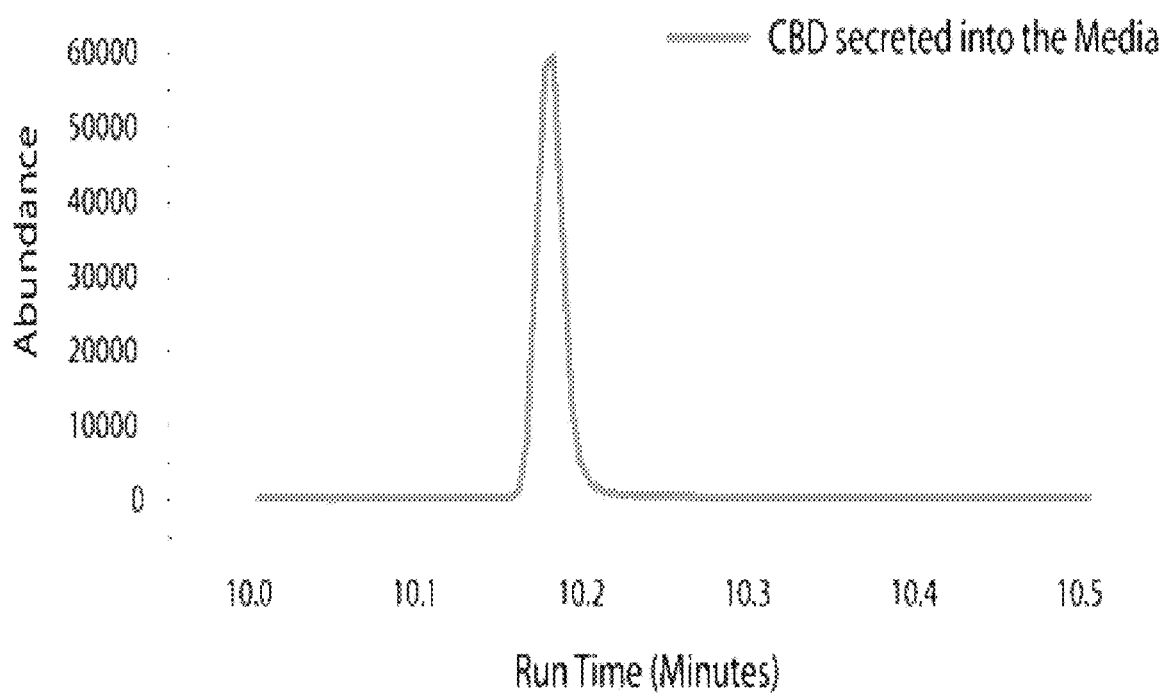

FIG. 6 shows exemplary experimental data achieved in connection with Example 6 of Appendix 1A titled "Additional Examples" for secretion of CBD into media by S. cerevisiae.

FIG. 6 shows gas chromatography-mass spectrometry of induced cannabidiol production (CBD) produced in S. cerevisiae and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in S. cerevisiae.

Through genetic engineering the inventors have reconstituted the cannabidiolic acid (CBDA) metabolic pathway found in Cannabis sativa into S. cerevisiae (a species of yeast).

Producing CBGA is an initial step in producing many cannabinoids from Cannabis sativa in S. cerevisiae. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
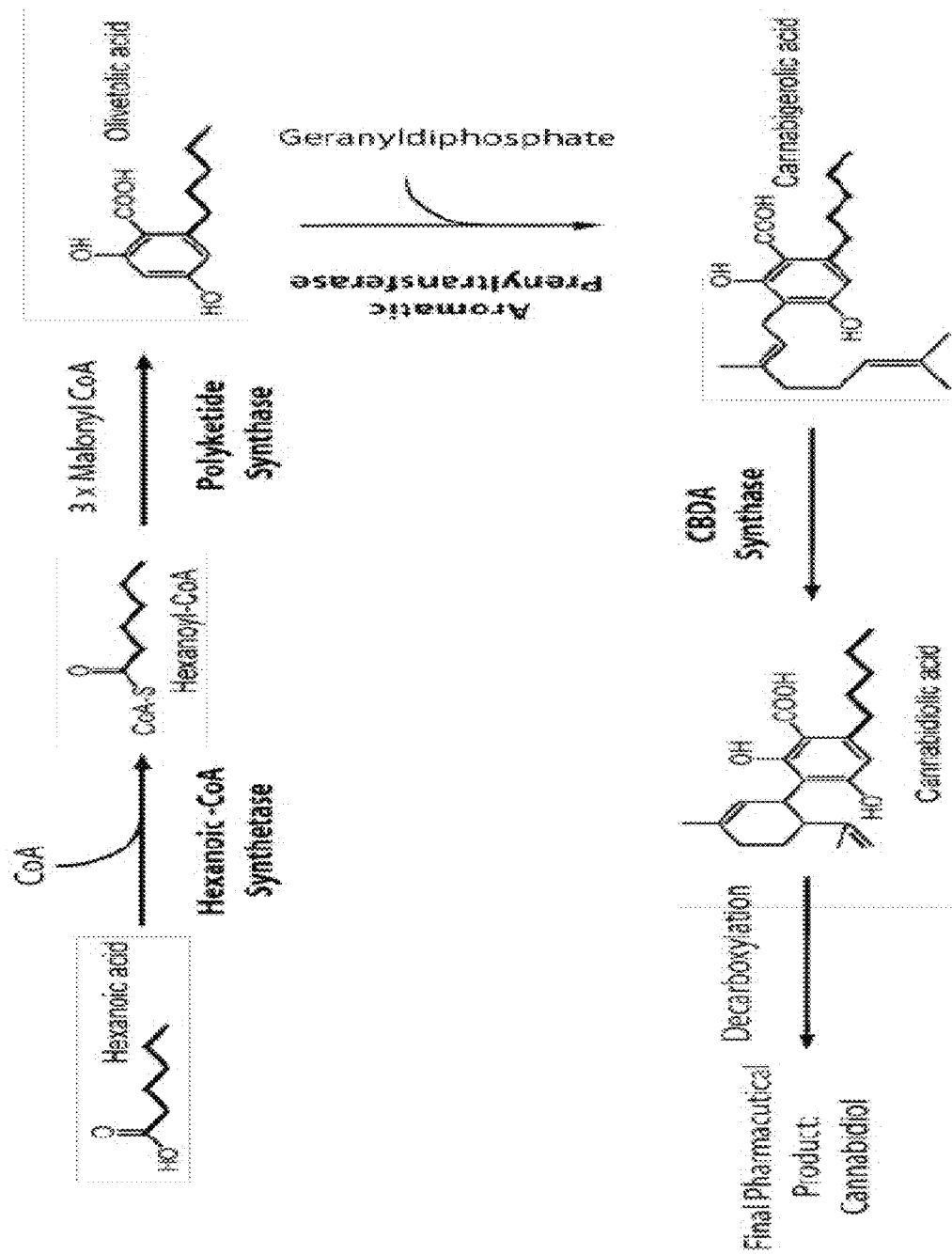
FIG. 7 shows an exemplary metabolic pathway for the production of cannabinoids by *Cannabis sativa*.

FIG. 7 shows an exemplary metabolic pathway for the production of cannabinoids by Cannabis sativa.

The biosynthetic route for the production of cannabidiolic acid in Cannabis sativa is shown in FIG. 7. The pathway begins with the conversion of Hexanoic acid (a simple fatty acid) to Hexanoyl-CoA by Hexanoyl-CoA Synthetase. Hexanoyl-CoA is converted to Olevolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into S. cerevisiae (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into S. cerevisiae.

Synthesis of Fusion Genes Required for CBDA Production in S. cerevisiae.

The genome of Cannabis sativa has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA. In addition to CsEE1, the Cannabis plant has several other acyl-activating enzymes with sequences that are similar to CsEE1. These enzymes can also be used for the conversation of hexanoic acid to hexanoyl-CoA. These are listed in Appendix 1C.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC. In addition to the tetraketide synthase, olivetolic synthase (OS), and the polyketide cyclase, olivetolic acid cyclase (OAC), the Cannabis plant has several other enzymes with sequences that are similar to the tetraketide synthase, olivetolic synthase (OS), and the polyketide cyclase, olivetolic acid cyclase (OAC). These enzymes can also be used for the conversation of hexanoyl-CoA to olivetolic acid. These are listed in Appendix 1C.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC). In addition to the aromatic prenyltransferase (CsPt1) the *Cannabis* plant has several other enzymes with sequences that are similar to the aromatic prenyltransferase (CsPt1). These enzymes can also be used for the conversation of olivetolic acid to CBGA. These are listed in Appendix 1C.

Creation of a Stable Yeast Strain Producing the Metabolic Pathway for CBDA.

Three stable transformations of *S. cerevesaie* where created utilizing selection for leucine, uracil and tryptophan. The inventors first transformed an auxotrophic yeast strain (his3D1/leu2/trp1-289/ura3-52) with the CsAAE1-T2A-Erg20(K197E)-FLAG gene in an integrating vector; other sequences listed in Appendix 1C number 85-91 can replace CsAAE1. 5 μg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, which contain the CsAAE1-T2A-Erg20(K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was designated as VscGPHA.

Using the VscGPHA strains the inventors added 5 μg of OS-T2A-OAC-HA in the vector containing a gene for leucine depletion resistance; other sequences listed in Appendix 1C number 60-84 can replace OS and OAC. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5 μg of this plasmid was linearized with EcoRV and transformed into chemically competent VscGPHOA; other sequences listed in Appendix 1C number 30-59 can replace CsPT. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs were taken for the final strain and designated VscCBDA.

Production of CBDA in Yeast.

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid-log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus*.

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Synthesis of Fusion Genes Required for CBDA Production in *K. marxianus*.

Figure 8:
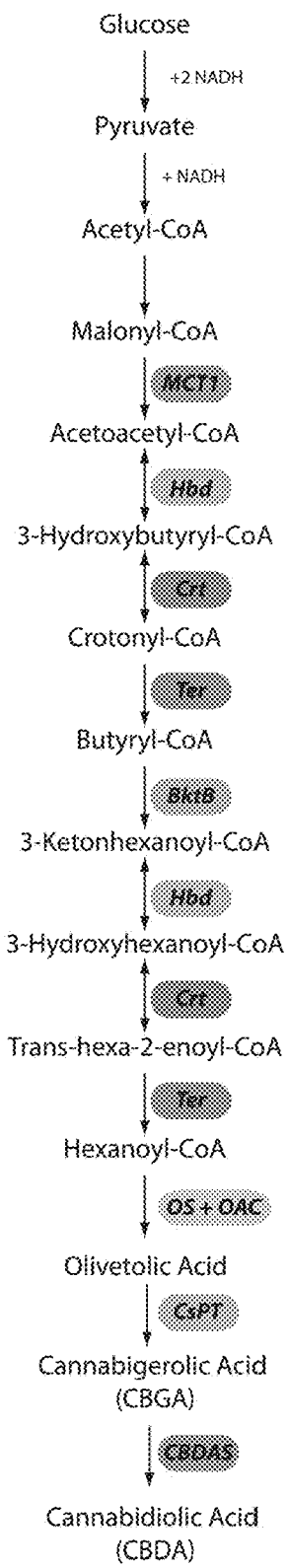
FIG. 8 shows an exemplary biosynthetic route for the production of CBDA from glucose.

FIG. 8 shows an exemplary biosynthetic route for the production of CBDA from glucose. The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reductase (Ter) from *Treponema denticola*. The Butyryl-CoA is converted to 3-Ketonhexanoyl-CoA by the enzyme β-ketothiolase (Bktb) from *Ralstonia eutropha*. 3-Ketonhexanoyl-CoA is converted to 3-Hydroxyhexanoyl-CoA by the enzyme Hbd. Hydroxyhexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus*.

Creation of a Stable *K. marxianus* Strain Producing the Metabolic Pathways for Hexonyl-coA and CBDA.

Two stable transformations of *K. marxianus* were created utilizing selection for uracil and G418 (Genenticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subcloned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement—Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (IRES), Ure2, into a galactose inducible vector and the final gene sequence pcen/arsGal-OSTOc-IRES-CsTCbds plasmid can be seen below. The plasmid pcen/arsGal-OSTOc-IRES-CstTCbds was used to synthesize a functional gene fragment that expresses the enzymes CBDAs, CsPt, OS, and OAC by using the primers GalIRES_F, GalIRES_R.

The Gibson Assembly method was used to subclone the PCR fragment from [0057] into the plasmid HO-polyKanMx4-HO (ATCC 87804) using the primers KmXIRES_F and KmXIRES_R to create the plasmid pHOOSCstKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement—Ura Clonetech 630416) 2% glucose, 1 mg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus*.

To initiate the reconstituted metabolic pathway of CBDA, a colony from k. Marx CBDA was freshly streaked onto an agar plate from a frozen glycerol stock of k. Marx CBDA. A small culture of VscCBDA was grown in YNBA base (YNB) supplemented with amino acid dropout mix (DO supplement—Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement—Ura Clonetech 630416) 2% glucose, and 1 mg/ml G418 (Gibco) and was grown at 30° C. until mid-log phase. Cells were pelleted by centrifugation then washed with 200 ml of phosphate buffered saline (PBS) and repelleted. Pelleted cells were resuspended with 1 L of YNBA supplemented with base (YNB)

supplemented with amino acid dropout mix (DO supplement—Ura Clonetech 630416) 2% galactose, and 1 mg/ml G418 (Gibco) and grown at 30° C. overnight.

Processing CBDA for Analysis of Cannabinoid Production.

Overnight 1 L cultures were pelleted by centrifugation, resuspended, washed one time in PBS and pelleted. The process for extracting cannabinoids from the yeast generally follows the following basic steps:
1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol Used for Cannabinoid Extraction from Yeast Cell Lysate
1. After lysising the cells using any mechanical technique, add 1 mL of 4M KCl, pH2.0 to each 1 mL of cell lysate.
2. Add 1-2 mLs of ethyl acetate for each 1 mL of cell lysate.
3. Rigorously mix for 1 min.
4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)
1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for k. Marx CBDA
1. Remove solvent from samples under vacuum.
2. Re-suspend dry samples in either 100 uL of dry hexane or dry ethyl acetate
3. Add 20 uL of N-Methyl-N-(trimethylsilyl) trifluoroacetamide (MSTFA)
4. Briefly mix
5. Heat solution to 60° C. for 10-15 minutes
6. GC-MS Method
   a. Instrument Agilent 6890-5975 GC-MS (Model Number: Agilent 19091S-433)
   b. Column HP-5MS 5% Phenyl Methyl Siloxane
   c. OVEN:

| | | | |
|---|---|---|---|
| i. Initial temp: 100 'C. (On) Maximum temp: 300 'C. | | | |
| ii. Initial time: 3.00 min Equilibration time: 0.50 min | | | |
| iii. Ramps: | | | |
| # | Rate | Final temp | Final time |
| 1 | 30.00 | 280 | 1.00 |
| 2 | 70.00 | 300 | 5.00 |
| 3 | 0.0 (Off) | | | iv. Post temp: 0° C.
v. Post time: 0.00 min
vi. Run time: 15.29 min

What is claimed is:

1. A method for making cannabigerolic acid, the method comprising:
   transforming a S. cerevisiae with a first nucleotide sequence of SEQ ID NO 1 expressing an acyl-activating enzyme;
   transforming the S. cerevisiae with a second nucleotide sequence of SEQ ID NO 22 expressing a mutant prenyltransferase;
   transforming the S. cerevisiae with a third nucleotide sequence of SEQ ID NO 10 expressing olivetolic synthase;
   transforming the S. cerevisiae with a fourth nucleotide sequence of SEQ ID NO 5 expressing olivetolic acid cyclase; and
   transforming the S. cerevisiae with a fifth nucleotide sequence of SEQ ID NO 39 expressing aromatic prenyltransferase.

2. A method for making cannabigerolic acid, the method comprising:
   transforming a S. cerevisiae with a first nucleotide sequence of SEQ ID NO 1 expressing an acyl-activating enzyme;
   transforming the S. cerevisiae with a second nucleotide sequence of SEQ ID NO 22 expressing a mutant prenyltransferase;
   transforming the S. cerevisiae with a third nucleotide sequence of SEQ ID NO 81 expressing olivetolic synthase;
   transforming the S. cerevisiae with a fourth nucleotide sequence of SEQ ID NO 5 expressing olivetolic acid cyclase; and
   transforming the S. cerevisiae with a fifth nucleotide sequence of SEQ ID NO 39 expressing aromatic prenyltransferase.

3. A method for making cannabigerolic acid, the method comprising:
   transforming a S. cerevisiae with a first nucleotide sequence of SEQ ID NO 85 expressing an acyl-activating enzyme;
   transforming the S. cerevisiae with a second nucleotide sequence of SEQ ID NO 22 expressing a mutant prenyltransferase;
   transforming the S. cerevisiae with a third nucleotide sequence of SEQ ID NO 81 expressing olivetolic synthase;
   transforming the S. cerevisiae with a fourth nucleotide sequence of SEQ ID NO 5 expressing olivetolic acid cyclase; and
   transforming the S. cerevisiae with a fifth nucleotide sequence of SEQ ID NO 39 expressing aromatic prenyltransferase.

4. A method for making cannabigerolic acid, the method comprising:
   transforming a S. cerevisiae with a first nucleotide sequence of SEQ ID NO 23 expressing an acyl-activating enzyme;
   transforming the S. cerevisiae with a second nucleotide sequence of SEQ ID NO 24 expressing a mutant prenyltransferase;
   transforming the S. cerevisiae with a third nucleotide sequence of SEQ ID NO 25 expressing olivetolic synthase;
   transforming the S. cerevisiae with a fourth nucleotide sequence of SEQ ID NO 26 expressing olivetolic acid cyclase; and
   transforming the S. cerevisiae with a fifth nucleotide sequence of SEQ ID NO 39 expressing aromatic prenyltransferase.

5. A method for making cannabigerolic acid, the method comprising:
   transforming a S. cerevisiae with a first nucleotide sequence of SEQ ID NO 81 expressing an acyl-activating enzyme, olivetolic synthase and olivetolic acid cyclase;

transforming the *S. cerevisiae* with a second nucleotide sequence of SEQ ID NO 22 expressing a mutant prenyltransferase; and transforming the *S. cerevisiae* with a third nucleotide sequence of SEQ ID NO 39 expressing aromatic prenyltransferase.

* * * * *

SEQUENCE LISTING

```
<160> NUMBER OF SEQ ID NOS: 117

<210> SEQ ID NO 1
<211> LENGTH: 7969
<212> TYPE: DNA
<213> ORGANISM: Artificial Sequence
<220> FEATURE:
<223> OTHER INFORMATION: Codon Optimized

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120 ttgcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta    300
ttactcttgg cctcctctag tacactctat atttttttat gcctcggtaa tgattttcat    360 ttttttttt cccctagcgg atgactcttt ttttttctta gcgattggca ttatcacata    420
atgaattata cattatataa agtaatgtga tttcttcgaa gaatatacta aaaaatgagc    480
```

-continued

| | |
|---|---|
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaaagag gcagaagcag tagcagaaca ggccacacaa tcgcaagtga | 660 |
| ttaacgtcca cacaggtata gggttttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag cttttaaaga ggccctactg gcgcgtggag | 840 |
| taaaaaggtt tggatcagga tttgcgcctt tggatgaggc actttccaga gcggtggtag | 900 |
| atctttcgaa caggccgtac gcagttgtcg aacttggttt gcaaagggag aaagtaggag | 960 |
| atctctcttg cgagatgatc ccgcattttc ttgaaagctt tgcagaggct agcagaatta | 1020 |
| ccctccacgt tgattgtctg cgaggcaaga atgatcatca ccgtagtgag agtgcgttca | 1080 |
| aggctcttgc ggttgccata agagaagcca cctcgcccaa tggtaccaac gatgttccct | 1140 |
| ccaccaaagg tgttcttatg tagtgacacc gattatttaa agctgcagca tacgatatat | 1200 |
| atacatgtgt atatatgtat acctatgaat gtcagtaagt atgtatacga acagtatgat | 1260 |
| actgaagatg acaaggtaat gcatcattct atacgtgtca ttctgaacga ggcgcgcttt | 1320 |
| cctttttttct ttttgctttt tctttttttt tctcttgaac tcgacggatc tatgcggtgt | 1380 |
| gaaataccgc acagatgcgt aaggagaaaa taccgcatca ggaaattgta aacgttaata | 1440 |
| ttttgttaaa attcgcgtta aattttttgtt aaatcagctc attttttaac caataggccg | 1500 |
| aaatcggcaa aatcccttat aaatcaaaag aatagaccga gatagggttg agtgttgttc | 1560 |
| cagtttggaa caagagtcca ctattaagaa acgtggactc caacgtcaaa gggcgaaaaa | 1620 |
| ccgtctatca gggcgatggc ccactacgtg aaccatcacc ctaatcaagt ttttgggggt | 1680 |
| cgaggtgccg taaagcacta atcggaacc ctaaagggag cccccgattt agagcttgac | 1740 |
| ggggaaagcc ggcgaacgtg gcgagaaagg aagggaagaa agcgaaagga gcgggcgcta | 1800 |
| gggcgctggc aagtgtagcg gtcacgctgc gcgtaaccac cacacccgcc gcgcttaatg | 1860 |
| cgccgctaca gggcgcgtcg cgccattcgc cattcaggct gcgcaactgt tgggaagggc | 1920 |
| gatcggtgcg ggcctcttcg ctattacgcc agctggcgaa aggggggatgt gctgcaaggc | 1980 |
| gattaagttg ggtaacgcca gggttttccc agtcacgacg ttgtaaaacg acggccagtg | 2040 |
| agcgcgcgta atacgactca ctatagggcg aattgggtac cggccgcaaa ttaaagcctt | 2100 |
| cgagcgtccc aaaaccttct caagcaaggt tttcagtata atgttacatg cgtacacgcg | 2160 |
| tctgtacaga aaaaaagaa aaatttgaaa tataaataac gttcttaata ctaacataac | 2220 |
| tataaaaaaa taaataggga cctagacttc aggttgtcta actccttcct tttcggttag | 2280 |
| agcggatgtg gggggagggc gtgaatgtaa gcgtgacata actaattaca tgactcgagg | 2340 |
| tcgactcatt cgaaatgact gaattgttgt ctcaaaactc ttctcatgat cttgtttgtt | 2400 |
| gcagttctag gtaaggatga caatgggaca actctagtaa ctttgaataa tgggttcaat | 2460 |
| ttcttttgca aacccaagtt aaaggataat ctcaattggt tcaaatcaat ggttgtgtcg | 2520 |
| tttgaatcct tcaatacgaa aaatatgacc aattgttctg gaccaccacc caaaggtgga | 2580 |
| acaccaatag cagtggtttc aaaaactctg tcatctactt cattacagac tctttcgatt | 2640 |
| tcgatagaac taattttgat accaccgatg ttcatagtgt catcggctct accgtgtgca | 2700 |
| tggtagtaac cgttagaggt caattcgaaa atgtcaccat gtcttctcaa tacttcacca | 2760 |
| ttcaaggttg gcatacccctt gaaatagaca tcgtgatgat taccgtttaa caatgttttt | 2820 |
| gaggcaccaa acataacagg acctaatgcc aattcaccga tacctggctt attttttaggc | 2880 |

```
attgggtaac cgttcttatc taatatgtac aaggtgcaac ccatacattg ggatgaaaaa    2940
gaacttaaag attgagcttg caaaaatgaa ccagcagaaa aagcaccacc gatttctgta    3000
ccaccacaca tttctataac tggcttgtag ttagctctac ccattaacca caaatattcg    3060
tctacattag aggcttcacc ggatgaagaa aagcatctta tggtggacca atcgtaacct    3120
gaaacacaat ttgtggattt ccatgatctt acaatagatg gtacgacacc caacattgtg    3180
acctttgcat cttgaacaaa tttagcgaaa ccagagacta aaggactacc gttgtacaag    3240
gcaatagatg caccatttaa caaactagca taaaccaacc aaggacccat catccaaccc    3300
aaattagttg gccatactat aacgtcacct tttctaatat ccaaatgaga ccaaccatca    3360
gcagcagcct tcaatggggt ggcttgtgtc caaggaattg cttttggttc acctgtagta    3420
ccactggaga ataagatgtt agtataagca tcaacaggtt gttctctggc agtaaactcg    3480
cagtttttaa actccttggc tctttctaaa aagtaatccc aagatatgtc accatctctc    3540
aattctgcac caatgttaga accactacaa gggataacta ttgccattgg ggatttagct    3600
tcaactactc ttgaatacaa tggtattctc ttttacctc tgatgatgtg atcttgtgtg    3660
aaaattgcct tagctttgga taatctcaat ctagttgaga tttcaggggc ggaaaatgaa    3720
tctgctatag agacaactac gtaaccagcc aatactatgg ccaaatatat aacaacagca    3780
tcaacatgca ttggcatatc gatggctatt gcacaacctt tttctaaacc catttcttcc    3840
aatgcataac caaccaacca aactctcttt ctcaattgat ctaatgtcaa cttattcaaa    3900
ggcaagtcat cgttaccctc gtctctccaa acgatcatag tatcgttcaa tttcttattg    3960
gagtttacgt tcaagcaatt tttagctgag ttcaagtaac caccaggtaa ccattcagaa    4020
ccacctgggt tgttgatgtc atctcttctc aagatacatt ctgggtcctt agagaaacta    4080
attttcattt catccatcaa tactgttctc caatagactt cagggtttct aacagaaaat    4140
tcttggaagt gagaaaaaga agaaattgga tctttgtact ttacacccaa aaattcttta    4200
cctctctttt ccaacaaagc acccaaatta gttgacttga ctttttcagg gtctggaatc    4260
caagcaggtg gggctggacc gaaatccttg tagcaaccat aaaacaacat ttggtgtaag    4320
gagaaaggca aatctggtga caagatatgg ttagcgatgt tgatccaagt ttgagggggtt    4380 gcagcaccat aattacaaac gatttctgcc aatctaccat gtaatgtttc tgctacttct    4440
gaggtgatac ccaatgcgat gaaatctgag gcaacgactg aatccaagga cttatagttt    4500
ttacccatac tagttctaga tccgtcgaaa ctaagttctt ggtgttttaa aactaaaaaa    4560
aagactaact ataaaagtag aatttaagaa gtttaagaaa tagatttaca gaattacaat    4620
caatacctac cgtctttata tacttattag tcaagtaggg gaataatttc agggaactgg    4680
tttaaacctt ttttttcagc tttttccaaa tcagagagag cagaaggtaa tagaaggtgt    4740
aagaaaatga gatagataca tgcgtgggtc aattgccttg tgtcatcatt tactccaggc    4800
aggttgcatc actccattga ggttgtgccc gttttttgcc tgtttgtgcc ctgttctctg    4860
tagttgcgct aagagaatgg acctatgaac tgatggttgg tgaagaaaac aatattttgg    4920
tgctgggatt cttttttttt ctggatgcca gcttaaaaag cgggctccat tatatttagt    4980
ggatgccagg aataaacctg ttcacccaag caccatcagt gttatatatt ctgtgtaacc    5040 cgcccccctat tttggcatgt acgggttaca gcagaattaa aaggctaatt ttttgactaa    5100
ataaagttag gaaaatcact actattaatt atttacgtat tctttgaaat ggcagtattg    5160
ataatgataa actcgagagc tccagctttt gttcccttta gtgagggtta attgcgcgct    5220
```

```
tggcgtaatc atggtcatag ctgtttcctg tgtgaaattg ttatccgctc acaattccac    5280
acaacatagg agccggaagc ataaagtgta aagcctgggg tgcctaatga gtgaggtaac    5340
tcacattaat tgcgttgcgc tcactgcccg ctttccagtc gggaaacctg tcgtgccagc    5400
tgcattaatg aatcggccaa cgcgcgggga gaggcggttt gcgtattggg cgctcttccg    5460
cttcctcgct cactgactcg ctgcgctcgg tcgttcggct gcggcgagcg gtatcagctc    5520
actcaaaggc ggtaatacgg ttatccacag aatcagggga taacgcagga agaacatgt    5580 gagcaaaagg ccagcaaaag gccaggaacc gtaaaaaggc cgcgttgctg gcgttttcc    5640 ataggctccg cccccctgac gagcatcaca aaaatcgacg ctcaagtcag aggtggcgaa    5700
acccgacagg actataaaga taccaggcgt ttccccctgg aagctccctc gtgcgctctc    5760
ctgttccgac cctgccgctt accggatacc tgtccgcctt ctcccttcg ggaagcgtgg    5820 cgctttctca tagctcacgc tgtaggtatc tcagttcggt gtaggtcgtt cgctccaagc    5880
tgggctgtgt gcacgaaccc cccgttcagc ccgaccgctg cgccttatcc ggtaactatc    5940
gtcttgagtc caacccggta agacacgact tatcgccact ggcagcagcc actggtaaca    6000
ggattagcag agcgaggtat gtaggcggtg ctacagagtt cttgaagtgg tggcctaact    6060
acggctacac tagaaggaca gtatttggta tctgcgctct gctgaagcca gttaccttcg    6120
gaaaaagagt tggtagctct tgatccggca acaaaccac cgctggtagc ggtggttttt    6180
ttgtttgcaa gcagcagatt acgcgcagaa aaaaggatc tcaagaagat cctttgatct    6240
tttctacggg gtctgacgct cagtggaacg aaaactcacg ttaagggatt ttggtcatga    6300
gattatcaaa aaggatcttc acctagatcc ttttaaatta aaaatgaagt tttaaatcaa    6360
tctaaagtat atatgagtaa acttggtctg acagttacca atgcttaatc agtgaggcac    6420
ctatctcagc gatctgtcta tttcgttcat ccatagttgc ctgactcccc gtcgtgtaga    6480
taactacgat acgggagggc ttaccatctg gccccagtgc tgcaatgata ccgcgagacc    6540
cacgctcacc ggctccagat ttatcagcaa taaaccagcc agccggaagg gccgagcgca    6600
gaagtggtcc tgcaacttta tccgcctcca tccagtctat taattgttgc cgggaagcta    6660
gagtaagtag ttcgccagtt aatagtttgc gcaacgttgt tgccattgct acaggcatcg    6720
tggtgtcacg ctcgtcgttt ggtatggctt cattcagctc cggttcccaa cgatcaaggc    6780
gagttacatg atcccccatg ttgtgcaaaa aagcggttag ctccttcggt cctccgatcg    6840
ttgtcagaag taagttggcc gcagtgttat cactcatggt tatggcagca ctgcataatt    6900
ctcttactgt catgccatcc gtaagatgct tttctgtgac tggtgagtac tcaaccaagt    6960
cattctgaga atagtgtatg cggcgaccga gttgctcttg cccggcgtca atacgggata    7020
ataccgcgcc acatagcaga actttaaaag tgctcatcat tggaaaacgt tcttcggggc    7080
gaaaactctc aaggatctta ccgctgttga tccagttc gatgtaaccc actcgtgcac    7140
ccaactgatc ttcagcatct tttactttca ccagcgtttc tgggtgagca aaaacaggaa    7200
ggcaaaatgc cgcaaaaaag gaataagggc gacacggaa atgttgaata ctcatactct    7260 tccttttca atattattga agcatttatc agggttattg tctcatgagc ggatacatat    7320
ttgaatgtat ttagaaaaat aaacaaatag gggttccgcg cacatttccc cgaaaagtgc    7380
cacctgggtc ttttcatca cgtgctataa aaataattat aatttaaatt ttttaatata    7440
aatatataaa ttaaaaatag aaagtaaaaa agaaattaa agaaaaaata gttttttgttt    7500 tccgaagatg taaaagactc taggggatc gccaacaaat actaccttt atcttgctct    7560 tcctgctctc aggtattaat gccgaattgt ttcatcttgt ctgtgtagaa gaccacacac    7620
```

```
gaaaatcctg tgattttaca ttttacttat cgttaatcga atgtatatct atttaatctg    7680
cttttcttgt ctaataaata tatatgtaaa gtacgctttt tgttgaaatt ttttaaacct    7740
ttgtttattt ttttttcttc attccgtaac tcttctacct tctttattta ctttctaaaa    7800
tccaaataca aaacataaaa ataaataaac acagagtaaa ttcccaaatt attccatcat    7860
taaaagatac gaggcgcgtg taagttacag gcaagcgatc cgtcctaaga aaccattatt    7920
atcatgacat taacctataa aaataggcgt atcacgaggc cctttcgtc              7969

<210> SEQ ID NO 2
<211> LENGTH: 10004
<212> TYPE: DNA
<213> ORGANISM: Artificial Sequence
<220> FEATURE:
<223> OTHER INFORMATION: Codon Optimized

<400> SEQUENCE: 2
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctttca attcatcatt ttttttttat tcttttttt gatttcggtt     360 tctttgaaat ttttttgatt cggtaatctc cgaacagaag gaagaacgaa ggaaggagca     420
cagacttaga ttggtatata tacgcatatg tagtgttgaa gaaacatgaa attgcccagt     480
attcttaacc caactgcaca gaacaaaaac ctgcaggaaa cgaagataaa tcatgtcgaa     540
agctacatat aaggaacgtg ctgctactca tcctagtcct gttgctgcca agctatttaa     600
tatcatgcac gaaaagcaaa caaacttgtg tgcttcattg gatgttcgta ccaccaagga     660
attactggag ttagttgaag cattaggtcc caaaatttgt ttactaaaaa cacatgtgga     720
tatcttgact gatttttcca tggagggcac agttaagccg ctaaaggcat atccgccaa     780 gtacaatttt ttactcttcg aagacagaaa atttgctgac attggtaata cagtcaaatt     840
gcagtactct gcgggtgtat acagaatagc agaatgggca gacattacga atgcacacgg     900
tgtggtgggc ccaggtattg ttagcggttt gaagcaggcg gcagaagaag taacaaagga     960
acctagaggc cttttgatgt tagcagaatt gtcatgcaag ggctccctat ctactggaga    1020
atatactaag ggtactgttg acattgcgaa gagcgacaaa gattttgtta tcggctttat    1080
tgctcaaaga gacatgggtg gaagagatga aggttacgat tggttgatta tgacacccgg    1140
tgtgggttta gatgacaagg gagacgcatt gggtcaacag tatagaaccg tggatgatgt    1200
ggtctctaca ggatctgaca ttattattgt tggaagagga ctatttgcaa agggaaggga    1260
tgctaaggta gagggtgaac gttacagaaa agcaggctgg gaagcatatt tgagaagatg    1320
cggccagcaa aactaatgac accgattatt taaagctgca gcatacgata tatatacatg    1380
tgtatatatg tataccatg aatgtcagta agtatgtata cgaacagtat gatactgaag    1440
atgacaaggt aatgcatcat tctatacgtg tcattctgaa cgaggcgcgc tttcctttt    1500 tcttttttgct ttttcttttt tttctcttg aactcgacgg atctatgcgg tgtgaaatac    1560
cgcacagatg cgtaaggaga aaataccgca tcaggaaatt gtaaacgtta atattttgtt    1620
aaaattcgcg ttaaattttt gttaaatcag ctcatttttt aaccaatagg ccgaaatcgg    1680
```

-continued

```
caaaatccct tataaatcaa agaatagac cgagatagg ttgagtgttg ttccagtttg    1740
gaacaagagt ccactattaa agaacgtgga ctccaacgtc aaagggcgaa aaaccgtcta    1800
tcagggcgat ggcccactac gtgaaccatc accctaatca agttttttgg ggtcgaggtg    1860
ccgtaaagca ctaaatcgga accctaaagg gagcccccga tttagagctt gacggggaaa    1920
gccggcgaac gtggcgagaa aggaagggaa gaaagcgaaa ggagcgggcg ctagggcgct    1980
ggcaagtgta gcggtcacgc tgcgcgtaac caccacaccc gccgcgctta atgcgccgct    2040
acagggcgcg tcgcgccatt cgccattcag gctgcgcaac tgttgggaag ggcgatcggt    2100
gcgggcctct tcgctattac gccagctggc gaaaggggga tgtgctgcaa ggcgattaag    2160
ttgggtaacg ccagggtttt cccagtcacg acgttgtaaa acgacggcca gtgagcgcgc    2220
gtaatacgac tcactatagg gcgaattggg taccggccgc aaattaaagc cttcgagcgt    2280
cccaaaacct tctcaagcaa ggttttcagt ataatgttac atgcgtacac gcgtctgtac    2340
agaaaaaaaa gaaaaatttg aaatataaat aacgttctta atactaacat aactataaaa    2400
aaataaatag ggacctagac ttcaggttgt ctaactcctt cctttttcggt tagagcggat    2460 gtgggggggag ggcgtgaatg taagcgtgac ataactaatt acatgactcg aggtcgactt    2520
acttgtcatc gtcatctttg tagtcaatat cgtggtcttt atagtcaccg tcatgatcct    2580
tgtaatcctt tgatctcttg tagaccttat tcaagaaagc tgtcaaaacg tcggctttaa    2640
aacctcttga ttcatcaact tgactaatct ttgcctttaa gtcttagcg atggattctt    2700 cgtattcatg gtacaattgt tcaatcttca aatcattaaa aattttctta cactttgctt    2760
cagcaactga gtccttttta ccgtagtttt catccaaagt ctttctttgt tcggcagatg    2820
ctaattccaa agccttgtta ataacccaac tgcacttatt gtcttgaata tctgtaccga    2880
ttttacctat ttgttctgga gtaccgaaac agtctaagta gtcatcttgg atttggaagt    2940
attcacccaa aggtatcaaa acatctcttg cttgcttcaa gtcttttca tcagtaatac    3000 cagctacgta catagccaag gcgactggca aatagaagga gtaataagca gtttcaaagg    3060
tgacgatgaa tgaatgtttc ttcaaggaaa actttgacaa gtcaacttta tcttcaggtg    3120
cagttatcaa atccatcaat tgacccaatt ctgtttggaa agtaacttcg tggaataatt    3180
cggtaatatc gatgtagtac ttttcgtttc tgaaatgtga cttcaacaat ttatagatag    3240
cggcttccaa cataaaagca tcatttatgg ctatttcacc aacttctgga actttgtacc    3300
agcatggttg acctcttctt gttatagact tatccatcat gtcatcggca accaaaaagt    3360
atgcttgcaa caattcaata caccaaccca agatagcgac cttttcgtat tcttcttgac    3420
ctaattgttc aacggttttg ttagacaaga tagcataagt atcaactaca ctcaaacctc    3480
tattcaattt accacctgga gtattgtagt ttaaagagtg agcataccaa tcgcaggctt    3540
ctttaggcat accataagct aacaaactag cgttcaattc ttcaactaac tttgggaata    3600
cgttcaagaa tctttctctt cttatttcct tttctgaagc cataggacct ggattttctt    3660
caacgtcacc acatgttaac aaagaacctc taccttcttc gaaatgactg aattgttgtc    3720
tcaaaactct tctcatgatc ttgtttgttg cagttctagg taaggatgac aatgggacaa    3780
ctctagtaac tttgaataat gggttcaatt tcttttgcaa acccaagtta aaggataatc    3840
tcaattggtt caaatcaatg gttgtgtcgt ttgaatcctt caatacgaaa aatatgacca    3900
attgttctgg accaccaccc aaaggtggaa caccaatagc agtggtttca aaaactctgt    3960
catctacttc attacagact ctttcgattt cgatagaact aatttgata ccaccgatgt    4020 tcatagtgtc atcggctcta ccgtgtgcat ggtagtaacc gttagaggtc aattcgaaaa    4080
```

```
tgtcaccatg tcttctcaat acttcaccat tcaaggttgg catacccttg aaatagacat   4140
cgtgatgatt accgtttaac aatgtttttg aggcaccaaa cataacagga cctaatgcca   4200
attcaccgat acctggctta ttttaggca ttgggtaacc gttcttatct aatatgtaca   4260
aggtgcaacc catacattgg gatgaaaaag aacttaaaga ttgagcttgc aaaaatgaac   4320
cagcagaaaa agcaccaccg atttctgtac caccacacat ttctataact ggcttgtagt   4380
tagctctacc cattaaccac aaatattcgt ctacattaga ggcttcaccg gatgaagaaa   4440
agcatcttat ggtggaccaa tcgtaacctg aaacacaatt tgtggatttc catgatctta   4500
caatagatgg tacgacaccc aacattgtga cctttgcatc ttgaacaaat ttagcgaaac   4560
cagagactaa aggactaccg ttgtacaagg caatagatgc accatttaac aaactagcat   4620
aaaccaacca aggacccatc atccaaccca aattagttgg ccatactata acgtcacctt   4680
ttctaatatc caaatgagac caaccatcag cagcagcctt caatggggtg gcttgtgtcc   4740
aaggaattgc ttttggttca cctgtagtac cactggagaa taagatgtta gtataagcat   4800
caacaggttg ttctctggca gtaaactcgc agttttaaa ctccttggct ctttctaaaa   4860
agtaatccca agatatgtca ccatctctca attctgcacc aatgttagaa ccactacaag   4920
ggataactat tgccattggg gatttagctt caactactct tgaatacaat ggtattctct   4980
ttttacctct gatgatgtga tcttgtgtga aaattgcctt agctttggat aatctcaatc   5040
tagttgagat ttcaggggcg gaaaatgaat ctgctataga gacaactacg taaccagcca   5100
atactatggc caaatatata acaacagcat caacatgcat tggcatatcg atggctattg   5160
cacaaccttt ttctaaaccc atttcttcca atgcataacc aaccaaccaa actctctttc   5220
tcaattgatc taatgtcaac ttattcaaag gcaagtcatc gttaccctcg tctctccaaa   5280
cgatcatagt atcgttcaat ttcttattgg agtttacgtt caagcaattt ttagctgagt   5340
tcaagtaacc accaggtaac cattcagaac cacctgggtt gttgatgtca tctcttctca   5400
agatacattc tgggtcctta gagaaactaa ttttcatttc atccatcaat actgttctcc   5460
aatagacttc agggtttcta acagaaaatt cttggaagtg agaaaaagaa gaaattggat   5520
ctttgtactt tacacccaaa aattctttac ctctcttttc caacaaagca cccaaattag   5580
ttgacttgac ttttttcaggg tctggaatcc aagcaggtgg ggctggaccg aaatccttgt   5640
agcaaccata aaacaacatt tggtgtaagg agaaaggcaa atctggtgac aagatatggt   5700
tagcgatgtt gatccaagtt tgaggggttg cagcaccata attacaaacg atttctgcca   5760
atctaccatg taatgtttct gctacttctg aggtgatacc caatgcgatg aaatctgagg   5820
caacgactga atccaaggac ttatagtttt tacccatact agttctagat ccgtcgaaac   5880
taagttcttg gtgtttttaaa actaaaaaaa agactaacta taaagtaga atttaagaag   5940 tttaagaaat agatttacag aattacaatc aatacctacc gtctttatat acttattagt   6000
caagtagggg aataatttca gggaactggt ttaaaccttt tttttcagct ttttccaaat   6060
cagagagagc agaaggtaat agaaggtgta agaaaatgag atagatacat gcgtgggtca   6120
attgccttgt gtcatcattt actccaggca ggttgcatca ctccattgag gttgtgcccg   6180 tttttgcct gtttgtgccc tgttctctgt agttgcgcta agagaatgga cctatgaact   6240
gatggttggt gaagaaaaca atattttggt gctgggattc ttttttttc tggatgccag   6300 cttaaaaagc gggctccatt atatttagtg gatgccagga ataaacctgt tcacccaagc   6360
accatcagtg ttatatattc tgtgtaaccc gccccctatt ttggcatgta cgggttacag   6420
```

```
cagaattaaa aggctaattt tttgactaaa taaagttagg aaaatcacta ctattaatta      6480
tttacgtatt cttttgaaatg gcagtattga taatgataaa ctcgagagct ccagcttttg     6540
ttcagttgat tgtatgcttg gtatagcttg aaatattgtg cagaaaaaga aacaaggaag      6600
aaagggaacg agaacaatga cgaggaaaca aaagattaat aattgcaggt ctatttatac     6660
ttgatagcaa gacagcaaac tttttttttat ttcaaattca agtaactgga aggaaggccg    6720
tataccgttg ctcattagag agtagtgtgc gtgaatgaag gaaggaaaaa gtttcgtgtg     6780
cttcgagata cccctcatca gctctggaac aacgacatct gttggtgctg tctttgtcgt     6840 taatttttc ctttagtgtc ttccatcatt tttttgtcat tgcggatatg gtgagacaac      6900
aacgggggag agagaaaaga aaaaaaaaga aaagaagttg catgcgccta ttattacttc     6960
aatagatggc aaatgaaaaa agggtagtga aacttcgata tgatgatggc tatcaagtct     7020
agggctacag tattagttcg ttatgtacca ccatcaatga ggcagtgtaa ttggtgtagt     7080
cttgtttagc ccattatgtc ttgtctggta tctgttctat tgtatatctc ccctccgcca     7140
cctacatgtt agggagacca acgaaggtat tataggaatc ccgatgtatg ggtttggttg     7200
ccagaaaaga ggaagtccat attgtacacc cggaaacaac aaaaggatgc gcgcttggcg    7260
taatcatggt catagctgtt tcctgtgtga aattgttatc cgctcacaat tccacacaac     7320
ataggagccg gaagcataaa gtgtaaagcc tggggtgcct aatgagtgag gtaactcaca     7380
ttaattgcgt tgcgctcact gcccgctttc cagtcgggaa acctgtcgtg ccagctgcat     7440
taatgaatcg gccaacgcgc ggggagaggc ggtttgcgta ttgggcgctc ttccgcttcc     7500
tcgctcactg actcgctgcg ctcggtcgtt cggctgcggc gagcggtatc agctcactca     7560
aaggcggtaa tacggttatc cacagaatca ggggataacg caggaaagaa catgtgagca     7620
aaaggccagc aaaaggccag gaaccgtaaa aaggccgcgt tgctggcgtt tttccatagg    7680
ctccgccccc ctgacgagca tcacaaaaat cgacgctcaa gtcagaggtg gcgaaacccg     7740
acaggactat aaagatacca ggcgtttccc cctggaagct ccctcgtgcg ctctcctgtt     7800
ccgaccctgc cgcttaccgg atacctgtcc gcctttctcc cttcgggaag cgtggcgctt    7860
tctcatagct cacgctgtag gtatctcagt tcggtgtagg tcgttcgctc caagctgggc     7920
tgtgtgcacg aaccccccgt tcagcccgac cgctgcgcct tatccggtaa ctatcgtctt     7980
gagtccaacc cggtaagaca cgacttatcg ccactggcag cagccactgg taacaggatt    8040
agcagagcga ggtatgtagg cggtgctaca gagttcttga agtggtggcc taactacggc     8100
tacactagaa ggacagtatt tggtatctgc gctctgctga agccagttac cttcggaaaa     8160
agagttggta gctcttgatc cggcaaacaa accaccgctg gtagcggtgg tttttttgtt     8220
tgcaagcagc agattacgcg cagaaaaaaa ggatctcaag aagatccttt gatcttttct     8280
acggggtctg acgctcagtg gaacgaaaac tcacgttaag ggattttggt catgagatta    8340
tcaaaaagga tcttcaccta gatccttta aattaaaaat gaagttttaa atcaatctaa      8400
agtatatatg agtaaacttg gtctgacagt taccaatgct taatcagtga ggcacctatc    8460
tcagcgatct gtctatttcg ttcatccata gttgcctgac tccccgtcgt gtagataact    8520
acgatacggg agggcttacc atctggcccc agtgctgcaa tgataccgcg agacccacgc    8580
tcaccggctc cagatttatc agcaataaac cagccagccg aagggccga gcgcagaagt     8640 ggtcctgcaa ctttatccgc ctccatccag tctattaatt gttgccggga agctagagta    8700
agtagttcgc cagttaatag tttgcgcaac gttgttgcca ttgctacagg catcgtggtg     8760
tcacgctcgt cgtttggtat ggcttcattc agctccggtt cccaacgatc aaggcgagtt     8820
```

| | |
|---|---|
| acatgatccc ccatgttgtg caaaaaagcg gttagctcct tcggtcctcc gatcgttgtc | 8880 |
| agaagtaagt tggccgcagt gttatcactc atggttatgg cagcactgca taattctctt | 8940 |
| actgtcatgc catccgtaag atgctttttct gtgactggtg agtactcaac caagtcattc | 9000 |
| tgagaatagt gtatgcggcg accgagttgc tcttgcccgg cgtcaatacg ggataatacc | 9060 |
| gcgccacata gcagaacttt aaaagtgctc atcattggaa aacgttcttc ggggcgaaaa | 9120 |
| ctctcaagga tcttaccgct gttgagatcc agttcgatgt aacccactcg tgcacccaac | 9180 |
| tgatcttcag catcttttac tttcaccagc gtttctgggt gagcaaaaac aggaaggcaa | 9240 |
| aatgccgcaa aaaagggaat aagggcgaca cggaaatgtt gaatactcat actcttcctt | 9300 |
| tttcaatatt attgaagcat ttatcagggt tattgtctca tgagcggata catatttgaa | 9360 |
| tgtatttaga aaaataaaca ataggggtt ccgcgcacat ttccccgaaa agtgccacct | 9420 |
| gggtcctttt catcacgtgc tataaaaata attataattt aaattttta atataaatat | 9480 |
| ataaattaaa aatagaaagt aaaaaagaa attaaagaaa aaatagtttt tgttttccga | 9540 |
| agatgtaaaa gactctaggg ggatcgccaa caaatactac cttttatctt gctcttcctg | 9600 |
| ctctcaggta ttaatgccga attgtttcat cttgtctgtg tagaagacca cacgaaaa | 9660 |
| tcctgtgatt ttacatttta cttatcgtta atcgaatgta tatctattta atctgctttt | 9720 |
| cttgtctaat aaatatatat gtaaagtacg cttttttgttg aaattttta aacctttgtt | 9780 |
| tatttttttt tcttcattcc gtaactcttc taccttcttt atttactttc taaaatccaa | 9840 |
| atacaaaaca taaaaataaa taaacacaga gtaaattccc aaattattcc atcattaaaa | 9900 |
| gatacgaggc gcgtgtaagt tacaggcaag cgatccgtcc taagaaacca ttattatcat | 9960 |
| gacattaacc tataaaaata ggcgtatcac gaggccctt cgtc | 10004 |

<210> SEQ ID NO 3
<211> LENGTH: 9508
<212> TYPE: DNA
<213> ORGANISM: Artificial Sequence
<220> FEATURE:
<223> OTHER INFORMATION: Codon Optimized

<400> SEQUENCE: 3

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgcgtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctaacg acattactat atatataata taggaagcat taatagaca | 360 |
| gcatcgtaat atatgtgtac tttgcagtta tgacgccaga tggcagtagt ggaagatatt | 420 |
| ctttattgaa aaatagcttg tcaccttacg tacaatcttg atccggagct ttctttttt | 480 |
| tgccgattaa gaattaattc ggtcgaaaaa agaaaaggag agggccaaga gggagggcat | 540 |
| tggtgactat tgagcacgtg agtatacgtg attaagcaca caaaggcagc ttggagtatg | 600 |
| tctgttatta atttcacagg tagttctggt ccattggtga agtttgcgg cttgcagagc | 660 |
| acagaggccg cagaatgtgc tctagattcc gatgctgact tgctgggtat tatatgtgtg | 720 |
| cccaatagaa agagaacaat tgacccggtt attgcaagga aatttcaag tcttgtaaaa | 780 |
| gcatataaaa atagttcagg cactccgaaa tacttggttg gcgtgtttcg taatcaacct | 840 |

```
aaggaggatg tttttggctct ggtcaatgat tacggcattg atatcgtcca actgcatgga      900
gatgagtcgt ggcaagaata ccaagagttc ctcggtttgc cagttattaa aagactcgta      960
tttccaaaag actgcaacat actactcagt gcagcttcac agaaacctca ttcgtttatt     1020
cccttgtttg attcagaagc aggtgggaca ggtgaacttt tggattggaa ctcgatttct     1080
gactgggttg gaaggcaaga gagccccgaa agcttacatt ttatgttagc tggtggactg     1140
acgccagaaa atgttggtga tgcgcttaga ttaaatggcg ttattggtgt tgatgtaagc     1200
ggaggtgtgg agacaaatgg tgtaaaagac tctaacaaaa tagcaaattt cgtcaaaaat     1260
gctaagaaat agtgacaccg attatttaaa gctgcagcat acgatatata tacatgtgta     1320
tatatgtata cctatgaatg tcagtaagta tgtatacgaa cagtatgata ctgaagatga     1380
caaggtaatg catcattcta tacgtgtcat tctgaacgag gcgcgctttc cttttttctt     1440
tttgctttttt cttttttttt ctcttgaact cgacggatct atgcggtgtg aaataccgca     1500
cagatgcgta aggagaaaat accgcatcag gaaattgtaa acgttaatat tttgttaaaa     1560
ttcgcgttaa attttttgtta aatcagctca tttttttaacc aataggccga aatcggcaaa     1620
atcccttata aatcaaaaga atagaccgag atagggttga gtgttgttcc agtttggaac     1680
aagagtccac tattaaagaa cgtggactcc aacgtcaaag gcgaaaaaac cgtctatcag     1740
ggcgatggcc cactacgtga accatcaccc taatcaagtt ttttggggtc gaggtgccgt     1800
aaagcactaa atcggaaccc taaagggagc ccccgattta gagcttgacg gggaaagccg     1860
gcgaacgtgg cgagaaagga agggaagaaa gcgaaaggag cgggcgctag gcgctggca     1920
agtgtagcgg tcacgctgcg cgtaaccacc acacccgccg cgcttaatgc gccgctacag     1980
ggcgcgtcgc gccattcgcc attcaggctg cgcaactgtt gggaagggcg atcggtgcgg     2040
gcctcttcgc tattacgcca gctggcgaaa ggggatgtg ctgcaaggcg attaagttgg     2100
gtaacgccag ggttttccca gtcacgacgt tgtaaaacga cggccagtga gcgcgcgtaa     2160
tacgactcac tatagggcga attgggtacc ggccgcaaat taaagccttc gagcgtccca     2220
aaaccttctc aagcaaggtt ttcagtataa tgttacatgc gtacacgcgt ctgtacagaa     2280
aaaaagaaa aatttgaaat ataaataacg ttcttaatac taacataact ataaaaaaat     2340
aaatagggac ctagacttca ggttgtctaa ctccttcctt ttcggttaga gcggatgtgg     2400
ggggagggcg tgaatgtaag cgtgacataa ctaattacat gactcgaggt cgacttacaa     2460
atcttcttca cttattaatt tttgttcgtg gtggtgaggt ggcaaaggtg ggatggattg     2520
ttcgtttctg aaaaagttgt tagggtcggc tttagtcttt actttaacta atctgttgaa     2580
attttttacca aagtactttt cacccccaaat tcttgcttgt gtatagttat ttggagattc     2640
agggttagtt ttacctaagt ccaaatctct gtagttcaaa tatgccaatc ttgggttttg     2700
actaacgtaa ggtgtagtga agttgtaaac ggatctgacc cagttgatat gcttttcgtt     2760
atcttcttgc ttttcccatg aggctgtgta ccataattca tacatgatac cagctctgtg     2820
aggaaatggt atgctgatt cagatatttc ttccataata ccaccgtatg gatacaaaac     2880
gtacatgccg acacctacat cttcttcgta caacttttcc aatatcttga ccattgcagt     2940
ttcagggatt ggtttcttaa cgtagtccaa tttaatagaa aaagcggtct ttttaccagc     3000
ggatctatcc aacaagattt cctttttgaa gttagcggtg ttgaagttta caacacctga     3060
atagaagatg gttgtgtcta tccaagaaaa ttccttgcaa tctgtctttt taatacccaa     3120
ttctgggaat gacttattca tcaaatcaac caaagaatct acaccaccat ggaaaattga     3180
agaaaaataa ccgtgaacag tggtcttatt tttaccatgg ttatctgtaa tatttttagt     3240
```

```
gatgaaatgg gtcatcaaaa ccaagtcctt atcgtacttg taagcgatgt tttgccactt    3300
attaaacaac ttaaccaaac cgtggatttc catgttcttt ttgacagaga aaatagtact    3360
tttggaagga acagcgacta acttaatttt ccaagcggca atgataccga aattttcacc    3420
accaccacct cttatggccc aaaacaaatc ttcacccata gactttctgt ccaaaacttt    3480
accatctacg ttaaccaaat gggcgtctat aatattatct gcagctaaac cgtagtttct    3540
catcaatgca ccataaccac caccagaaaa gtgaccaccg acacctactg ttggacagta    3600
accaccaggg aaagaaaagt tttcattctt ttcgttgatc cagtagtaaa cttcacccaa    3660
ggtggcacct gcttctaccc atgctgtttg actgtgaacg tcgatctttta tggaatgcat    3720 atttctcaaa tcgactacaa cgaatggaac ttgtgagatg taagacatgc cttctgcatc    3780
atgaccacct gatctagttc tgatttgcaa acctactttc ttagagcaca atatagaagc    3840
ttgaatgtga ctaacattgg aaggtgtaac aatgactaaa ggttttggtg tagtgtcaga    3900
agtgaatctc aaattttgga tggtactgtt caaaacggac atgtacaatt gatcatgttg    3960
agtatatata aactttgggt tagcagggtt gtttgggatg tattcggaga aacacttcaa    4020
aaagttttct tgtggatttg cgatggagat ttggatgttg aaggacaaga agaagaagat    4080
tattttacag acgaaccaga aagagaatgc ggagcagttc ataggacctg gattttcttc    4140
aacgtcacca caggtcaaca aagaacctct accttcaata aaaacgtata ccaaatattc    4200
agcgtagtac aatttccaca taaactcgta gaatcttcta cctgcttcag ggtcataatt    4260
tgtcaaagcg aaatctctag tttgcaagat caaccagaaa gccaagatgg catgtgacaa    4320
caacataacg ttagaattaa aggcttgtgg ccaaatgata cctgccaaaa tggctgcgac    4380
gtaacttaac aaaacgatac cggagcagaa caaagtcaaa tttcttgaac cgtacttaga    4440
agccaaggta ctaataccga actttgtgtc accttcaacg tcagaggcat ccttgatcaa    4500
ggctaatgca gaacccatac ttttcatgaa tgccaacaaa aatgtgaatg aaggtctcaa    4560
ttcgaatggc aaacctaaag cagctcttga agcgtagtag aaggtgaagt ttgtgatgat    4620
atgagctaag aaattcaaca aaaaggcagt actagggttt tgtttccatc taaaaggtgg    4680
tacggaatag acaataccac cgaagatacc gaaacagtaa ccgaagatgt acaatggacc    4740
acccttcatt ttaattgtga tgatcaaacc gaacaaggct actatgatag acatgatcca    4800
tgcagtattg acggatattt cacctgaagc caaaggcaaa tctggtttgt taattctgtc    4860
gatgtgcaaa tcgtatattt gattaattgt agtggtgaat gaagcgatgc acaagatggc    4920
aactaaaaag aaaaatgcct tgaacatcaa ggaccatgaa attaagttag tgttatgcaa    4980
caattcttta ccgaataaac cgcatgcaca agaagtaaaa gcgattatgg tgtatggtct    5040
ttgcaacttc caacatgctt taccgaagtt caaaatttttt gtggcaacag agtgattatc    5100
actttcaggt ggttcagttt gatttgtagt tgcagctctg atagagttct tagctataga    5160
caaactttcg gagcacttat tttgtaagtg aaggacttg gttgaacaat gttttgatgg    5220
aaagttgttg taagagtact taataggtgt ctttggatgt ctgtaacaca acaatgatgt    5280
ttttggattg ttgttgtgag gattcaataa ggtatgatag ttagtttgga aggagaaagt    5340
acagacggat gataaaccca tactagttct agatccgtcg aaactaagtt cttggtgttt    5400
taaaactaaa aaaagactaa actataaaag tagaatttaa gaagtttaag aaatagattt    5460
acagaattac aatcaatacc taccgtcttt atatacttat tagtcaagta ggggaataat    5520
ttcagggaac tggtttaaac cttttttttc agcttttttcc aaatcagaga gagcagaagg    5580
```

```
taatagaagg tgtaagaaaa tgagatagat acatgcgtgg gtcaattgcc ttgtgtcatc    5640
atttactcca ggcaggttgc atcactccat tgaggttgtg cccgttttt gcctgtttgt    5700 gccctgttct ctgtagttgc gctaagagaa tggacctatg aactgatggt tggtgaagaa    5760
aacaatattt tggtgctggg attctttttt tttctggatg ccagcttaaa aagcgggctc    5820
cattatattt agtggatgcc aggaataaac ctgttcaccc aagcaccatc agtgttatat    5880
attctgtgta acccgccccc tattttggca tgtacgggtt acagcagaat taaaaggcta    5940 atttttttgac taaataaagt taggaaaatc actactatta attatttacg tattctttga    6000
aatggcagta ttgataatga taaactcgag agctccagct tttgttcagt tgattgtatg    6060
cttggtatag cttgaaatat tgtgcagaaa aagaaacaag gaagaaaggg aacgagaaca    6120
atgacgagga aacaaaagat taataattgc aggtctattt atacttgata gcaagacagc    6180
aaactttttt ttatttcaaa ttcaagtaac tggaaggaag gccgtatacc gttgctcatt    6240
agagagtagt gtgcgtgaat gaaggaagga aaaagtttcg tgtgcttcga gatacccctc    6300
atcagctctg gaacaacgac atctgttggt gctgtctttg tcgttaattt tttcctttag    6360
tgtcttccat catttttttg tcattgcgga tatggtgaga caacaacggg ggagagagaa    6420
aagaaaaaaa aagaaaagaa gttgcatgcg cctattatta cttcaataga tggcaaatgg    6480
aaaaagggta gtgaaacttc gatatgatga tggctatcaa gtctagggct acagtattag    6540
ttcgttatgt accaccatca atgaggcagt gtaattggtg tagtcttgtt tagcccatta    6600
tgtcttgtct ggtatctgtt ctattgtata tctcccctcc gccacctaca tgttagggag    6660
accaacgaag gtattatagg aatcccgatg tatgggtttg gttgccagaa aagaggaagt    6720
ccatattgta cacccggaaa caacaaaagg atgcgcgctt ggcgtaatca tggtcatagc    6780
tgtttcctgt gtgaaattgt tatccgctca caattccaca caacatagga gccggaagca    6840
taaagtgtaa agcctggggt gcctaatgag tgaggtaact cacattaatt gcgttgcgct    6900
cactgcccgc tttccagtcg ggaaacctgt cgtgccagct gcattaatga atcggccaac    6960
gcgcggggag aggcggtttg cgtattgggc gctcttccgc ttcctcgctc actgactcgc    7020
tgcgctcggt cgttcggctg cggcgagcgg tatcagctca ctcaaaggcg gtaatacggt    7080
tatccacaga atcaggggat aacgcaggaa agaacatgtg agcaaaaggc cagcaaaagg    7140
ccaggaaccg taaaaaggcc gcgttgctgg cgttttttcca taggctccgc ccccctgacg    7200
agcatcacaa aaatcgacgc tcaagtcaga ggtggcgaaa cccgacagga ctataaagat    7260
accaggcgtt tccccctgga agctccctcg tgcgctctcc tgttccgacc ctgccgctta    7320
ccggatacct gtccgccttt ctcccttcgg gaagcgtggc gctttctcat agctcacgct    7380
gtaggtatct cagttcggtg taggtcgttc gctccaagct gggctgtgtg cacgaacccc    7440
ccgttcagcc cgaccgctgc gccttatccg gtaactatcg tcttgagtcc aacccggtaa    7500
gacacgactt atcgccactg gcagcagcca ctggtaacag gattagcaga gcgaggtatg    7560
taggcggtgc tacagagttc ttgaagtggt ggcctaacta cggctacact agaaggacag    7620
tatttggtat ctgcgctctg ctgaagccag ttaccttcgg aaaaagagtt ggtagctctt    7680
gatccggcaa acaaaccacc gctggtagcg gtggtttttt tgtttgcaag cagcagatta    7740
cgcgcagaaa aaaaggatct caagaagatc ctttgatctt ttctacgggg tctgacgctc    7800
agtggaacga aaactcacgt taagggattt tggtcatgag attatcaaaa aggatcttca    7860
cctagatcct tttaaattaa aaatgaagtt ttaaatcaat ctaaagtata tatgagtaaa    7920
cttggtctga cagttaccaa tgcttaatca gtgaggcacc tatctcagcg atctgtctat    7980
```

```
ttcgttcatc catagttgcc tgactccccg tcgtgtagat aactacgata cgggagggct    8040
taccatctgg ccccagtgct gcaatgatac cgcgagaccc acgctcaccg gctccagatt    8100
tatcagcaat aaaccagcca gccggaaggg ccgagcgcag aagtggtcct gcaactttat    8160
ccgcctccat ccagtctatt aattgttgcc gggaagctag agtaagtagt tcgccagtta    8220
atagtttgcg caacgttgtt gccattgcta caggcatcgt ggtgtcacgc tcgtcgtttg    8280
gtatggcttc attcagctcc ggttcccaac gatcaaggcg agttacatga tcccccatgt    8340
tgtgcaaaaa agcggttagc tccttcggtc ctccgatcgt tgtcagaagt aagttggccg    8400
cagtgttatc actcatggtt atggcagcac tgcataattc tcttactgtc atgccatccg    8460
taagatgctt ttctgtgact ggtgagtact caaccaagtc attctgagaa tagtgtatgc    8520
ggcgaccgag ttgctcttgc ccggcgtcaa tacgggataa taccgcgcca catagcagaa    8580
ctttaaaagt gctcatcatt ggaaaacgtt cttcggggcg aaaactctca aggatcttac    8640
cgctgttgag atccagttcg atgtaaccca ctcgtgcacc caactgatct tcagcatctt    8700
ttactttcac cagcgtttct gggtgagcaa aaacaggaag gcaaaatgcc gcaaaaaagg    8760
gaataagggc gacacggaaa tgttgaatac tcatactctt cctttttcaa tattattgaa    8820
gcatttatca gggttattgt ctcatgagcg gatacatatt tgaatgtatt tagaaaaata    8880
aacaaatagg ggttccgcgc acatttcccc gaaaagtgcc acctgggtcc ttttcatcac    8940
gtgctataaa aataattata atttaaattt tttaatataa atatataaat taaaaataga    9000
aagtaaaaaa agaaattaaa gaaaaaatag tttttgtttt ccgaagatgt aaaagactct    9060 aggggatcg ccaacaaata ctaccttta tcttgctctt cctgctctca ggtattaatg    9120
ccgaattgtt tcatcttgtc tgtgtagaag accacacacg aaaatcctgt gatttacat    9180 tttacttatc gttaatcgaa tgtatatcta tttaatctgc ttttcttgtc taataaatat    9240
atatgtaaag tacgcttttt gttgaaattt tttaaacctt tgtttatttt tttttcttca    9300
ttccgtaact cttctacctt cttatttac tttctaaaat ccaaatacaa acataaaaa    9360 taaataaaca cagagtaaat tcccaaatta ttccatcatt aaaagatacg aggcgcgtgt    9420
aagttacagg caagcgatcc gtcctaagaa accattatta tcatgacatt aacctataaa    9480
aataggcgta tcacgaggcc ctttcgtc                                       9508

<210> SEQ ID NO 4
<211> LENGTH: 9505
<212> TYPE: DNA
<213> ORGANISM: Artificial Sequence
<220> FEATURE:
<223> OTHER INFORMATION: Codon Optimized

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctaacg acattactat atatataata taggaagcat taatagaca    360 gcatcgtaat atatgtgtac tttgcagtta tgacgccaga tggcagtagt ggaagatatt     420
ctttattgaa aaatagcttg tcaccttacg tacaatcttg atccggagct tttctttttt     480
```

```
tgccgattaa gaattaattc ggtcgaaaaa agaaaaggag agggccaaga gggagggcat    540
tggtgactat tgagcacgtg agtatacgtg attaagcaca caaaggcagc ttggagtatg    600
tctgttatta atttcacagg tagttctggt ccattggtga agtttgcgg cttgcagagc    660 acagaggccg cagaatgtgc tctagattcc gatgctgact tgctgggtat tatatgtgtg    720
cccaatagaa agagaacaat tgacccggtt attgcaagga aaatttcaag tcttgtaaaa    780
gcatataaaa atagttcagg cactccgaaa tacttggttg gcgtgtttcg taatcaacct    840
aaggaggatg ttttggctct ggtcaatgat tacggcattg atatcgtcca actgcatgga    900
gatgagtcgt ggcaagaata ccaagagttc ctcggtttgc cagttattaa agactcgta    960 tttccaaaag actgcaacat actactcagt gcagcttcac agaaacctca ttcgtttatt   1020
cccttgtttg attcagaagc aggtgggaca ggtgaacttt tggattggaa ctcgatttct   1080
gactgggttg aaggcaaga gagccccgaa agcttacatt ttatgttagc tggtggactg   1140
acgccagaaa atgttggtga tgcgcttaga ttaaatggcg ttattggtgt tgatgtaagc   1200
ggaggtgtgg agacaaatgg tgtaaaagac tctaacaaaa tagcaaattt cgtcaaaaat   1260
gctaagaaat agtgacaccg attatttaaa gctgcagcat acgatatata tacatgtgta   1320
tatatgtata cctatgaatg tcagtaagta tgtatacgaa cagtatgata ctgaagatga   1380
caaggtaatg catcattcta tacgtgtcat tctgaacgag gcgcgctttc cttttttctt   1440 tttgctttt ctttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa attttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag gcgaaaaac cgtctatcag   1740 ggcgatggcc cactacgtga accatcaccc taatcaagtt ttttgggtc gaggtgccgt   1800 aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa ggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280 aaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg tctatgtcta ggtaaaggtg aatggattg   2520 ttcgtttcta aagaagttgt ttgggtcaac caatgtctta acctttacta atctatcgaa   2580
atttttaccg aagtattttt caccccaaat tctagcttgg gtatagttgt taggattctt   2640
tggatcgtta ataccgatgt ccaaatctct gtagttcaaa tatgccaatc tagggttttt   2700
agaaacgtat ggagtcatga agttatagat gtttctaatc cagtttaagt gcttttcgtt   2760
atcttcttgc ttttcccatg aacaaatgta ccacaattcg tataagatac cagctctatg   2820
aggaaatgga atggcagatt cactgatttc gtccattata ccaccgtatg gatacaaggc   2880
```

```
gtacatgcct gcaccaatat cttcttcgta caatttttct aagatttgga cgaaaactga    2940
ttcaggtatt ggcttttta acgtagtctaa cttaatttta aaggcaccgt tttgacctgc    3000
```

```
gtacatgcct gcaccaatat cttcttcgta caatttttct aagatttgga cgaaaactga    2940
ttcaggtatt ggctttttaa cgtagtctaa cttaatttta aaggcaccgt tttgacctgc    3000
ggatctatcc aataatattt ctttgttgaa gttgtctgta tcgtagttga caacacctga    3060
ataaaagatg atggtgtcga tccaagacaa ttgtctacaa tcagttttct taatacctaa    3120
ttctggaaaa gacttattca tcaagtctac taaggaatcg acaccaccca agaaaactga    3180
agaaaagtat gtgtggatag cagtcttatt tttaccttgg ttatcggtga tgtttcttgt    3240
gatgaaatga gtcatcaaca acaagtcctt atcgtacttg tatgcgatgt tttgccactt    3300
attgaccaat ttaactaatt catggatttc cattatcttt ttgactgaga acatagtaga    3360
ctttggtact gcgactaatc ttatcttcca agcaactatg ataccgaatg attctgcacc    3420
accacctctc aaagcccaaa ataagtcttc acccatagac tttctatcca aaactttacc    3480
gtgaacattt accaaatgag cgtcgattat gttatcagcg gccaaaccgt agtttctcat    3540
taaaggacca taaccaccac caccaaaatg accacctgcg caaactgttg gacagtaacc    3600
agcagccaat gataagtttt cattcttttc gttaacccag tagtatactt cacccaatgt    3660
tgcaccagct tcaacccaag cagtttgtga gtgtacgtct attttaattg atctcatgtt    3720
tctcaaatca acgataacga atggaacttg ggagatgtat gacatgcctt cactatcatg    3780
accaccggat ctagttctaa tttgcaaacc aacctttta gaacataaga tagtaccttg    3840
gatgtgagat acatgactag gggttacaat gaccaaaggt tttggagtgg tatcagaagt    3900
gaatctcaaa ttatggattg tactgttcaa gacggacatg tacaatgggt tgttttgagt    3960
gtaaaccaac ttcaaattgg tggcgttatt aggtatgtat tgtgagaagc acttcaaaaa    4020
gttttctctt gggtttgcga tacttgtttg gatgttaaag gaaagaaaa agaagatgat    4080
cttgcatacg aaccaaaagg agaaagttga acatttcata ggacctggat tttcttcaac    4140
gtcaccacag gtcaacaaag aacctctacc ttcaataaaa acgtatacca aatattcagc    4200
gtagtacaat ttccacataa actcgtagaa tcttctacct gcttcagggt cataatttgt    4260
caaagcgaaa tctctagttt gcaagatcaa ccagaaagcc aagatggcat gtgacaacaa    4320
cataacgtta gaattaaagg cttgtggcca aatgatacct gccaaaatgg ctgcgacgta    4380
acttaacaaa acgataccgg agcagaacaa agtcaaattt cttgaaccgt acttagaagc    4440
caaggtacta ataccgaact ttgtgtcacc ttcaacgtca gaggcatcct tgatcaaggc    4500
taatgcagaa cccatacttt tcatgaatgc caacaaaaat gtgaatgaag gtctcaattc    4560
gaatggcaaa cctaaagcag ctcttgaagc gtagtagaag gtgaagtttg tgatgatatg    4620
agctaagaaa ttcaacaaaa aggcagtact agggttttgt ttccatctaa aaggtggtac    4680
ggaatagaca ataccaccga agataccgaa acagtaaccg aagatgtaca atggaccacc    4740
cttcattta attgtgatga tcaaaccgaa caaggctact atgatagaca tgatccatgc    4800
agtattgacg atatttcac ctgaagccaa aggcaaatct ggtttgttaa ttctgtcgat    4860
gtgcaaatcg tatatttgat taattgtagt ggtgaatgaa gcgatgcaca agatggcaac    4920
taaaagaaa aatgccttga acatcaagga ccatgaaatt aagttagtgt tatgcaacaa    4980
ttctttaccg aataaaccgc atgcacaaga agtaaaagcg attatggtgt atggtctttg    5040
caacttccaa catgctttac cgaagttcaa aattttgtg gcaacagagt gattatcact    5100
ttcaggtggt tcagtttgat ttgtagttgc agctctgata gagttcttag ctatagacaa    5160
actttcggag cacttatttt gtaagtggaa ggacttggtt gaacaatgtt ttgatggaaa    5220
```

| | |
|---|---|
| gttgttgtaa gagtacttaa taggtgtctt tggatgtctg taacacaaca atgatgtttt | 5280 |
| tggattgttg ttgtgaggat tcaataaggt atgatagtta gtttggaagg agaaagtaca | 5340 |
| gacggatgat aaacccatac tagttctaga tccgtcgaaa ctaagttctt ggtgttttaa | 5400 |
| aactaaaaaa aagactaact ataaaagtag aatttaagaa gtttaagaaa tagatttaca | 5460 |
| gaattacaat caatacctac cgtctttata tacttattag tcaagtaggg gaataaattc | 5520 |
| agggaactgg tttaaacctt ttttttcagc ttttttccaaa tcagagagag cagaaggtaa | 5580 |
| tagaaggtgt aagaaaatga gatagataca tgcgtgggtc aattgccttg tgtcatcatt | 5640 |
| tactccaggc aggttgcatc actccattga ggttgtgccc gttttttgcc tgtttgtgcc | 5700 |
| ctgttctctg tagttgcgct aagagaatgg acctatgaac tgatggttgg tgaagaaaac | 5760 |
| aatattttgg tgctgggatt ctttttttttt ctggatgcca gcttaaaaag cgggctccat | 5820 |
| tatatttagt ggatgccagg aataaacctg ttcacccaag caccatcagt gttatatatt | 5880 |
| ctgtgtaacc cgcccccctat tttggcatgt acgggttaca gcagaattaa aaggctaatt | 5940 |
| ttttgactaa ataaagttag gaaaatcact actattaatt atttacgtat tctttgaaat | 6000 |
| ggcagtattg ataatgataa actcgagagc tccagctttt gttcagttga ttgtatgctt | 6060 |
| ggtatagctt gaaatattgt gcagaaaaag aaacaaggaa gaaagggaac gagaacaatg | 6120 |
| acgaggaaac aaaagattaa taattgcagg tctatttata cttgatagca agacagcaaa | 6180 |
| cttttttta tttcaaattc aagtaactgg aaggaaggcc gtataccgtt gctcattaga | 6240 |
| gagtagtgtg cgtgaatgaa ggaaggaaaa agtttcgtgt gcttcgagat accctcatc | 6300 |
| agctctggaa caacgacatc tgttggtgct gtctttgtcg ttaattttttt cctttagtgt | 6360 |
| cttccatcat ttttttgtca ttgcggatat ggtgagacaa caacggggga gagagaaaag | 6420 |
| aaaaaaaaag aaaagaagtt gcatgcgcct attattactt caatagatgg caaatggaaa | 6480 |
| aagggtagtg aaacttcgat atgatgatgg ctatcaagtc tagggctaca gtattagttc | 6540 |
| gttatgtacc accatcaatg aggcagtgta attggtgtag tcttgtttag cccattatgt | 6600 |
| cttgtctggt atctgttcta ttgtatatct ccccctccgcc acctacatgt tagggagacc | 6660 |
| aacgaaggta ttataggaat cccgatgtat gggtttggtt gccagaaaag aggaagtcca | 6720 |
| tattgtacac ccggaaacaa caaaaggatg cgcgcttggc gtaatcatgg tcatagctgt | 6780 |
| ttcctgtgtg aaattgttat ccgctcacaa ttccacacaa cataggagcc ggaagcataa | 6840 |
| agtgtaaagc ctggggtgcc taatgagtga ggtaactcac attaattgcg ttgcgctcac | 6900 |
| tgcccgcttt ccagtcggga aacctgtcgt gccagctgca ttaatgaatc ggccaacgcg | 6960 |
| cggggagagg cggtttgcgt attgggcgct cttccgcttc ctcgctcact gactcgctgc | 7020 |
| gctcggtcgt tcggctgcgg cgagcggtat cagctcactc aaaggcggta atacggttat | 7080 |
| ccacagaatc agggggataac gcaggaaaga acatgtgagc aaaaggccag caaaaggcca | 7140 |
| ggaaccgtaa aaaggccgcg ttgctggcgt ttttccatag gctccgcccc cctgacgagc | 7200 |
| atcacaaaaa tcgacgctca gtcagaggt ggcgaaaccc gacaggacta taaagatacc | 7260 |
| aggcgtttcc ccctggaagc tccctcgtgc gctctcctgt tccgaccctg ccgcttaccg | 7320 |
| gatacctgtc cgcctttctc ccttcgggaa gcgtggcgct ttctcatagc tcacgctgta | 7380 |
| ggtatctcag ttcggtgtag tcgttcgct ccaagctggg ctgtgtgcac gaaccccccg | 7440 |
| ttcagcccga ccgctgcgcc ttatccggta actatcgtct tgagtccaac ccggtaagac | 7500 |
| acgacttatc gccactggca gcagccactg gtaacaggat tagcagagcg aggtatgtag | 7560 |
| gcggtgctac agagttcttg aagtggtggc ctaactacgg ctacactaga aggacagtat | 7620 |

```
ttggtatctg cgctctgctg aagccagtta ccttcggaaa aagagttggt agctcttgat      7680
ccggcaaaca aaccaccgct ggtagcggtg gttttttgt ttgcaagcag cagattacgc       7740
gcagaaaaaa aggatctcaa gaagatcctt tgatcttttc tacggggtct gacgctcagt      7800
ggaacgaaaa ctcacgttaa gggattttgg tcatgagatt atcaaaaagg atcttcacct     7860
agatcctttt aaattaaaaa tgaagtttta aatcaatcta agtatatat gagtaaactt       7920 ggtctgacag ttaccaatgc ttaatcagtg aggcacctat ctcagcgatc tgtctatttc      7980
gttcatccat agttgcctga ctccccgtcg tgtagataac tacgatacgg gagggcttac     8040
catctggccc cagtgctgca atgataccgc gagacccacg ctcaccggct ccagatttat     8100
cagcaataaa ccagccagcc ggaagggccg agcgcagaag tggtcctgca actttatccg     8160
cctccatcca gtctattaat tgttgccggg aagctagagt aagtagttcg ccagttaata     8220
gtttgcgcaa cgttgttgcc attgctacag gcatcgtggt gtcacgctcg tcgtttggta     8280
tggcttcatt cagctccggt tcccaacgat caaggcgagt tacatgatcc cccatgttgt     8340
gcaaaaaagc ggttagctcc ttcggtcctc cgatcgttgt cagaagtaag ttggccgcag     8400
tgttatcact catggttatg gcagcactgc ataattctct tactgtcatg ccatccgtaa     8460
gatgcttttc tgtgactggt gagtactcaa ccaagtcatt ctgagaatag tgtatgcggc     8520
gaccgagttg ctcttgcccg gcgtcaatac gggataatac cgcgccacat agcagaactt    8580
taaaagtgct catcattgga aaacgttctt cggggcgaaa actctcaagg atcttaccgc    8640
tgttgagatc cagttcgatg taacccactc gtgcacccaa ctgatcttca gcatctttta    8700
ctttcaccag cgtttctggg tgagcaaaaa caggaaggca aaatgccgca aaaagggaa     8760 taagggcgac acggaaatgt tgaatactca tactcttcct ttttcaatat tattgaagca    8820
tttatcaggg ttattgtctc atgagcggat acatatttga atgtatttag aaaaataaac    8880
aaataggggt tccgcgcaca tttccccgaa aagtgccacc tgggtccttt tcatcacgtg    8940
ctataaaaat aattataatt taaattttttt aatataaata tataaattaa aaatagaaag   9000
taaaaaaaga aattaaagaa aaaatagttt ttgttttccg aagatgtaaa agactctagg    9060
gggatcgcca acaaatacta cctttatctc tgctcttcct gctctcaggt attaatgccg    9120
aattgtttca tcttgtctgt gtagaagacc acacacgaaa atcctgtgat tttacatttt    9180
acttatcgtt aatcgaatgt atatctattt aatctgcttt tcttgtctaa taaatatata    9240
tgtaaagtac gcttttttgtt gaaatttttt aaacctttgt ttatttttttt ttcttcattc   9300 cgtaactctt ctaccttctt tatttacttt ctaaaatcca aatacaaaac ataaaaataa    9360
ataaacacag agtaaattcc caaattattc catcattaaa agatacgagg cgcgtgtaag    9420
ttacaggcaa gcgatccgtc ctaagaaacc attattatca tgacattaac ctataaaaat    9480
aggcgtatca cgaggccctt tcgtc                                          9505
```

<210> SEQ ID NO 5
<211> LENGTH: 8696
<212> TYPE: DNA
<213> ORGANISM: Artificial Sequence
<220> FEATURE:
<223> OTHER INFORMATION: Codon Optimized

<400> SEQUENCE: 5

```
tcgcgcgttt cggtgatgac ggtgaaaacc tctgacacat gcagctcccg gagacggtca       60
cagcttgtct gtaagcggat gccggagca gacaagcccg tcagggcgcg tcagcgcgtg       120
```

```
ttggcgggtg tcgggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tcttttcta    300
ttactcttgg cctcctaact gtgggaatac tcaggtatcg taagatgcaa gagttcgaat    360
ctcttagcaa ccattatttt tttcctcaac ataacgagaa cacacagggg cgctatcgca    420
cagaatcaaa ttcgatgact ggaaattttt tgttaatttc agaggtcgcc tgacgcatat    480
accttttca actgaaaaat tgggagaaaa aggaaggtg agaggccgga accggctttt       540
catatagaat agagaagcgt tcatgactaa atgcttgcat cacaatactt gaagttgaca    600
atattattta aggacctatt gttttttcca ataggtggtt agcaatcgtc ttactttcta    660
acttttctta ccttttacat ttcagcaata tatatatata tttcaaggat ataccattct    720
aatgtctgcc cctatgtctg cccctaagaa gatcgtcgtt ttgccaggtg accacgttgg    780
tcaagaaatc acagccgaag ccattaaggt tcttaaagct atttctgatg ttcgttccaa    840
tgtcaagttc gatttcgaaa atcatttaat tggtggtgct gctatcgatg ctacaggtgt    900
cccacttcca gatgaggcgc tggaagcctc caagaaggtt gatgccgttt tgttaggtgc    960
tgtgggtggt cctaaatggg gtaccggtag tgttagacct gaacaaggtt tactaaaaat   1020
ccgtaaagaa cttcaattgt acgccaactt aagaccatgt aactttgcat ccgactctct   1080
tttagactta tctccaatca agccacaatt tgctaaaggt actgacttcg ttgttgtcag   1140
agaattagtg ggaggtattt actttggtaa gagaaaggaa gacgatggtg atggtgtcgc   1200
tgggatagt gaacaataca ccgttccaga agtgcaaaga atcacaagaa tggccgcttt    1260
catggcccta caacatgagc caccattgcc tatttggtcc ttggataaag ctaatgtttt   1320
ggcctcttca agattatgga gaaaaactgt ggaggaaacc atcaagaacg aattccctac   1380
attgaaggtt caacatcaat tgattgattc tgccgccatg atcctagtta agaacccaac   1440
ccacctaaat ggtattataa tcaccagcaa catgttggt gatatcatct ccgatgaagc     1500
ctccgttatc ccaggttcct ggggtttgtt gccatctgcg tccttggcct ctttgccaga   1560
caagaacacc gcatttggtt tgtacgaacc atgccacggt tctgctccag atttgccaaa   1620
gaataaggtt gaccctatcg ccactatctt gtctgctgca atgatgttga aattgtcatt   1680
gaacttgcct gaagaaggta aggccattga agatgcagtt aaaaaggttt tggatgcagg   1740
tatcagaact ggtgatttag gtggttccaa cagtaccacc gaagtcggtg atgctgtcgc   1800
cgaagaagtt aagaaaatcc ttgcttaatg acaccgatta tttaaagctg cagcatacga   1860
tatatataca tgtgtatata tgtataccta tgaatgtcag taagtatgta tacgaacagt   1920
atgatactga agatgacaag gtaatgcatc attctatacg tgtcattctg aacgaggcgc   1980
gctttccttt tttctttttg cttttctctt tttttctct tgaactcgac ggatctatgc     2040
ggtgtgaaat accgcacaga tgcgtaagga gaaataccg catcaggaaa ttgtaaacgt     2100
taatattttg ttaaaattcg cgttaaattt ttgttaaatc agctcatttt ttaaccaata   2160
ggccgaaatc ggcaaaatcc cttataaatc aaaagaatag accgagatag ggttgagtgt   2220
tgttccagtt tggaacaaga gtccactatt aagaacgtg gactccaacg tcaagggcg     2280
aaaaccgtc tatcagggcg atgccccact acgtgaacca tcaccctaat caagttttt     2340
ggggtcgagg tgccgtaaag cactaaatcg gaacccttaaa gggagccccc gatttagagc   2400
ttgacgggga agccggcga acgtggcgag aaggaaggg aagaaagcga aggagcggg      2460
cgctagggcg ctggcaagtg tagcggtcac gctgcgcgta accaccacac ccgccgcgct   2520
```

```
taatgcgccg ctacagggcg cgtcgcgcca ttcgccattc aggctgcgca actgttggga    2580
agggcgatcg gtgcgggcct cttcgctatt acgccagctg gcgaaagggg gatgtgctgc    2640
aaggcgatta agttgggtaa cgccagggtt ttcccagtca cgacgttgta aaacgacggc    2700
cagtgagcgc gcgtaatacg actcactata gggcgaattg ggtaccggcc gcaaattaaa    2760
gccttcgagc gtcccaaaac cttctcaagc aaggttttca gtataatgtt acatgcgtac    2820
acgcgtctgt acagaaaaaa agaaaaatt tgaaatataa ataacgttct taatactaac    2880
ataactataa aaaataaat agggacctag acttcaggtt gtctaactcc ttccttttcg    2940
gttagagcgg atgtgggggg agggcgtgaa tgtaagcgtg acataactaa ttacatgact    3000
cgaggtcgac ttatgcatag tctggaacat cgtaaggggta ctttcttggg gtgtaatcga    3060
agatcaacaa tttttcccag aaggatctgt aaacgtcacc aaaaccaacg tgagctggat    3120
gaatgatgta atcttggata gtttcaactg attcgaaggt tacttcgaca atgtgtgtat    3180
aaccttcttc tttcttttgt gtaacgtctt taccccagta tacatctttc atagcaggta    3240
taatgttgac caaattaacg taggtcttga aaaattcttc cttttgagct tctgtgattt    3300 catcttttaaa cttcaatact atcaaatgct tgacggccat aggacctggg ttttcttcaa    3360
cgtcaccaca agttaacaag gaacctctac cttcatattt aattggtact gatctgacaa    3420
ctactctttc gacggtcaaa ccaggaccga aaccaaataa gacacccat tcaaaaccgt    3480 caccagtagt agatttaccc tcttctaatg atctctttct caattcatcc attacgaaca    3540
agacagtgga tgaagacatg ttaccgtgtt cagataaaac atgtctacta tctacaaact    3600 tttcttttctt caaatccaat ttttcttcaa ccttatccaa aatggcttta ccacctggat    3660
gtgttatcca gaaatagag ttccaatctg agatacctat aggagtgaat gcttctatca    3720 aacactttc tatgttgtta gagattaaca ttggaacgtc tttgtgcaaa tcgaagatca    3780
aacctgcttc tcttatatga ccaccaattg taccttcaga attaggcaag atggtttgac    3840
ctgtactgac taattcaaat attggtcttt caccaacaga ttcgtcaggt tctgcaccaa    3900
caataacagc agcagcaccg tcaccgaaga tagcttgacc aactaacaat tccaagtcag    3960
aatcacttgg acctctaaac aagcaagcca taatgtcgca acaaacagct aatactctgg    4020 caccccttgtt gttttctgca atatccttag cgattctcaa aacagtacca ccaccgtagc    4080
aacctaattg atacatcatg actctcttaa cggatggtga caaacctaac aatttggcac    4140
agtggtagtc tgcaccaggc atatctgtag tagatgcact tgtaaaaatc aaatgagtga    4200
tctttgactt tggttgaccc cattccttaa tggcttttgc acaagcatct ttacccaatt    4260
taggaacttc gacaactaac atgtcttgtc tggcatccaa tgtttgcatt tcgtgttcta    4320
ccaatcttgg attttgcttc aaatgttctt cgttcaagaa gcagtttctc tttctgatca    4380
tagacttatc acatatttttt ctaaacttttt ccttcaattg agtcatgtgt tcactcttgg    4440
taactctgaa gtaataatca ggaaattcat cttggatcaa tatgttttct ggggttggctg    4500 tacctatggc taatacggag gcaggacctt cggctctcaa atggttcata ctagttctag    4560
atccgtcgaa actaagttct tggtgtttta aactaaaaa aaagactaac tataaaagta    4620
gaatttaaga agtttaagaa atagatttac agaattacaa tcaataccta ccgtctttat    4680
atacttatta gtcaagtagg ggaataattt cagggaactg gtttaaacct ttttttttcag    4740 cttttttccaa atcagagaga gcagaaggta ataagaaggtg taagaaaatg agatagatac    4800
atgcgtgggt caattgcctt gtgtcatcat ttactccagg caggttgcat cactccattg    4860
```

```
aggttgtgcc cgttttttgc ctgtttgtgc cctgttctct gtagttgcgc taagagaatg    4920
gacctatgaa ctgatggttg gtgaagaaaa caatattttg gtgctgggat tcttttttt    4980
tctggatgcc agcttaaaaa gcgggctcca ttatatttag tggatgccag gaataaacct    5040
gttcacccaa gcaccatcag tgttatatat tctgtgtaac ccgcccccta ttttggcatg    5100
tacgggttac agcagaatta aaaggctaat ttttgactaa ataaagtta ggaaaatcac     5160
tactattaat tatttacgta ttcttgaaa tggcagtatt gataatgata aactcgagag     5220
ctccagcttt tgttcagttg attgtatgct tggtatagct tgaaatattg tgcagaaaaa    5280
gaaacaagga agaagggaa cgagaacaat gacgaggaaa caaagatta ataattgcag      5340
gtctatttat acttgatagc aagacagcaa acttttttt atttcaaatt caagtaactg     5400
gaaggaaggc cgtataccgt tgctcattag agagtagtgt gcgtgaatga aggaaggaaa    5460
aagtttcgtg tgcttcgaga taccctcat cagctctgga caacgacat ctgttggtgc      5520
tgtctttgtc gttaatttt tcctttagtg tcttccatca ttttttgtc attgcggata      5580
tggtgagaca acaacggggg agagagaaaa gaaaaaaaa gaaagaagt tgcatgcgcc      5640
tattattact tcaatagatg gcaaatggaa aaagggtagt gaaacttcga tatgatgatg    5700
gctatcaagt ctagggctac agtattagtt cgttatgtac caccatcaat gaggcagtgt    5760
aattggtgta gtcttgttta gcccattatg tcttgtctgg tatctgttct attgtatatc    5820
tccctccgc cacctacatg ttaggagac caacgaaggt attataggaa tcccgatgta     5880
tgggtttggt tgccagaaaa gaggaagtcc atattgtaca cccggaaaca acaaaaggat    5940
gcgcgcttgg cgtaatcatg gtcatagctg tttcctgtgt gaaattgtta ccgctcaca    6000
attccacaca acataggagc cggaagcata aagtgtaaag cctggggtgc ctaatgagtg    6060
aggtaactca cattaattgc gttgcgctca ctgcccgctt tccagtcggg aaacctgtcg    6120
tgccagctgc attaatgaat cggccaacgc gcggggagag gcggtttgcg tattgggcgc    6180
tcttccgctt cctcgctcac tgactcgctg cgctcggtcg ttcggctgcg gcgagcggta    6240
tcagctcact caaaggcggt aatacggtta tccacagaat caggggataa cgcaggaaag    6300
aacatgtgag caaaaggcca gcaaaaggcc aggaaccgta aaaaggccgc gttgctggcg    6360
ttttcccata ggctccgccc ccctgacgag catcacaaaa atcgacgctc aagtcagagg    6420
tggcgaaacc cgacaggact ataaagatac caggcgtttc ccctggaag ctccctcgtg     6480
cgctctcctg ttccgaccct gccgcttacc ggatacctgt ccgcctttct cccttcggga    6540
agcgtggcgc tttctcatag ctcacgctgt aggtatctca gttcggtgta ggtcgttcgc    6600
tccaagctgg gctgtgtgca cgaaccccc gttcagcccg accgctgcgc cttatccggt     6660
aactatcgtc ttgagtccaa cccggtaaga cacgacttat cgccactggc agcagccact    6720
ggtaacagga ttagcagagc gaggtatgta ggcggtgcta cagagttctt gaagtggtgg    6780
cctaactacg gctacactag aaggacagta tttggtatct gcgctctgct gaagccagtt    6840
accttcggaa aaagagttgg tagctcttga tccggcaaac aaaccaccgc tggtagcggt    6900
ggtttttttg tttgcaagca gcagattacg cgcagaaaaa aaggatctca agaagatcct    6960
ttgatctttt ctacggggtc tgacgctcag tggaacgaaa actcacgtta agggattttg    7020
gtcatgagat tatcaaaaag gatcttcacc tagatccttt taaattaaaa atgaagtttt    7080
aaatcaatct aaagtatata tgagtaaact tggtctgaca gttaccaatg cttaatcagt    7140
gaggcaccta tctcagcgat ctgtctattt cgttcatcca tagttgcctg actccccgtc    7200
gtgtagataa ctacgatacg ggagggctta ccatctggcc ccagtgctgc aatgataccg    7260
```

```
cgagacccac gctcaccggc tccagattta tcagcaataa accagccagc cggaagggcc      7320
gagcgcagaa gtggtcctgc aactttatcc gcctccatcc agtctattaa ttgttgccgg      7380
gaagctagag taagtagttc gccagttaat agtttgcgca acgttgttgc cattgctaca      7440
ggcatcgtgg tgtcacgctc gtcgtttggt atggcttcat tcagctccgg ttcccaacga      7500
tcaaggcgag ttacatgatc ccccatgttg tgcaaaaaag cggttagctc cttcggtcct      7560
ccgatcgttg tcagaagtaa gttggccgca gtgttatcac tcatggttat ggcagcactg      7620
cataattctc ttactgtcat gccatccgta agatgctttt ctgtgactgg tgagtactca      7680
accaagtcat tctgagaata gtgtatgcgg cgaccgagtt gctcttgccc ggcgtcaata      7740
cgggataata ccgcgccaca tagcagaact ttaaaagtgc tcatcattgg aaaacgttct      7800
tcggggcgaa aactctcaag gatcttaccg ctgttgagat ccagttcgat gtaacccact      7860
cgtgcaccca actgatcttc agcatctttt actttcacca gcgtttctgg gtgagcaaaa      7920
acaggaaggc aaaatgccgc aaaaaaggga ataagggcga cacggaaatg ttgaatactc      7980
atactcttcc tttttcaata ttattgaagc atttatcagg gttattgtct catgagcgga      8040
tacatatttg aatgtattta gaaaaataaa caaatagggg ttccgcgcac atttccccga      8100
aaagtgccac ctgggtcctt ttcatcacgt gctataaaaa taattataat ttaaattttt      8160
taatataaat atataaatta aaaatagaaa gtaaaaaaag aaattaaaga aaaaatagtt      8220
tttgttttcc gaagatgtaa aagactctag ggggatcgcc aacaaatact accttttatc      8280
ttgctcttcc tgctctcagg tattaatgcc gaattgtttc atcttgtctg tgtagaagac      8340
cacacacgaa aatcctgtga ttttacattt tacttatcgt taatcgaatg tatatctatt      8400
taatctgctt ttcttgtcta ataaatatat atgtaaagta cgcttttgt tgaaattttt      8460 taaacctttg tttattttt tttcttcatt ccgtaactct tctaccttct ttatttactt      8520
tctaaaatcc aaatacaaaa cataaaaata aataaacaca gagtaaattc ccaaattatt      8580
ccatcattaa aagatacgag gcgcgtgtaa gttacaggca agcgatccgt cctaagaaac      8640
cattattatc atgacattaa cctataaaaa taggcgtatc acgaggccct ttcgtc        8696
```

<210> SEQ ID NO 6
<211> LENGTH: 4322
<212> TYPE: DNA
<213> ORGANISM: Artificial Sequence
<220> FEATURE:
<223> OTHER INFORMATION: Codon Optimized

<400> SEQUENCE: 6

```
aggaaacgaa gataaatctc gagtttatca ttatcaatac tgccatttca agaatacgt       60 aaataattaa tagtagtgat tttcctaact ttatttagtc aaaaaattag ccttttaatt      120
ctgctgtaac ccgtacatgc caaataggg ggcgggttac acagaatata taacactgat       180
ggtgcttggg tgaacaggtt tattcctggc atccactaaa tataatggag cccgcttttt      240
aagctggcat ccagaaaaaa aaagaatccc agcaccaaaa tattgttttc ttcaccaacc      300
atcagttcat aggtccattc tcttagcgca actacagaga acagggcaca aacaggcaaa      360
aaacgggcac aacctcaatg gagtgatgca acctgcctgg agtaaatgat gacacaaggc      420
aattgaccca cgcatgtatc tatctcattt tcttacacct tctattacct tctgctctct      480
ctgatttgga aaaagctgaa aaaaaaggtt taaaccagtt ccctgaaatt attccctac      540 ttgactaata agtatataaa gacggtaggt attgattgta attctgtaaa tctatttctt      600
```

```
aaacttctta aattctactt ttatagttag tctttttttt agttttaaaa caccaagaac      660
ttagtttcga cggatctaga actagtatgg gtaaaaacta taagtccttg gattcagtcg      720
ttgcctcaga tttcatcgca ttgggtatca cctcagaagt agcagaaaca ttacatggta      780
gattggcaga atcgtttgt aattatggtg ctgcaacccc tcaaacttgg atcaacatcg       840
ctaaccatat cttgtcacca gatttgcctt tctccttaca ccaaatgttg ttttatggtt     900
gctacaagga tttcggtcca gccccacctg cttggattcc agaccctgaa aaagtcaagt      960
caactaattt gggtgctttg ttggaaaaga gaggtaaaga attttgggt gtaaagtaca      1020 aagatccaat ttcttctttt tctcacttcc aagaattttc tgttagaaac cctgaagtct     1080
attggagaac agtattgatg gatgaaatga aaattagttt ctctaaggac ccagaatgta    1140
tcttgagaag agatgacatc aacaacccag gtggttctga atggttacct ggtggttact    1200
tgaactcagc taaaaattgc ttgaacgtaa actccaataa gaaattgaac gatactatga     1260
tcgtttggag agacgagggt aacgatgact tgccttttgaa taagttgaca ttagatcaat    1320
tgagaaagag agtttggttg gttggttatg cattggaaga aatgggttta gaaaaaggtt     1380
gtgcaatagc catcgatatg ccaatgcatg ttgatgctgt tgttatatat ttggccatag     1440
tattggctgg ttacgtagtt gtctctatag cagattcatt ttccgcccct gaaatctcaa     1500
ctagattgag attatccaaa gctaaggcaa ttttcacaca agatcacatc atcagaggta     1560
aaaagagaat accattgtat tcaagagtag ttgaagctaa atccccaatg gcaatagtta    1620
tcccttgtag tggttctaac attggtgcag aattgagaga tggtgacata tcttgggatt    1680 acttttaga aagagccaag gagtttaaaa actgcgagtt tactgccaga gaacaacctg     1740
ttgatgctta tactaacatc ttattctcca gtggtactac aggtgaacca aaagcaattc     1800 cttgacaca agccaccca ttgaaggctg ctgctgatgg ttggtctcat ttggatatta     1860
gaaaaggtga cgttatagta tggccaacta atttgggttg gatgatgggt ccttggttgg   1920
tttatgctag tttgttaaat ggtgcatcta ttgccttgta caacggtagt cctttagtct     1980
ctggtttcgc taaatttgtt caagatgcaa aggtcacaat gttgggtgtc gtaccatcta    2040
ttgtaagatc atggaaatcc acaaattgtg tttcaggtta cgattggtcc accataagat    2100
gcttttcttc atccggtgaa gcctctaatg tagacgaata tttgtggtta atgggtagag    2160
ctaactacaa gccagttata gaaatgtgtg gtggtacaga aatcggtggt gcttttctg    2220 ctggttcatt tttgcaagct caatctttaa gttcttttc atcccaatgt atgggttgca    2280
ccttgtacat attagataag aacggttacc caatgcctaa aaataagcca ggtatcggtg    2340
aattggcatt aggtcctgtt atgtttggtg cctcaaaaac attgttaaac ggtaatcatc    2400
acgatgtcta tttcaagggt atgccaacct tgaatggtga agtattgaga agacatggtg    2460
acattttcga attgacctct aacggttact accatgcaca cggtagagcc gatgacacta    2520
tgaacatcgg tggtatcaaa attagttcta tcgaaatcga aagagtctgt aatgaagtag    2580
atgacagagt ttttgaaacc actgctattg gtgttccacc tttgggtggt ggtccagaac    2640
aattggtcat attttcgta ttgaaggatt caaacgacac aaccattgat ttgaaccaat    2700
tgagattatc ctttaacttg ggtttgcaaa agaaattgaa cccattattc aaagttacta    2760
gagttgtccc attgtcatcc ttacctagaa ctgcaacaaa caagatcatg agaagagttt    2820
tgagacaaca attcagtcat ttcgaagaag gtagaggttc tttgttaaca tgtggtgacg   2880
ttgaagaaaa tccaggtcct atggcttcag aaaaggaaat aagaagagaa agattcttga   2940
acgtattccc aaagttagtt gaagaattga acgctagttt gttagcttat ggtatgccta    3000
```

```
aagaagcctg cgattggtat gctcactctt taaactacaa tactccaggt ggtaaattga    3060
atagaggttt gagtgtagtt gatacttatg ctatcttgtc taacaaaacc gttgaacaat    3120
taggtcaaga agaatacgaa aaggtcgcta tcttgggttg gtgtattgaa ttgttgcaag    3180 catactttt ggttgccgat gacatgatgg ataagtctat aacaagaaga ggtcaaccat    3240
gctggtacaa agttccagaa gttggtgaaa tagccataaa tgatgctttt atgttggaag    3300
ccgctatcta taaattgttg aagtcacatt tcagaaacga aaagtactac atcgatatta    3360
ccgaattatt ccacgaagtt actttccaaa cagaattggg tcaattgatg gatttgataa    3420
ctgcacctga agataaagtt gacttgtcaa agttttcctt gaagaaacat tcattcatcg    3480
tcacctttga aactgcttat tactccttct atttgccagt cgccttggct atgtacgtag    3540
ctggtattac tgatgaaaaa gacttgaagc aagcaagaga tgttttgata cctttgggtg    3600
aatacttcca atccaagat gactacttag actgtttcgg tactccagaa caaataggta    3660
aaatcggtac agatattcaa gacaataagt gcagttgggt tattaacaag ctttggaat    3720 tagcatctgc cgaacaaaga aagactttgg atgaaaacta cggtaaaaag gactcagttg    3780
ctgaagcaaa gtgtaagaaa atttttaatg atttgaagat tgaacaattg taccatgaat    3840
acgaagaatc catcgctaaa gacttaaagg caaagattag tcaagttgat gaatcaagag    3900
gttttaaagc cgacgttttg acagctttct tgaataaggt ctacaagaga tcaaaggatt    3960
acaaggatca tgacggtgac tataaagacc acgatattga ctacaaagat gacgatgaca    4020
agtaagtcga cctcgagtca tgtaattagt tatgtcacgc ttacattcac gccctccccc    4080
cacatccgct ctaaccgaaa aggaaggagt tagacaacct gaagtctagg tccctattta    4140
tttttttata gttatgttag tattaagaac gttatttata tttcaaattt ttcttttttt    4200
tctgtacaga cgcgtgtacg catgtaacat tatactgaaa accttgcttg agaaggtttt    4260
gggacgctcg aaggctttaa tttgcgtgac ataactaatt acatgacttg actgattttt    4320
cc                                                                   4322
```

<210> SEQ ID NO 7
<211> LENGTH: 2522
<212> TYPE: DNA
<213> ORGANISM: Artificial Sequence
<220> FEATURE:
<223> OTHER INFORMATION: Codon Optimized

<400> SEQUENCE: 7

```
aggaaacgaa gataaatctc gagtttatca ttatcaatac tgccatttca aagaatacgt      60
aaataattaa tagtagtgat tttcctaact ttatttagtc aaaaaattag ccttttaatt     120
ctgctgtaac ccgtacatgc caaaataggg ggcgggttac acagaatata taacactgat     180
ggtgctgggg tgaacaggtt tattcctggc atccactaaa tataatggag cccgcttttt     240
aagctggcat ccagaaaaaa aaagaatccc agcaccaaaa tattgttttc ttcaccaacc     300
atcagttcat aggtccattc tcttagcgca actacagaga cagggcaca aacaggcaaa      360 aaacgggcac aacctcaatg gagtgatgca acctgcctgg agtaaatgat gacacaaggc     420
aattgaccca cgcatgtatc tatctcattt tcttacacct tctattacct tctgctctct     480
ctgatttgga aaaagctgaa aaaaaaggtt taaaccagtt ccctgaaatt attcccctac     540
ttgactaata agtatataaa gacggtaggt attgattgta attctgtaaa tctatttctt     600
aaacttctta aattctactt ttatagttag tctttttttt agttttaaaa caccaagaac     660
```

-continued

```
ttagtttcga cggatctaga actagtatga accatttgag agccgaaggt cctgcctccg      720
tattagccat aggtacagcc aacccagaaa acatattgat ccaagatgaa tttcctgatt      780
attacttcag agttaccaag agtgaacaca tgactcaatt gaaggaaaag tttagaaaaa      840
tatgtgataa gtctatgatc agaaagagaa actgcttctt gaacgaagaa catttgaagc      900
aaaatccaag attggtagaa cacgaaatgc aaacattgga tgccagacaa gacatgttag      960
ttgtcgaagt tcctaaattg ggtaaagatg cttgtgcaaa agccattaag gaatggggtc     1020
aaccaaagtc aaagatcact catttgattt ttacaagtgc atctactaca gatatgcctg     1080
gtgcagacta ccactgtgcc aaattgttag gtttgtcacc atccgttaag agagtcatga     1140
tgtatcaatt aggttgctac ggtggtggta ctgttttgag aatcgctaag gatattgcag     1200
aaaacaacaa gggtgccaga gtattagctg tttgttgcga cattatggct tgcttgttta     1260
gaggtccaag tgattctgac ttggaattgt tagttggtca agctatcttc ggtgacggtg     1320
ctgctgctgt tattgttggt gcagaacctg acgaatctgt tggtgaaaga ccaatatttg     1380
aattagtcag tacaggtcaa accatcttgc ctaattctga aggtacaatt ggtggtcata     1440
taagagaagc aggtttgatc ttcgatttgc acaaagacgt tccaatgtta atctctaaca     1500
acatagaaaa gtgtttgata gaagcattca ctcctatagg tatctcagat tggaactcta     1560
ttttctggat aacacatcca ggtggtaaag ccatttttgga taaggttgaa gaaaaattgg     1620
atttgaagaa agaaaagttt gtagatagta gacatgtttt atctgaacac ggtaacatgt     1680
cttcatccac tgtcttgttc gtaatggatg aattgagaaa gagatcatta aagagggta     1740
aatctactac tggtgacggt tttgaatggg gtgtcttatt tggtttcggt cctggttga     1800
ccgtcgaaag agtagttgtc agatcagtac caattaaata tgaaggtaga ggttccttgt     1860
taacttgtgg tgacgttgaa gaaacccag gtcctatggc cgtcaagcat ttgatagtat     1920
tgaagtttaa agatgaaatc acagaagctc aaaaggaaga ttttttcaag acctacgtta     1980
atttggtcaa cattataccct gctatgaaag atgtatactg gggtaaagac gttacacaaa     2040
agaaagaaga aggttataca cacattgtcg aagtaaccctt cgaatcagtt gaaactatcc     2100
aagattacat cattcatcca gctcacgttg gttttggtga cgtttacaga tccttctggg     2160
aaaaattgtt gatcttcgat tacaccccaa gaaagtaccc ttacgatgtt ccagactatg     2220
cataagtcga cctcgagtca tgtaattagt tatgtcacgc ttacattcac gccctccccc     2280
cacatccgct ctaaccgaaa aggaaggagt tagacaacct gaagtctagg tccctattta     2340
tttttttata gttatgttag tattaagaac gttatttata tttcaaattt ttcttttttt     2400
tctgtacaga cgcgtgtacg catgtaacat tatactgaaa accttgcttg agaaggtttt     2460
gggacgctcg aaggctttaa tttgcgtgac ataactaatt acatgacttg actgattttt     2520
cc                                                                    2522
```

<210> SEQ ID NO 8
<211> LENGTH: 3887
<212> TYPE: DNA
<213> ORGANISM: Artificial Sequence
<220> FEATURE:
<223> OTHER INFORMATION: Codon Optimized

<400> SEQUENCE: 8

```
aggaaacgaa gataaatctc gagtttatca ttatcaatac tgccatttca agaatacgt       60
aaataattaa tagtagtgat tttcctaact ttatttagtc aaaaaattag cctttaatt      120
ctgctgtaac ccgtacatgc caaaataggg ggcgggttac acagaatata taacactgat     180
```

```
ggtgcttggg tgaacaggtt tattcctggc atccactaaa tataatggag cccgcttttt    240
aagctggcat ccagaaaaaa aaagaatccc agcaccaaaa tattgttttc ttcaccaacc    300
atcagttcat aggtccattc tcttagcgca actacagaga acagggcaca aacaggcaaa    360
aaacgggcac aacctcaatg gagtgatgca acctgcctgg agtaaatgat gacacaaggc    420
aattgaccca cgcatgtatc tatctcattt tcttacacct tctattacct tctgctctct    480
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tctttttttt agttttaaaa caccaagaac    660
ttagtttcga cggatctaga actagtatgg gtttatcatc cgtctgtact ttctccttcc    720
aaactaacta tcatacctta ttgaatcctc acaacaacaa tccaaaaaca tcattgttgt    780
gttacagaca tccaaagaca cctattaagt actcttacaa caactttcca tcaaaacatt    840
gttcaaccaa gtccttccac ttacaaaata agtgctccga aagtttgtct atagctaaga    900
actctatcag agctgcaact acaaatcaaa ctgaaccacc tgaaagtgat aatcactctg    960
ttgccacaaa aattttgaac ttcggtaaag catgttggaa gttgcaaaga ccatacacca   1020
taatcgcttt tacttcttgt gcatgcggtt tattcggtaa agaattgttg cataacacta   1080
acttaatttc atggtccttg atgttcaagg cattttttctt tttagttgcc atcttgtgca   1140
tcgcttcatt caccactaca attaatcaaa tatacgattt gcacatcgac agaattaaca   1200
aaccagattt gcctttggct tcaggtaaaa tatccgtcaa tactgcatgg atcatgtcta   1260
tcatagtagc cttgttcggt ttgatcatca caattaaaat gaagggtggt ccattgtaca   1320
tcttcggtta ctgtttcggt atcttcggtg gtattgtcta ttccgtacca cctttttagat  1380 ggaaacaaaa ccctagtact gccttttttgt tgaatttctt agctcatatc atcacaaact   1440
tcaccttcta ctacgcttca agagctgctt taggtttgcc attcgaattg agaccttcat   1500
tcacattttt gttggcattc atgaaaagta tgggttctgc attagccttg atcaaggatg   1560
cctctgacgt tgaaggtgac acaaagttcg gtattagtac cttggcttct aagtacggtt   1620
caagaaattt gactttgttc tgctccggta tcgttttgtt aagttacgtc gcagccattt   1680
tggcaggtat catttggcca caagccttta attctaacgt tatgttgttg tcacatgcca   1740
tcttggcttt ctggttgatc ttgcaaacta gagatttcgc tttgacaaat tatgaccctg   1800
aagcaggtag aagattctac gagtttatgt ggaaattgta ctacgctgaa tatttggtat   1860
acgtttttat tgaaggtaga ggttcttgt tgacctgtgg tgacgttgaa gaaaatccag   1920
gtcctatgaa atgttcaact ttctcctttt ggttcgtatg caagatcatc ttcttttct    1980 tttccttttaa catccaaaca agtatcgcaa acccaagaga aaacttttg aagtgcttct    2040 cacaatacat acctaataac gccaccaatt tgaagttggt ttacactcaa acaacccat    2100 tgtacatgtc cgtcttgaac agtacaatcc ataatttgag attcacttct gataccactc   2160
caaaaccttt ggtcattgta acccctagtc atgtatctca catccaaggt actatcttat   2220
gttctaaaaa ggttggtttg caaattagaa ctagatccgg tggtcatgat agtgaaggca   2280
tgtcatacat ctcccaagtt ccattcgtta tcgttgattt gagaaacatg agatcaatta   2340
aaatagacgt acactcacaa actgcttggg ttgaagctgg tgcaacattg ggtgaagtat   2400
actactgggt taacgaaaag aatgaaaact tatcattggc tgctggttac tgtccaacag   2460
tttgcgcagg tggtcatttt ggtggtggtg gttatggtcc tttaatgaga aactacggtt   2520
```

```
tggccgctga taacataatc gacgctcatt tggtaaatgt tcacggtaaa gttttggata    2580
gaaagtctat gggtgaagac ttatttgggg ctttgagagg tggtggtgca gaatcattcg    2640
gtatcatagt tgcttggaag ataagattag tcgcagtacc aaagtctact atgttctcag    2700
tcaaaaagat aatggaaatc catgaattag ttaaattggt caataagtgg caaaacatcg    2760
catacaagta cgataaggac ttgttgttga tgactcattt catcacaaga acatcaccg    2820 ataaccaagg taaaaataag actgctatcc acacatactt tcttcagtt ttcttgggtg    2880 gtgtcgattc cttagtagac ttgatgaata agtcttttcc agaattaggt attaagaaaa    2940
ctgattgtag acaattgtct tggatcgaca ccatcatctt ttattcaggt gttgtcaact    3000
acgatacaga caacttcaac aaagaaatat tattggatag atccgcaggt caaaacggtg    3060
cctttaaaat taagtttagac tacgttaaaa agccaatacc tgaatcagtt ttcgtccaaa    3120
tcttagaaaa attgtacgaa gaagatattg gtgcaggcat gtacgccttg tatccatacg    3180
gtggtataat ggacgaaatc agtgaatctg ccattccatt tcctcataga gctggtatct    3240
tatacgaatt gtgtacatt tgttcatggg aaaagcaaga agataacgaa aagcacttaa    3300
actggattag aaacatctat aacttcatga ctccatacgt ttctaaaaac cctagattgg    3360
catatttgaa ctacagagat ttggacatcg gtattaacga tccaagaat cctaacaact    3420 atacccaagc tagaatttgg ggtgaaaaat acttcggtaa aaatttcgat agattagtaa    3480
aggttaagac attggttgac ccaaacaact tctttagaaa cgaacaatcc attccacctt    3540
tacctagaca tagacacgaa caaaaattaa taagtgaaga gatttgtaa gtcgacctcg    3600 agtcatgtaa ttagttatgt cacgcttaca ttcacgccct cccccacat ccgctctaac    3660 cgaaaaggaa ggagttagac aacctgaagt ctaggtccct atttatttt ttatagttat    3720 gttagtatta agaacgttat ttatatttca aatttttctt ttttttctgt acagacgcgt    3780
gtacgcatgt aacattatac tgaaaacctt gcttgaaagg ttttgggac gctcgaaggc    3840 tttaatttgc gtgacataac taattacatg acttgactga tttttcc                 3887
```

<210> SEQ ID NO 9
<211> LENGTH: 8963
<212> TYPE: DNA
<213> ORGANISM: Artificial Sequence
<220> FEATURE:
<223> OTHER INFORMATION: Codon Optimized

<400> SEQUENCE: 9

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accataaacg acattactat atatataata taggaagcat taatagaca gcatcgtaat     240 atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aatttcaag tcttgtaaaa gcatataaaa     660
atagttcagg cactccgaaa tacttggttg gcgtgtttcg taatcaacct aaggaggatg     720
```

```
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaagaa tagaccgaga tagggttgag tgttgttcca    1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg    1500 aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cccgccgc gcttaatgcg    1680 ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact ataggggcgaa ttgggtaccg ccgcaaatt aaagccttcg   1920 agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttacttg tcatcgtcat ctttgtagtc aatatcgtgg tctttatagt caccgtcatg   2220
atccttgtaa tccttgatc tcttgtagac cttattcaag aaagctgtca aaacgtcggc    2280
tttaaaacct cttgattcat caacttgact aatctttgcc tttaagtctt tagcgatgga   2340
ttcttcgtat tcatggtaca attgttcaat cttcaaatca ttaaaatttt tcttacactt   2400
tgcttcagca actgagtcct ttttaccgta gttttcatcc aaagtctttc tttgttcggc   2460
agatgctaat tccaaagcct tgttaataac ccaactgcac ttattgtctt gaatatctgt   2520
accgatttta cctatttgtt ctggagtacc gaaacagtct aagtagtcat cttggatttg   2580
gaagtattca cccaaaggta tcaaaacatc tcttgcttgc ttcaagtctt tttcatcagt   2640
aataccagct acgtacatag ccaaggcgac tggcaaatag aaggagtaat aagcagtttc   2700
aaaggtgacg atgaatgaat gtttcttcaa ggaaaacttt gacaagtcaa ctttatcttc   2760
aggtgcagtt atcaaatcca tcaattgacc caattctgtt tggaaagtaa cttcgtggaa   2820
taattcggta atatcgatgt agtacttttc gtttctgaaa tgtgacttca acaatttata   2880
gatagcggct tccaacataa agcatcatt tatggctatt tcaccaactt ctggaacttt    2940
gtaccagcat ggttgacctc ttcttgttat agacttatcc atcatgtcat cggcaaccaa   3000
aaagtatgct tgcaacaatt caatacacca acccaagata gcgaccttt cgtattcttc    3060
```

```
ttgacctaat tgttcaacgg ttttgttaga caagatagca taagtatcaa ctacactcaa    3120
acctctattc aatttaccac ctggagtatt gtagtttaaa gagtgagcat accaatcgca    3180
ggcttcttta ggcataccat aagctaacaa actagcgttc aattcttcaa ctaactttgg    3240
gaatacgttc aagaatcttt ctcttcttat ttccttttct gaagccatag gacctggatt    3300
ttcttcaacg tcaccacatg ttaacaaaga acctctacct tcttcgaaat gactgaattg    3360
ttgtctcaaa actcttctca tgatcttgtt tgttgcagtt ctaggtaagg atgacaatgg    3420
gacaactcta gtaactttga ataatgggtt caatttcttt tgcaaaccca agttaaagga    3480
taatctcaat tggttcaaat caatggttgt gtcgtttgaa tccttcaata cgaaaaatat    3540
gaccaattgt tctggaccac acccaaagg tggaacacca atagcagtgg tttcaaaaac    3600
tctgtcatct acttcattac agactctttc gatttcgata gaactaattt tgataccacc    3660
gatgttcata gtgtcatcgg ctctaccgtg tgcatggtag taaccgttag aggtcaattc    3720
gaaaatgtca ccatgtcttc tcaatacttc accattcaag gttggcatac ccttgaaata    3780
gacatcgtga tgattaccgt ttaacaatgt ttttgaggca ccaaacataa caggacctaa    3840
tgccaattca ccgatacctg gcttattttt aggcattggg taaccgttct tatctaatat    3900
gtacaaggtg caacccatac attgggatga aaagaacttt aaagattgag cttgcaaaaa    3960
tgaaccagca gaaaagcac accgatttc tgtaccacca cacatttcta taactggctt    4020
gtagttagct ctaccattta accacaaata ttcgtctaca ttagaggctt caccggatga    4080
agaaaagcat cttatggtgg accaatcgta acctgaaaca caatttgtgg atttccatga    4140
tcttacaata gatggtacga cacccaacat tgtgaccttt gcatcttgaa caaatttagc    4200
gaaaccagag actaaaggac taccgttgta caaggcaata gatgcaccat ttaacaaact    4260
agcataaacc aaccaaggac ccatcatcca acccaaatta gttggccata ctataacgtc    4320
acctttctat atatccaaat gagaccaacc atcagcagca gccttcaatg gggtggcttg    4380
tgtccaagga attgcttttg gttcacctgt agtaccactg gagaataaga tgttagtata    4440
agcatcaaca ggttgttctc tggcagtaaa ctcgcagttt ttaaactcct ggctctttc    4500 taaaaagtaa tcccaagata tgtcaccatc tctcaattct gcaccaatgt tagaaccact    4560
acaagggata actattgcca ttggggattt agcttcaact actcttgaat acaatggtat    4620
tctcttttta cctctgatga tgtgatcttg tgtgaaaatt gccttagctt tggataatct    4680
caatctagtt gagatttcag gggcggaaaa tgaatctgct atagagacaa ctacgtaacc    4740
agccaatact atggccaaat atataacaac agcatcaaca tgcattggca tatcgatggc    4800
tattgcacaa cctttttcta aacccatttc ttccaatgca taaccaacca accaaactct    4860
ctttctcaat tgatctaatg tcaacttatt caaaggcaag tcatcgttac cctcgtctct    4920
ccaaacgatc atagtatcgt tcaatttctt attggagttt acgttcaagc aatttttagc    4980
tgagttcaag taaccaccag gtaaccattc agaaccacct gggttgttga tgtcatctct    5040
tctcaagata cattctgggt ccttagagaa actaattttc atttcatcca tcaatactgt    5100
tctccaatag acttcagggt ttctaacaga aaattcttgg aagtgagaaa agaagaaat    5160 tggatctttg tactttacac ccaaaaattc tttacctctc ttttccaaca aagcaccaa    5220 attagttgac ttgactttt cagggtctgg aatccaagca ggtggggctg gaccgaaatc    5280
cttgtagcaa cctaaaaaca acatttggtg taaggagaaa ggcaaatctg gtgacaagat    5340
atggttagcg atgttgatcc aagtttgagg ggttgcagca ccataattac aaacgatttc    5400
tgccaatcta ccatgtaatg tttctgctac ttctgaggtg atacccaatg cgatgaaatc    5460
```

```
tgaggcaacg actgaatcca aggacttata gttttacccc atactagttc tagatccgtc   5520
gaaactaagt tcttggtgtt ttaaaactaa aaaaagact aactataaaa gtagaattta    5580
agaagtttaa gaaatagatt tacagaatta caatcaatac ctaccgtctt tatatactta   5640
ttagtcaagt aggggaataa tttcagggaa ctggtttaaa ccttttttt cagcttttc     5700 caaatcagag agagcagaag gtaatagaag gtgtaagaaa atgagataga tacatgcgtg   5760
ggtcaattgc cttgtgtcat catttactcc aggcaggttg catcactcca ttgaggttgt   5820
gcccgttttt tgcctgtttg tgccctgttc tctgtagttg cgctaagaga atggacctat   5880
gaactgatgg ttggtgaaga aaacaatatt ttggtgctgg gattcttttt ttttctggat   5940
gccagcttaa aaagcgggct ccattatatt tagtggatgc caggaataaa cctgttcacc   6000
caagcaccat cagtgttata tattctgtgt aacccgcccc ctattttggc atgtacgggt   6060
tacagcagaa ttaaaaggct aatttttga ctaaataaag ttaggaaaat cactactatt    6120
aattatttac gtattctttg aaatggcagt attgataatg ataaactcga gagctccagc   6180
ttttgttccc tttagtgagg gttaattgcg cgcttggcgt aatcatggtc atagctgttt   6240
cctgtgtgaa attgttatcc gctcacaatt ccacacaaca taggagccgg aagcataaag   6300
tgtaaagcct ggggtgccta atgagtgagg taactcacat taattgcgtt gcgctcactg   6360
cccgctttcc agtcgggaaa cctgtcgtgc cagctgcatt aatgaatcgg ccaacgcgcg   6420
gggagaggcg gtttgcgtat tgggcgctct tccgcttcct cgctcactga ctcgctgcgc   6480
tcggtcgttc ggctgcggcg agcggtatca gctcactcaa aggcggtaat acggttatcc   6540
acagaatcag gggataacgc aggaaagaac atgtgagcaa aaggccagca aaaggccagg   6600
aaccgtaaaa aggccgcgtt gctggcgttt ttccataggc tccgcccccc tgacgagcat   6660
cacaaaaatc gacgctcaag tcagaggtgg cgaaacccga caggactata aagataccag   6720
gcgtttcccc ctggaagctc cctcgtgcgc tctcctgttc cgaccctgcc gcttaccgga   6780
tacctgtccg cctttctccc ttcgggaagc gtggcgcttt ctcatagctc acgctgtagg   6840
tatctcagtt cggtgtaggt cgttcgctcc aagctgggct gtgtgcacga accccccgtt   6900
cagcccgacc gctgcgcctt atccggtaac tatcgtcttg agtccaaccc ggtaagacac   6960
gacttatcgc cactggcagc agccactggt aacaggatta gcagagcgag gtatgtaggc   7020
ggtgctacag agttcttgaa gtggtggcct aactacggct acactagaag gacagtattt   7080
ggtatctgcg ctctgctgaa gccagttacc ttcggaaaaa gagttggtag ctcttgatcc   7140
ggcaaacaaa ccaccgctgg tagcggtggt ttttttgttt gcaagcagca gattacgcgc   7200
agaaaaaaag gatctcaaga agatcctttg atcttttcta cggggtctga cgctcagtgg   7260
aacgaaaact cacgttaagg gattttggtc atgagattat caaaaaggat cttcacctag   7320 atcctttaa attaaaaatg aagttttaaa tcaatctaaa gtatatatga gtaaacttgg   7380
tctgacagtt accaatgctt aatcagtgag gcacctatct cagcgatctg tctatttcgt   7440
tcatccatag ttgcctgact ccccgtcgtg tagataacta cgatacggga gggcttacca   7500
tctggcccca gtgctgcaat gataccgcga gacccacgct caccggctcc agatttatca   7560
gcaataaacc agccagccgg aagggccgag cgcagaagtg gtcctgcaac tttatccgcc   7620
tccatccagt ctattaattg ttgccgggaa gctagagtaa gtagttcgcc agttaatagt   7680
ttgcgcaacg ttgttgccat tgctacaggc atcgtggtgt cacgctcgtc gtttggtatg   7740
gcttcattca gctccggttc ccaacgatca aggcgagtta catgatcccc catgttgtgc   7800
```

```
aaaaaagcgg ttagctcctt cggtcctccg atcgttgtca aagtaagtt ggccgcagtg    7860 ttatcactca tggttatggc agcactgcat aattctctta ctgtcatgcc atccgtaaga    7920
tgctttcctg tgactggtga gtactcaacc aagtcattct gagaatagtg tatgcggcga    7980
ccgagttgct cttgcccggc gtcaatacgg gataataccg cgccacatag cagaactta     8040 aaagtgctca tcattggaaa acgttcttcg gggcgaaaac tctcaaggat cttaccgctg    8100
ttgagatcca gttcgatgta acccactcgt gcacccaact gatcttcagc atctttact     8160 ttcaccagcg tttctgggtg agcaaaaaca ggaaggcaaa atgccgcaaa aagggaata     8220 agggcgacac ggaaatgttg aatactcata ctcttccttt ttcaatatta ttgaagcatt    8280
tatcagggtt attgtctcat gagcggatac atatttgaat gtatttagaa aaataaacaa    8340
ataggggttc cgcgcacatt tccccgaaaa gtgccacctg ggtcctttc atcacgtgct     8400 ataaaaataa ttataattta aattttttaa tataaatata taaattaaaa atagaaagta    8460
aaaaaagaaa ttaaagaaaa aatagtttt gttttccgaa gatgtaaaag actctagggg     8520
gatcgccaac aaatactacc ttttatcttg ctcttcctgc tctcaggtat taatgccgaa    8580
ttgtttcatc ttgtctgtgt agaagaccac acacgaaaat cctgtgattt tacattttac    8640
ttatcgttaa tcgaatgtat atctatttaa tctgcttttc ttgtctaata aatatatatg    8700
taaagtacgc ttttgttga aatttttaa acctttgttt atttttttt cttcattccg       8760 taactcttct accttcttta tttacttct aaaatccaaa tacaaaacat aaaaataat      8820 aaacacagag taaattccca aattattcca tcattaaaag atacgaggcg cgtgtaagtt    8880
acaggcaagc gatccgtcct aagaaaccat tattatcatg acattaacct ataaaaatag    8940
gcgtatcacg aggccctttc gtc                                            8963

<210> SEQ ID NO 10
<211> LENGTH: 7163
<212> TYPE: DNA
<213> ORGANISM: Artificial Sequence
<220> FEATURE:
<223> OTHER INFORMATION: Codon Optimized

<400> SEQUENCE: 10
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga agtttgcgg cttgcagagc acagaggccg     540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg cgtgtttcg taatcaacct aaggaggatg     720
ttttggctct ggtcaatgat tacggcattg atatcgtcca actgcatgga gatgagtcgt    780
ggcaagaata ccaagagttc ctcggttttgc cagttattaa aagactcgta tttccaaaag    840
actgcaacat actactcagt gcagcttcac agaaacctca ttcgtttatt cccttgtttg    900
```

```
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttgttaa atcagctcat tttttaacca ataggccgaa    1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg ttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaagaaaaa atttgaaata taaataacgt tcttaatact aacataacta   2040
taaaaaata aatagggacc tagacttcag gttgtctaac tccttccttt tcggttagag    2100
cggatgtggg gggagggcgt gaatgtaagc gtgacataac taattcatg actcgaggtc    2160
gacttatgca tagtctggaa catcgtaagg gtactttctt ggggtgtaat cgaagatcaa   2220
caattttcc cagaaggatc tgtaaacgtc accaaaacca acgtgagctg atgaatgat     2280
gtaatcttgg atagtttcaa ctgattcgaa ggttacttcg acaatgtgtg tataaccttc   2340
ttctttcttt tgtgtaacgt cttaccccca gtatacatct ttcatagcag gtataatgtt   2400
gaccaaatta acgtaggtct tgaaaaattc ttccttttga gcttctgtga tttcatcttt   2460
aaacttcaat actatcaaat gcttgacggc ataggacct gggttttctt caacgtcacc    2520
acaagttaac aaggaacctc taccttcata tttaattggt actgatctga caactactct   2580
ttcgacggtc aaaccaggac cgaaaccaaa taagacaccc cattcaaaac cgtcaccagt   2640
agtagattta ccctcttcta atgatctctt tctcaattca tccattacga acaagacagt   2700
ggatgaagac atgttaccgt gttcagataa aacatgtcta ctatctacaa acttttcttt   2760
cttcaaatcc aatttttctt caaccttatc caaaatggct ttaccacctg gatgtgttat   2820
ccagaaaata gagttccaat ctgagatacc tataggagtg aatgcttcta tcaaacactt   2880
ttctatgttg ttagagatta acattggaac gtctttgtgc aaatcgaaga tcaaacctgc   2940
ttctcttata tgaccaccaa ttgtaccttc agaattaggc aagatggttt gacctgtact   3000
gactaattca aatattggtc tttcaccaac agattcgtca ggttctgcac caacaataac   3060
agcagcagca ccgtcaccga agatagcttg accaactaac aattccaagt cagaatcact   3120
tggacctcta aacaagcaag ccataatgtc gcaacaaaca gctaatactc tggcaccctt   3180
gttgttttct gcaatatcct tagcgattct caaaacagta ccaccaccgt agcaacctaa   3240
```

```
ttgatacatc atgactctct taacggatgg tgacaaacct aacaatttgg cacagtggta    3300
gtctgcacca ggcatatctg tagtagatgc acttgtaaaa atcaaatgag tgatctttga    3360 cttttggttga ccccattcct taatggcttt tgcacaagca tctttaccca atttaggaac   3420
ttcgacaact aacatgtctt gtctggcatc caatgtttgc atttcgtgtt ctaccaatct    3480
tggattttgc ttcaaatgtt cttcgttcaa gaagcagttt ctctttctga tcatagactt    3540
atcacatatt tttctaaact tttccttcaa ttgagtcatg tgttcactct tggtaactct    3600
gaagtaataa tcaggaaatt catcttggat caatatgttt tctggttgg ctgtacctat     3660 ggctaatacg gaggcaggac cttcggctct caaatggttc atactagttc tagatccgtc    3720
gaaactaagt tcttggtgtt ttaaaactaa aaaaaagact aactataaaa gtagaattta    3780
agaagtttaa gaaatagatt tacagaatta caatcaatac ctaccgtctt tatatactta    3840
ttagtcaagt aggggaataa tttcagggaa ctggtttaaa cctttttttt cagcttttttc   3900 caaatcagag agagcagaag gtaatagaag gtgtaagaaa atgagataga tacatgcgtg    3960
ggtcaattgc cttgtgtcat catttactcc aggcaggttg catcactcca ttgaggttgt    4020
gcccgttttt tgcctgtttg tgccctgttc tctgtagttg cgctaagaga atggacctat    4080
gaactgatgg ttggtgaaga aaacaatatt ttggtgctgg gattctttttt ttttctggat   4140 gccagcttaa aaagcgggct ccattatatt tagtggatgc caggaataaa cctgttcacc    4200
caagcaccat cagtgttata tattctgtgt aacccgcccc ctattttggc atgtacgggt    4260
tacagcagaa ttaaaaggct aattttttga ctaaataaag ttaggaaaat cactactatt    4320
aattatttac gtattctttg aaatggcagt attgataatg ataaactcga gagctccagc    4380
ttttgttccc tttagtgagg gttaattgcg cgcttggcgt aatcatggtc atagctgttt    4440
cctgtgtgaa attgttatcc gctcacaatt ccacacaaca taggagccgg aagcataaag    4500
tgtaaagcct ggggtgccta atgagtgagg taactcacat taattgcgtt gcgctcactg    4560
cccgctttcc agtcgggaaa cctgtcgtgc cagctgcatt aatgaatcgg ccaacgcgcg    4620
gggagaggcg gtttgcgtat tgggcgctct tccgcttcct cgctcactga ctcgctgcgc    4680
tcggtcgttc ggctgcggcg agcggtatca gctcactcaa aggcggtaat acggttatcc    4740
acagaatcag gggataacgc aggaaagaac atgtgagcaa aaggccagca aaaggccagg    4800
aaccgtaaaa aggccgcgtt gctggcgttt ttccataggc tccgcccccc tgacgagcat    4860
cacaaaaatc gacgctcaag tcagaggtgg cgaaacccga caggactata agataccag    4920 gcgtttcccc ctggaagctc cctcgtgcgc tctcctgttc cgaccctgcc gcttaccgga    4980
tacctgtccg cctttctccc ttcgggaagc gtggcgcttt ctcatagctc acgctgtagg    5040
tatctcagtt cggtgtaggt cgttcgctcc aagctgggct gtgtgcacga acccccgtt    5100 cagcccgacc gctgcgcctt atccggtaac tatcgtcttg agtccaaccc ggtaagacac    5160
gacttatcgc cactggcagc agccactggt aacaggatta gcagagcgag gtatgtaggc    5220
ggtgctacag agttcttgaa gtggtggcct aactacggct acactagaag gacagtattt    5280
ggtatctgcg ctctgctgaa gccagttacc ttcggaaaaa gagttggtag ctcttgatcc    5340
ggcaaacaaa ccaccgctgg tagcggtggt ttttttgttt gcaagcagca gattacgcgc    5400
agaaaaaaag gatctcaaga gatcctttg atcttttcta cggggtctga cgctcagtgg    5460
aacgaaaact cacgttaagg gattttggtc atgagattat caaaaaggat cttcacctag    5520
atccttttaa attaaaaatg aagttttaaa tcaatctaaa gtatatatga gtaaacttgg    5580
tctgacagtt accaatgctt aatcagtgag gcacctatct cagcgatctg tctatttcgt    5640
```

| | |
|---|---|
| tcatccatag ttgcctgact ccccgtcgtg tagataacta cgatacggga gggcttacca | 5700 |
| tctggcccca gtgctgcaat gataccgcga gacccacgct caccggctcc agatttatca | 5760 |
| gcaataaacc agccagccgg aagggccgag cgcagaagtg gtcctgcaac tttatccgcc | 5820 |
| tccatccagt ctattaattg ttgccgggaa gctagagtaa gtagttcgcc agttaatagt | 5880 |
| ttgcgcaacg ttgttgccat tgctacaggc atcgtggtgt cacgctcgtc gtttggtatg | 5940 |
| gcttcattca gctccggttc ccaacgatca aggcgagtta catgatcccc catgttgtgc | 6000 |
| aaaaaagcgg ttagctcctt cggtcctccg atcgttgtca gaagtaagtt ggccgcagtg | 6060 |
| ttatcactca tggttatggc agcactgcat aattctctta ctgtcatgcc atccgtaaga | 6120 |
| tgcttttctg tgactggtga gtactcaacc aagtcattct gagaatagtg tatgcggcga | 6180 |
| ccgagttgct cttgcccggc gtcaatacgg gataataccg cgccacatag cagaacttta | 6240 |
| aaagtgctca tcattggaaa acgttcttcg gggcgaaaac tctcaaggat cttaccgctg | 6300 |
| ttgagatcca gttcgatgta acccactcgt gcacccaact gatcttcagc atcttttact | 6360 |
| ttcaccagcg tttctgggtg agcaaaaaca ggaaggcaaa atgccgcaaa aaagggaata | 6420 |
| agggcgacac ggaaatgttg aatactcata ctcttccttt ttcaatatta ttgaagcatt | 6480 |
| tatcagggtt attgtctcat gagcggatac atatttgaat gtatttagaa aaataaacaa | 6540 |
| ataggggttc cgcgcacatt tccccgaaaa gtgccacctg ggtccttttc atcacgtgct | 6600 |
| ataaaaataa ttataattta aattttttaa tataaatata taaattaaaa atagaaagta | 6660 |
| aaaaaagaaa ttaaagaaaa aatagttttt gttttccgaa gatgtaaaag actctagggg | 6720 |
| gatcgccaac aaatactacc ttttatcttg ctcttcctgc tctcaggtat taatgccgaa | 6780 |
| ttgtttcatc ttgtctgtgt agaagaccac acacgaaaat cctgtgattt tacattttac | 6840 |
| ttatcgttaa tcgaatgtat atctatttaa tctgcttttc ttgtctaata aatatatatg | 6900 |
| taaagtacgc tttttgttga aattttttaa acctttgttt atttttttt cttcattccg | 6960 |
| taactcttct accttcttta tttactttct aaaatccaaa tacaaaacat aaaaataaat | 7020 |
| aaacacagag taaattccca aattattcca tcattaaaag atacgaggcg cgtgtaagtt | 7080 |
| acaggcaagc gatccgtcct aagaaaccat tattatcatg acattaacct ataaaaatag | 7140 |
| gcgtatcacg aggccctttc gtc | 7163 |

<210> SEQ ID NO 11
<211> LENGTH: 8710
<212> TYPE: DNA
<213> ORGANISM: Artificial Sequence
<220> FEATURE:
<223> OTHER INFORMATION: Codon Optimized

<400> SEQUENCE: 11

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgcgtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| tttttttttt cccctagcgg atgactcttt tttttcttagcgattggca ttatcacata | 420 |
| atgaattata cattatataa agtaatgtga tttcttcgaa gaatatacta aaaaatgagc | 480 |

-continued

| | |
|---|---|
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaaagag gcagaagcag tagcagaaca ggccacacaa tcgcaagtga | 660 |
| ttaacgtcca cacaggtata gggttttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag cttttaaaga ggccctactg gcgcgtggag | 840 |
| taaaaaggtt tggatcagga tttgcgcctt tggatgaggc actttccaga gcggtggtag | 900 |
| atctttcgaa caggccgtac gcagttgtcg aacttggttt gcaaagggag aaagtaggag | 960 |
| atctctcttg cgagatgatc ccgcattttc ttgaaagctt tgcagaggct agcagaatta | 1020 |
| ccctccacgt tgattgtctg cgaggcaaga atgatcatca ccgtagtgag agtgcgttca | 1080 |
| aggctcttgc ggttgccata agagaagcca cctcgcccaa tggtaccaac gatgttccct | 1140 |
| ccaccaaagg tgttcttatg tagtgacacc gattatttaa agctgcagca tacgatatat | 1200 |
| atacatgtgt atatatgtat acctatgaat gtcagtaagt atgtatacga acagtatgat | 1260 |
| actgaagatg acaaggtaat gcatcattct atacgtgtca ttctgaacga ggcgcgcttt | 1320 |
| cctttttct ttttgctttt tctttttttt tctcttgaac tcgacggatc tatgcggtgt | 1380 |
| gaaataccgc acagatgcgt aaggagaaaa taccgcatca ggaaattgta aacgttaata | 1440 |
| ttttgttaaa attcgcgtta aattttttgtt aaatcagctc atttttttaac caataggccg | 1500 |
| aaatcggcaa aatcccttat aaatcaaaag aatagaccga gatagggttg agtgttgttc | 1560 |
| cagtttggaa caagagtcca ctattaaaga acgtggactc caacgtcaaa gggcgaaaaa | 1620 |
| ccgtctatca gggcgatggc ccactacgtg aaccatcacc ctaatcaagt tttttggggt | 1680 |
| cgaggtgccg taaagcacta atcggaacc ctaaagggag cccccgattt agagcttgac | 1740 |
| ggggaaagcc ggcgaacgtg gcgagaaagg aagggaagaa agcgaaagga gcgggcgcta | 1800 |
| gggcgctggc aagtgtagcg gtcacgctgc gcgtaaccac cacacccgcc gcgcttaatg | 1860 |
| cgccgctaca gggcgcgtcg cgccattcgc cattcaggct gcgcaactgt tgggaagggc | 1920 |
| gatcggtgcg ggcctcttcg ctattacgcc agctggcgaa aggggatgt gctgcaaggc | 1980 |
| gattaagttg ggtaacgcca gggttttccc agtcacgacg ttgtaaaacg acggccagtg | 2040 |
| agcgcgcgta atacgactca ctatagggcg aattgggtac cggccgcaaa ttaaagcctt | 2100 |
| cgagcgtccc aaaaccttct caagcaaggt tttcagtata atgttacatg cgtacacgcg | 2160 |
| tctgtacaga aaaaaagaa aaatttgaaa tataaataac gttcttaata ctaacataac | 2220 |
| tataaaaaaa taaataggga cctagacttc aggttgtcta actccttcct tttcggttag | 2280 |
| agcggatgtg gggggagggc gtgaatgtaa gcgtgacata actaattaca tgactcgagg | 2340 |
| tcgacttaca aatcttcttc acttattaat ttttgttcgt gtctatgtct aggtaaaggt | 2400 |
| ggaatggatt gttcgtttct aaagaagttg tttgggtcaa ccaatgtctt aacctttact | 2460 |
| aatctatcga aattttacc gaagtatttt tcaccccaaa ttctagcttg ggtatagttg | 2520 |
| ttaggattct ttggatcgtt aataccgatg tccaaatctc tgtagttcaa atatgccaat | 2580 |
| ctagggtttt tagaaacgta tggagtcatg aagttataga tgtttctaat ccagtttaag | 2640 |
| tgcttttcgt tatcttcttg cttttcccat gaacaaatgt accacaattc gtataagata | 2700 |
| ccagctctat gaggaaatgg aatggcagat tcactgattt cgtccattat accaccgtat | 2760 |
| ggatacaagg cgtacatgcc tgcaccaata tcttcttcgt acaattttc taagatttgg | 2820 |
| acgaaaactg attcaggtat tggcttttta acgtagtcta acttaatttt aaaggcaccg | 2880 |

```
ttttgacctg cggatctatc caataatatt tctttgttga agttgtctgt atcgtagttg    2940
acaacacctg aataaaagat gatggtgtcg atccaagaca attgtctaca atcagttttc    3000
ttaataccta attctggaaa agacttattc atcaagtcta ctaaggaatc gacaccaccc    3060
aagaaaactg aagaaaagta tgtgtggata gcagtcttat ttttaccttg gttatcggtg    3120
atgtttcttg tgatgaaatg agtcatcaac aacaagtcct tatcgtactt gtatgcgatg    3180
ttttgccact tattgaccaa tttaactaat tcatggattt ccattatctt tttgactgag    3240
aacatagtag actttggtac tgcgactaat cttatcttcc aagcaactat gataccgaat    3300
gattctgcac caccacctct caaagcccaa aataagtctt cacccataga ctttctatcc    3360
aaaactttac cgtgaacatt taccaaatga gcgtcgatta tgttatcagc ggccaaaccg    3420
tagtttctca ttaaaggacc ataaccacca ccaccaaaat gacccctgc gcaaactgtt    3480
ggacagtaac cagcagccaa tgataagttt tcattctttt cgttaaccca gtagtatact    3540
tcacccaatg ttgcaccagc ttcaacccaa gcagtttgtg agtgtacgtc tattttaatt    3600
gatctcatgt ttctcaaatc aacgataacg aatggaactt gggagatgta tgacatgcct    3660
tcactatcat gaccaccgga tctagttcta atttgcaaac caacctttt agaacataag    3720
atagtacctt ggatgtgaga tacatgacta ggggttacaa tgaccaaagg ttttggagtg    3780
gtatcagaag tgaatctcaa attatggatt gtactgttca agacggacat gtacaatggg    3840
ttgttttgag tgtaaaccaa cttcaaattg gtggcgttat taggtatgta ttgtgagaag    3900
cacttcaaaa agttttctct tgggtttgcg atacttgttt ggatgttaaa ggaaaagaaa    3960
aagaagatga tcttgcatac gaaccaaaag gagaaagttg aacatttcat aggacctgga    4020
ttttcttcaa cgtcaccaca ggtcaacaaa gaacctctac cttcaataaa aacgtatacc    4080
aaatattcag cgtagtacaa tttccacata aactcgtaga atcttctacc tgcttcaggg    4140
tcataatttg tcaaagcgaa atctctagtt tgcaagatca accagaaagc caagatggca    4200
tgtgacaaca acataacgtt agaattaaag gcttgtggcc aaatgatacc tgccaaaatg    4260
gctgcgacgt aacttaacaa aacgataccg gagcagaaca aagtcaaatt tcttgaaccg    4320
tacttagaag ccaaggtact aataccgaac tttgtgtcac cttcaacgtc agaggcatcc    4380
ttgatcaagg ctaatgcaga acccatactt tcatgaatg ccaacaaaaa tgtgaatgaa    4440
ggtctcaatt cgaatggcaa acctaaagca gctcttgaag cgtagtagaa ggtgaagttt    4500
gtgatgatat gagctaagaa attcaacaaa aaggcagtac tagggttttg tttccatcta    4560
aaaggtggta cggaatagac aataccaccg aagataccga aacagtaacc gaagatgtac    4620
aatggaccac ccttcatttt aattgtgatg atcaaaccga acaaggctac tatgatagac    4680
atgatccatg cagtattgac ggatatttca cctgaagcca aagcaaatc tggtttgtta    4740
attctgtcga tgtgcaaatc gtatatttga ttaattgtag tggtgaatga agcgatgcac    4800
aagatggcaa ctaaaaagaa aaatgccttg aacatcaagg accatgaaat taagttagtg    4860
ttatgcaaca attctttacc gaataaaccg catgcacaag aagtaaaagc gattatggtg    4920
tatggtcttt gcaacttcca acatgcttta ccgaagttca aattttttgt ggcaacagag    4980
tgattatcac tttcaggtgg ttcagtttga tttgtagttg cagctctgat agagttctta    5040
gctatagaca aactttcgga gcacttattt tgtaagtgga aggacttggt tgaacaatgt    5100
tttgatggaa agttgttgta agagtactta ataggtgtct ttggatgtct gtaacacaac    5160
aatgatgttt ttggattgtt gttgtgagga ttcaataagg tatgatagtt agtttggaag    5220
```

```
gagaaagtac agacggatga taaacccata ctagttctag atccgtcgaa actaagttct    5280
tggtgtttta aaactaaaaa aaagactaac tataaaagta gaatttaaga agtttaagaa    5340
atagatttac agaattacaa tcaataccta ccgtctttat atacttatta gtcaagtagg    5400
ggaataattt cagggaactg gtttaaacct ttttttcag cttttccaa atcagagaga    5460 gcagaaggta atagaaggtg taagaaaatg agatagatac atgcgtgggt caattgcctt    5520
gtgtcatcat ttactccagg caggttgcat cactccattg aggttgtgcc cgttttttgc    5580
ctgtttgtgc cctgttctct gtagttgcgc taagagaatg gacctatgaa ctgatggttg    5640
gtgaagaaaa caatattttg gtgctgggat tcttttttt tctggatgcc agcttaaaaa    5700
gcgggctcca ttatatttag tggatgccag gaataaacct gttcacccaa gcaccatcag    5760
tgttatatat tctgtgtaac ccgcccccta ttttggcatg tacgggttac agcagaatta    5820
aaaggctaat ttttgacta aataaagtta ggaaaatcac tactattaat tatttacgta    5880
ttctttgaaa tggcagtatt gataatgata aactcgagag ctccagcttt tgttcccttt    5940
agtgagggtt aattgcgcgc ttggcgtaat catggtcata gctgtttcct gtgtgaaatt    6000
gttatccgct cacaattcca cacaacatag gagccggaag cataaagtgt aaagcctggg    6060
gtgcctaatg agtgaggtaa ctcacattaa ttgcgttgcg ctcactgccc gctttccagt    6120
cgggaaacct gtcgtgccag ctgcattaat gaatcggcca acgcgcgggg agaggcggtt    6180
tgcgtattgg gcgctcttcc gcttcctcgc tcactgactc gctgcgctcg tcgttcggc    6240 tgcggcgagc ggtatcagct cactcaaagg cggtaatacg ttatccaca gaatcagggg    6300 ataacgcagg aaagaacatg tgagcaaaag gccagcaaaa ggccaggaac cgtaaaaagg    6360
ccgcgttgct ggcgtttttc cataggctcc gcccccctga cgagcatcac aaaaatcgac    6420
gctcaagtca gaggtggcga aacccgacag gactataaag ataccaggcg tttccccctg    6480
gaagctccct cgtgcgctct cctgttccga ccctgccgct taccggatac ctgtccgcct    6540 ttctccccttc gggaagcgtg gcgctttctc atagctcacg ctgtaggtat ctcagttcgg    6600
tgtaggtcgt tcgctccaag ctgggctgtg tgcacgaacc ccccgttcag cccgaccgct    6660
gcgccttatc cggtaactat cgtcttgagt ccaacccggt aagacacgac ttatcgccac    6720
tggcagcagc cactggtaac aggattagca gagcgaggta tgtaggcggt gctacagagt    6780
tcttgaagtg gtggcctaac tacggctaca ctagaaggac agtatttggt atctgcgctc    6840
tgctgaagcc agttaccttc ggaaaaagag ttggtagctc ttgatccggc aaacaaacca    6900
ccgctggtag cggtggtttt tttgtttgca agcagcagat tacgcgcaga aaaaaaggat    6960
ctcaagaaga tcctttgatc ttttctacgg ggtctgacgc tcagtggaac gaaaactcac    7020
gttaagggat tttggtcatg agattatcaa aaaggatctt cacctagatc cttttaaatt    7080
aaaaatgaag ttttaaatca atctaaagta tatatgagta aacttggtct gacagttacc    7140
aatgcttaat cagtgaggca cctatctcag cgatctgtct atttcgttca tccatagttg    7200
cctgactccc cgtcgtgtag ataactacga tacgggaggg cttaccatct ggccccagtg    7260
ctgcaatgat accgcgagac ccacgctcac cggctccaga tttatcagca ataaaccagc    7320
cagccggaag ggccgagcgc agaagtggtc ctgcaacttt atccgcctcc atccagtcta    7380
ttaattgttg ccgggaagct agagtaagta gttcgccagt taatagtttg cgcaacgttg    7440
ttgccattgc tacaggcatc gtggtgtcac gctcgtcgtt tggtatggct tcattcagct    7500
ccggttccca acgatcaagg cgagttacat gatcccccat gttgtgcaaa aaagcggtta    7560
gctccttcgg tcctccgatc gttgtcagaa gtaagttggc cgcagtgtta tcactcatgg    7620
```

```
ttatggcagc actgcataat tctcttactg tcatgccatc cgtaagatgc ttttctgtga    7680
ctggtgagta ctcaaccaag tcattctgag aatagtgtat gcggcgaccg agttgctctt    7740
gcccggcgtc aatacgggat aataccgcgc cacatagcag aactttaaaa gtgctcatca    7800
ttggaaaacg ttcttcgggg cgaaaactct caaggatctt accgctgttg agatccagtt    7860
cgatgtaacc cactcgtgca cccaactgat cttcagcatc ttttactttc accagcgttt    7920
ctgggtgagc aaaaacagga aggcaaaatg ccgcaaaaaa gggaataagg gcgacacgga    7980
aatgttgaat actcatactc ttcctttttc aatattattg aagcatttat cagggttatt    8040
gtctcatgag cggatacata tttgaatgta tttagaaaaa taaacaaata ggggttccgc    8100
gcacatttcc ccgaaaagtg ccacctgggt ccttttcatc acgtgctata aaaataatta    8160
taatttaaat tttttaatat aaatatataa attaaaaata gaaagtaaaa aaagaaatta    8220
aagaaaaaat agtttttgtt ttccgaagat gtaaagact  ctaggggat cgccaacaaa    8280 tactacccttt tatcttgctc ttcctgctct caggtattaa tgccgaattg tttcatcttg    8340
tctgtgtaga agaccacaca cgaaaatcct gtgattttac attttactta tcgttaatcg    8400
aatgtatatc tatttaatct gcttttcttg tctaataaat atatatgtaa agtacgcttt    8460
ttgttgaaat tttttaaacc tttgtttatt tttttttctt cattccgtaa ctcttctacc    8520
ttctttattt actttctaaa atccaaatac aaaacataaa aataaataaa cacagagtaa    8580
attcccaaat tattccatca ttaaaagata cgaggcgcgt gtaagttaca ggcaagcgat    8640
ccgtcctaag aaaccattat tatcatgaca ttaacctata aaaataggcg tatcacgagg    8700
ccctttcgtc                                                         8710

<210> SEQ ID NO 12
<211> LENGTH: 9617
<212> TYPE: DNA
<213> ORGANISM: Artificial Sequence
<220> FEATURE:
<223> OTHER INFORMATION: Codon Optimized

<400> SEQUENCE: 12
ttatcatgac attaacctat aaaaataggc gtatcacgag gccctttcgt ctcgcgcgtt      60
tcggtgatga cggtgaaaac ctctgacaca tgcagctccc ggagacggtc acagcttgtc     120
tgtaagcgga tgccgggagc agacaagccc gtcagggcgc gtcagcgggt gttggcgggt     180
gtcggggctg gcttaactat gcggcatcag agcagattgt actgagagtg caccacgctt     240
ttcaattcaa ttcatcattt ttttttttatt ctttttttttg atttcggttt ctttgaaatt    300
tttttgattc ggtaatctcc gaacagaagg aagaacgaag gaaggagcac agacttagat     360
tggtatatat acgcatatgt agtgttgaag aaacatgaaa ttgcccagta ttcttaaccc     420
aactgcacag aacaaaaacc tgcaggaaac gaagataaat catgtcgaaa gctacatata     480
aggaacgtgc tgctactcat cctagtcctg ttgctgccaa gctatttaat atcatgcacg     540
aaaagcaaac aaacttgtgt gcttcattgg atgttcgtac caccaaggaa ttactggagt     600
tagttgaagc attaggtccc aaaatttgtt tactaaaaac acatgtggat atcttgactg     660
atttttccat ggagggcaca gttaagccgc taaaggcatt atccgccaag tacaattttt     720
tactcttcga agacagaaaa tttgctgaca ttggtaatac agtcaaattg cagtactctg     780
cgggtgtata cagaatagca gaatgggcag acattacgaa tgcacacggt gtggtgggcc     840
caggtattgt tagcggtttg aagcaggcgg cagaagaagt aacaaaggaa cctagaggcc     900
```

```
tttt gatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
ataccgcatc aggaaattgt aaacgttaat attttgttaa aattcgcgtt aaattttgt    1440
taaatcagct cattttttaa ccaataggcc gaaatcggca aaatccctta taaatcaaaa   1500
gaatagaccg atagggtt gagtgttgtt ccagtttgga acaagagtcc actattaaag    1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga agggggatg tgctgcaagg cgattaagtt gggtaacgcc agggttttcc    1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga acgcagatg tgcctcgcgc    2160
cgcactgctc cgaacaataa agattctaca atactagctt ttatggttat gaagaggaaa   2220
aattggcagt aacctggccc cacaaacctt caaattaacg aatcaaatta caaccatag    2280
gatgataatg cgattagttt tttagcctta tttctggggt aattaatcag cgaagcgatg   2340
attttgatc tattaacaga tatataaatg gaaaagctgc ataaccactt taactaatac    2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatgaac catttgagag ccgaaggtcc tgcctccgta ttagccatag   2580
gtacagccaa cccagaaaac atattgatcc aagatgaatt tcctgattat tacttcagag   2640
ttaccaagag tgaacacatg actcaattga aggaaaagtt tagaaaaata tgtgataagt   2700
ctatgatcag aaagagaaac tgcttcttga acgaagaaca tttgaagcaa atccaagat    2760
tggtagaaca cgaaatgcaa acattggatg ccagacaaga catgttagtt gtcgaagttc   2820
ctaaattggg taaagatgct tgtgcaaaag ccattaagga atggggtcaa ccaaagtcaa   2880
agatcactca tttgatttt acaagtgcat ctactacaga tatgcctggt gcagactacc    2940
actgtgccaa attgttaggt ttgtcaccat ccgttaagag agtcatgatg tatcaattag   3000
gttgctacgg tggtggtact gttttgagaa tcgctaagga tattgcagaa acaacaagg    3060
gtgccagagt attagctgtt tgttgcgaca ttatggcttg cttgtttaga ggtccaagtg   3120
attctgactt ggaattgtta gttggtcaag ctatcttcgg tgacggtgct gctgctgtta   3180
ttgttggtgc agaacctgac gaatctgttg gtgaaagacc aatatttgaa ttagtcagta   3240
caggtcaaac catcttgcct aattctgaag gtacaattgg tggtcatata agagaagcag   3300
```

-continued

```
gtttgatctt cgatttgcac aaagacgttc caatgttaat ctctaacaac atagaaaagt  3360
gtttgataga agcattcact cctataggta tctcagattg gaactctatt ttctggataa  3420
cacatccagg tggtaaagcc attttggata aggttgaaga aaaattggat ttgaagaaag  3480
aaaagtttgt agatagtaga catgttttat ctgaacacgg taacatgtct tcatccactg  3540
tcttgttcgt aatggatgaa ttgagaaaga gatcattaga agagggtaaa tctactactg  3600
gtgacggttt tgaatgggt gtcttatttg gtttcggtcc tggtttgacc gtcgaaagag  3660
tagttgtcag atcagtacca attaaatatg aaggtagagg ttccttgtta acttgtggtg  3720
acgttgaaga aaacccaggt cctatggccg tcaagcattt gatagtattg aagtttaaag  3780
atgaaatcac agaagctcaa aaggaagaat ttttcaagac ctacgttaat ttggtcaaca  3840
ttatacctgc tatgaaagat gtatactggg gtaaagacgt tacacaaaag aaagaagaag  3900
gttatacaca cattgtcgaa gtaaccttcg aatcagttga aactatccaa gattacatca  3960
ttcatccagc tcacgttggt tttggtacgt tttacagatc cttctgggaa aaattgttga  4020
tcttcgatta caccccaaga aagttaaagc caaaataatg ataacgagaa taatatcaag  4080
aataccttag aacaacatcg acaacaacaa caggcatttt cggatatgag tcacgtggag  4140
tattccagaa ttacaaaatt ttttcaagaa caaccactgg agggatatac ccttttctct  4200
cacaggtctg cgccatgggt ttatcatccg tctgtacttt ctccttccaa actaactatc  4260
ataccttatt gaatcctcac aacaacaatc caaaacatc attgttgtgt tacagacatc  4320
caaagacacc tattaagtac tcttacaaca actttccatc aaaacattgt tcaaccaagt  4380
ccttccactt acaaaataag tgctccgaaa gtttgtctat agctaagaac tctatcagag  4440
ctgcaactac aaatcaaact gaaccacctg aaagtgataa tcactctgtt gccacaaaaa  4500
ttttgaactt cggtaaagca tgttggaagt tgcaaagacc atacaccata atcgctttta  4560
cttcttgtgc atgcggttta ttcggtaaag aattgttgca taacactaac ttaatttcat  4620
ggtccttgat gttcaaggca ttttttcttt tagttgccat cttgtgcatc gcttcattca  4680
ccactacaat taatcaaata tacgatttgc acatcgacag aattaacaaa ccagatttgc  4740
ctttggcttc aggtgaaata tccgtcaata ctgcatggat catgtctatc atagtagcct  4800
tgttcggttt gatcatcaca attaaaatga agggtggtcc attgtacatc ttcggttact  4860
gtttcggtat cttcggtggt attgtctatt ccgtaccacc ttttagatgg aaacaaaacc  4920
ctagtactgc cttttgttg aatttcttag ctcatatcat cacaaacttc accttctact  4980
acgcttcaag agctgcttta ggtttgccat tcgaattgag accttcattc acattttgt  5040 tggcattcat gaaaagtatg ggttctgcat tagccttgat caaggatgcc tctgacgttg  5100
aaggtgacac aaagttcggt attagtacct ggcttctaa gtacggttca agaaatttga  5160
ctttgttctg ctccggtatc gttttgttaa gttacgtcgc agccattttg gcaggtatca  5220
tttggccaca agcctttaat tctaacgtta tgttgttgtc acatgccatc ttggctttct  5280
ggttgatctt gcaaactaga gatttcgctt tgacaaatta tgaccctgaa gcaggtagaa  5340
gattctacga gttatgtgg aaattgtact acgctgaata tttggtatac gtttttattg  5400
aaggtagagg ttctttgttg acctgtggtg acgttgaaga aaatccaggt cctatgaaat  5460
gttcaacttt ctcctttggg ttcgtatgca agatcatctt ctttttcttt tccttttaaca  5520 tccaaacaag tatcgcaaac ccaagagaaa acttttgaa gtgcttctca caatacatac  5580
ctaataacgc caccaatttg aagttggttt acactcaaaa caacccattg tacatgtccg  5640
```

```
tcttgaacag tacaatccat aatttgagat tcacttctga taccactcca aaacctttgg    5700
tcattgtaac ccctagtcat gtatctcaca tccaaggtac tatcttatgt tctaaaaagg    5760
ttggtttgca aattagaact agatccggtg gtcatgatag tgaaggcatg tcatacatct    5820
cccaagttcc attcgttatc gttgatttga gaaacatgag atcaattaaa atagacgtac    5880
actcacaaac tgcttgggtt gaagctggtg caacattggg tgaagtatac tactgggtta    5940
acgaaaagaa tgaaaactta tcattggctg ctggttactg tccaacagtt tgcgcaggtg    6000
gtcattttgg tggtggtggt tatggtcctt taatgagaaa ctacggtttg gccgctgata    6060
acataatcga cgctcatttg gtaaatgttc acggtaaagt tttggataga agtctatgg     6120 gtgaagactt attttgggct ttgagaggtg gtggtgcaga atcattcggt atcatagttg    6180
cttggaagat aagattagtc gcagtaccaa agtctactat gttctcagtc aaaaagataa    6240
tggaaatcca tgaattagtt aaattggtca ataagtggca aaacatcgca tacaagtacg    6300
ataaggactt gttgttgatg actcatttca tcacaagaaa catcaccgat aaccaaggta    6360
aaaataagac tgctatccac acatactttt cttcagtttt cttgggtggt gtcgattcct    6420
tagtagactt gatgaataag tcttttccag aattaggtat taagaaaact gattgtagac    6480
aattgtcttg gatcgacacc atcatctttt attcaggtgt tgtcaactac gatacagaca    6540
acttcaacaa agaaatatta ttggatagat ccgcaggtca aaacggtgcc tttaaaatta    6600
agttagacta cgttaaaaag ccaataccty aatcagtttt cgtccaaatc ttagaaaaat    6660
tgtacgaaga agatattggt gcaggcatgt acgccttgta tccatacggt ggtataatgg    6720
acgaaatcag tgaatctgcc attccatttc ctcatagagc tggtatctta tacgaattgt    6780
ggtacatttg ttcatgggaa aagcaagaag ataacgaaaa gcacttaaac tggattagaa    6840
acatctataa cttcatgact ccatacgttt ctaaaacccc tagattggca tatttgaact    6900
acagagattt ggacatcggt attaacgatc caaagaatcc taacaactat acccaagcta    6960
gaatttgggg tgaaaaatac ttcggtaaaa atttcgatag attagtaaag gttaagacat    7020
tggttgaccc aaacaacttc tttagaaacg aacaatccat tccacctta cctagacata    7080 gacactgatg ggctgcagga attcgatatc aagcttatcg ataccgtcga cctcgagtca    7140
tgtaattagt tatgtcacgc ttacattcac gccctccccc cacatccgct ctaaccgaaa    7200
aggaaggagt tagacaacct gaagtctagg tccctattta ttttttttata gttatgttag    7260 tattaagaac gttatttata tttcaaattt ttcttttttt tctgtacaga cgcgtgtacg    7320
catgtaacat tatactgaaa accttgcttg agaaggtttt gggacgctcg aaggctttaa    7380
tttgcggccg gtacccagct tttgttccct ttagtgaggg ttaattccga gcttggcgta    7440
atcatggtca tagctgtttc ctgtgtgaaa ttgttatccg ctcacaattc cacacaacat    7500
aggagccgga agcataaagt gtaaagcctg gggtgcctaa tgagtgaggt aactcacatt    7560
aattgcgttg cgctcactgc ccgctttcca gtcgggaaac ctgtcgtgcc agctgcatta    7620
atgaatcggc caacgcgcgg ggagaggcgg tttgcgtatt gggcgctctt ccgcttcctc    7680
gctcactgac tcgctgcgct cggtcgttcg gctgcggcga gcggtatcag ctcactcaaa    7740
ggcggtaata cggttatcca cagaatcagg ggataacgca ggaaagaaca tgtgagcaaa    7800
aggccagcaa aaggccagga accgtaaaaa ggccgcgttg ctggcgtttt tccataggct    7860
cggcccccct gacgagcatc acaaaaatcg acgctcaagt cagaggtggc gaaacccgac    7920
aggactataa agataccagg cgttcccccc tggaagctcc ctcgtgcgct ctcctgttcc    7980
gaccctgccg cttaccggat acctgtccgc ctttctccct tcgggaagcg tggcgctttc    8040
```

```
tcaatgctca cgctgtaggt atctcagttc ggtgtaggtc gttcgctcca agctgggctg    8100
tgtgcacgaa ccccccgttc agcccgaccg ctgcgcctta ccggtaact atcgtcttga    8160 gtccaacccg gtaagacacg acttatcgcc actggcagca gccactggta acaggattag    8220
cagagcgagg tatgtaggcg gtgctacaga gttcttgaag tggtggccta actacggcta    8280
cactagaagg acagtatttg gtatctgcgc tctgctgaag ccagttacct tcggaaaaag    8340
agttggtagc tcttgatccg gcaaacaaac caccgctggt agcggtggtt ttttgtttg    8400 caagcagcag attacgcgca gaaaaaagg atctcaagaa gatcctttga tcttttctac    8460
ggggtctgac gctcagtgga acgaaaactc acgttaaggg attttggtca tgagattatc    8520
aaaaaggatc ttcacctaga tccttttaaa ttaaaatga agttttaaat caatctaaag    8580
tatatatgag taaacttggt ctgacagtta ccaatgctta atcagtgagg cacctatctc    8640
agcgatctgt ctatttcgtt catccatagt tgcctgactg cccgtcgtgt agataactac    8700
gatacgggag ggcttaccat ctggccccag tgctgcaatg ataccgcgag acccacgctc    8760
accggctcca gatttatcag caataaacca gccagccgga agggccgagc gcagaagtgg    8820
tcctgcaact ttatccgcct ccatccagtc tattaattgt tgccgggaag ctagagtaag    8880
tagttcgcca gttaatagtt tgcgcaacgt tgttgccatt gctacaggca tcgtggtgtc    8940
acgctcgtcg tttggtatgg cttcattcag ctccggttcc caacgatcaa ggcgagttac    9000
atgatccccc atgttgtgaa aaaagcggt tagctccttc ggtcctccga tcgttgtcag    9060
aagtaagttg gccgcagtgt tatcactcat ggttatggca gcactgcata attctcttac    9120
tgtcatgcca tccgtaagat gcttttctgt gactggtgag tactcaacca agtcattctg    9180
agaatagtgt atgcggcgac cgagttgctc ttgcccggcg tcaatacggg ataataccgc    9240
gccacatagc agaactttaa aagtgctcat cattggaaaa cgttcttcgg ggcgaaaact    9300
ctcaaggatc ttaccgctgt tgagatccag ttcgatgtaa cccactcgtg cacccaactg    9360
atcttcagca tcttttactt tcaccagcgt ttctgggtga gcaaaacag gaaggcaaaa    9420 tgccgcaaaa aagggaataa gggcgacacg gaaatgttga atactcatac tcttcctttt    9480
tcaatattat tgaagcattt atcagggtta ttgtctcatg agcggataca tatttgaatg    9540
tatttagaaa aataaacaaa taggggttcc gcgcacattt ccccgaaaag tgccacctga    9600
cgtctaagaa accatta                                                  9617
```

<210> SEQ ID NO 13
<211> LENGTH: 7879
<212> TYPE: DNA
<213> ORGANISM: Artificial Sequence
<220> FEATURE:
<223> OTHER INFORMATION: Codon Optimized

<400> SEQUENCE: 13

```
aacctataaa aataggcgta tcacgaggcc ctttcgtctc gcgcgtttcg gtgatgacgg      60
tgaaaacctc tgacacatgc agctcccgga gacggtcaca gcttgtctgt aagcggatgc     120
cgggagcaga caagcccgtc agggcgcgtc agcgggtgtt ggcgggtgtc ggggctggct     180
taactatgcg gcatcagagc agattgtact gagagtgcac cacgctttc aattcaattc     240 atcattttt ttttattctt tttttgatt tcggtttctt tgaaatttt ttgattcggt       300 aatctccgaa cagaaggaag aacgaaggaa ggagcacaga cttagattgg tatatatacg     360
catatgtagt gttgaagaaa catgaaattg cccagtattc ttaacccaac tgcacagaac     420
```

```
aaaaacctgc aggaaacgaa gataaatcat gtcgaaagct acatataagg aacgtgctgc    480
tactcatcct agtcctgttg ctgccaagct atttaatatc atgcacgaaa agcaaacaaa    540
cttgtgtgct tcattggatg ttcgtaccac caaggaatta ctggagttag ttgaagcatt    600
aggtcccaaa atttgtttac taaaaacaca tgtggatatc ttgactgatt tttccatgga    660
gggcacagtt aagccgctaa aggcattatc cgccaagtac aattttttac tcttcgaaga    720
cagaaaattt gctgacattg gtaatacagt caaattgcag tactctgcgg gtgtatacag    780
aatagcagaa tgggcagaca ttacgaatgc acacggtgtg gtgggcccag gtattgttag    840
cggtttgaag caggcggcag aagaagtaac aaaggaacct agaggccttt tgatgttagc    900
agaattgtca tgcaagggct ccctatctac tggagaatat actaagggta ctgttgacat    960
tgcgaagagc gacaaagatt ttgttatcgg ctttattgct caaagagaca tgggtggaag   1020
agatgaaggt tacgattggt tgattatgac acccggtgtg ggtttagatg acaagggaga   1080
cgcattgggt caacagtata gaaccgtgga tgatgtggtc tctacaggat ctgacattat   1140
tattgttgga agaggactat ttgcaaaggg aagggatgct aagtagagg gtgaacgtta   1200 cagaaaagca ggctgggaag catatttgag aagatgcggc cagcaaaact aaaaaactgt   1260
attataagta aatgcatgta tactaaactc acaaattaga gcttcaattt aattatatca   1320
gttattaccc tgcggtgtga ataccgcac agatgcgtaa ggagaaaata ccgcatcagg   1380
aaattgtaaa cgttaatatt ttgttaaaat tcgcgttaaa ttttttgttaa atcagctcat   1440 tttttaacca ataggccgaa atcggcaaaa tcccttataa atcaaaagaa tagaccgaga   1500
tagggttgag tgttgttcca gtttggaaca agagtccact attaaagaac gtggactcca   1560
acgtcaaagg gcgaaaaacc gtctatcagg gcgatggccc actacgtgaa ccatcaccct   1620
aatcaagttt ttggggtcg aggtgccgta aagcactaaa tcggaaccct aaagggagcc   1680
cccgatttag agcttgacgg ggaaagccgg cgaacgtggc gagaaaggaa gggaagaaag   1740
cgaaaggagc gggcgctagg gcgctggcaa gtgtagcggt cacgctgcgc gtaaccacca   1800
cacccgccgc gcttaatgcg ccgctacagg gcgcgtcgcg ccattcgcca ttcaggctgc   1860
gcaactgttg ggaagggcga tcggtgcggg cctcttcgct attacgccag ctggcgaagg   1920
ggggatgtgc tgcaaggcga ttaagttggg taacgccagg gttttcccag tcacgacgtt   1980
gtaaaacgac ggccagtgaa ttgtaatacg actcactata gggcgaattg gagctctagt   2040
acggattaga agccgccgag cgggcgacag ccctccgacg gaagactctc ctccgtgcgt   2100
cctcgtcttc accggtcgcg ttcctgaaac gcagatgtgc ctcgcgccgc actgctccga   2160
acaataaaga ttctacaata ctagctttta tggttatgaa gaggaaaaat tggcagtaac   2220
ctggccccac aaaccttcaa attaacgaat caaattaaca accataggat gataatgcga   2280
ttagtttttt agccttattt ctggggtaat taatcagcga agcgatgatt tttgatctat   2340
taacagatat ataaatggaa aagctgcata accacttta ctaatacttt caacattttc   2400
agtttgtatt acttcttatt caaatgtcat aaaagtatca caaaaaaatt gttaatatac   2460
ctctatactt taacgtcaag gagaaaaaac cccggattct agaactagtg gatcatgaac   2520
catttgagag ccgaaggtcc tgcctccgta ttagccatag gtacagccaa cccagaaaac   2580
atattgatcc aagatgaatt tcctgattat tacttcagag ttaccaagag tgaacacatg   2640
actcaattga aggaaaagtt tagaaaaata tgtgataagt ctatgatcag aaagagaaac   2700
tgcttcttga acgaagaaca tttgaagcaa aatccaagat tggtagaaca cgaaatgcaa   2760
acattggatg ccagacaaga catgttagtt gtcgaagttc ctaaattggg taaagatgct   2820
```

```
tgtgcaaaag ccattaagga atggggtcaa ccaaagtcaa agatcactca tttgatttt      2880 acaagtgcat ctactacaga tatgcctggt gcagactacc actgtgccaa attgttaggt    2940
ttgtcaccat ccgttaagag agtcatgatg tatcaattag gttgctacgg tggtggtact    3000
gttttgagaa tcgctaagga tattgcagaa acaacaagg gtgccagagt attagctgtt     3060
tgttgcgaca ttatggcttg cttgtttaga ggtccaagtg attctgactt ggaattgtta    3120
gttggtcaag ctatcttcgg tgacggtgct gctgctgtta ttgttggtgc agaacctgac    3180
gaatctgttg gtgaaagacc aatatttgaa ttagtcagta caggtcaaac catcttgcct    3240
aattctgaag gtacaattgg tggtcatata agagaagcag gtttgatctt cgatttgcac    3300
aaagacgttc caatgttaat ctctaacaac atagaaaagt gtttgataga agcattcact    3360
cctataggta tctcagattg gaactctatt ttctggataa cacatccagg tggtaaagcc    3420
attttggata aggttgaaga aaaattggat ttgaagaaag aaaagtttgt agatagtaga    3480
catgttttat ctgaacacgg taacatgtct tcatccactg tcttgttcgt aatggatgaa    3540
ttgagaaaga gatcattaga agagggtaaa tctactactg gtgacggttt tgaatggggt    3600
gtcttatttg gtttcggtcc tggtttgacc gtcgaaagag tagttgtcag atcagtacca    3660
attaaatatg aaggtagagg ttccttgtta acttgtggtg acgttgaaga aaacccaggt    3720
cctatggccg tcaagcattt gatagtattg aagtttaaag atgaaatcac agaagctcaa    3780
aaggaagaat ttttcaagac ctacgttaat ttggtcaaca ttatacctgc tatgaaagat    3840
gtatactggg gtaaagacgt tacacaaaag aaagaagaag gttatacaca cattgtcgaa    3900
gtaaccttcg aatcagttga aactatccaa gattacatca ttcatccagc tcacgttggt    3960
tttggtgacg tttacagatc cttctgggaa aaattgttga tcttcgatta caccccaaga    4020
aagtgataac gagaataata tcaagaatac cttagaacaa catcgacaac aacaacaggc    4080 atttcggat atgagtcacg tggagtattc cagaattaca aaattttttc aagaacaacc    4140
actggaggga tataccctt tctctcacag gtctgcgcca tgggtttatc atccgtctgt    4200
actttctcct tccaaactaa ctatcatacc ttattgaatc ctcacaacaa caatccaaaa    4260
acatcattgt tgtgttacag acatccaaag acacctatta agtactctta caacaacttt    4320
ccatcaaaac attgttcaac caagtccttc cacttacaaa ataagtgctc cgaaagtttg    4380
tctatagcta agaactctat cagagctgca actacaaatc aaactgaacc acctgaaagt    4440
gataatcact ctgttgccac aaaaaatttg aacttcggta agcatgttg gaagttgcaa    4500 agaccataca ccataatcgc ttttacttct tgtgcatgcg gttattcgg taagaattg     4560 ttgcataaca ctaacttaat ttcatggtcc ttgatgttca aggcatttt ctttttagtt    4620 gccatcttgt gcatcgcttc attcaccact acaattaatc aaatatacga tttgcacatc    4680
gacagaatta acaaaccaga tttgcctttg gcttcaggtg aaatatccgt caatactgca    4740
tggatcatgt ctatccatagt agccttgttc ggtttgatca tcacaattaa aatgaagggt   4800
ggtccattgt acatcttcgg ttactgtttc ggtatcttcg gtggtattgt ctattccgta   4860
ccacctttta gatggaaaca aaaccctagt actgcctttt tgttgaattt cttagctcat   4920
atcatcacaa acttccacctt ctactacgct tcaagagctg ctttaggttt gccattcgaa   4980
ttgagacctt cattcacatt tttgttggca ttcatgaaaa gtatgggttc tgcattagcc   5040
ttgatcaagg atgcctctga cgttgaaggt gacacaaagt tcggtattag taccttggct   5100
tctaagtacg gttcaagaaa tttgactttg ttctgctccg gtatcgtttt gttaagttac   5160
```

```
gtcgcagcca tttttggcagg tatcatttgg ccacaagcct ttaattctaa cgttatgttg   5220
ttgtcacatg ccatcttggc tttctggttg atcttgcaaa ctagagattt cgctttgaca   5280
aattatgacc ctgaagcagg tagaagattc tacgagttta tgtggaaatt gtactacgct   5340
gaatatttgg tatacgtttt tatttaacga taccgtcgac ctcgagtcat gtaattagtt   5400
atgtcacgct tacattcacg ccctcccccc acatccgctc taaccgaaaa ggaaggagtt   5460
agacaacctg aagtctaggt ccctatttat tttttatag ttatgttagt attaagaacg   5520
ttatttatat ttcaaatttt tcttttttttt ctgtacagac gcgtgtacgc atgtaacatt   5580
atactgaaaa ccttgcttga aaggttttg ggacgctcga aggctttaat ttgcggccgg   5640
tacccagctt ttgttcccctt tagtgagggt taattccgag cttggcgtaa tcatggtcat   5700
agctgtttcc tgtgtgaaat tgttatccgc tcacaattcc acacaacata ggagccggaa   5760
gcataaagtg taaagcctgg ggtgcctaat gagtgaggta actcacatta attgcgttgc   5820
gctcactgcc cgctttccag tcgggaaacc tgtcgtgcca gctgcattaa tgaatcggcc   5880
aacgcgcggg gagaggcggt ttgcgtattg ggcgctcttc cgcttcctcg ctcactgact   5940
cgctgcgctc ggtcgttcgg ctgcggcgag cggtatcagc tcactcaaag gcggtaatac   6000
ggttatccac agaatcaggg gataacgcag gaaagaacat gtgagcaaaa ggccagcaaa   6060
aggccaggaa ccgtaaaaag gccgcgttgc tggcgttttt ccataggctc ggcccccctg   6120
acgagcatca caaaaatcga cgctcaagtc agaggtggcg aaacccgaca ggactataaa   6180
gataccaggc gttccccccct ggaagctccc tcgtgcgctc tcctgttccg accctgccgc   6240
ttaccggata ccctgtccgcc tttctccctt cgggaagcgt ggcgctttct caatgctcac   6300
gctgtaggta tctcagttcg gtgtaggtcg ttcgctccaa gctgggctgt gtgcacgaac   6360
cccccgttca gcccgaccgc tgcgccttat ccggtaacta tcgtcttgag tccaacccgg   6420
taagacacga cttatcgcca ctggcagcag ccactggtaa caggattagc agagcgaggt   6480
atgtaggcgg tgctacagag ttcttgaagt ggtggcctaa ctacggctac actagaagga   6540
cagtatttgg tatctgcgct ctgctgaagc cagttacctt cggaaaaaga gttggtagct   6600
cttgatccgg caaacaaacc accgctggta gcggtggttt ttttgtttgc aagcagcaga   6660
ttacgcgcag aaaaaaagga tctcaagaag atcctttgat cttttctacg ggtctgacg   6720 ctcagtggaa cgaaaactca cgttaaggga ttttggtcat gagattatca aaaaggatct   6780
tcacctagat ccttttaaat taaaaatgaa gttttaaatc aatctaaagt atatatgagt   6840
aaacttggtc tgacagttac caatgcttaa tcagtgaggc acctatctca gcgatctgtc   6900
tatttcgttc atccatagtt gcctgactgc ccgtcgtgta gataactacg atacgggagg   6960
gcttaccatc tggccccagt gctgcaatga taccgcgaga cccacgctca ccggctccag   7020
atttatcagc aataaaccag ccagccggaa gggccgagcg cagaagtggt cctgcaactt   7080
tatccgcctc catccagtct attaattgtt gccgggaagc tagagtaagt agttcgccag   7140
ttaatagttt gcgcaacgtt gttgccattg ctacaggcat cgtggtgtca cgctcgtcgt   7200
ttggtatggc ttcattcagc tccggttccc aacgatcaag gcgagttaca tgatccccca   7260
tgttgtgaaa aaaagcggtt agctccttcg gtcctccgat cgttgtcaga agtaagttgg   7320
ccgcagtgtt atcactcatg gttatggcag cactgcataa ttctcttact gtcatgccat   7380
ccgtaagatg cttttctgtg actggtgagt actcaaccaa gtcattctga gaatagtgta   7440
tgcggcgacc gagttgctct tgcccggcgt caatacggga taataccgcg ccacatagca   7500
gaactttaaa agtgctcatc attggaaaac gttcttcggg gcgaaaactc tcaaggatct   7560
```

| | | |
|---|---|---|
| taccgctgtt gagatccagt tcgatgtaac ccactcgtgc acccaactga tcttcagcat | 7620 | |
| cttttacttt caccagcgtt tctgggtgag caaaaacagg aaggcaaaat gccgcaaaaa | 7680 | |
| agggaataag ggcgacacgg aaatgttgaa tactcatact cttcctttt caatattatt | 7740 | |
| gaagcattta tcagggttat tgtctcatga gcggatacat atttgaatgt atttagaaaa | 7800 | |
| ataaacaaat aggggttccg cgcacatttc cccgaaaagt gccacctgac gtctaagaaa | 7860 | |
| ccattattat catgacatt | 7879 | |

<210> SEQ ID NO 14
<211> LENGTH: 3353
<212> TYPE: DNA
<213> ORGANISM: Artificial Sequence
<220> FEATURE:
<223> OTHER INFORMATION: Codon Optimized

<400> SEQUENCE: 14

| | | |
|---|---|---|
| actagtatgg gtaaaaacta taagtccttg gattcagtcg ttgcctcaga tttcatcgca | 60 | |
| ttgggtatca cctcagaagt agcagaaaca ttacatggta gattggcaga aatcgtttgt | 120 | |
| aattatggtg ctgcaacccc tcaaacttgg atcaacatcg ctaaccatat cttgtcacca | 180 | |
| gatttgcctt tctccttaca ccaaatgttg ttttatggtt gctacaagga tttcggtcca | 240 | |
| gccccacctg cttggattcc agaccctgaa aaagtcaagt caactaattt gggtgctttg | 300 | |
| ttggaaaaga gaggtaaaga attttgggt gtaaagtaca aagatccaat ttcttctttt | 360 | |
| tctcacttcc aagaattttc tgttagaaac cctgaagtct attggagaac agtattgatg | 420 | |
| gatgaaatga aaattagttt ctctaaggac ccagaatgta tcttgagaag atgacacatc | 480 | |
| aacaacccag gtggttctga atggttacct ggtggttact tgaactcagc taaaaattgc | 540 | |
| ttgaacgtaa actccaataa gaaattgaac gatactatga tcgtttggag agacgagggt | 600 | |
| aacgatgact tgcctttgaa taagttgaca ttagatcaat tgagaaagag agtttggttg | 660 | |
| gttggttatg cattggaaga aatgggttta gaaaaaggtt gtgcaatagc catcgatatg | 720 | |
| ccaatgcatg ttgatgctgt tgttatatat ttggccatag tattggctgg ttacgtagtt | 780 | |
| gtctctatag cagattcatt ttccgcccct gaaatctcaa ctagattgag attatccaaa | 840 | |
| gctaaggcaa ttttcacaca agatcacatc atcagaggta aaagagaat accattgtat | 900 | |
| tcaagagtag ttgaagctaa atccccaatg gcaatagtta tcccttgtag tggttctaac | 960 | |
| attggtgcag aattgagaga tggtgacata tcttgggatt acttttaga aagagccaag | 1020 | |
| gagtttaaaa actgcgagtt tactgccaga gaacaacctg ttgatgctta tactaacatc | 1080 | |
| ttattctcca gtggtactac aggtgaacca aaagcaattc cttggacaca agccaccca | 1140 | |
| ttgaaggctg ctgctgatgg ttggtctcat ttggatatta gaaaggtgac gttatagta | 1200 | |
| tggccaacta atttgggttg gatgatgggt ccttggttgg tttatgctag tttgttaaat | 1260 | |
| ggtgcatcta ttgccttgta acggtagt ccttagtct ctggtttcgc taaatttgtt | 1320 | |
| caagatgcaa aggtcacaat gttgggtgtc gtaccatcta ttgtaagatc atggaaatcc | 1380 | |
| acaaattgtg tttcaggtta cgattggtcc accataagat gcttttcttc atccggtgaa | 1440 | |
| gcctctaatg tagacgaata tttgtggtta atgggtagac taactacaa gccagttata | 1500 | |
| gaaatgtgtg gtggtacaga aatcggtggt gcttttctg ctggttcatt tttgcaagct | 1560 | |
| caatctttaa gttcttttc atcccaatgt atggggttgca ccttgtacat attagataag | 1620 | |
| aacggttacc caatgcctaa aaataagcca ggtatcggtg aattggcatt aggtcctgtt | 1680 | |

```
atgtttggtg cctcaaaaac attgttaaac ggtaatcatc acgatgtcta tttcaagggt    1740
atgccaacct tgaatggtga agtattgaga agacatggtg acattttcga attgacctct    1800
aacggttact accatgcaca cggtagagcc gatgacacta tgaacatcgg tggtatcaaa    1860
attagttcta tcgaaatcga aagagtctgt aatgaagtag atgacagagt ttttgaaacc    1920
actgctattg gtgttccacc tttgggtggt ggtccagaac aattggtcat atttttcgta    1980
ttgaaggatt caaacgacac aaccattgat ttgaaccaat tgagattatc ctttaacttg    2040
ggtttgcaaa agaaattgaa cccattattc aaagttacta gagttgtccc attgtcatcc    2100
ttacctagaa ctgcaacaaa caagatcatg agaagagttt tgagacaaca attcagtcat    2160
ttcgaagaag gtagaggttc tttgttaaca tgtggtgacg ttgaagaaaa tccaggtcct    2220
atggcttcag aaaaggaaat aagaagagaa agattcttga acgtattccc aaagttagtt    2280
gaagaattga acgctagttt gttagcttat ggtatgccta agaagcctg cgattggtat    2340 gctcactctt taaactacaa tactccaggt ggtaaattga atagaggttt gagtgtagtt    2400
gatacttatg ctatcttgtc taacaaaacc gttgaacaat taggtcaaga agaatacgaa    2460
aaggtcgcta tcttgggttg gtgtattgaa ttgttgcaag catacttttt ggttgccgat    2520
gacatgatgg ataagtctat aacaagaaga ggtcaaccat gctggtacaa agttccagaa    2580
gttggtgaaa tagccataaa tgatgctttt atgttggaag ccgctatcta taaattgttg    2640
aagtcacatt tcagaaacga aaagtactac atcgatatta ccgaattatt ccacgaagtt    2700
actttccaaa cagaattggg tcaattgatg gatttgataa ctgcacctga agataaagtt    2760
gacttgtcaa agttttcctt gaagaaacat tcattcatcg tcacctttga aactgcttat    2820
tactccttct atttgccagt cgccttggct atgtacgtag ctggtattac tgatgaaaaa    2880
gacttgaagc aagcaagaga tgtttttgata cctttgggtg aatacttcca aatccaagat    2940
gactacttag actgtttcgg tactccagaa caaataggta aaatcggtac agatattcaa    3000
gacaataagt gcagttgggt tattaacaag gctttggaat tagcatctgc cgaacaaaga    3060
aagactttgg atgaaaacta cggtaaaaag gactcagttg ctgaagcaaa gtgtaagaaa    3120
atttttaatg atttgaagat tgaacaattg taccatgaat acgaagaatc catcgctaaa    3180
gacttaaagg caaagattag tcaagttgat gaatcaagag gttttaaagc cgacgttttg    3240
acagctttct tgaataaggt ctacaagaga tcaaaggatt acaaggatca tgacggtgac    3300
tataaagacc acgatattga ctacaaagat gacgatgaca gtaagcggc cgc            3353

<210> SEQ ID NO 15
<211> LENGTH: 1553
<212> TYPE: DNA
<213> ORGANISM: Artificial Sequence
<220> FEATURE:
<223> OTHER INFORMATION: Codon Optimized

<400> SEQUENCE: 15
actagtatga accatttgag agccgaaggt cctgcctccg tattagccat aggtacagcc      60
aacccagaaa acatattgat ccaagatgaa tttcctgatt attacttcag agttaccaag     120
agtgaacaca tgactcaatt gaaggaaaag tttagaaaaa tatgtgataa gtctatgatc     180
agaaagagaa actgcttctt gaacgaagaa catttgaagc aaaatccaag attggtagaa     240
cacgaaatgc aaacattgga tgccagacaa gacatgttag ttgtcgaagt tcctaaattg     300
ggtaaagatg cttgtgcaaa agccattaag gaatggggtc aaccaaagtc aaagatcact     360
catttgattt ttacaagtgc atctactaca gatatgcctg gtgcagacta ccactgtgcc     420
```

| | |
|---|---|
| aaaattgttag gtttgtcacc atccgttaag agagtcatga tgtatcaatt aggttgctac | 480 |
| ggtggtggta ctgttttgag aatcgctaag gatattgcag aaaacaacaa gggtgccaga | 540 |
| gtattagctg tttgttgcga cattatggct tgcttgttta gaggtccaag tgattctgac | 600 |
| ttggaattgt tagttggtca agctatcttc ggtgacggtg ctgctgctgt tattgttggt | 660 |
| gcagaacctg acgaatctgt tggtgaaaga ccaatatttg aattagtcag tacaggtcaa | 720 |
| accatcttgc ctaattctga aggtacaatt ggtggtcata agagaagc aggtttgatc | 780 |
| ttcgatttgc acaaagacgt tccaatgtta atctctaaca acatagaaaa gtgtttgata | 840 |
| gaagcattca ctcctatagg tatctcagat tggaactcta ttttctggat aacacatcca | 900 |
| ggtggtaaag ccattttgga taaggttgaa gaaaaattgg atttgaagaa agaaaagttt | 960 |
| gtagatagta gacatgtttt atctgaacac ggtaacatgt cttcatccac tgtcttgttc | 1020 |
| gtaatggatg aattgagaaa gagatcatta aagagggta atctactac tggtgacggt | 1080 |
| tttgaatggg gtgtcttatt tggtttcggt cctggtttga ccgtcgaaag agtagttgtc | 1140 |
| agatcagtac caattaaata tgaaggtaga ggttccttgt taacttgtgg tgacgttgaa | 1200 |
| gaaaacccag gtcctatggc cgtcaagcat ttgatagtat tgaagtttaa agatgaaatc | 1260 |
| acagaagctc aaaaggaaga attttcaag acctacgtta atttggtcaa cattataccct | 1320 |
| gctatgaaag atgtatactg gggtaaagac gttacacaaa agaaagaaga aggttataca | 1380 |
| cacattgtcg aagtaacctt cgaatcagtt gaaactatcc aagattacat cattcatcca | 1440 |
| gctcacgttg ttttggtga cgtttacaga tccttctggg aaaaattgtt gatcttcgat | 1500 |
| tacaccccaa gaaagtaccc ttacgatgtt ccagactatg cataagcggc cgc | 1553 |

<210> SEQ ID NO 16
<211> LENGTH: 2918
<212> TYPE: DNA
<213> ORGANISM: Artificial Sequence
<220> FEATURE:
<223> OTHER INFORMATION: Codon Optimized

<400> SEQUENCE: 16

| | |
|---|---|
| actagtatgg gttatcatc cgtctgtact ttctccttcc aaactaacta tcataccta | 60 |
| ttgaatcctc acaacaacaa tccaaaaaca tcattgttgt gttacagaca tccaaagaca | 120 |
| cctattaagt actcttacaa caactttcca tcaaaacatt gttcaaccaa gtccttccac | 180 |
| ttacaaaata agtgctccga aagtttgtct atagctaaga actctatcag agctgcaact | 240 |
| acaaatcaaa ctgaaccacc tgaaagtgat aatcactctg ttgccacaaa aattttgaac | 300 |
| ttcggtaaag catgttggaa gttgcaaaga ccatacacca taatcgcttt tacttcttgt | 360 |
| gcatgcggtt tattcggtaa agaattgttg cataacacta acttaatttc atggtccttg | 420 |
| atgttcaagg cattttttctt tttagttgcc atcttgtgca tcgcttcatt caccactaca | 480 |
| attaatcaaa tatcgatttt gcacatcgac agaattaaca aaccagattt gcctttggct | 540 |
| tcaggtgaaa tatccgtcaa tactgcatgg atcatgtcta tcatagtagc cttgttcggt | 600 |
| ttgatcatca caattaaaat gaagggtggt ccattgtaca tcttcggtta ctgtttcggt | 660 |
| atcttcggtg gtattgtcta ttccgtacca ccttttagat ggaaacaaaa ccctagtact | 720 |
| gcctttttgt tgaatttctt agctcatatc atcacaaact tcaccttcta ctacgcttca | 780 |
| agagctgctt taggtttgcc attcgaattg agaccttcat tcacatttt gttggcattc | 840 |
| atgaaaagta tgggttctgc attagccttg atcaaggatg cctctgacgt tgaaggtgac | 900 |

```
acaaagttcg gtattagtac cttggcttct aagtacggtt caagaaattt gactttgttc      960
tgctccggta tcgttttgtt aagttacgtc gcagccattt ggcaggtat catttggcca     1020
caagccttta attctaacgt tatgttgttg tcacatgcca tcttggcttt ctggttgatc     1080
ttgcaaacta gagatttcgc tttgacaaat tatgaccctg aagcaggtag aagattctac     1140
gagtttatgt ggaaattgta ctacgctgaa tatttggtat acgttttat tgaaggtaga     1200
ggttctttgt tgacctgtgg tgacgttgaa gaaaatccag gtcctatgaa atgttcaact     1260
ttctcctttt ggttcgtatg caagatcatc ttctttttct tttcctttaa catccaaaca     1320
agtatcgcaa acccaagaga aaacttttg aagtgcttct cacaatacat acctaataac     1380
gccaccaatt tgaagttggt ttacactcaa aacaacccat tgtacatgtc cgtcttgaac     1440
agtacaatcc ataatttgag attcacttct gataccactc caaaaccttt ggtcattgta     1500
accctagtc atgtatctca catccaaggt actatcttat gttctaaaaa ggttggtttg     1560
caaattagaa ctagatccgg tggtcatgat agtgaaggca tgtcatacat ctcccaagtt     1620
ccattcgtta tcgttgattt gagaaacatg agatcaatta aaatagacgt acactcacaa     1680
actgcttggg ttgaagctgg tgcaacattg ggtgaagtat actactgggt taacgaaaag     1740
aatgaaaact tatcattggc tgctggttac tgtccaacag tttgcgcagg tggtcatttt     1800
ggtggtggtg gttatggtcc tttaatgaga aactacggtt tggccgctga taacataatc     1860
gacgctcatt tggtaaatgt tcacggtaaa gttttggata aaagtctat gggtgaagac     1920
ttatttggg ctttgagagg tggtggtgca gaatcattcg gtatcatagt tgcttggaag     1980
ataagattag tcgcagtacc aaagtctact atgttctcag tcaaaaagat aatggaaatc     2040
catgaattag ttaaattggt caataagtgg caaaacatcg catacaagta cgataaggac     2100
ttgttgttga tgactcattt catcacaaga aacatcaccg ataaccaagg taaaaataag     2160
actgctatcc acacatactt ttcttcagtt ttcttgggtg gtgtcgattc cttagtagac     2220
ttgatgaata agtcttttcc agaattaggt attaagaaaa ctgattgtag acaattgtct     2280
tggatcgaca ccatcatctt ttattcaggt gttgtcaact acgatacaga caacttcaac     2340
aaagaaatat tattggatag atccgcaggt caaaacggtg cctttaaaat taagttagac     2400
tacgttaaaa agccaatacc tgaatcagtt ttcgtccaaa tcttagaaaa attgtacgaa     2460
gaagatattg gtgcaggcat gtacgccttg tatccatacg gtggtataat ggacgaaatc     2520
agtgaatctg ccattccatt tcctcataga gctggtatct tatacgaatt gtggtacatt     2580
tgttcatggg aaaagcaaga agataacgaa aagcacttaa actggattag aaacatctat     2640
aacttcatga ctccatacgt ttctaaaaac cctagattgg catatttgaa ctacagagat     2700
ttggacatcg gtattaacga tccaaagaat cctaacaact ataccaagc tagaatttgg     2760
ggtgaaaaat acttcggtaa aaatttcgat agattagtaa aggttaagac attggttgac     2820
ccaaacaact tctttagaaa cgaacaatcc attccaccctt tacctagaca tagacacgaa     2880
caaaaattaa taagtgaaga agatttgtaa gcggccgc                             2918
```

<210> SEQ ID NO 17
<211> LENGTH: 167
<212> TYPE: DNA
<213> ORGANISM: Artificial Sequence
<220> FEATURE:
<223> OTHER INFORMATION: Codon Optimized

<400> SEQUENCE: 17

```
agccaaaata atgataacga gaataatatc aagaatacct agaacaaca tcgacaacaa       60
```
caacaggcat tttcggatat gagtcacgtg gagtattcca gaattacaaa atttttttcaa        120 gaacaaccac tggagggata tacccttttc tctcacaggt ctgcgcc                      167

<210> SEQ ID NO 18
<211> LENGTH: 1518
<212> TYPE: DNA
<213> ORGANISM: Artificial Sequence
<220> FEATURE:
<223> OTHER INFORMATION: Codon Optimized

<400> SEQUENCE: 18
atggtttcca atcacttgtt tgacgcaatg agagccgctg cccctggtaa cgccccttc         60 ataagaatag ataatactag aacttggaca tacgatgacg cctttgcttt atctggtaga        120
atagcatcag ctatggatgc tttgggtatc agaccaggtg acagagtcgc agttcaagta        180
gaaaaatccg ctgaagcatt gatcttgtat ttggcttgtt tgagaagtgg tgcagtttat       240
ttgccattga atactgccta cacattagct gaattggatt acttcatagg tgacgcagaa       300
cctagattgg ttgtagtcgc ctcttcagcc agagctggtg tagaaacaat gctaaaacca      360
agaggtgcaa tagtcgaaac cttagatgct gctggttctg gtagtttgtt agatttggcc      420
agagacgaac ctgctgattt tgttgacgct tcaagatcag ccgatgactt agccgctatt      480
ttgtacacct ctggtactac aggtagatca aaggtgcta tgttgactca tggtaattg       540 ttgtcaaacg cattaaccctt gagagatttc tggagagtta ctgccggtga cagattaatc    600
cacgctttgc caattttca tactcacggt ttattcgttg ctaccaacgt aactttgtta      660
gcaggtgcct ccatgttctt gttgagtaag ttcgatccag aagaaatatt atctttgatg      720
cctcaagcta ctatgttgat gggtgtccca acattctacg ttagattgtt acaatcacct     780
agattagata agcaagctgt tgcaaacatc agattgttta tatccggtag tgctccattg      840
ttagcagaaa cccatactga atttcaagca agaacaggtc acgccatttt agaaagatac     900
ggtatgacag aaaccaatat gaacacttct aaccctatg aaggtaaaag aatagctggt     960
acagttggtt ttccattgcc tgatgtcaca gttagagtaa ccgacccagc cactggttta    1020
gctttgccac tgaacaaaac tggtatgatc gaaattaaag gtccaaacgt ttttaagggt    1080
tactggagaa tgcctgaaaa gactgctgct gagtttactg ctgatggttt cttatctct     1140 ggtgacttag gtaaattga tagagacggt tatgtccata ttgttggtcg tggtaaagat    1200
ttggttatat ccggtggtta taacatctac cctaaggaag tagaaggtga aatagatcaa    1260
atcgaaggtg ttgtagaatc agctgtaata ggtgtcccac atcctgattt tggtgaaggt    1320
gttacagcag tcgttgtaag aaaaccaggt gctgcattag atgaaaaggc aattgtttct    1380
gccttacaag acagattggc tagatacaag caaccaaaga gaataatctt cgcagaagat    1440
ttgcctagaa atactatggg taaagtacaa aagaacatct tgagacaaca atacgccgac    1500
ttatacacca gaacctga                                                  1518

<210> SEQ ID NO 19
<211> LENGTH: 2092
<212> TYPE: DNA
<213> ORGANISM: Artificial Sequence
<220> FEATURE:
<223> OTHER INFORMATION: Codon Optimized

<400> SEQUENCE: 19
actagtatgg gtttatcatc cgtctgtact ttctccttcc aaactaacta tcataccta        60

```
ttgaatcctc acaacaacaa tccaaaaaca tcattgttgt gttacagaca tccaaagaca        120
cctattaagt actcttacaa caactttcca tcaaaacatt gttcaaccaa gtccttccac        180
ttacaaaata agtgctccga agtttgtct atagctaaga actctatcag agctgcaact         240
acaaatcaaa ctgaaccacc tgaaagtgat aatcactctg ttgccacaaa aattttgaac        300
ttcggtaaag catgttggaa gttgcaaaga ccatacacca taatcgcttt tacttcttgt       360
gcatgcggtt tattcggtaa agaattgttg cataacacta acttaatttc atggtcctat        420
gaactgctcc gcattctctt tctggttcgt ctgtaaaata atcttcttct tcttgtcctt       480
caacatccaa atctccatcg caaatccaca agaaaacttt tgaagtgtt tctccgaata        540 catcccaaac aaccctgcta acccaaagtt tatatatact caacatgatc aattgtacat       600
gtccgttttg aacagtacca tccaaaattt gagattcact tctgacacta caccaaaacc       660
tttagtcatt gttacacctt ccaatgttag tcacattcaa gcttctatat tgtgctctaa       720
gaaagtaggt ttgcaaatca gaactagatc aggtggtcat gatgcagaag gcatgtctta      780
catctcacaa gttccattcg ttgtagtcga tttgagaaat atgcattcca taaagatcga       840
cgttcacagt caaacagcat gggtagaagc aggtgccacc ttgggtgaag tttactactg      900
gatcaacgaa aagaatgaaa acttttcttt ccctggtggt tactgtccaa cagtaggtgt      960
cggtggtcac tttctggtg gtggttatgg tgcattgatg agaaactacg gtttagctgc      1020
agataatatt ataggacgccc atttggttaa cgtagatggt aaagttttgg acagaaagtc    1080
tatgggtgaa gatttgtttt gggccataag aggtggtggt ggtgaaaatt cggtatcat     1140 tgccgcttgg aaaattaagt tagtcgctgt tccttccaaa agtactattt tctctgtcaa    1200
aaagaacatg gaaatccacg gtttggttaa gttgtttaat aagtggcaaa acatcgctta    1260
caagtacgat aaggacttgg tttttgatgac ccatttcatc actaaaaata ttacagataa   1320
ccatggtaaa aataagacca ctgttcacgg ttattttct tcaatttcc atggtggtgt      1380 agattctttg gttgatttga tgaataagtc attcccagaa ttgggtatta aaaagacaga    1440
ttgcaaggaa ttttcttgga tagacacaac catcttctat tcaggtgttg taaacttcaa    1500
caccgctaac ttcaaaaagg aaatcttgtt ggatagatcc gctggtaaaa agaccgcttt    1560
ttctattaaa ttggactacg ttaagaaacc aatccctgaa actgcaatgg tcaagatatt    1620
ggaaaagttg tacgaagaag atgtaggtgt cggcatgtac gttttgtatc catacggtgg    1680
tattatggaa gaaatatctg aatcagccat accatttcct cacagagctg gtatcatgta    1740
tgaattatgg tacacagcct catgggaaaa gcaagaagat aacgaaaagc atatcaactg    1800
ggtcagatcc gtttacaact tcactacacc ttacgttagt caaaacccaa gattggcata    1860
tttgaactac agagatttgg acttaggtaa aactaaccct gaatctccaa ataactatac     1920
acaagcaaga atttggggtg aaaagtactt tggtaaaaat ttcaacagat tagttaaagt     1980
aaagactaaa gccgaccctca acactttttt cagaaacgaa caatccatcc cacctttgcc    2040
acctcaccac cacgaacaaa aattaataag tgaagaagat ttgtaagtcg ac             2092
```

<210> SEQ ID NO 20
<211> LENGTH: 7904
<212> TYPE: DNA
<213> ORGANISM: Artificial Sequence
<220> FEATURE:
<223> OTHER INFORMATION: Codon Optimized

<400> SEQUENCE: 20

```
tcgcgcgttt cggtgatgac ggtgaaaacc tctgacacat gcagctcccg gagacggtca      60
```

```
cagcttgtct gtaagcggat gccgggagca gacaagcccg tcaggcgcg  tcagcgggtg    120 ttggcgggtg tcgggctgg  cttaactatg cggcatcaga gcagattgta ctgagagtgc    180
accatatcga ctacgtcgta aggccgtttc tgacagagta aaattcttga gggaactttc    240
accattatgg gaaatggttc aagaaggtat tgacttaaac tccatcaaat ggtcaggtca    300
ttgagtgttt tttatttgtt gtatttttt  tttttagag  aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tccttttct  ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaacctttt  aactgcatct    780 tcaatggcct taccttcttc aggcaagttc aatgacaatt tcaacatcat tgcagcagac    840
aagatagtgg cgataggtc  aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc  tccataatct tgaagaggcc aaaacattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg attttagta  aaccttgttc aggtctaaca   1500
ctaccggtac cccatttagg accacccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa acgacgatc    1740 ttcttagggg cagacatagg ggcagacatt agaatgtat  atccttgaaa tatatatata   1800
tattgctgaa atgtaaaagg taagaaaagt tagaaagtaa gacgattgct aaccacctat   1860
tggaaaaaac aataggtcct taaataatat tgtcaacttc aagtattgtg atgcaagcat   1920
ttagtcatga acgcttctct attctatatg aaaagccggt tccggcctct cacctttcct   1980
ttttctccca attttcagt  tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agtaactgc  ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
```

```
gaagttctcc tcgagggtcg atatgcggtg tgaaataccg cacagatgcg taaggagaaa      2460
ataccgcatc aggaaattgt aaacgttaat attttgttaa aattcgcgtt aaattttgt       2520 taaatcagct cattttttaa ccataggcc gaaatcggca aaatcccta taaatcaaaa        2580 gaatagaccg atagggtt gagtgttgtt ccagtttgga acaagagtcc actattaaag        2640
aacgtggact ccaacgtcaa agggcgaaaa accgtctatc agggcgatgg cccactacgt      2700
gaaccatcac cctaatcaag ttttttgggg tcgaggtgcc gtaaagcact aaatcggaac      2760
cctaaaggga gcccccgatt tagagcttga cggggaaagc cggcgaacgt ggcgagaaag      2820
gaagggaaga aagcgaaagg agcgggcgct agggcgctgg caagtgtagc ggtcacgctg      2880
cgcgtaacca ccacacccgc cgcgcttaat gcgccgctac agggcgcgtc gcgccattcg      2940
ccattcaggc tgcgcaactg ttgggaaggg cgatcggtgc gggcctcttc gctattacgc      3000
cagctggcga agggggatg tgctgcaagg cgattaagtt gggtaacgcc agggttttcc       3060
cagtcacgac gttgtaaaac gacggccagt gaattgtaat acgactcact ataggcgaa      3120 ttggagctct agtacggatt agaagccgcc gagcgggcga cagccctccg acggaagact      3180
ctcctccgtg cgtcctcgtc ttcaccggtc gcgttcctga aacgcagatg tgcctcgcgc      3240
cgcactgctc cgaacaataa agattctaca atactagctt ttatggttat gaagaggaaa      3300
aattggcagt aacctggccc cacaaacctt caaattaacg aatcaaatta caaccatag       3360 gatgataatg cgattagttt tttagcctta tttctgggt aattaatcag cgaagcgatg       3420
atttttgatc tattaacaga tatataaatg gaaaagctgc ataaccactt taactaatac      3480
tttcaacatt ttcagtttgt attacttctt attcaaatgt cataaaagta tcaacaaaaa      3540
attgttaata tacctctata ctttaacgtc aaggagaaaa accccggat tctagaacta      3600 gtggatcccc catcacaagt ttgtacaaaa aagctgaacg agaaacgtaa aatgatataa      3660
atatcaatat attaaattag attttgcata aaaaacagac tacataatac tgtaaaacac      3720
aacatatcca gtcactatgg cggccgcatt aggcaccca ggctttacac tttatgcttc      3780
cggctcgtat aatgtgtgga ttttgagtta ggatccgtcg agattttcag gagctaagga     3840
agctaaaatg gagaaaaaaa tcactggata taccaccgtt gatatatccc aatggcatcg      3900
taaagaacat tttgaggcat ttcagtcagt tgctcaatgt acctataacc agaccgttca      3960
gctggatatt acggcctttt taagaccgt aagaaaaat aagcacaagt tttatccggc       4020
ctttattcac attcttgccc gcctgatgaa tgctcatccg gaattccgta tggcaatgaa      4080
agacggtgag ctggtgatat gggatagtgt tcacccttgt tacaccgttt tccatgagca     4140
aactgaaacg ttttcatcgc tctggagtga ataccacgac gatttccggc agtttctaca     4200
catatattcg caagatgtgg cgtgttacgg tgaaaacctg gcctatttcc ctaaaggtt      4260 tattgagaat atgtttttcg tctcagccaa tccctgggtg agtttcacca gttttgattt     4320
aaacgtggcc aatatggaca acttcttcgc ccccgttttc accatgggca aatattatac     4380
gcaaggcgac aaggtgctga tgccgctggc gattcaggtt catcatgccg tctgtgatgg    4440
cttccatgtc ggcagaatgc ttaatgaatt acaacagtac tgcgatgagt ggcagggcgg    4500
ggcgtaaacg ccgcgtggat ccggcttact aaaagccaga taacagtatg cgtatttgcg     4560
cgctgatttt tgcggtataa gaatatatac tgatatgtat acccgaagta tgtcaaaaag    4620
aggtatgcta tgaagcagcg tattacagtg acagttgaca gcgacagcta tcagttgctc    4680
aaggcatata tgatgtcaat atctccggtc tggtaagcac aaccatgcag aatgaagccc    4740
gtcgtctgcg tgccgaacgc tggaaagcgg aaaatcagga agggatggct gaggtcgccc    4800
```

-continued

```
ggtttattga aatgaacggc tcttttgctg acgagaacag gggctggtga aatgcagttt    4860
aaggtttaca cctataaaag agagagccgt tatcgtctgt ttgtggatgt acagagtgat    4920
attattgaca cgcccgggcg acggatggtg atcccctgg ccagtgcacg tctgctgtca     4980
gataaagtct cccgtgaact ttacccggtg gtgcatatcg gggatgaaag ctggcgcatg    5040
atgaccaccg atatggccag tgtgccggtc tccgttatcg gggaagaagt ggctgatctc    5100
agccaccgcg aaaatgacat caaaaacgcc attaacctga tgttctgggg aatataaatg    5160
tcaggctccc ttatacacag ccagtctgca ggtcgaccat agtgactgga tatgttgtgt    5220
tttacagtat tatgtagtct gttttttatg caaaatctaa tttaatatat tgatatttat    5280
atcattttac gtttctcgtt cagctttctt gtacaaagtg gtgatgggct gcaggaattc    5340
gatatcaagc ttatcgatac cgtcgacctc gagtcatgta attagttatg tcacgcttac    5400
attcacgccc tccccccaca tccgctctaa ccgaaaagga aggagttaga caacctgaag    5460
tctaggtccc tatttatttt tttatagtta tgttagtatt aagaacgtta tttatatttc    5520 aaattttct ttttttctg tacagacgcg tgtacgcatg taacattata ctgaaaacct      5580
tgcttgagaa ggttttggga cgctcgaagg ctttaatttg cggccggtac ccagcttttg    5640
ttccctttag tgagggttaa ttccgagctt ggcgtaatca tggtcatagc tgtttcctgt    5700
gtgaaattgt tatccgctca caattccaca acatagga gccggaagca taaagtgtaa      5760
agcctggggt gcctaatgag tgaggtaact cacattaatt gcgttgcgct cactgcccgc    5820
tttccagtcg ggaaacctgt cgtgccagct gcattaatga atcggccaac gcgcggggag    5880
aggcggtttg cgtattgggc gctcttccgc ttcctcgctc actgactcgc tgcgctcggt    5940
cgttcggctg cggcgagcgg tatcagctca ctcaaaggcg gtaatacggt tatccacaga    6000 atcagggat aacgcaggaa agaacatgtg agcaaaaggc cagcaaaagg ccaggaaccg      6060
taaaaaggcc gcgttgctgg cgttttttcca taggctcggc cccctgacg agcatcacaa     6120 aaatcgacgc tcaagtcaga ggtggcgaaa cccgacagga ctataaagat accaggcgtt    6180 ccccctgga agctccctcg tgcgctctcc tgttccgacc ctgccgctta ccggatacct      6240
gtccgccttt ctcccttcgg gaagcgtggc gctttctcaa tgctcacgct gtaggtatct    6300
cagttcggtg taggtcgttc gctccaagct gggctgtgtg cacgaacccc cgttcagcc      6360 cgaccgctgc gccttatccg gtaactatcg tcttgagtcc aacccggtaa gacacgactt    6420
atcgccactg gcagcagcca ctggtaacag gattagcaga gcgaggtatg taggcggtgc    6480
tacagagttc ttgaagtggt ggcctaacta cggctacact agaaggacag tatttggtat    6540
ctgcgctctg ctgaagccag ttaccttcgg aaaagagtt ggtagctctt gatccggcaa      6600
acaaaccacc gctggtagcg gtggtttttt tgtttgcaag cagcagatta cgcgcagaaa    6660
aaaaggatct caagaagatc ctttgatctt ttctacgggg tctgacgctc agtggaacga    6720
aaactcacgt taagggattt tggtcatgag attatcaaaa aggatcttca cctagatcct    6780
tttaaattaa aaatgaagtt ttaaatcaat ctaaagtata tatgagtaaa cttggtctga    6840
cagttaccaa tgcttaatca gtgaggcacc tatctcagcg atctgtctat ttcgttcatc    6900
catagttgcc tgactgcccg tcgtgtagat aactacgata cgggagggct taccatctgg    6960
ccccagtgct gcaatgatac cgcgagaccc acgctcaccg gctccagatt tatcagcaat    7020
aaaccagcca gccggaaggg ccgagcgcag aagtggtcct gcaactttat ccgcctccat    7080
ccagtctatt aattgttgcc gggaagctag agtaagtagt tcgccagtta atagtttgcg    7140
```

```
caacgttgtt gccattgcta caggcatcgt ggtgtcacgc tcgtcgtttg gtatggcttc      7200
attcagctcc ggttcccaac gatcaaggcg agttacatga tcccccatgt tgtgaaaaaa      7260
agcggttagc tccttcggtc ctccgatcgt tgtcagaagt aagttggccg cagtgttatc      7320
actcatggtt atggcagcac tgcataattc tcttactgtc atgccatccg taagatgctt      7380
ttctgtgact ggtgagtact caaccaagtc attctgagaa tagtgtatgc ggcgaccgag      7440
ttgctcttgc ccggcgtcaa tacgggataa taccgcgcca catagcagaa ctttaaaagt      7500
gctcatcatt ggaaaacgtt cttcggggcg aaaactctca aggatcttac cgctgttgag      7560
atccagttcg atgtaaccca ctcgtgcacc caactgatct tcagcatctt ttactttcac      7620
cagcgtttct gggtgagcaa aacaggaag gcaaaatgcc gcaaaaaagg gaataagggc       7680
gacacggaaa tgttgaatac tcatactctt ccttttcaa tattattgaa gcatttatca       7740
gggttattgt ctcatgagcg atacatatt tgaatgtatt tagaaaaata aacaaatagg       7800
ggttccgcgc acatttcccc gaaaagtgcc acctgacgtc taagaaacca ttattatcat      7860
gacattaacc tataaaaata ggcgtatcac gaggccctt cgtc                        7904
```

<210> SEQ ID NO 21
<211> LENGTH: 6773
<212> TYPE: DNA
<213> ORGANISM: Artificial Sequence
<220> FEATURE:
<223> OTHER INFORMATION: Codon Optimized

<400> SEQUENCE: 21

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accacgcttt tcaattcaat tcatcatttt ttttttattc ttttttttga tttcggtttc       240
tttgaaattt ttttgattcg gtaatctccg aacagaagga agaacgaagg aaggagcaca       300
gacttagatt ggtatatata cgcatatgta gtgttgaaga acatgaaat tgcccagtat       360 tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttccatg gagggcacag ttaagccgct aaaggcatta tccgccaagt       660
acaatttttt actcttcgaa gacagaaaat tgctgacat tggtaataca gtcaaattgc      720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct ttgatgtta gcagaattgt catgcaaggg ctccctatct actggagaat       900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg gaagaggact atttgcaaag ggaagggatg     1140
ctaaggtaga gggtgaacgt tacagaaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
```

```
aaggagaaaa taccgcatca ggaaattgta aacgttaata tttttgttaaa attcgcgtta    1380 aattttttgtt aaatcagctc atttttttaac caataggccg aaatcggcaa aatcccttat   1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt ttttttgggt cgaggtgccg taaagcacta    1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc     2280
gaagcgatga tttttgatct attaacagat atataaatgg aaaagctgca taaccacttt      2340
aactaatact ttcaacattt tcagtttgta ttacttctta ttcaaatgtc ataaaagtat        2400
caacaaaaaa ttgttaatat acctctatac tttaacgtca aggagaaaaa accccggatt       2460
ctagaactag tggatccccc atcacaagtt tgtacaaaaa agctgaacga gaacgtaaa       2520 atgatataaa tatcaatata ttaaattaga ttttgcataa aaaacagact acataatact      2580
gtaaaacaca acatatccag tcactatggc ggccgcatta ggcacccag gctttacact        2640 ttatgcttcc ggctcgtata atgtgtggat tttgagttag gatccgtcga gattttcagg       2700
agctaaggaa gctaaaatgg agaaaaaaat cactggatat accaccgttg atatatccca      2760
atggcatcgt aaagaacatt tgaggcatt tcagtcagtt gctcaatgta cctataacca         2820
gaccgttcag ctggatatta cggcctttt aaagaccgta agaaaaata agcacaagtt          2880 ttatccggcc tttattcaca ttcttgcccg cctgatgaat gctcatccgg aattccgtat       2940
ggcaatgaaa gacggtgagc tggtgatatg ggatagtgtt cacccttgtt acaccgtttt     3000
ccatgagcaa actgaaacgt tttcatcgct ctggagtgaa taccacgacg atttccggca     3060
gtttctacac atatattcgc aagatgtggc gtgttacggt gaaaacctgg cctatttccc    3120
taaagggttt attgagaata tgttttttcgt ctcagccaat ccctgggtga gtttcaccag     3180
ttttgattta aacgtggcca atatggacaa cttcttcgcc cccgttttca ccatgggcaa      3240
atattatacg caaggcgaca aggtgctgat gccgctggcg attcaggttc atcatgccgt     3300
ctgtgatggc ttccatgtcg cagaatgct taatgaatta caacagtact gcgatgagtg     3360
gcagggcggg gcgtaaacgc cgcgtggatc cggcttacta aaagccagat aacagtatgc     3420
gtatttgcgc gctgattttt gcggtataag aatatatact gatatgtata cccgaagtat       3480
gtcaaaaaga ggtatgctat gaagcagcgt attacagtga cagttgacag cgacagctat       3540
cagttgctca aggcatatat gatgtcaata tctccggtct ggtaagcaca accatgcaga        3600
atgaagcccg tcgtctgcgt gccgaacgct ggaaagcgga aaatcaggaa gggatggctg       3660
```

```
aggtcgcccg gtttattgaa atgaacggct cttttgctga cgagaacagg ggctggtgaa    3720
atgcagttta aggtttacac ctataaaaga gagagccgtt atcgtctgtt tgtggatgta    3780
cagagtgata ttattgacac gcccgggcga cggatggtga tcccctggc cagtgcacgt    3840 ctgctgtcag ataaagtctc ccgtgaactt tacccggtgg tgcatatcgg ggatgaaagc    3900
tggcgcatga tgaccaccga tatggccagt gtgccggtct ccgttatcgg ggaagaagtg    3960
gctgatctca gccaccgcga aaatgacatc aaaaacgcca ttaacctgat gttctgggga    4020
atataaatgt caggctccct tatacacagc cagtctgcag gtcgaccata gtgactggat    4080
atgttgtgtt ttacagtatt atgtagtctg tttttatgc aaaatctaat ttaatatatt    4140
gatatttata tcattttacg tttctcgttc agctttcttg tacaaagtgg tgatgggctg    4200
caggaattcg atatcaagct tatcgatacc gtcgacctcg agtcatgtaa ttagttatgt    4260
cacgcttaca ttcacgccct ccccccacat ccgctctaac cgaaaggaa ggagttagac    4320 aacctgaagt ctaggtccct atttattttt ttatagttat gttagtatta agaacgttat    4380
ttatatttca aattttctt tttttctgt acagacgcgt gtacgcatgt aacattatac    4440 tgaaaaccttt gcttgagaag gttttgggac gctcgaaggc tttaatttgc ggccggtacc    4500
cagcttttgt tcccttagt gagggttaat tccgagcttg gcgtaatcat ggtcatagct    4560
gtttcctgtg tgaaattgtt atccgctcac aattccacac aacataggag ccggaagcat    4620
aaagtgtaaa gcctggggtg cctaatgagt gaggtaactc acattaattg cgttgcgctc    4680
actgcccgct ttccagtcgg gaaacctgtc gtgccagctg cattaatgaa tcggccaacg    4740
cgcggggaga ggcggtttgc gtattgggcg ctcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgtga gcaaaaggcc agcaaaaggc    4920
caggaaccgt aaaaaggccg cgttgctggc gtttttccat aggctcggcc cccctgacga    4980
gcatcacaaa aatcgacgct caagtcagag gtggcgaaac ccgacaggac tataaagata    5040
ccaggcgttc cccctggaa gctccctcgt gcgctctcct gttccgaccc tgccgcttac    5100
cggatacctg tccgcctttc tcccttcggg aagcgtggcg ctttctcaat gctcacgctg    5160
taggtatctc agttcggtgt aggtcgttcg ctccaagctg ggctgtgtgc acgaacccc    5220 cgttcagccc gaccgctgcg ccttatccgg taactatcgt cttgagtcca acccggtaag    5280
acacgactta tcgccactgg cagcagccac tggtaacagg attagcagag cgaggtatgt    5340
aggcggtgct acagagttct tgaagtggtg gcctaactac ggctacacta aaggacagt    5400 atttggtatc tgcgctctgc tgaagccagt taccttcgga aaaagagttg gtagctcttg    5460
atccggcaaa caaccaccg ctggtagcgg tggtttttt gtttgcaagc agcagattac    5520
gcgcagaaaa aaaggatctc aagaagatcc tttgatcttt tctacggggt ctgacgctca    5580
gtggaacgaa aactcacgtt aagggatttt ggtcatgaga ttatcaaaaa ggatcttcac    5640
ctagatcctt ttaaattaaa aatgaagttt taaatcaatc taaagtatat atgagtaaac    5700
ttggtctgac agttaccaat gcttaatcag tgaggcacct atctcagcga tctgtctatt    5760
tcgttcatcc atagttgcct gactgcccgt cgtgtagata actacgatac gggagggctt    5820
accatctggc cccagtgctg caatgatacc gcgagaccca cgctcaccgg ctccagattt    5880
atcagcaata aaccagccag ccggaagggc cgagcgcaga agtggtcctg caactttatc    5940
cgcctccatc cagtctatta attgttgccg ggaagctaga gtaagtagtt cgccagttaa    6000
tagtttgcgc aacgttgttg ccattgctac aggcatcgtg gtgtcacgct cgtcgtttgg    6060
```

-continued

| | |
|---|---|
| tatggcttca ttcagctccg gttcccaacg atcaaggcga gttacatgat ccccccatgtt | 6120 |
| gtgaaaaaaa gcggttagct ccttcggtcc tccgatcgtt gtcagaagta agttggccgc | 6180 |
| agtgttatca ctcatggtta tggcagcact gcataattct cttactgtca tgccatccgt | 6240 |
| aagatgcttt tctgtgactg gtgagtactc aaccaagtca ttctgagaat agtgtatgcg | 6300 |
| gcgaccgagt tgctcttgcc cggcgtcaat acgggataat accgcgccac atagcagaac | 6360 |
| tttaaaagtg ctcatcattg gaaaacgttc ttcggggcga aaactctcaa ggatcttacc | 6420 |
| gctgttgaga tccagttcga tgtaacccac tcgtgcaccc aactgatctt cagcatcttt | 6480 |
| tactttcacc agcgtttctg ggtgagcaaa acaggaagg caaatgccg caaaaaggg | 6540 |
| aataagggcg acacggaaat gttgaatact catactcttc cttttttcaat attattgaag | 6600 |
| catttatcag ggttattgtc tcatgagcgg atacatattt gaatgtattt agaaaaataa | 6660 |
| acaaataggg gttccgcgca catttccccg aaaagtgcca cctgacgtct aagaaaccat | 6720 |
| tattatcatg acattaacct ataaaaatag gcgtatcacg aggcccttc gtc | 6773 |

<210> SEQ ID NO 22
<211> LENGTH: 7690
<212> TYPE: DNA
<213> ORGANISM: Artificial Sequence
<220> FEATURE:
<223> OTHER INFORMATION: Codon Optimized

<400> SEQUENCE: 22

| | |
|---|---|
| ttatcatgac attaacctat aaaaataggc gtatcacgag gccctttcgt ctcgcgcgtt | 60 |
| tcggtgatga cggtgaaaac tctgacaca tgcagctccc ggagacggtc acagcttgtc | 120 |
| tgtaagcgga tgccgggagc agacaagccc gtcaggcgc gtcagcgggt gttggcgggt | 180 |
| gtcgggctg gcttaactat gcggcatcag agcagattgt actgagagtg caccacgctt | 240 |
| ttcaattcaa ttcatcattt ttttttttatt ctttttttttg atttcggttt ctttgaaatt | 300 |
| tttttgattc ggtaatctcc gaacagaagg aagaacgaag gaaggagcac agacttagat | 360 |
| tggtatatat acgcatatgt agtgttgaag aaacatgaaa ttgcccagta ttcttaaccc | 420 |
| aactgcacag aacaaaaacc tgcaggaaac gaagataaat catgtcgaaa gctacatata | 480 |
| aggaacgtgc tgctactcat cctagtcctg ttgctgccaa gctatttaat atcatgcacg | 540 |
| aaaagcaaac aaacttgtgt gcttcattgg atgttcgtac caccaaggaa ttactggagt | 600 |
| tagttgaagc attaggtccc aaaatttgtt tactaaaaac acatgtggat atcttgactg | 660 |
| atttttccat ggagggcaca gttaagccgc taaaggcatt atccgccaag tacaatttt | 720 |
| tactcttcga agacagaaaa tttgctgaca ttggtaatac agtcaaattg cagtactctg | 780 |
| cgggtgtata cagaatagca gaatgggcag acattacgaa tgcacacggt gtggtgggcc | 840 |
| caggtattgt tagcggtttg aagcaggcgg cagaagaagt aacaaaggaa cctagaggcc | 900 |
| ttttgatgtt agcagaattg tcatgcaagg gctccctatc tactggagaa tatactaagg | 960 |
| gtactgttga cattgcgaag agcgacaaag attttgttat cggctttatt gctcaaagag | 1020 |
| acatgggtgg aagagatgaa ggttacgatt ggttgattat gacacccggt gtgggtttag | 1080 |
| atgacaaggg agacgcattg ggtcaacagt atagaaccgt ggatgatgtg gtctctacag | 1140 |
| gatctgacat tattattgtt ggaagaggac tatttgcaaa gggaagggat gctaaggtag | 1200 |
| agggtgaacg ttacagaaaa gcaggctggg aagcatattt gagaagatgc ggccagcaaa | 1260 |
| actaaaaaac tgtattataa gtaaatgcat gtatactaaa ctcacaaatt agagcttcaa | 1320 |

```
tttaattata tcagttatta ccctgcggtg tgaaataccg cacagatgcg taaggagaaa   1380
ataccgcatc aggaaattgt aaacgttaat attttgttaa aattcgcgtt aaattttttgt  1440 taaatcagct cattttttaa ccaataggcc gaaatcggca aaatccctta taaatcaaaa   1500
gaatagaccg atatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga agggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta caaccatag    2280 gatgataatg cgattagttt tttagcctta tttctggggt aattaatcag cgaagcgatg   2340 attttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa accccggat tctagaacta   2520 gtggatcccc catcatggtt tccaatcact tgtttgacgc aatgagagcc gctgcccctg   2580
gtaacgcccc tttcataaga atagataata ctagaacttg acatacgat gacgcctttg    2640 cttatctgg tagaatagca tcagctatgg atgctttggg tatcagacca ggtgacagag    2700
tcgcagttca agtagaaaaa tccgctgaag cattgatctt gtatttggct tgtttgagaa   2760
gtggtgcagt ttatttgcca ttgaatactg cctacacatt agctgaattg gattacttca   2820
taggtgacgc agaacctaga ttggttgtag tcgcctcttc agccagagct ggtgtagaaa   2880
caattgctaa accaagagt gcaatagtcg aaaccttaga tgctgctggt tctggtagtt    2940
tgttagattt ggccagagac gaacctgctg attttgttga cgcttcaaga tcagccgatg   3000
acttagccgc tattttgtac acctctggta ctacaggtag atcaaagggt gctatgttga   3060
ctcatggtaa tttgttgtca aacgcattaa ccttgagaga tttctggaga gttactgccg   3120
gtgacagatt aatccacgct tgccaatttt tcatactca cggtttattc gttgctacca   3180
acgtaacttt gttagcaggt gcctccatgt tcttgttgag taagttcgat ccagaagaaa   3240
tattatcttt gatgcctcaa gctactatgt tgatgggtgt cccaacattc tacgttagat   3300
tgttacaatc acctagatta gataagcaag ctgttgcaaa catcagattg tttatatccg   3360
gtagtgctcc attgttagca gaaacccata ctgaatttca agcaagaaca ggtcacgcca   3420
ttttagaaag atacggtatg acagaaacca atatgaacac ttctaaccct tatgaaggta   3480
aaagaatagc tggtacagtt ggttttccat tgcctgatgt cacagttaga gtaaccgacc   3540
cagccactgg tttagctttg ccacctgaac aaactggtat gatcgaaatt aaaggtccaa   3600 acgttttaa gggttactgg agaatgcctg aaaagactgc tgctgagttt actgctgatg    3660
gtttctttat ctctggtgac ttaggtaaaa ttgatagaga cggttatgtc catattgttg   3720
```

```
gtcgtggtaa agatttggtt atatccggtg gttataacat ctaccctaag gaagtagaag    3780
gtgaaataga tcaaatcgaa ggtgttgtag aatcagctgt aataggtgtc ccacatcctg    3840
attttggtga aggtgttaca gcagtcgttg taagaaaacc aggtgctgca ttagatgaaa    3900
aggcaattgt ttctgcctta caagacagat tggctagata caagcaacca aagagaataa    3960
tcttcgcaga agatttgcct agaaatacta tgggtaaagt acaaaagaac atcttgagac    4020
aacaatacgc cgacttatac accagaaccg aaggtagagg ttctttgtta acatgtggtg    4080
acgttgaaga aaatccaggt cctatggctt cagaaaagga aataagaaga gaaagattct    4140
tgaacgtatt cccaaagtta gttgaagaat tgaacgctag tttgttagct tatggtatgc    4200
ctaaagaagc ctgcgattgg tatgctcact ctttaaacta caatactcca ggtggtaaat    4260
tgaatagagg tttgagtgta gttgatactt atgctatctt gtctaacaaa accgttgaac    4320
aattaggtca agaagaatac gaaaaggtcg ctatcttggg ttggtgtatt gaattgttgc    4380
aagcatactt tttggttgcc gatgacatga tggataagtc tataacaaga agaggtcaac    4440
catgctggta caaagttcca gaagttggtg aaatagccat aaatgatgct tttatgttgg    4500
aagccgctat ctataaattg ttgaagtcac atttcagaaa cgaaaagtac tacatcgata    4560
ttaccgaatt attccacgaa gttactttcc aaacagaatt gggtcaattg atggatttga    4620
taactgcacc tgaagataaa gttgacttgt caaagttttc cttgaagaaa cattcattca    4680
tcgtcacctt tgaaactgct tattactcct tctatttgcc agtcgccttg gctatgtacg    4740
tagctggtat tactgatgaa aaagacttga agcaagcaag agatgttttg atacctttgg    4800
gtgaatactt ccaaatccaa gatgactact agactgtttt cggtactcca gaacaaatag    4860
gtaaaatcgg tacagatatt caagacaata agtgcagttg ggttattaac aaggctttgg    4920
aattagcatc tgccgaacaa agaaagactt tggatgaaaa ctacggtaaa aaggactcag    4980
ttgctgaagc aaagtgtaag aaaatttta atgatttgaa gattgaacaa ttgtaccatg    5040
aatacgaaga atccatcgct aaagacttaa aggcaaagat tagtcaagtt gatgaatcaa    5100
gaggtttaa agccgacgtt ttgacagctt tcttgaataa ggtctacaag agatcaaagt    5160
gatgggctgc aggaattcga tatcaagctt atcgataccg tcgacctcga gtcatgtaat    5220
tagttatgtc acgcttacat tcacgccctc cccccacatc cgctctaacc gaaaaggaag    5280
gagttagaca acctgaagtc taggtcccta tttattttt tatagttatg ttagtattaa    5340
gaacgttatt tatatttcaa attttttctt tttttctgta cagacgcgtg tacgcatgta    5400
acattatact gaaaaccttg cttgagaagg ttttgggacg ctcgaaggct ttaatttgcg    5460
gccggtaccc agcttttgtt ccctttagtg agggttaatt ccgagcttgg cgtaatcatg    5520
gtcatagctg tttcctgtgt gaaattgtta tccgctcaca attccacaca ataggagc    5580
cggaagcata aagtgtaaag cctggggtgc ctaatgagtg aggtaactca cattaattgc    5640
gttgcgctca ctgcccgctt tccagtcggg aaacctgtcg tgccagctgc attaatgaat    5700
cggccaacgc gcggggagag gcggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat cagggggataa cgcaggaaaa acatgtgag caaaaggcca    5880
gcaaaaggcc aggaaccgta aaaaggccgc gttgctggcg tttttccata ggctccgccc    5940
ccctgacgag catcacaaaa atcgacgctc aagtcagagg tggcgaaacc cgacaggact    6000
ataaagatac caggcgttcc cccctggaag ctccctcgtg cgctctcctg ttccgaccct    6060
```

```
gccgcttacc ggatacctgt ccgcctttct cccttcggga agcgtggcgc tttctcaatg    6120
ctcacgctgt aggtatctca gttcggtgta ggtcgttcgc tccaagctgg gctgtgtgca    6180
cgaaccccc gttcagcccg accgctgcgc cttatccggt aactatcgtc ttgagtccaa     6240
cccggtaaga cacgacttat cgccactggc agcagccact ggtaacagga ttagcagagc    6300
gaggtatgta ggcggtgcta cagagttctt gaagtggtgg cctaactacg gctacactag    6360
aaggacagta tttggtatct gcgctctgct gaagccagtt accttcggaa aaagagttgg    6420
tagctcttga tccggcaaac aaaccaccgc tggtagcggt ggttttttg tttgcaagca     6480
gcagattacg cgcagaaaaa aaggatctca agaagatcct ttgatcttt ctacggggtc     6540
tgacgctcag tggaacgaaa actcacgtta agggattttg gtcatgagat tatcaaaaag   6600
gatcttcacc tagatccttt taaattaaaa atgaagtttt aaatcaatct aaagtatata    6660
tgagtaaact tggtctgaca gttaccaatg cttaatcagt gaggcaccta tctcagcgat    6720
ctgtctattt cgttcatcca tagttgcctg actgcccgtc gtgtagataa ctacgatacg    6780
ggagggctta ccatctggcc ccagtgctgc aatgataccg cgagacccac gctcaccggc    6840
tccagattta tcagcaataa accagccagc cggaagggcc gagcgcagaa gtggtcctgc    6900
aactttatcc gcctccatcc agtctattaa ttgttgccgg gaagctagag taagtagttc    6960
gccagttaat agtttgcgca acgttgttgc cattgctaca ggcatcgtgg tgtcacgctc    7020
gtcgtttggt atggcttcat tcagctccgg ttcccaacga tcaaggcgag ttacatgatc    7080
ccccatgttg tgaaaaaaag cggttagctc cttcggtcct ccgatcgttg tcagaagtaa    7140
gttggccgca gtgttatcac tcatggttat ggcagcactg cataattctc ttactgtcat    7200
gccatccgta agatgctttt ctgtgactgg tgagtactca accaagtcat tctgagaata    7260
gtgtatgcgg cgaccgagtt gctcttgccc ggcgtcaata cgggataata ccgcgccaca    7320
tagcagaact ttaaaagtgc tcatcattgg aaaacgttct cggggcgaaa actctcaag    7380
gatcttaccg ctgttgagat ccagttcgat gtaacccact cgtgcaccca actgatcttc    7440
agcatctttt actttcacca gcgtttctgg gtgagcaaaa acaggaaggc aaaatgccgc    7500
aaaaaaggga ataagggcga cacggaaatg ttgaatactc atactcttcc ttttcaata    7560
ttattgaagc atttatcagg gttattgtct catgagcgga tacatatttg aatgtattta    7620
gaaaaataaa caaatagggg ttccgcgcac atttccccga aagtgccac ctgacgtcta     7680
agaaaccatt                                                           7690

<210> SEQ ID NO 23
<211> LENGTH: 2163
<212> TYPE: DNA
<213> ORGANISM: Artificial Sequence
<220> FEATURE:
<223> OTHER INFORMATION: Codon Optimized

<400> SEQUENCE: 23
atgggtaaaa actataagtc cttggattca gtcgttgcct cagatttcat cgcattgggt      60
atcacctcag aagtagcaga acattacat ggtagattgg cagaaatcgt ttgtaattat      120
ggtgctgcaa cccctcaaac ttggatcaac atcgctaacc atatcttgtc accagatttg    180
cctttctcct tacaccaaat gttgttttat ggttgctaca aggatttcgg tccagcccca   240
cctgcttgga ttccagaccc tgaaaaagtc aagtcaacta atttgggtgc tttgttggaa    300
aagagaggta agaatttttt gggtgtaaag tacaaagatc caatttcttc ttttttctcac   360
ttccaagaat tttctgttag aaaccctgaa gtctattgga gaacagtatt gatggatgaa    420
```

```
atgaaaatta gtttctctaa ggacccagaa tgtatcttga aaagagatga catcaacaac    480
ccaggtggtt ctgaatggtt acctggtggt tacttgaact cagctaaaaa ttgcttgaac    540
gtaaactcca ataagaaatt gaacgatact atgatcgttt ggagagacga gggtaacgat    600
gacttgcctt tgaataagtt gacattagat caattgagaa agagagtttg gttggttggt    660
tatgcattgg aagaaatggg tttagaaaaa ggttgtgcaa tagccatcga tatgccaatg    720
catgttgatg ctgttgttat atatttggcc atagtattgg ctggttacgt agttgtctct    780
atagcagatt catttccgc ccctgaaatc tcaactagat tgagattatc caaagctaag    840
gcaattttca cacaagatca catcatcaga ggtaaaaaga gaataccatt gtattcaaga    900
gtagttgaag ctaaatcccc aatggcaata gttatccctt gtagtggttc taacattggt    960
gcagaattga gagatggtga catatcttgg gattacttt tagaaagagc caaggagttt    1020
aaaaactgcg agtttactgc cagagaacaa cctgttgatg cttatactaa catcttattc    1080
tccagtggta ctacaggtga accaaaagca attccttgga cacaagccac cccattgaag    1140
gctgctgctg atggttggtc tcatttggat attagaaaag gtgacgttat agtatggcca    1200
actaatttgg gttggatgat gggtccttgg ttggtttatg ctagtttgtt aaatggtgca    1260
tctattgcct tgtacaacgg tagtccttta gtctctggtt tcgctaaatt tgttcaagat    1320
gcaaaggtca caatgttggg tgtcgtacca tctattgtaa gatcatggaa atccacaaat    1380 tgtgttcag gttacgattg gtccaccata agatgctttt cttcatccgg tgaagcctct    1440
aatgtagacg aatatttgtg gttaatgggt agagctaact acaagccagt tatagaaatg    1500
tgtggtggta cagaaatcgg tggtgctttt tctgctggtt cattttttgca agctcaatct    1560 ttaagttctt tttcatccca atgtatgggt tgcaccttgt acatattaga taagaacggt    1620
tacccaatgc ctaaaaataa gccaggtatc ggtgaattgg cattaggtcc tgttatgttt    1680
ggtgcctcaa aaacattgtt aaacggtaat catcacgatg tctatttcaa gggtatgcca    1740
accttgaatg gtgaagtatt gagaagacat ggtgacattt cgaattgac ctctaacggt    1800 tactaccatg cacacggtag agccgatgac actatgaaca tcggtggtat caaaattagt    1860
tctatcgaaa tcgaaagagt ctgtaatgaa gtagatgaca gagttttga aaccactgct    1920 attggtgttc caccttgg gtggtggtcca gaacaattgg tcatatttt cgtattgaag    1980 gattcaaacg acacaaccat tgatttgaac caattgagat tatcctttaa cttgggtttg    2040
caaaagaaat tgaaccccatt attcaaagtt actagagttg tcccattgtc atccttacct    2100
agaactgcaa caaacaagat catgagaaga gttttgagac aacaattcag tcatttcgaa    2160
tga                                                                 2163
```

<210> SEQ ID NO 24
<211> LENGTH: 1059
<212> TYPE: DNA
<213> ORGANISM: Artificial Sequence
<220> FEATURE:
<223> OTHER INFORMATION: Codon Optimized

<400> SEQUENCE: 24

```
atggcttcag aaaaggaaat aagaagagaa agattcttga acgtattccc aaagttagtt     60
gaagaattga acgctagttt gttagcttat ggtatgccta agaagcctg cgattggtat    120 gctcactctt taaactacaa tactccaggt ggtaaattga atagaggttt gagtgtagtt    180
gatacttatg ctatccttgtc taacaaaacc gttgaacaat taggtcaaga agaatacgaa    240
```

| | |
|---|---:|
| aaggtcgcta tcttgggttg gtgtattgaa ttgttgcaag catactttt ggttgccgat | 300 |
| gacatgatgg ataagtctat aacaagaaga ggtcaaccat gctggtacaa agttccagaa | 360 |
| gttggtgaaa tagccataaa tgatgctttt atgttggaag ccgctatcta taaattgttg | 420 |
| aagtcacatt tcagaaacga aaagtactac atcgatatta ccgaattatt ccacgaagtt | 480 |
| actttccaaa cagaattggg tcaattgatg gatttgataa ctgcacctga agataaagtt | 540 |
| gacttgtcaa agttttcctt gaagaaacat tcattcatcg tcacctttga aactgcttat | 600 |
| tactccttct atttgccagt cgccttggct atgtacgtag ctggtattac tgatgaaaaa | 660 |
| gacttgaagc aagcaagaga tgttttgata cctttgggtg aatacttcca aatccaagat | 720 |
| gactacttag actgtttcgg tactccagaa caaataggta aaatcggtac agatattcaa | 780 |
| gacaataagt gcagttgggt tattaacaag gctttggaat tagcatctgc cgaacaaaga | 840 |
| aagactttgg atgaaaacta cggtaaaaag gactcagttg ctgaagcaaa gtgtaagaaa | 900 |
| attttaatg atttgaagat tgaacaattg taccatgaat acgaagaatc catcgctaaa | 960 |
| gacttaaagg caaagattag tcaagttgat gaatcaagag ttttaaagc cgacgttttg | 1020 |
| acagctttct tgaataaggt ctacaagaga tcaaagtag | 1059 |

<210> SEQ ID NO 25
<211> LENGTH: 1158
<212> TYPE: DNA
<213> ORGANISM: Artificial Sequence
<220> FEATURE:
<223> OTHER INFORMATION: Codon Optimized

<400> SEQUENCE: 25

| | |
|---|---:|
| atgaaccatt tgagagccga aggtcctgcc tccgtattag ccataggtac agccaaccca | 60 |
| gaaaacatat tgatccaaga tgaatttcct gattattact tcagagttac caagagtgaa | 120 |
| cacatgactc aattgaagga aaagtttaga aaaatatgtg ataagtctat gatcagaaag | 180 |
| agaaactgct tcttgaacga agaacatttg aagcaaaatc caagattggt agaacacgaa | 240 |
| atgcaaacat tggatgccag acaagacatg ttagttgtcg aagttcctaa attgggtaaa | 300 |
| gatgcttgtg caaaagccat taaggaatgg ggtcaaccaa agtcaaagat cactcatttg | 360 |
| attttacaa gtgcatctac tacagatatg cctggtgcag actaccactg tgccaaattg | 420 |
| ttaggttttgt caccatccgt taagagagtc atgatgtatc aattaggttg ctacggtggt | 480 |
| ggtactgttt tgagaatcgc taaggatatt gcagaaaaca caagggtgc cagagtatta | 540 |
| gctgtttgtt gcgacattat ggcttgcttg tttagaggtc aagtgattc tgacttggaa | 600 |
| ttgttagttg gtcaagctat cttcggtgac ggtgctgctg ctgttattgt tggtgcagaa | 660 |
| cctgacgaat ctgttggtga agaccaata tttgaattag tcagtacagg tcaaaccatc | 720 |
| ttgcctaatt ctgaaggtac aattggtggt catataagag aagcaggttt gatcttcgat | 780 |
| ttgcacaaag acgttccaat gttaatctct aacaacatag aaaagtgttt gatagaagca | 840 |
| ttcactccta taggtatctc agattggaac tctattttct ggataacaca tccaggtggt | 900 |
| aaagccattt tggataaggt tgaagaaaaa ttggatttga agaaagaaaa gtttgtagat | 960 |
| agtagacatg tttatctga acacggtaac atgtcttcat ccactgtctt gttcgtaatg | 1020 |
| gatgaattga gaaagagatc attagaagag ggtaaatcta ctactggtga cggttttgaa | 1080 |
| tggggtgtct tatttggttt cggtcctggt ttgaccgtcg aaagagtagt tgtcagatca | 1140 |
| gtaccaatta aatattag | 1158 |

<210> SEQ ID NO 26
<211> LENGTH: 315
<212> TYPE: DNA
<213> ORGANISM: Artificial Sequence
<220> FEATURE:
<223> OTHER INFORMATION: Codon Optimized

<400> SEQUENCE: 26

```
atggccgtca agcatttgat agtattgaag tttaaagatg aaatcacaga agctcaaaag      60
gaagaatttt tcaagaccta cgttaatttg gtcaacatta tacctgctat gaaagatgta     120
tactggggta agacgttac acaaaagaaa gaagaaggtt atacacacat tgtcgaagta     180
accttcgaat cagttgaaac tatccaagat tacatcattc atccagctca cgttggtttt     240
ggtgacgttt acagatcctt ctgggaaaaa ttgttgatct tcgattacac cccaagaaag     300
ttaaagccaa aataa                                                      315
```

<210> SEQ ID NO 27
<211> LENGTH: 1188
<212> TYPE: DNA
<213> ORGANISM: Artificial Sequence
<220> FEATURE:
<223> OTHER INFORMATION: Codon Optimized

<400> SEQUENCE: 27

```
atgggtttat catccgtctg tactttctcc ttccaaacta actatcatac cttattgaat      60
cctcacaaca caatccaaa acatcattg ttgtgttaca gacatccaaa gacacctatt      120
aagtactctt acaacaactt tccatcaaaa cattgttcaa ccaagtcctt ccacttacaa     180
aataagtgct ccgaaagttt gtctatagct aagaactcta tcagagctgc aactacaaat     240
caaactgaac cacctgaaag tgataatcac tctgttgcca caaaattttt gaacttcggt     300
aaagcatgtt ggaagttgca aagaccatac accataatcg cttttacttc ttgtgcatgc     360
ggtttattcg gtaaagaatt gttgcataac actaacttaa tttcatggtc cttgatgttc     420
aaggcatttt tcttttttagt tgccatcttg tgcatcgctt cattcaccac tacaattaat     480
caaatatacg atttgcacat cgacagaatt aacaaaccag atttgccttt ggcttcaggt     540
gaaatatccg tcaatactgc atggatcatg tctatcatag tagccttgtt cggtttgatc     600
atcacaatta aaatgaaggg tggtccattg tacatcttcg ttactgtttt cggtatcttc     660
ggtggtattg tctattccgt accaccttt agatggaaac aaaaccctag tactgccttt     720
ttgttgaatt tcttagctca tatcatcaca aacttcacct tctactacgc ttcaagagct     780
gctttaggtt tgccattcga attgagacct tcattccat ttttgttggc attcatgaaa     840
agtatgggtt ctgcattagc cttgatcaag gatgcctctg acgttgaagg tgacacaaag     900
ttcggtatta gtaccttggc ttctaagtac ggttcaagaa atttgacttt gttctgctcc     960
ggtatcgttt tgttaagtta cgtcgcagcc attttggcag gtatcatttg ccacaagcc    1020
tttaattcta cgttatgtt gttgtcacat gccatcttgg ctttctggtt gatcttgcaa    1080
actagagatt tcgctttgac aaattatgac cctgaagcag gtagaagatt ctacgagttt    1140
atgtggaaat tgtactacgc tgaatatttg gtatacgttt ttatttag                 1188
```

<210> SEQ ID NO 28
<211> LENGTH: 1635
<212> TYPE: DNA
<213> ORGANISM: Artificial Sequence
<220> FEATURE:
<223> OTHER INFORMATION: Codon Optimized

<400> SEQUENCE: 28

```
atgaaatgtt caactttctc cttttggttc gtatgcaaga tcatcttctt tttcttttcc      60
tttaacatcc aaacaagtat cgcaaaccca agagaaaact ttttgaagtg cttctcacaa     120
tacataccta ataacgccac caatttgaag ttggtttaca ctcaaaacaa cccattgtac     180
atgtccgtct tgaacagtac aatccataat ttgagattca cttctgatac cactccaaaa     240
cctttggtca ttgtaacccc tagtcatgta tctcacatcc aaggtactat cttatgttct     300
aaaaaggttg gtttgcaaat tagaactaga tccggtggtc atgatagtga aggcatgtca     360
tacatctccc aagttccatt cgttatcgtt gatttgagaa acatgagatc aattaaaata     420
gacgtacact cacaaactgc ttgggttgaa gctggtgcaa cattgggtga agtatactac     480
tgggttaacg aaaagaatga aaacttatca ttggctgctg ttactgtcc aacagtttgc      540
gcaggtggtc attttggtgg tggtggttat ggtcctttaa tgagaaacta cggtttggcc     600
gctgataaca taatcgacgc tcatttggta aatgttcacg gtaaagtttt ggatagaaag     660
tctatgggtg aagacttatt tgggctttg agaggtggtg gtgcagaatc attcggtatc     720
atagttgctt ggaagataag attagtcgca gtaccaaagt ctactatgtt ctcagtcaaa     780
aagataatgg aaatccatga attagttaaa ttggtcaata agtggcaaaa catcgcatac     840
aagtacgata aggacttgtt gttgatgact catttcatca aagaaacat caccgataac      900
caaggtaaaa ataagactgc tatccacaca tactttctt cagttttctt gggtggtgtc      960
gattccttag tagacttgat gaataagtct tttccagaat taggtattaa gaaaactgat    1020
tgtagacaat tgtcttggat cgacaccatc atcttttatt caggtgttgt caactacgat    1080
acagacaact tcaacaaaga atattattg gatagatccg caggtcaaaa cggtgccttt    1140
aaaattaagt tagactacgt taaaaagcca atacctgaat cagttttcgt ccaaatctta    1200
gaaaaattgt acgaagaaga tattggtgca ggcatgtacg ccttgtatcc atacggtggt    1260
ataatggacg aaatcagtga atctgccatt ccatttcctc atagagctgg tatcttatac    1320
gaattgtggt acatttgttc atgggaaaag caagaagata cgaaaagca cttaaactgg    1380
attagaaaca tctataactt catgactcca tacgtttcta aaaaccctag attggcatat    1440
ttgaactaca gagatttgga catcggtatt aacgatccaa agaatcctaa caactatacc    1500
caagctagaa tttgggtga aaaatacttc ggtaaaaatt tcgatagatt agtaaaggtt    1560
aagacattgg ttgacccaaa caacttcttt agaaacgaac aatccattcc acctttacct    1620
agacatagac actga                                                    1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon Optimized

<400> SEQUENCE: 29

```
atgaactgct ccgcattctc tttctggttc gtctgtaaaa taatcttctt cttcttgtcc      60
ttcaacatcc aaatctccat cgcaaatcca caagaaaact ttttgaagtg tttctccgaa     120
tacatcccaa acaaccctgc taacccaaag tttatatata ctcaacatga tcaattgtac     180
atgtccgttt tgaacagtac catccaaaat ttgagattca cttctgacac tacaccaaaa     240
cctttagtca ttgttacacc ttccaatgtt agtcacattc aagcttctat attgtgctct     300
aagaaagtag gtttgcaaat cagaactaga tcaggtggtc atgatgcaga aggcatgtct     360
```

```
tacatctcac aagttccatt cgttgtagtc gatttgagaa atatgcattc cataaagatc    420
gacgttcaca gtcaaacagc atgggtagaa gcaggtgcca ccttgggtga agtttactac    480
tggatcaacg aaaagaatga aaactttcct ttccctggtg gttactgtcc aacagtaggt    540
gtcggtggtc acttttctgg tggtggttat ggtgcattga tgagaaacta cggtttagct    600
gcagataata ttatagacgc ccatttggtt aacgtagatg gtaaagtttt ggacagaaag    660
tctatgggtg aagatttgtt ttgggccata agaggtggtg gtggtgaaaa tttcggtatc    720
attgccgctt ggaaaattaa gttagtcgct gttccttcca aaagtactat tttctctgtc    780
aaaaagaaca tggaaatcca cggtttggtt aagttgttta ataagtggca aaacatcgct    840
tacaagtacg ataaggactt ggttttgatg acccatttca tcactaaaaa tattacagat    900
aaccatggta aaaataagac cactgttcac ggttattttt cttcaatttt ccatggtggt    960
gtagattctt tggttgattt gatgaataag tcattcccag aattgggtat taaaaagaca   1020
gattgcaagg aattttcttg gatagacaca accatcttct attcaggtgt tgtaaacttc   1080
aacaccgcta acttcaaaaa ggaaatcttg ttggatagat ccgctggtaa aaagaccgct   1140
ttttctatta aattggacta cgttaagaaa ccaatccctg aaactgcaat ggtcaagata   1200
ttggaaaagt tgtacgaaga agatgtaggt gtcggcatgt acgttttgta tccatacggt   1260
ggtattatgg aagaaatatc tgaatcagcc ataccatttc ctcacagagc tggtatcatg   1320
tatgaattat ggtacacagc ctcatgggaa aagcaagaag ataacgaaaa gcatatcaac   1380
tgggtcagat ccgtttacaa cttcactaca ccttacgtta gtcaaaaccc aagattggca   1440
tatttgaact acagagattt ggacttaggt aaaactaacc ctgaatctcc aaataactat   1500
acacaagcaa gaatttgggg tgaaaagtac tttggtaaaa atttcaacag attagttaaa   1560
gtaaagacta agccgaccc taacaacttt ttcagaaacg aacaatccat cccacctttg   1620
ccacctcacc accactaa                                                 1638
```

<210> SEQ ID NO 30
<211> LENGTH: 960
<212> TYPE: DNA
<213> ORGANISM: Artificial Sequence
<220> FEATURE:
<223> OTHER INFORMATION: Codon Optimized

<400> SEQUENCE: 30

```
atggctaatc aaacagaacc tccagaatct aatacgaaat atagtgtagt taccaaaatc     60
ctaagttttg gccacacttg ttggaaattg cagagaccgt atactttcat tggagtgatt    120
agttgcgcct gtggattgtt cggtagagag ttattccata atactaattt gctatcatgg    180
tctctgatgt tgaaagcttt cagctcattg atggtaatac tgtcagtgaa tctatgtacc    240
aatatcataa accagatcac tgacctggac atagacagaa tcaataagcc ggacttgcca    300
ttggcgagcg gggaaatgtc cattgaaaca gcatggatta tgagtattat agttgcacta    360
actggattga tacttacgat aaagcttaat tgcggcccctt tgtttatatc tctatattgt    420
gtcagcatac tagtcggggc actatattca gtaccgccat tcagatggaa gcaaaatccc    480
aataccgcat tctcaagtta ttttatggga ctggtgatcg tcaattttac ctgctattac    540
gcaagcaggg ccgccttgg actgccattc gagatgtcac ccccgttcac attcattctt    600
gcctttgtca gtcaatggg tagcgcactt ttttgtgta agatgtctc tgacattgaa    660 ggagattcta agcacggtat atctaccctt gcgacgaggt atggagcaaa aaacattact    720
```

```
ttcctttgct caggaatcgt actgctaacc tacgtaagcg cgatattggc tgcgattatt      780
tggccacaag ccttcaagtc caacgtgatg ctgttgagtc acgcaaccct ggccttttgg      840
cttatctttc agactagaga gttcgcgtta actaattaca atccagaggc agggaggaag      900
ttttacgagt tcatgtggaa gctgcactac gctgaatact tagtctatgt atttatatag      960
```

<210> SEQ ID NO 31
<211> LENGTH: 960
<212> TYPE: DNA
<213> ORGANISM: Artificial Sequence
<220> FEATURE:
<223> OTHER INFORMATION: Codon Optimized

<400> SEQUENCE: 31

```
atggctaatc aaacagaacc tccagaatct aatacgaaat atagtgtagt taccaaaatc       60
ctaagttttg gccacacttg ttggaaattg cagagaccgt atactttcat tggagtgatt      120
agttgcgcct gtggattgtt cggtagagag ttattccata atactaattt gctatcatgg      180
tctctgatgt tgaaagcttt cagctcattg atggtaatac tgtcagtgaa tctatgtacc      240
aatatcataa accagatcac tgacctggac atagacagaa tcaataagcc ggacttgcca      300
ttggcgagcg ggaaatgtcc attgaaaca gcatggatta tgagtattat agttgcacta      360
actggattga tacttacgat aaagcttaat tgcggccctt tgtttatatc tctatattgt      420
gtcagcatac tagtcggggc actatattca gtaccgccat tcagatggaa gcaaaatccc      480
aataccgcat tctcaagtta ttttatggga ctggtgatcg tcaattttac ctgctattac      540
gcaagcaggg ccgcctttgg actgccattc gagatgtcac cccgttcac attcattctt       600 gcctttgtca agtcaatggg tagcgcactt ttttgtgta agatgtctc tgacattgaa        660 ggagattcta agcacggtat atctaccctt gcgacgagg atggagcaaa aacattact       720 ttcctttgct caggaatcgt actgctaacc tacgtaagcg cgatattggc tgcgattatt      780
tggccacaag ccttcaagtc caacgtgatg ctgttgagtc acgcaaccct ggccttttgg      840
cttatctttc agactagaga gttcgcgtta actaattaca atccagaggc agggaggaag      900
ttttacgagt tcatgtggaa gctgcactac gctgaatact tagtctatgt atttatatag      960
```

<210> SEQ ID NO 32
<211> LENGTH: 1023
<212> TYPE: DNA
<213> ORGANISM: Artificial Sequence
<220> FEATURE:
<223> OTHER INFORMATION: Codon Optimized

<400> SEQUENCE: 32

```
atgagattcc catctatttt cactgctgtt ttgttcgctg cttcttctgc tttggctgct       60
ccagttgcta atcaaacaga acctccagaa tctaatacga aatatagtgt agttaccaaa      120
atcctaagtt ttggccacac ttgttggaaa ttgcagagac cgtatacttt cattggagtg      180
attagttgcg cctgtggatt gttcggtaga gagttattcc ataatactaa tttgctatca      240
tggtctctga tgttgaaagc tttcagctca ttgatggtaa tactgtcagt gaatctatgt      300
accaatatca taaaccagat cactgacctg gacatagaca gaatcaataa gccggacttg      360
ccattggcga gcggggaaat gtccattgaa acagcatgga ttatgagtat tatagttgca      420
ctaactggat tgatacttac gataaagctt aattgcggcc ctttgtttat atctctatat      480
tgtgtcagca tactagtcgg ggcactatat tcagtaccgc cattcagatg gaagcaaaat      540
cccaataccg cattctcaag ttattttatg ggactggtga tcgtcaattt tacctgctat      600
```

```
tacgcaagca gggccgcctt tggactgcca ttcgagatgt cacccccgtt cacattcatt      660
cttgcctttg tcaagtcaat gggtagcgca cttttttttgt gtaaagatgt ctctgacatt      720
gaaggagatt ctaagcacgg tatatctacc cttgcgacga ggtatggagc aaaaaacatt      780
actttccttt gctcaggaat cgtactgcta acctacgtaa cgcgatatt ggctgcgatt      840 atttggccac aagccttcaa gtccaacgtg atgctgttga gtcacgcaac cctggccttt      900
tggcttatct ttcagactag agagttcgcg ttaactaatt acaatccaga ggcagggagg      960
aagttttacg agttcatgtg gaagctgcac tacgctgaat acttagtcta tgtatttata     1020
tag                                                                    1023

<210> SEQ ID NO 33
<211> LENGTH: 6025
<212> TYPE: DNA
<213> ORGANISM: Artificial Sequence
<220> FEATURE:
<223> OTHER INFORMATION: Codon Optimized

<400> SEQUENCE: 33
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accacgcttt tcaattcaat tcatcatttt ttttttattc tttttttttga tttcggtttc      240 tttgaaattt ttttgattcg gtaatctccg aacagaagga agaacgaagg aaggagcaca      300
gacttagatt ggtatatata cgcatatgta gtgttgaaga acatgaaat tgcccagtat      360 tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttttccatg gagggcacag ttaagccgct aaaggcatta tccgccaagt      660
acaatttttt actcttcgaa gacagaaaat ttgctgacat tggtaataca gtcaaattgc      720
agtactctgc gggtgtatac agaatagcag aatgggcaga cattacgaat gcacacggtg      780
tggtgggccc aggtattgtt agcggttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggcttttattg      960 ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg gaagaggact atttgcaaag ggaagggatg     1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta acgttaata ttttgttaaa attcgcgtta     1380
aatttttgtt aaatcagctc attttttaac caataggccg aaatcggcaa atcccttat      1440 aaatcaaaag aatagaccga gatagggttg agtgttgttc cagtttggaa caagagtcca     1500
ctattaaaga acgtggactc caacgtcaaa gggcgaaaaa ccgtctatca gggcgatggc     1560
```

```
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggcta atcaaacaga acctccagaa tctaatacga   2520
aatatagtgt agttaccaaa atcctaagtt ttggccacac ttgttggaaa ttgcagagac   2580
cgtatacttt cattggagtg attagttgcg cctgtggatt gttcggtaga gagttattcc   2640
ataatactaa tttgctatca tggtctctga tgttgaaagc tttcagctca ttgatggtaa   2700
tactgtcagt gaatctatgt accaatatca taaaccagat cactgacctg gacatagaca   2760
gaatcaataa gccggacttg ccattggcga gcggggaaat gtccattgaa acagcatgga   2820
ttatgagtat tatagttgca ctaactggat tgatacttac gataaagctt aattgcggcc   2880
ctttgtttat atctctatat tgtgtcagca tactagtcgg ggcactatat tcagtaccgc   2940
cattcagatg gaagcaaaat cccaataccg cattctcaag ttatttatg ggactggtga   3000 tcgtcaattt tacctgctat tacgcaagca gggccgcctt tggactgcca ttcgagatgt   3060
cacccccgtt cacattcatt cttgcctttg tcaagtcaat gggtagcgca ctttttttgt   3120
gtaaagatgt ctctgacatt gaaggagatt ctaagcacgg tatatctacc cttgcgacga   3180
ggtatggagc aaaaaacatt actttccttt gctcaggaat cgtactgcta acctacgtaa   3240
gcgcgatatt ggctgcgatt atttggccac aagccttcaa gtccaacgtg atgctgttga   3300
gtcacgcaac cctggccttt tggcttatct ttcagactag agagttcgcg ttaactaatt   3360
acaatccaga ggcagggagg aagttttacg agttcatgtg gaagctgcac tacgctgaat   3420
acttagtcta tgtatttata taggatgggc tgcaggaatt cgatatcaag cttatcgata   3480
ccgtcgacct cgagtcatgt aattagttat gtcacgctta cattcacgcc ctccccccac   3540
atccgctcta accgaaaagg aaggagttag acaacctgaa gtctaggtcc ctatttattt   3600
ttttatagtt atgttagtat taagaacgtt atttatattt caaattttc ttttttttct   3660 gtacagacgc gtgtacgcat gtaacattat actgaaaacc ttgcttgaga aggttttggg   3720
acgctcgaag gctttaattt gcggccggta cccagctttt gttcccttta gtgagggtta   3780
attccgagct ggcgtaatc atggtcatag ctgtttcctg tgtgaaattg ttatccgctc   3840
acaattccac acaacatagg agccggaagc ataaagtgta aagcctgggg tgcctaatga   3900
gtgaggtaac tcacattaat tgcgttgcgc tcactgcccg ctttccagtc gggaaacctg   3960
```

```
tcgtgccagc tgcattaatg aatcggccaa cgcgcgggga gaggcggttt gcgtattggg    4020
cgctcttccg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgttttttcc ataggctcgg ccccctgac gagcatcaca aaaatcgacg ctcaagtcag    4260
aggtggcgaa acccgacagg actataaaga taccaggcgt tcccccctgg aagctccctc    4320
gtgcgctctc ctgttccgac cctgccgctt accggatacc tgtccgcctt tctcccttcg    4380
ggaagcgtgg cgctttctca atgctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc aacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac cgctggtagc    4740
ggtggttttt tgtttgcaa gcagcagatt acgcgcagaa aaaaggatc tcaagaagat    4800
cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactgccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgaaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga tccagttc gatgtaaccc    5700
actcgtgcac ccaactgatc ttcagcatct tttactttca ccagcgtttc tgggtgagca    5760
aaaacaggaa ggcaaaatgc cgcaaaaaag gaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgt ctaagaaacc attattatca tgacattaac ctataaaaat    6000
aggcgtatca cgaggccctt tcgtc                                         6025
```

<210> SEQ ID NO 34
<211> LENGTH: 6025
<212> TYPE: DNA
<213> ORGANISM: Artificial Sequence
<220> FEATURE:
<223> OTHER INFORMATION: Codon Optimized

<400> SEQUENCE: 34

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt tttttttattc ttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaat tgcccagtat      360
tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga tttttccatg gagggcacag ttaagccgct aaaggcatta tccgccaagt     660
acaatttttt actcttcgaa gacagaaaat ttgctgacat tggtaataca gtcaaattgc     720
agtactctgc gggtgtatac agaatagcag aatgggcaga cattacgaat gcacacggtg     780
tggtgggccc aggtattgtt agcggttga agcaggcggc agaagaagta acaaaggaac      840
ctagaggcct tttgatgtta gcagaattgt catgcaaggg ctccctatct actggagaat     900
atactaaggg tactgttgac attgcgaaga gcgacaaaga ttttgttatc ggctttattg     960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact atttgcaaag gaagggatg     1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta aacgttaata ttttgttaaa attcgcgtta    1380
aattttttgtt aaatcagctc atttttttaac caataggccg aaatcggcaa aatcccttat    1440
aaatcaaaag aatagaccga datagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt ttttgggt cgaggtgccg taaagcacta      1620
aatcggaacc ctaaagggag ccccgatt agagcttgac gggaaagcc ggcgaacgtg      1680
gcgagaaagg aagggaagaa agcgaaagga gcggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta aagccgccg agcgggcgac agccctccga     2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagcccttat ttctggggta attaatcagc    2280
gaagcgatga ttttttgatct attaacagat atataaatgg aaaagctgca taaccacttt    2340
```

```
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggcta atcaaacaga acctccagaa tctaatacga    2520
aatatagtgt agttaccaaa atcctaagtt ttggccacac ttgttggaaa ttgcagagac    2580
cgtatacttt cattggagtg attagttgcg cctgtggatt gttcggtaga gagttattcc    2640
ataatactaa tttgctatca tggtctctga tgttgaaagc tttcagctca ttgatggtaa    2700
tactgtcagt gaatctatgt accaatatca taaaccagat cactgacctg acatagaca     2760 gaatcaataa gccggacttg ccattggcga gcggggaaat gtccattgaa acagcatgga    2820
ttatgagtat tatagttgca ctaactggat tgatacttac gataaagctt aattgcggcc    2880
ctttgtttat atctctatat tgtgtcagca tactagtcgg ggcactatat tcagtaccgc    2940
cattcagatg gaagcaaaat cccaataccg cattctcaag ttattttatg ggactggtga    3000
tcgtcaattt tacctgctat tacgcaagca gggccgcctt tggactgcca ttcgagatgt    3060
cacccccgtt cacattcatt cttgcctttg tcaagtcaat gggtagcgca cttttttgt     3120 gtaaagatgt ctctgacatt gaaggagatt ctaagcacgg tatatctacc cttgcgacga    3180
ggtatggagc aaaaaacatt actttccttt gctcaggaat cgtactgcta acctacgtaa    3240
gcgcgatatt ggctgcgatt atttggccac aagccttcaa gtccaacgtg atgctgttga    3300
gtcacgcaac cctggccttt tggcttatct ttcagactag agagttcgcg ttaactaatt    3360
acaatccaga ggcagggagg aagttttacg agttcatgtg gaagctgcac tacgctgaat    3420
acttagtcta tgtatttata taggatgggc tgcaggaatt cgatatcaag cttatcgata    3480
ccgtcgacct cgagtcatgt aattagttat gtcacgctta cattcacgcc ctcccccac    3540 atccgctcta accgaaaagg aaggagttag acaacctgaa gtctaggtcc ctatttattt    3600
ttttatagtt atgttagtat taagaacgtt atttatattt caaatttttc ttttttttct    3660
gtacagacgc gtgtacgcat gtaacattat actgaaaacc ttgcttgaga aggttttggg    3720
acgctcgaag gctttaattt gcggccggta cccagctttt gttccccttta gtgagggtta    3780 attccgagct tggcgtaatc atggtcatag ctgtttcctg tgtgaaattg ttatccgctc    3840
acaattccac acaacatagg agccggaagc ataaagtgta aagcctgggg tgcctaatga    3900
gtgaggtaac tcacattaat tgcgttgcgc tcactgcccg ctttccagtc gggaaacctg    3960
tcgtgccagc tgcattaatg aatcggccaa cgcgcgggga gaggcggttt gcgtattggg    4020
cgctcttccg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgtttttcc ataggctcgg cccccctgac gagcatcaca aaaatcgacg ctcaagtcag    4260
aggtggcgaa acccgacagg actataaaga taccaggcgt tcccccctgg aagctccctc    4320
gtgcgctctc ctgttccgac cctgccgctt accggatacc tgtccgcctt tctcccttcg    4380
ggaagcgtgg cgctttctca atgctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
```

```
gttaccttcg gaaaaagagt tggtagctct tgatccggca acaaaccac cgctggtagc      4740 ggtggttttt ttgtttgcaa gcagcagatt acgcgcagaa aaaaggatc tcaagaagat      4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc   4980
agtgaggcac ctatctcagc gatctgtcta tttcgttcat ccatagttgc ctgactgccc    5040
gtcgtgtaga taactacgat acgggagggc ttaccatctg gccccagtgc tgcaatgata   5100
ccgcgagacc cacgctcacc ggctccagat ttatcagcaa taaccagcc agccggaagg   5160 gccgagcgca gaagtggtcc tgcaacttta tccgcctcca tccagtctat taattgttgc   5220
cgggaagcta gagtaagtag ttcgccagtt aatagtttgc gcaacgttgt tgccattgct   5280
acaggcatcg tggtgtcacg ctcgtcgttt ggtatggctt cattcagctc cggttcccaa   5340
cgatcaaggc gagttacatg atcccccatg ttgtgaaaaa aagcggttag ctccttcggt    5400
cctccgatcg ttgtcagaag taagttggcc gcagtgttat cactcatggt tatgcagca    5460 ctgcataatt ctcttactgt catgccatcc gtaagatgct tttctgtgac tggtgagtac   5520
tcaaccaagt cattctgaga atagtgtatg cggcgaccga gttgctcttg cccggcgtca   5580
atacgggata taccgcgcc acatagcaga actttaaaag tgctcatcat tggaaaacgt    5640 tcttcgggc gaaaactctc aaggatctta ccgctgttga gatccagttc gatgtaaccc    5700
actcgtgcac ccaactgatc ttcagcatct tttactttca ccagcgtttc tgggtgagca   5760
aaaacaggaa ggcaaaatgc cgcaaaaaag gaataaggg cgacacggaa atgttgaata   5820
ctcatactct ccttttttca atattattga agcatttatc agggttattg tctcatgagc   5880
ggatacatat ttgaatgtat ttagaaaaat aaacaaatag gggttccgcg cacatttccc    5940
cgaaaagtgc cacctgacgt ctaagaaacc attattatca tgacattaac ctataaaaat    6000
aggcgtatca cgaggccctt tcgtc                                          6025
```

<210> SEQ ID NO 35
<211> LENGTH: 6088
<212> TYPE: DNA
<213> ORGANISM: Artificial Sequence
<220> FEATURE:
<223> OTHER INFORMATION: Codon Optimized

<400> SEQUENCE: 35

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg      120
ttggcgggtg tcggggctgg cttaactatg cggcatcaga gcagattgta ctgagagtgc     180
accacgcttt tcaattcaat tcatcatttt tttttattc tttttttga tttcggtttc      240 tttgaaattt ttttgattcg gtaatctccg aacagaagga agaacgaagg aaggagcaca    300
gacttagatt ggtatatata cgcatatgta gtgttgaaga aacatgaaat tgcccagtat   360
tcttaaccca actgcacaga acaaaaacct gcaggaaacg aagataaatc atgtcgaaag   420
ctacatataa ggaacgtgct gctactcatc ctagtcctgt tgctgccaag ctatttaata    480
tcatgcacga aaagcaaaca aacttgtgtg cttcattgga tgttcgtacc accaaggaat   540
tactggagtt agttgaagca ttaggtccca aaatttgttt actaaaaaca catgtggata   600
tcttgactga ttttttccatg gagggcacag ttaagccgct aaaggcatta tccgccaagt   660 acaattttttt actcttcgaa gacagaaaat ttgctgacat tggtaataca gtcaaattgc   720
```

```
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata  ttttgttaaa attcgcgtta   1380
aatttttgtt aaatcagctc attttttaac caataggccg aaatcggcaa aatcccttat   1440
aaatcaaaag aatagaccga datagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttgggt  cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tccatctat  tttcactgct gttttgttcg   2520
ctgcttcttc tgctttggct gctccagttg ctaatcaaac agaacctcca gaatctaata   2580
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
gcccttgtt  tatatctcta tattgtgtca gcatactagt cggggcacta tattcagtac   3000
cgccattcag atggaagcaa aatcccaata ccgcattctc aagttatttt atgggactgg   3060
```

```
tgatcgtcaa ttttacctgc tattacgcaa gcagggccgc ctttggactg ccattcgaga    3120
tgtcaccccc gttcacattc attcttgcct ttgtcaagtc aatgggtagc gcactttttt    3180
tgtgtaaaga tgtctctgac attgaaggag attctaagca cggtatatct acccttgcga    3240
cgaggtatgg agcaaaaaac attactttcc tttgctcagg aatcgtactg ctaacctacg    3300
taagcgcgat attggctgcg attatttggc cacaagcctt caagtccaac gtgatgctgt    3360
tgagtcacgc aaccctggcc ttttggctta tctttcagac tagagagttc gcgttaacta    3420
attacaatcc agaggcaggg aggaagtttt acgagttcat gtggaagctg cactacgctg    3480
aatacttagt ctatgtattt atataggatg ggctgcagga attcgatatc aagcttatcg    3540
ataccgtcga cctcgagtca tgtaattagt tatgtcacgc ttacattcac gccctccccc    3600
cacatccgct ctaaccgaaa aggaaggagt tagacaacct gaagtctagg tccctattta    3660
tttttttata gttatgttag tattaagaac gttatttata tttcaaattt ttctttttttt    3720 tctgtacaga cgcgtgtacg catgtaacat tatactgaaa accttgcttg agaaggtttt    3780
gggacgctcg aaggctttaa tttgcggccg gtacccagct tttgttccct ttagtgaggg    3840
ttaattccga gcttggcgta atcatggtca tagctgtttc ctgtgtgaaa ttgttatccg    3900
ctcacaattc cacacaacat aggagccgga agcataaagt gtaaagcctg gggtgcctaa    3960
tgagtgaggt aactcacatt aattgcgttg cgctcactgc ccgctttcca gtcgggaaac    4020
ctgtcgtgcc agctgcatta atgaatcggc caacgcgcgg ggagaggcgg tttgcgtatt    4080
gggcgctctt ccgcttcctc gctcactgac tcgctgcgct cggtcgttcg gctgcggcga    4140
gcggtatcag ctcactcaaa ggcggtaata cggttatcca cagaatcagg ggataacgca    4200
ggaaagaaca tgtgagcaaa aggccagcaa aaggccagga accgtaaaaa ggccgcgttg    4260
ctggcgtttt tccataggct cggccccccct gacgagcatc acaaaaatcg acgctcaagt    4320
cagaggtggc gaaacccgac aggactataa agataccagg cgttcccccc tggaagctcc    4380
ctcgtgcgct ctcctgttcc gaccctgccg cttaccggat acctgtccgc ctttctccct    4440
tcgggaagcg tggcgctttc tcaatgctca cgctgtaggt atctcagttc ggtgtaggtc    4500
gttcgctcca agctgggctg tgtgcacgaa ccccccgttc agcccgaccg ctgcgcctta    4560
tccggtaact atcgtcttga gtccaacccg gtaagacacg acttatcgcc actggcagca    4620
gccactggta acaggattag cagagcgagg tatgtaggcg gtgctacaga gttcttgaag    4680
tggtggccta actacggcta cactagaagg acagtatttg gtatctgcgc tctgctgaag    4740
ccagttacct tcggaaaaag agttggtagc tcttgatccg gcaaacaaac caccgctggt    4800
agcggtggtt ttttgtttg caagcagcag attacgcgca gaaaaaaagg atctcaagaa    4860
gatcctttga tcttttctac ggggtctgac gctcagtgga acgaaaactc acgttaaggg    4920
attttggtca tgagattatc aaaaaggatc ttcacctaga tccttttaaa ttaaaaatga    4980
agttttaaat caatctaaag tatatatgag taaacttggt ctgacagtta ccaatgctta    5040
atcagtgagg cacctatctc agcgatctgt ctatttcgtt catccatagt tgcctgactg    5100
cccgtcgtgt agataactac gatacgggag ggcttaccat ctggccccag tgctgcaatg    5160
ataccgcgag acccacgctc accggctcca gatttatcag caataaacca gccagccgga    5220
agggccgagc gcagaagtgg tcctgcaact ttatccgcct ccatccagtc tattaattgt    5280
tgccgggaag ctagagtaag tagttcgcca gttaatagtt tgcgcaacgt tgttgccatt    5340
gctacaggca tcgtggtgtc acgctcgtcg tttggtatgg cttcattcag ctccggttcc    5400
caacgatcaa ggcgagttac atgatccccc atgttgtgaa aaaagcggtt agctccttc     5460
```

```
ggtcctccga tcgttgtcag aagtaagttg gccgcagtgt tatcactcat ggttatggca    5520
gcactgcata attctcttac tgtcatgcca tccgtaagat gcttttctgt gactggtgag    5580
tactcaacca agtcattctg agaatagtgt atgcggcgac cgagttgctc ttgcccggcg    5640
tcaatacggg ataataccgc gccacatagc agaactttaa aagtgctcat cattggaaaa    5700
cgttcttcgg ggcgaaaact ctcaaggatc ttaccgctgt tgagatccag ttcgatgtaa    5760
cccactcgtg cacccaactg atcttcagca tcttttactt tcaccagcgt ttctgggtga    5820
gcaaaaacag gaaggcaaaa tgccgcaaaa agggaataag ggcgacacg gaaatgttga    5880 atactcatac tcttcctttt tcaatattat tgaagcattt atcagggtta ttgtctcatg    5940
agcggataca tatttgaatg tatttagaaa aataaacaaa taggggttcc gcgcacattt    6000
ccccgaaaag tgccacctga cgtctaagaa accattatta tcatgacatt aacctataaa    6060
aataggcgta tcacgaggcc ctttcgtc                                       6088
```

<210> SEQ ID NO 36
<211> LENGTH: 1197
<212> TYPE: DNA
<213> ORGANISM: Artificial Sequence
<220> FEATURE:
<223> OTHER INFORMATION: Codon Optimized

<400> SEQUENCE: 36

```
atgggcctta gtctagtttg tacgttttct tttcagacga actaccacac gttgctgaat      60
ccgcacaata agaacccaaa aaactctcta ttgagctatc agcatcctaa gaccccgata     120
ataaagtctt cttacgataa cttteettet aaatactgtt taacaaagaa cttteattta     180 ctggactga actctcataa ccgtataagt agccaatcca ggagcattcg tgcgggctca     240
gatcagattg aaggttcccc ccaccacgaa agtgacaact ccatagcgac caaaattctt     300
aattttgggc acacttgttg gaagttacaa agaccctacg tagtgaaagg tatgatatcc     360
atagcgtgtg gtctgtttgg ccgtgaattg tttaataaca gacacttatt cagttggggg     420
ttaatgtgga aggctttttt tgctctagtt cccatcttga gttttaactt cttcgcggct     480
ataatgaacc aaatctacga cgtcgacatc gacaggatta taaaaccgga tcttccactt     540
gtgtccggag aaatgtccat tgaaacggct tggatcctta gtattattgt tgcccttact     600
ggtcttattg tgaccattaa gctaaaatca gccccacttt ttgtttttat ctatatattt     660
ggcatctttg ccggattcgc gtattcagtt cccccctatc cgttggaaaca atacccttt      720 acgaacttcc ttataacaat ttcctcccat gttgggttgg ccttcacatc atactcagcg     780
acaacttcag cactaggatt gccttcgtg tggaggcccg catttagctt tatcattgct     840
tttatgacgg ttatgggcat gacaatagca ttcgccaaag acattagtga tattgaaggt     900
gatgcaaaat acggtgtgtc aacggtcgcc actaagttag gagcaagaaa tatgacattc     960
gtggtgtcag gtgttttatt gcttaattat cttgtgtcca ttagcatcgg tataatctgg    1020
cctcaggttt tcaaatcaaa tatcatgatc ctatctcacg caattctagc tttctgcttg    1080
atctttcaga cgagagaatt ggctctagcc aactacgcat cagcacctag taggcagttc    1140
ttcgaattta tttggctatt gtattacgca gagtatttcg tgtatgtgtt catttaa       1197
```

<210> SEQ ID NO 37
<211> LENGTH: 969
<212> TYPE: DNA
<213> ORGANISM: Artificial Sequence
<220> FEATURE:

<223> OTHER INFORMATION: Codon Optimized

<400> SEQUENCE: 37

```
atggcgggct cagatcagat tgaaggttcc ccccaccacg aaagtgacaa ctccatagcg      60
accaaaattc ttaattttgg cacacttgt tggaagttac aaagaccccta cgtagtgaaa     120
ggtatgatat ccatagcgtg tggtctgttt ggccgtgaat tgtttaataa cagacactta    180
ttcagttggg ggttaatgtg gaaggctttt tttgctctag ttcccatctt gagttttaac    240
ttcttcgcgg ctataatgaa ccaaatctac gacgtcgaca tcgacaggat taataaaccg    300
gatcttccac ttgtgtccgg agaaatgtcc attgaaacgg cttggatcct tagtattatt    360
gttgccctta ctggtcttat tgtgaccatt aagctaaaat cagccccact ttttgttttt    420
atctatatat ttggcatctt tgccggattc gcgtattcag ttcccctat ccgttggaaa     480
caatacccct ttacgaactt ccttataaca atttcctccc atgttgggtt ggccttcaca    540
tcatactcag cgacaacttc agcactagga ttgcccttcg tgtggaggcc cgcatttagc    600
tttatcattg cttttatgac ggttatgggc atgacaatag cattcgccaa agacattagt    660
gatattgaag gtgatgcaaa atacggtgtg tcaacggtcg ccactaagtt aggagcaaga    720
aatatgacat cgtggtgtc aggtgtttta ttgcttaatt atcttgtgtc cattagcatc    780
ggtataatct ggcctcaggt tttcaaatca aatatcatga tcctatctca cgcaattcta    840
gctttctgct tgatcttca gacgagagaa ttggctctag ccaactacgc atcagcacct    900
agtaggcagt tcttcgaatt tatttggcta ttgtattacg cagagtattt cgtgtatgtg    960
ttcatttaa                                                            969
```

<210> SEQ ID NO 38
<211> LENGTH: 1032
<212> TYPE: DNA
<213> ORGANISM: Artificial Sequence
<220> FEATURE:
<223> OTHER INFORMATION: Codon Optimized

<400> SEQUENCE: 38

```
atgagattcc catctatttt cactgctgtt ttgttcgctg cttcttctgc tttggctgct      60
ccagttgcgg gctcagatca gattgaaggt tccccccacc acgaaagtga caactccata     120
gcgaccaaaa ttcttaattt tgggcacact tgttggaagt tacaaagacc ctacgtagtg    180
aaaggtatga tatccatagc gtgtggtctg tttggccgtg aattgtttaa tacagacac      240
ttattcagtt gggggttaat gtggaaggct ttttttgctc tagttcccat cttgagtttt    300
aacttcttcg cggctataat gaaccaaatc tacgacgtcg acatcgacag gattaataaa    360
ccggatcttc cacttgtgtc cggagaaatg tccattgaaa cggcttggat ccttagtatt    420
attgttgccc ttactggtct tattgtgacc attaagctaa atcagcccc acttttgtt      480
tttatctata tatttggcat ctttgccgga ttcgcgtatt cagttccccc tatccgttgg    540
aaacaatacc cctttacgaa cttccttata acaatttcct cccatgttgg gttggccttc    600
acatcatact cagcgacaac ttcagcacta ggattgccct tcgtgtggag gcccgcattt    660
agctttatca ttgcttttat gacggttatg ggcatgacaa tagcattcgc caaagacatt    720
agtgatattg aaggtgatgc aaaatacggt gtgtcaacgg tcgccactaa gttaggagca    780
agaaatatga cattcgtggt gtcaggtgtt ttattgctta attatcttgt gtccattagc    840
atcggtataa tctggcctca ggttttcaaa tcaaatatca tgatcctatc tcacgcaatt    900
ctagctttct gcttgatctt tcagacgaga gaattggctc tagccaacta cgcatcagca    960
```

```
cctagtaggc agttcttcga atttatttgg ctattgtatt acgcagagta tttcgtgtat    1020
gtgttcattt aa                                                        1032

<210> SEQ ID NO 39
<211> LENGTH: 6262
<212> TYPE: DNA
<213> ORGANISM: Artificial Sequence
<220> FEATURE:
<223> OTHER INFORMATION: Codon Optimized

<400> SEQUENCE: 39
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accacgcttt tcaattcaat tcatcatttt ttttttattc ttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaat tgcccagtat      360 tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga ttttccatg gagggcacag ttaagccgct aaaggcatta tccgccaagt      660
acaatttttt actcttcgaa gacagaaaat tgctgacat tggtaataca gtcaaattgc      720
agtactctgc gggtgtatac agaatagcag aatgggcaga cattacgaat gcacacggtg     780
tggtgggccc aggtattgtt agcggtttga agcaggcggc agaagaagta acaaaggaac     840
ctagaggcct tttgatgtta gcagaattgt catgcaaggg ctccctatct actggagaat     900
atactaaggg tactgttgac attgcgaaga gcgacaaaga ttttgttatc ggctttattg     960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact attttgcaaag ggaagggatg    1140 ctaaggtaga gggtgaacgt tacagaaaag caggctggga gcatatttg agaagatgcg     1200 gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta     1380
aatttttgtt aaatcagctc atttttaac caataggccg aaatcggcaa atcccttat     1440 aaatcaaaag aatagaccga datagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggt cgaggtgccg taaagcacta     1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
```

```
gggttttccc agtcacgacg ttgtaaaacg acggccagtg aattgtaata cgactcacta    1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga tttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatgggcc ttagtctagt ttgtacgttt tcttttcaga    2520
cgaactacca cacgttgctg aatccgcaca ataagaaccc aaaaaactct ctattgagct    2580
atcagcatcc taagacccg ataataaagt cttcttacga taactttcct tctaaatact    2640
gtttaacaaa gaactttcat ttactgggac tgaactctca taaccgtata agtagccaat    2700
ccaggagcat tcgtgcgggc tcagatcaga ttgaaggttc cccccaccac gaaagtgaca    2760
actccatagc gaccaaaatt cttaattttg ggcacacttg ttggaagtta caagacccct    2820
acgtagtgaa aggtatgata tccatagcgt gtggtctgtt tggccgtgaa ttgtttaata    2880
acagacactt attcagttgg gggttaatgt ggaaggcttt ttttgctcta gttcccatct    2940
tgagttttaa cttcttcgcg gctataatga accaaatcta cgacgtcgac atcgacagga    3000
ttaataaacc ggatcttcca cttgtgtccg gagaaatgtc cattgaaacg gcttggatcc    3060
ttagtattat tgttgccctt actggtctta ttgtgaccat taagctaaaa tcagccccac    3120
tttttgtttt tatctatata tttggcatct ttgccggatt cgcgtattca gttccccta    3180 tccgttggaa acaataccc tttacgaact tccttataac aatttcctcc catgttgggt    3240
tggccttcac atcatactca gcgacaactt cagcactagg attgcccttc gtgtggaggc    3300
ccgcatttag ctttatcatt gcttttatga cggttatggg catgacaata gcattcgcca    3360
aagacattag tgatattgaa ggtgatgcaa aatacggtgt gtcaacggtc gccactaagt    3420
taggagcaag aaatatgaca ttcgtggtgt caggtgtttt attgcttaat tatcttgtgt    3480
ccattagcat cggtataatc tggcctcagg ttttcaaatc aaatatcatg atcctatctc    3540
acgcaattct agctttctgc ttgatctttc agacgagaga attggctcta gccaactacg    3600
catcagcacc tagtaggcag ttcttcgaat ttatttggct attgtattac gcagagtatt    3660
tcgtgtatgt gttcatttaa gatgggctgc aggaattcga tatcaagctt atcgataccg    3720
tcgacctcga gtcatgtaat tagttatgtc acgcttacat tcacgccctc cccccacatc    3780
cgctctaacc gaaaggaag gagttagaca acctgaagtc taggtcccta tttattttt    3840 tatagttatg ttagtattaa gaacgttatt tatatttcaa attttctttt tttttctgta    3900
cagacgcgtg tacgcatgta acattatact gaaaaccttg cttgagaagg ttttgggacg    3960
ctcgaaggct ttaatttgcg gccggtaccc agcttttgtt ccctttagtg agggttaatt    4020
ccgagcttgg cgtaatcatg gtcatagctg tttcctgtgt gaaattgtta tccgctcaca    4080
attccacaca acataggagc cggaagcata agtgtaaag cctgggtgc ctaatgagtg    4140 aggtaactca cattaattgc gttgcgctca ctgcccgctt tccagtcggg aaacctgtcg    4200
tgccagctgc attaatgaat cggccaacgc gcggggagag gcggtttgcg tattgggcgc    4260
tcttccgctt cctcgctcac tgactcgctg cgctcggtcg ttcggctgcg gcgagcggta    4320
```

```
tcagctcact caaaggcggt aatacggtta tccacagaat cagggataa cgcaggaaag      4380 aacatgtgag caaaaggcca gcaaaaggcc aggaaccgta aaaaggccgc gttgctggcg      4440 ttttccata ggctcggccc ccctgacgag catcacaaaa atcgacgctc aagtcagagg      4500
tggcgaaacc cgacaggact ataaagatac caggcgttcc ccctggaag ctccctcgtg      4560 cgctctcctg ttccgaccct gccgcttacc ggatacctgt ccgcctttct cccttcggga      4620
agcgtggcgc tttctcaatg ctcacgctgt aggtatctca gttcggtgta ggtcgttcgc      4680
tccaagctgg gctgtgtgca cgaaccccc gttcagcccg accgctgcgc cttatccggt      4740
aactatcgtc ttgagtccaa cccggtaaga cacgacttat cgccactggc agcagccact      4800
ggtaacagga ttagcagagc gaggtatgta ggcggtgcta cagagttctt gaagtggtgg      4860
cctaactacg gctacactag aaggacagta tttggtatct gcgctctgct gaagccagtt      4920
accttcggaa aaagagttgg tagctcttga tccggcaaac aaaccaccgc tggtagcggt      4980
ggtttttttg tttgcaagca gcagattacg cgcagaaaaa aaggatctca agaagatcct      5040
ttgatctttt ctacggggtc tgacgctcag tggaacgaaa actcacgtta agggattttg      5100
gtcatgagat tatcaaaaag gatcttcacc tagatccttt taaattaaaa atgaagtttt      5160
aaatcaatct aaagtatata tgagtaaact tggtctgaca gttaccaatg cttaatcagt      5220
gaggcaccta tctcagcgat ctgtctattt cgttcatcca tagttgcctg actgcccgtc      5280
gtgtagataa ctacgatacg ggagggctta ccatctggcc ccagtgctgc aatgataccg      5340
cgagacccac gctcaccggc tccagattta tcagcaataa accagccagc cggaagggcc      5400
gagcgcagaa gtggtcctgc aactttatcc gcctccatcc agtctattaa ttgttgccgg      5460
gaagctagag taagtagttc gccagttaat agtttgcgca acgttgttgc cattgctaca      5520
ggcatcgtgg tgtcacgctc gtcgtttggt atggcttcat tcagctccgg ttcccaacga      5580
tcaaggcgag ttacatgatc ccccatgttg tgaaaaaaag cggttagctc cttcggtcct      5640
ccgatcgttg tcagaagtaa gttggccgca gtgttatcac tcatggttat ggcagcactg      5700
cataattctc ttactgtcat gccatccgta agatgctttt ctgtgactgg tgagtactca      5760
accaagtcat tctgagaata gtgtatgcgg cgaccgagtt gctcttgccc ggcgtcaata      5820
cgggataata ccgcgccaca tagcagaact ttaaaagtgc tcatcattgg aaaacgttct      5880
tcggggcgaa aactctcaag gatcttaccg ctgttgagat ccagttcgat gtaacccact      5940
cgtgcaccca actgatcttc agcatctttt actttcacca gcgtttctgg gtgagcaaaa      6000
acaggaaggc aaaatgccgc aaaaaaggga ataaggcga cacggaaatg ttgaatactc      6060
atactcttcc ttttttcaata ttattgaagc atttatcagg gttattgtct catgagcgga      6120
tacatatttg aatgtattta gaaaaataaa caaatagggg ttccgcgcac atttccccga      6180
aaagtgccac ctgacgtcta agaaaccatt attatcatga cattaaccta taaaaatagg      6240
cgtatcacga ggccctttcg tc                                                6262
```

<210> SEQ ID NO 40
<211> LENGTH: 6034
<212> TYPE: DNA
<213> ORGANISM: Artificial Sequence
<220> FEATURE:
<223> OTHER INFORMATION: Codon Optimized

<400> SEQUENCE: 40

```
tcgcgcgttt cggtgatgac ggtgaaaacc tctgacacat gcagctcccg gagacggtca       60
```

```
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accacgcttt tcaattcaat tcatcatttt ttttttattc tttttttga tttcggtttc    240 tttgaaattt ttttgattcg gtaatctccg aacagaagga agaacgaagg aaggagcaca    300
gacttagatt ggtatatata cgcatatgta gtgttgaaga acatgaaat tgcccagtat    360 tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660 acaattttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact attttgcaaag ggaagggatg   1140 ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttgatct attaacagat atataatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
```

```
ctagaactag tggatccccc atcatggcgg gctcagatca gattgaaggt tccccccacc    2520
acgaaagtga caactccata gcgaccaaaa ttcttaattt tgggcacact tgttggaagt    2580
tacaaagacc ctacgtagtg aaaggtatga tatccatagc gtgtggtctg tttggccgtg    2640
aattgtttaa taacagacac ttattcagtt gggggttaat gtggaaggct tttttttgctc   2700 tagttcccat cttgagtttt aacttcttcg cggctataat gaaccaaatc tacgacgtcg    2760
acatcgacag gattaataaa ccggatcttc cacttgtgtc cggagaaatg tccattgaaa    2820
cggcttggat ccttagtatt attgttgccc ttactggtct tattgtgacc attaagctaa    2880
aatcagcccc acttttttgtt tttatctata tatttggcat ctttgccgga ttcgcgtatt    2940
cagttccccc tatccgttgg aaacaatacc cctttacgaa cttccttata acaatttcct    3000
cccatgttgg gttggccttc acatcatact cagcgacaac ttcagcacta ggattgccct    3060
tcgtgtggag gcccgcattt agctttatca ttgcttttat gacggttatg ggcatgacaa    3120
tagcattcgc caaagacatt agtgatattg aaggtgatgc aaaatacggt gtgtcaacgg    3180
tcgccactaa gttaggagca agaaatatga cattcgtggt gtcaggtgtt ttattgctta    3240
attatcttgt gtccattagc atcggtataa tctggcctca ggttttcaaa tcaaatatca    3300
tgatcctatc tcacgcaatt ctagctttct gcttgatctt tcagacgaga gaattggctc    3360
tagccaacta cgcatcagca cctagtaggc agttcttcga atttatttgg ctattgtatt    3420
acgcagagta tttcgtgtat gtgttcattt aagatgggct gcaggaattc gatatcaagc    3480
ttatcgatac cgtcgacctc gagtcatgta attagttatg tcacgcttac attcacgccc    3540
tccccccaca tccgctctaa ccgaaaagga aggagttaga caacctgaag tctaggtccc    3600
tatttatttt tttatagtta tgttagtatt aagaacgtta tttatatttc aaattttttct   3660 ttttttttctg tacagacgcg tgtacgcatg taacattata ctgaaaacct tgcttgagaa    3720
ggttttggga cgctcgaagg ctttaatttg cggccggtac ccagcttttg ttccctttag    3780
tgagggttaa ttccgagctt ggcgtaatca tggtcatagc tgtttcctgt gtgaaattgt    3840
tatccgctca caattccaca caacatagga gccggaagca taaagtgtaa agcctggggt    3900
gcctaatgag tgaggtaact cacattaatt gcgttgcgct cactgcccgc tttccagtcg    3960
ggaaacctgt cgtgccagct gcattaatga atcggccaac gcgcggggag aggcggtttg    4020
cgtattgggc gctcttccgc ttcctcgctc actgactcgc tgcgctcggt cgttcggctg    4080
cggcgagcgg tatcagctca ctcaaaggcg gtaatacggt tatccacaga atcaggggat    4140
aacgcaggaa agaacatgtg agcaaaaggc cagcaaaagg ccaggaaccg taaaaaggcc    4200
gcgttgctgg cgtttttcca taggctcggc cccctgacg agcatcacaa aaatcgacgc    4260
tcaagtcaga ggtggcgaaa cccgacagga ctataaagat accaggcgtt ccccctggaa    4320
agctccctcg tgcgctctcc tgttccgacc ctgccgctta ccggatacct gtccgccttt    4380
ctcccttcgg gaagcgtggc gctttctcaa tgctcacgct gtaggtatct cagttcggtg    4440
taggtcgttc gctccaagct gggctgtgtg cacgaacccc ccgttcagcc cgaccgctgc    4500
gccttatccg gtaactatcg tcttgagtcc aacccggtaa gacacgactt atcgccactg    4560
gcagcagcca ctggtaacag gattagcaga gcgaggtatg taggcggtgc tacagagttc    4620
ttgaagtggt ggcctaacta cggctacact agaaggacag tatttggtat ctgcgctctg    4680
ctgaagccag ttaccttcgg aaaaagagtt ggtagctctt gatccggcaa acaaaccacc    4740
gctggtagcg gtggtttttt tgtttgcaag cagcagatta cgcgcagaaa aaaaggatct    4800
```

```
caagaagatc ctttgatctt ttctacgggg tctgacgctc agtggaacga aaactcacgt      4860
taagggattt tggtcatgag attatcaaaa aggatcttca cctagatcct tttaaattaa      4920
aaatgaagtt ttaaatcaat ctaaagtata tatgagtaaa cttggtctga cagttaccaa      4980
tgcttaatca gtgaggcacc tatctcagcg atctgtctat ttcgttcatc catagttgcc      5040
tgactgcccg tcgtgtagat aactacgata cgggagggct taccatctgg ccccagtgct      5100
gcaatgatac cgcgagaccc acgctcaccg gctccagatt tatcagcaat aaaccagcca      5160
gccggaaggg ccgagcgcag aagtggtcct gcaactttat ccgcctccat ccagtctatt      5220
aattgttgcc gggaagctag agtaagtagt tcgccagtta atagtttgcg caacgttgtt      5280
gccattgcta caggcatcgt ggtgtcacgc tcgtcgtttg gtatggcttc attcagctcc      5340
ggttcccaac gatcaaggcg agttacatga tcccccatgt tgtgaaaaaa agcggttagc      5400
tccttcggtc ctccgatcgt tgtcagaagt aagttggccg cagtgttatc actcatggtt      5460
atggcagcac tgcataattc tcttactgtc atgccatccg taagatgctt ttctgtgact      5520
ggtgagtact caaccaagtc attctgagaa tagtgtatgc ggcgaccgag ttgctcttgc      5580
ccggcgtcaa tacgggataa taccgcgcca catagcagaa ctttaaaagt gctcatcatt      5640
ggaaaacgtt cttcggggcg aaaactctca aggatcttac cgctgttgag atccagttcg      5700
atgtaaccca ctcgtgcacc caactgatct tcagcatctt ttactttcac cagcgtttct      5760
gggtgagcaa aaacaggaag gcaaaatgcc gcaaaaaagg gaataagggc gacacggaaa      5820
tgttgaatac tcatactctt ccttttttcaa tattattgaa gcatttatca gggttattgt      5880
ctcatgagcg gatacatatt tgaatgtatt tagaaaaata aacaaatagg ggttccgcgc      5940
acatttcccc gaaaagtgcc acctgacgtc taagaaacca ttattatcat gacattaacc      6000
tataaaaata ggcgtatcac gaggcccttt cgtc                                  6034
```

<210> SEQ ID NO 41
<211> LENGTH: 6088
<212> TYPE: DNA
<213> ORGANISM: Artificial Sequence
<220> FEATURE:
<223> OTHER INFORMATION: Codon Optimized

<400> SEQUENCE: 41

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accacgcttt tcaattcaat tcatcatttt ttttttattc ttttttttga tttcggtttc       240
tttgaaattt ttttgattcg gtaatctccg aacagaagga agaacgaagg aaggagcaca       300
gacttagatt ggtatatata cgcatatgta gtgttgaaga aacatgaaat tgcccagtat       360
tcttaaccca actgcacaga acaaaaacct gcaggaaacg aagataaatc atgtcgaaag       420
ctacatataa ggaacgtgct gctactcatc ctagtcctgt tgctgccaag ctatttaata       480
tcatgcacga aaagcaaaca aacttgtgtg cttcattgga tgttcgtacc accaaggaat       540
tactggagtt agttgaagca ttaggtccca aaatttgttt actaaaaaca catgtggata       600
tcttgactga ttttccatg gagggcacag ttaagccgct aaaggcatta tccgccaagt       660 acaattttttt actcttcgaa gacagaaaat ttgctgacat tggtaataca gtcaaattgc       720
agtactctgc gggtgtatac agaatagcag aatgggcaga cattacgaat gcacacggtg       780
tggtgggccc aggtattgtt agcggtttga agcaggcggc agaagaagta acaaaggaac       840
```

```
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aatttttgtt aaatcagctc attttttaac caataggccg aaatcggcaa aatcccttat   1440
aaatcaaaag aatagaccga datagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttgggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tcccatctat tttcactgct gttttgttcg   2520
ctgcttcttc tgctttggct gctccagttg ctaatcaaac agaacctcca gaatctaata   2580
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
gcccttttgtt tatatctcta tattgtgtca gcatactagt cggggcacta tattcagtac   3000
cgccattcag atggaagcaa aatcccaata ccgcattctc aagttatttt atgggactgg   3060
tgatcgtcaa ttttacctgc tattacgcaa gcagggccgc ctttggactg ccattcgaga   3120
tgtcaccccc gttcacattc attcttgcct ttgtcaagtc aatgggtagc gcactttttt   3180
```

```
tgtgtaaaga tgtctctgac attgaaggag attctaagca cggtatatct acccttgcga    3240
cgaggtatgg agcaaaaaac attactttcc tttgctcagg aatcgtactg ctaacctacg    3300
taagcgcgat attggctgcg attatttggc cacaagcctt caagtccaac gtgatgctgt    3360
tgagtcacgc aaccctggcc ttttggctta tctttcagac tagagagttc gcgttaacta    3420
attacaatcc agaggcaggg aggaagtttt acgagttcat gtggaagctg cactacgctg    3480
aatacttagt ctatgtattt ataggatg gctgcagga attcgatatc aagcttatcg    3540
ataccgtcga cctcgagtca tgtaattagt tatgtcacgc ttacattcac gccctccccc    3600
cacatccgct ctaaccgaaa ggaaggagt tagacaacct gaagtctagg tccctattta    3660
tttttttata gttatgttag tattaagaac gttatttata tttcaaattt ttcttttttt    3720
tctgtacaga cgcgtgtacg catgtaacat tatactgaaa accttgcttg agaaggtttt    3780
gggacgctcg aaggctttaa tttgcggccg gtacccagct tttgttccct ttagtgaggg    3840
ttaattccga gcttggcgta atcatggtca tagctgtttc ctgtgtgaaa ttgttatccg    3900
ctcacaattc cacacaacat aggagccgga agcataaagt gtaaagcctg gggtgcctaa    3960
tgagtgaggt aactcacatt aattgcgttg cgctcactgc ccgctttcca gtcgggaaac    4020
ctgtcgtgcc agctgcatta atgaatcggc caacgcgcgg ggagaggcgg tttgcgtatt    4080
gggcgctctt ccgcttcctc gctcactgac tcgctgcgct cggtcgttcg gctgcggcga    4140
gcggtatcag ctcactcaaa ggcggtaata cggttatcca cagaatcagg ggataacgca    4200
ggaaagaaca tgtgagcaaa aggccagcaa aaggccagga accgtaaaaa ggccgcgttg    4260
ctggcgtttt tccataggct cggcccccct gacgagcatc acaaaaatcg acgctcaagt    4320
cagaggtggc gaaacccgac aggactataa agataccagg cgttcccccc tggaagctcc    4380
ctcgtgcgct ctcctgttcc gaccctgccg cttaccggat acctgtccgc ctttctccct    4440
tcgggaagcg tggcgctttc tcaatgctca cgctgtaggt atctcagttc ggtgtaggtc    4500
gttcgctcca agctgggctg tgtgcacgaa ccccccgttc agcccgaccg ctgcgcctta    4560
tccggtaact atcgtcttga gtccaacccg gtaagacacg acttatcgcc actggcagca    4620
gccactggta acaggattag cagagcgagg tatgtaggcg gtgctacaga gttcttgaag    4680
tggtggccta actacggcta cactagaagg acagtatttg gtatctgcgc tctgctgaag    4740
ccagttacct tcggaaaaag agttggtagc tcttgatccg gcaaacaaac caccgctggt    4800
agcggtggtt tttttgtttg caagcagcag attacgcgca gaaaaaaagg atctcaagaa    4860
gatcctttga tcttttctac ggggtctgac gctcagtgga acgaaaactc acgttaaggg    4920
attttggtca tgagattatc aaaaaggatc ttcacctaga tccttttaaa ttaaaaatga    4980
agttttaaat caatctaaag tatatatgag taaacttggt ctgacagtta ccaatgctta    5040
atcagtgagg cacctatctc agcgatctgt ctatttcgtt catccatagt tgcctgactg    5100
cccgtcgtgt agataactac gatacgggag ggcttaccat ctggccccag tgctgcaatg    5160
ataccgcgag acccacgctc accggctcca gatttatcag caataaacca gccagccgga    5220
agggccgagc gcagaagtgg tcctgcaact ttatccgcct ccatccagtc tattaattgt    5280
tgccgggaag ctagagtaag tagttcgcca gttaatagtt tgcgcaacgt tgttgccatt    5340
gctacaggca tcgtggtgtc acgctcgtcg tttggtatgg cttcattcag ctccggttcc    5400
caacgatcaa ggcgagttac atgatccccc atgttgtgaa aaaagcggt tagctccttc    5460 ggtcctccga tcgttgtcag aagtaagttg gccgcagtgt tatcactcat ggttatggca    5520
gcactgcata attctcttac tgtcatgcca tccgtaagat gcttttctgt gactggtgag    5580
```

```
tactcaacca agtcattctg agaatagtgt atgcggcgac cgagttgctc ttgcccggcg    5640
tcaatacggg ataataccgc gccacatagc agaactttaa aagtgctcat cattggaaaa    5700
cgttcttcgg ggcgaaaact ctcaaggatc ttaccgctgt tgagatccag ttcgatgtaa    5760
cccactcgtg cacccaactg atcttcagca tcttttactt tcaccagcgt ttctgggtga    5820
gcaaaaacag gaaggcaaaa tgccgcaaaa aagggaataa gggcgacacg gaaatgttga    5880
atactcatac tcttcctttt tcaatattat tgaagcattt atcagggtta ttgtctcatg    5940
agcggataca tatttgaatg tatttagaaa aataaacaaa taggggttcc gcgcacattt    6000
ccccgaaaag tgccacctga cgtctaagaa accattatta tcatgacatt aacctataaa    6060
aataggcgta tcacgaggcc ctttcgtc                                       6088
```

<210> SEQ ID NO 42
<211> LENGTH: 1203
<212> TYPE: DNA
<213> ORGANISM: Artificial Sequence
<220> FEATURE:
<223> OTHER INFORMATION: Codon Optimized

<400> SEQUENCE: 42

```
atggtatttt cctcagtgtg tagttttccg tcctctcttg gtacaaactt taagctggtg      60
cctagatcta attttaaggc ttcaagttca cattaccacg aaatcaacaa tttcattaac     120
aacaaaccca ttaaatttag ttatttctct tcaaggttgt attgcagtgc caagccaata     180
gtacacagag aaaacaagtt cacaaaatca ttctcactat cacacttaca acgtaaatct     240
tctatcaagg cccatggaga gatagaggct gatggaagta acgggacttc tgagttcaac     300
gtaatgaagt ccggaaatgc tatctggaga tttgtgaggc cgtatgccgc taaaggtgtc     360
ctgtttaact ccgcggcaat gttcgctaag gaacttgttg gaaatctgaa cttatttagc     420
tggccgttga tgttcaagat cctttcattt actcttgtca ttctgtgtat ctttgtatct     480
acatcaggca taaatcagat atatgatcta gacatcgata gactgaacaa accgaacttg     540
cccgtggcaa gcggggaaat tagcgtagaa ttggcatggt tacttactat agtatgtacg     600
attagtggac ttaccttaac cattataact aatagtggcc ccttttttcc gttcctttac     660
tcagcctcca tattctttgg tttcctatac tccgcccccc cgttccgttg aagaaaaac     720 ccccttaccg cctgcttttg caatgtgatg ttatacgtgg gaaccagtgt tggggtttat     780
tatgcctgca aagccagttt gggccttcct gccaattggt ctccagcatt ctgcctttta     840
ttttggttta ttagtctgct ttccatacct atcagcatag ctaaggattt atctgatatt     900
gaaggtgata ggaagtttgg aatcattact ttctctacta agttcggggc aaaaccgatc     960
gcgtacatat gtcacgggct tatgcttttg aattacgtga gtgttatggc cgcggccata    1020
atatggcctc aattcttcaa ctcctcagta atactgttat cacatgcctt catggcgatc    1080
tgggttttgt accaagcgtg gatactggag aaaagtaact atgcaacgga aacttgccag    1140
aaatattaca tcttcttatg gataatattc tcccttgagc acgctttta cctattcatg    1200 tag                                                                 1203
```

<210> SEQ ID NO 43
<211> LENGTH: 1128
<212> TYPE: DNA
<213> ORGANISM: Artificial Sequence
<220> FEATURE:
<223> OTHER INFORMATION: Codon Optimized

<400> SEQUENCE: 43

```
atggcttcaa gttcacatta ccacgaaatc aacaatttca ttaacaacaa acccattaaa      60
tttagttatt tctcttcaag gttgtattgc agtgccaagc caatagtaca cagagaaaac     120
aagttcacaa atcattctc actatcacac ttacaacgta atcttctat caaggcccat      180
ggagagatag aggctgatgg aagtaacggg acttctgagt tcaacgtaat gaagtccgga     240
aatgctatct ggagatttgt gaggccgtat gccgctaaag gtgtcctgtt taactccgcg     300
gcaatgttcg ctaaggaact tgttggaaat ctgaacttat ttagctggcc gttgatgttc     360
aagatccttt catttactct tgtcattctg tgtatctttg tatctacatc aggcataaat     420
cagatatatg atctagacat cgatagactg aacaaaccga acttgcccgt ggcaagcggg     480
gaaattagcg tagaattggc atggttactt actatagtat gtacgattag tggacttacc     540
ttaaccatta taactaatag tggccccttt tttccgttcc tttactcagc ctccatattc     600
tttggtttcc tatactccgc cccccgttc cgttggaaga aaacccctt taccgcctgc       660
ttttgcaatg tgatgttata cgtgggaacc agtgttgggg tttattatgc ctgcaaagcc     720
agtttgggcc ttcctgccaa ttggtctcca gcattctgcc ttttattttg gtttattagt     780
ctgctttcca tacctatcag catagctaag gatttatctg atattgaagg tgataggaag     840
tttggaatca ttactttctc tactaagttc ggggcaaaac cgatcgcgta catatgtcac     900
gggcttatgc ttttgaatta cgtgagtgtt atggccgcgg ccataatatg gcctcaattc     960
ttcaactcct cagtaatact gttatcacat gccttcatgg cgatctgggt tttgtaccaa    1020
gcgtggatac tggagaaaag taactatgca acggaaactt gccagaaata ttacatcttc    1080
ttatggataa tattctccct tgagcacgct ttttacctat tcatgtag                 1128
```

<210> SEQ ID NO 44
<211> LENGTH: 1191
<212> TYPE: DNA
<213> ORGANISM: Artificial Sequence
<220> FEATURE:
<223> OTHER INFORMATION: Codon Optimized

<400> SEQUENCE: 44

```
atgagattcc catctatttt cactgctgtt ttgttcgctg cttcttctgc tttggctgct      60
ccagttgctt caagttcaca ttaccacgaa atcaacaatt tcattaacaa caaacccatt     120
aaatttagtt atttctcttc aaggttgtat tgcagtgcca agccaatagt acacagagaa     180
aacaagttca caaatcattc tcactatcac acttacaacg taaatcttc tatcaaggcc      240
catggagaga tagaggctga tggaagtaac gggacttctg agttcaacgt aatgaagtcc     300
ggaaatgcta tctggagatt tgtgaggccg tatgccgcta aaggtgtcct gtttaactcc     360
gcggcaatgt tcgctaagga acttgttgga aatctgaact tatttagctg gccgttgatg     420
ttcaagatcc tttcatttac tcttgtcatt ctgtgtatct tgtatctac atcaggcata     480
aatcagatat atgatctaga catcgataga ctgaacaaac cgaacttgcc cgtggcaagc     540
ggggaaatta gcgtagaatt ggcatggtta cttactatag tatgtacgat tagtggactt     600
acctttaacca ttataactaa tagtggcccc ttttttccgt tccttactc agcctccata     660
ttctttggtt tcctatactc cgcccccccg ttccgttgga agaaaaaccc ctttaccgcc     720
tgcttttgca atgtgatgtt atacgtggga accagtgttg gggtttatta tgcctgcaaa     780
gccagtttgg gccttcctgc caattggtct ccagcattct gccttttatt ttggtttatt     840
agtctgcttt ccatacctat cagcatagct aaggatttat ctgatattga aggtgatagg     900
```

| aagtttggaa tcattacttt ctctactaag ttcggggcaa aaccgatcgc gtacatatgt | 960 |
| cacgggctta tgcttttgaa ttacgtgagt gttatggccg cggccataat atggcctcaa | 1020 |
| ttcttcaact cctcagtaat actgttatca catgccttca tggcgatctg ggttttgtac | 1080 |
| caagcgtgga tactggagaa aagtaactat gcaacgaaaa cttgccagaa atattacatc | 1140 |
| ttcttatgga taatattctc ccttgagcac gcttttacc tattcatgta g | 1191 |

<210> SEQ ID NO 45
<211> LENGTH: 6268
<212> TYPE: DNA
<213> ORGANISM: Artificial Sequence
<220> FEATURE:
<223> OTHER INFORMATION: Codon Optimized

<400> SEQUENCE: 45

| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accacgcttt tcaattcaat tcatcatttt ttttttattc tttttttga tttcggtttc | 240 |
| tttgaaattt tttgattcg gtaatctccg aacagaagga agaacgaagg aaggagcaca | 300 |
| gacttagatt ggtatatata cgcatatgta gtgttgaaga aacatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |
| tactggagtt agttgaagca ttaggtccca aaatttgttt actaaaaaca catgtggata | 600 |
| tcttgactga ttttttccatg gagggcacag ttaagccgct aaaggcatta tccgccaagt | 660 |
| acaattttt actcttcgaa gacagaaaat ttgctgacat tggtaataca gtcaaattgc | 720 |
| agtactctgc gggtgtatac agaatagcag aatgggcaga cattacgaat gcacacggtg | 780 |
| tggtgggccc aggtattgtt agcggtttga gcaggcggc agaagaagta acaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag gttacgattg gttgattatg acacccggtg | 1020 |
| tgggtttaga tgacaaggga gacgcattgg gtcaacagta tagaaccgtg atgatgtgg | 1080 |
| tctctacagg atctgacatt attattgttg gaagaggact attgcaaag gaagggatg | 1140 |
| ctaaggtaga gggtgaacgt tacagaaaag caggctggga agcatatttg agaagatgcg | 1200 |
| gccagcaaaa ctaaaaaact gtattataag taaatgcatg tatactaaac tcacaaatta | 1260 |
| gagcttcaat ttaattatat cagttattac cctgcggtgt gaaataccgc acagatgcgt | 1320 |
| aaggagaaaa taccgcatca ggaaattgta acgttaata ttttgttaaa attcgcgtta | 1380 |
| aatttttgtt aaatcagctc attttttaac caataggccg aaatcggcaa atcccttat | 1440 |
| aaatcaaaag aatagaccga gatagggttg agtgttgttc cagtttggaa caagagtcca | 1500 |
| ctattaaaga acgtggactc caacgtcaaa gggcgaaaaa ccgtctatca gggcgatggc | 1560 |
| ccactacgtg aaccatcacc ctaatcaagt ttttggggt cgaggtgccg taaagcacta | 1620 |
| aatcggaacc ctaaagggag cccccgattt agagcttgac ggggaaagcc ggcgaacgtg | 1680 |
| gcgagaaagg aagggaagaa agcgaaagga gcgggcgcta gggcgctggc aagtgtagcg | 1740 |

```
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggtat tttcctcagt gtgtagtttt ccgtcctctc   2520
ttggtacaaa ctttaagctg gtgcctagat ctaattttaa ggcttcaagt tcacattacc   2580
acgaaatcaa caatttcatt aacaacaaac ccattaaatt tagttatttc tcttcaaggt   2640
tgtattgcag tgccaagcca atagtacaca gagaaaacaa gttcacaaaa tcattctcac   2700
tatcacactt acaacgtaaa tcttctatca aggcccatgg agagatagag gctgatggaa   2760
gtaacgggac ttctgagttc aacgtaatga agtccggaaa tgctatctgg agatttgtga   2820
ggccgtatgc cgctaaaggt gtcctgttta actccgcggc aatgttcgct aaggaacttg   2880
ttggaaatct gaacttattt agctggccgt tgatgttcaa gatcctttca tttactcttg   2940
tcattctgtg tatctttgta tctacatcag gcataaatca gatatatgat ctagacatcg   3000
atagactgaa caaaccgaac ttgcccgtgg caagcgggga aattagcgta gaattggcat   3060
ggttacttac tatagtatgt acgattagtg gacttacctt aaccattata actaatagtg   3120
gccccttttt tccgttcctt tactcagcct ccatattctt tggtttccta tactccgccc   3180
ccccgttccg ttggaagaaa aacccctttta ccgcctgctt ttgcaatgtg atgttatacg   3240
tgggaaccag tgttggggtt tattatgcct gcaaagccag tttgggcctt cctgccaatt   3300
ggtctccagc attctgcctt ttattttggt ttattagtct gctttccata cctatcagca   3360
tagctaagga tttatctgat attgaaggtg ataggaagtt tggaatcatt actttctcta   3420
ctaagttcgg ggcaaaaccg atcgcgtaca tatgtcacgg gcttatgctt ttgaattacg   3480
tgagtgttat ggccgcggcc ataatatggc ctcaattctt caactcctca gtaatactgt   3540
tatcacatgc cttcatggcg atctgggttt tgtaccaagc gtggatactg gagaaaagta   3600
actatgcaac ggaaacttgc cagaaatatt acatcttctt atggataata ttctcccttg   3660
agcacgcttt ttacctattc atgtaggatg ggctgcagga attcgatatc aagcttatcg   3720
ataccgtcga cctcgagtca tgtaattagt tatgtcacgc ttacattcac gccctccccc   3780
cacatccgct ctaaccgaaa aggaaggagt tagacaacct gaagtctagg tccctattta   3840 ttttttttata gttatgttag tattaagaac gttatttata tttcaaattt ttcttttttt   3900
tctgtacaga cgcgtgtacg catgtaacat tatactgaaa accttgcttg agaaggtttt   3960
gggacgctcg aaggctttaa tttgcggccg gtacccagct tttgttccct ttagtgaggg   4020
ttaattccga gcttggcgta atcatggtca tagctgtttc ctgtgtgaaa ttgttatccg   4080
ctcacaattc cacacaacat aggagccgga agcataaagt gtaaagcctg ggtgcctaa    4140
```

```
tgagtgaggt aactcacatt aattgcgttg cgctcactgc ccgctttcca gtcgggaaac    4200
ctgtcgtgcc agctgcatta atgaatcggc caacgcgcgg ggagaggcgg tttgcgtatt    4260
gggcgctctt ccgcttcctc gctcactgac tcgctgcgct cggtcgttcg gctgcggcga    4320
gcggtatcag ctcactcaaa ggcggtaata cggttatcca cagaatcagg ggataacgca    4380
ggaaagaaca tgtgagcaaa aggccagcaa aaggccagga accgtaaaaa ggccgcgttg    4440
ctggcgtttt tccataggct cggcccccct gacgagcatc acaaaaatcg acgctcaagt    4500
cagaggtggc gaaacccgac aggactataa agataccagg cgttccccc tggaagctcc    4560 ctcgtgcgct ctcctgttcc gaccctgccg cttaccggat acctgtccgc ctttctccct    4620
tcgggaagcg tggcgctttc tcaatgctca cgctgtaggt atctcagttc ggtgtaggtc    4680
gttcgctcca agctgggctg tgtgcacgaa ccccccgttc agcccgaccg ctgcgcctta    4740
tccggtaact atcgtcttga gtccaacccg gtaagacacg acttatcgcc actggcagca    4800
gccactggta acaggattag cagagcgagg tatgtaggcg gtgctacaga gttcttgaag    4860
tggtggccta actacggcta cactagaagg acagtatttg gtatctgcgc tctgctgaag    4920
ccagttacct tcggaaaaag agttggtagc tcttgatccg gcaaacaaac caccgctggt    4980
agcggtggtt tttttgtttg caagcagcag attacgcgca gaaaaaaagg atctcaagaa    5040
gatcctttga tcttttctac ggggtctgac gctcagtgga acgaaaactc acgttaaggg    5100
attttggtca tgagattatc aaaaaggatc ttcacctaga tccttttaaa ttaaaaatga    5160
agttttaaat caatctaaag tatatatgag taaacttggt ctgacagtta ccaatgctta    5220
atcagtgagg cacctatctc agcgatctgt ctatttcgtt catccatagt tgcctgactg    5280
cccgtcgtgt agataactac gatacgggag ggcttaccat ctggccccag tgctgcaatg    5340
ataccgcgag acccacgctc accggctcca gatttatcag caataaacca gccagccgga    5400
agggccgagc gcagaagtgg tcctgcaact ttatccgcct ccatccagtc tattaattgt    5460
tgccgggaag ctagagtaag tagttcgcca gttaatagtt tgcgcaacgt tgttgccatt    5520
gctacaggca tcgtggtgtc acgctcgtcg tttggtatgg cttcattcag ctccggttcc    5580
caacgatcaa ggcgagttac atgatccccc atgttgtgaa aaaaagcggt tagctccttc    5640
ggtcctccga tcgttgtcag aagtaagttg gccgcagtgt tatcactcat ggttatggca    5700
gcactgcata attctcttac tgtcatgcca tccgtaagat gcttttctgt gactggtgag    5760
tactcaacca agtcattctg agaatagtgt atgcggcgac cgagttgctc ttgcccggcg    5820
tcaatacggg ataataccgc gccacatagc agaactttaa aagtgctcat cattggaaaa    5880
cgttcttcgg ggcgaaaact ctcaaggatc ttaccgctgt tgagatccag ttcgatgtaa    5940
cccactcgtg cacccaactg atcttcagca tcttttactt tcaccagcgt ttctgggtga    6000
gcaaaaacag gaaggcaaaa tgccgcaaaa aagggaataa gggcgacacg gaaatgttga    6060
atactcatac tcttcctttt tcaatattat tgaagcattt atcagggtta ttgtctcatg    6120
agcggataca tatttgaatg tatttagaaa aataaacaaa taggggttcc gcgcacattt    6180
ccccgaaaag tgccacctga cgtctaagaa accattatta tcatgacatt aacctataaa    6240
aataggcgta tcacgaggcc ctttcgtc                                       6268
```

<210> SEQ ID NO 46
<211> LENGTH: 6268
<212> TYPE: DNA
<213> ORGANISM: Artificial Sequence
<220> FEATURE:

<223> OTHER INFORMATION: Codon Optimized

<400> SEQUENCE: 46

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accacgcttt tcaattcaat tcatcatttt ttttttattc ttttttttga tttcggtttc      240
tttgaaattt ttttgattcg gtaatctccg aacagaagga agaacgaagg aaggagcaca      300
gacttagatt ggtatatata cgcatatgta gtgttgaaga acatgaaat tgcccagtat      360
tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttccatg gagggcacag ttaagccgct aaaggcatta tccgccaagt      660
acaattttt actcttcgaa acagaaaat ttgctgacat tggtaataca gtcaaattgc      720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg gaagaggact atttgcaaag gaagggatg     1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta acgttaata ttttgttaaa attcgcgtta     1380
aatttttgtt aaatcagctc attttttaac caataggccg aaatcggcaa atcccttat     1440
aaatcaaaag aatagaccga gatagggttg agtgttgttc agtttggaa caagagtcca     1500
ctattaaaga acgtggactc caacgtcaaa gggcgaaaaa ccgtctatca gggcgatggc     1560
ccactacgtg aaccatcacc ctaatcaagt tttttgggt cgaggtgccg taaagcacta     1620
aatcggaacc ctaaagggag cccccgattt agagcttgac ggggaaagcc ggcgaacgtg     1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca     1920
gggttttccc agtcacgacg ttgtaaaacg acggccagtg aattgtaata cgactcacta     1980
tagggcgaat ggagctcta gtacggatta gaagccgccg agcgggcgac agccctccga     2040
cggaagactc tcctccgtgc gtcctcgtct tcaccggtcg cgttcctgaa acgcagatgt     2100
gcctcgcgcc gcactgctcc gaacaataaa gattctacaa tactagcttt tatggttatg     2160
aagaggaaaa attggcagta acctggcccc acaaaccttc aaattaacga atcaaattaa     2220
caaccatagg atgataatgc gattagtttt ttagccttat ttctggggta attaatcagc     2280
```

```
gaagcgatga ttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggtat tttcctcagt gtgtagtttt ccgtcctctc    2520
ttggtacaaa ctttaagctg gtgcctagat ctaattttaa ggcttcaagt tcacattacc    2580
acgaaatcaa caatttcatt aacaacaaac ccattaaatt tagttatttc tcttcaaggt    2640
tgtattgcag tgccaagcca atagtacaca gagaaaacaa gttcacaaaa tcattctcac    2700
tatcacactt acaacgtaaa tcttctatca aggcccatgg agagatagag gctgatggaa    2760
gtaacgggac ttctgagttc aacgtaatga agtccggaaa tgctatctgg agatttgtga    2820
ggccgtatgc cgctaaaggt gtcctgttta actccgcggc aatgttcgct aaggaacttg    2880
ttggaaatct gaacttattt agctggccgt tgatgttcaa gatcctttca tttactcttg    2940
tcattctgtg tatctttgta tctacatcag gcataaatca gatatatgat ctagacatcg    3000
atagactgaa caaaccgaac ttgcccgtgg caagcgggga aattagcgta gaattggcat    3060
ggttacttac tatagtatgt acgattagtg gacttacctt aaccattata actaatagtg    3120
gccccttttt tccgttcctt tactcagcct ccatattctt tggtttccta tactccgccc    3180
ccccgttccg ttggaagaaa aaccccttta ccgcctgctt ttgcaatgtg atgttatacg    3240
tgggaaccag tgttggggtt tattatgcct gcaaagccag tttgggcctt cctgccaatt    3300
ggtctccagc attctgcctt ttattttggt ttattagtct gctttccata cctatcagca    3360
tagctaagga tttatctgat attgaaggtg ataggaagtt tggaatcatt actttctcta    3420
ctaagttcgg ggcaaaaccg atcgcgtaca tatgtcacgg gcttatgctt ttgaattacg    3480
tgagtgttat ggccgcggcc ataatatggc ctcaattctt caactcctca gtaatactgt    3540
tatcacatgc cttcatggcg atctgggttt tgtaccaagc gtggatactg agaaaaagta    3600
actatgcaac ggaaacttgc cagaaatatt acatcttctt atggataata ttctcccttg    3660
agcacgcttt ttacctattc atgtaggatg ggctgcagga attcgatatc aagcttatcg    3720
ataccgtcga cctcgagtca tgtaattagt tatgtcacgc ttacattcac gccctccccc    3780
cacatccgct ctaaccgaaa aggaaggagt tagacaacct gaagtctagg tccctattta    3840 ttttttata gttatgttag tattaagaac gttatttata tttcaaattt ttctttttt    3900 tctgtacaga cgcgtgtacg catgtaacat tatactgaaa accttgcttg agaaggtttt    3960
gggacgctcg aaggctttaa tttgcggccg gtacccagct tttgttccct ttagtgaggg    4020
ttaattccga gcttggcgta atcatggtca tagctgtttc ctgtgtgaaa ttgttatccg    4080
ctcacaattc cacacaacat aggagccgga agcataaagt gtaaagcctg ggtgcctaa    4140 tgagtgaggt aactcacatt aattgcgttg cgctcactgc ccgctttcca gtcgggaaac    4200
ctgtcgtgcc agctgcatta tgaatcggc caacgcgcgg ggagaggcgg tttgcgtatt    4260
gggcgctctt ccgcttcctc gctcactgac tcgctgcgct cggtcgttcg gctgcggcga    4320
gcggtatcag ctcactcaaa ggcggtaata cggttatcca cagaatcagg ggataacgca    4380
ggaaagaaca tgtgagcaaa aggccagcaa aaggccagga accgtaaaaa ggccgcgttg    4440
ctggcgtttt tccataggct cggccccct gacgagcatc acaaaaatcg acgctcaagt    4500
cagaggtggc gaaacccgac aggactataa agataccagg cgttccccc tggaagctcc    4560 ctcgtgcgct ctcctgttcc gaccctgccg cttaccggat acctgtccgc ctttctccct    4620
```

| | |
|---|---:|
| tcgggaagcg tggcgctttc tcaatgctca cgctgtaggt atctcagttc ggtgtaggtc | 4680 |
| gttcgctcca agctgggctg tgtgcacgaa cccccgttc agcccgaccg ctgcgcctta | 4740 |
| tccggtaact atcgtcttga gtccaacccg gtaagacacg acttatcgcc actggcagca | 4800 |
| gccactggta acaggattag cagagcgagg tatgtaggcg gtgctacaga gttcttgaag | 4860 |
| tggtggccta actacggcta cactagaagg acagtatttg gtatctgcgc tctgctgaag | 4920 |
| ccagttacct tcggaaaaag agttggtagc tcttgatccg gcaaacaaac caccgctggt | 4980 |
| agcggtggtt ttttgtttg caagcagcag attacgcgca gaaaaaagg atctcaagaa | 5040 |
| gatcctttga tcttttctac ggggtctgac gctcagtgga acgaaaactc acgttaaggg | 5100 |
| attttggtca tgagattatc aaaaaggatc ttcacctaga tccttttaaa ttaaaaatga | 5160 |
| agttttaaat caatctaaag tatatatgag taaacttggt ctgacagtta ccaatgctta | 5220 |
| atcagtgagg cacctatctc agcgatctgt ctatttcgtt catccatagt tgcctgactg | 5280 |
| cccgtcgtgt agataactac gatacgggag ggcttaccat ctggccccag tgctgcaatg | 5340 |
| ataccgcgag acccacgctc accggctcca gatttatcag caataaacca gccagccgga | 5400 |
| agggccgagc gcagaagtgg tcctgcaact ttatccgcct ccatccagtc tattaattgt | 5460 |
| tgccgggaag ctagagtaag tagttcgcca gttaatagtt tgcgcaacgt tgttgccatt | 5520 |
| gctacaggca tcgtggtgtc acgctcgtcg tttggtatgg cttcattcag ctccggttcc | 5580 |
| caacgatcaa ggcgagttac atgatccccc atgttgtgaa aaaagcggt tagctccttc | 5640 |
| ggtcctccga tcgttgtcag aagtaagttg gccgcagtgt tatcactcat ggttatggca | 5700 |
| gcactgcata attctcttac tgtcatgcca tccgtaagat gcttttctgt gactggtgag | 5760 |
| tactcaacca agtcattctg agaatagtgt atgcggcgac cgagttgctc ttgcccggcg | 5820 |
| tcaatacggg ataataccgc gccacatagc agaactttaa aagtgctcat cattggaaaa | 5880 |
| cgttcttcgg ggcgaaaact ctcaaggatc ttaccgctgt tgagatccag ttcgatgtaa | 5940 |
| cccactcgtg cacccaactg atcttcagca tcttttactt tcaccagcgt ttctgggtga | 6000 |
| gcaaaaacag gaaggcaaaa tgccgcaaaa aagggaataa gggcgacacg gaaatgttga | 6060 |
| atactcatac tcttcctttt tcaatattat tgaagcattt atcagggtta ttgtctcatg | 6120 |
| agcggataca tatttgaatg tatttagaaa aataaacaaa taggggttcc gcgcacattt | 6180 |
| ccccgaaaag tgccacctga cgtctaagaa accattatta tcatgacatt aacctataaa | 6240 |
| aataggcgta tcacgaggcc ctttcgtc | 6268 |

<210> SEQ ID NO 47
<211> LENGTH: 6256
<212> TYPE: DNA
<213> ORGANISM: Artificial Sequence
<220> FEATURE:
<223> OTHER INFORMATION: Codon Optimized

<400> SEQUENCE: 47

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accacgcttt tcaattcaat tcatcatttt ttttttattc ttttttttga tttcggtttc | 240 |
| tttgaaattt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |

```
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttccatg gagggcacag ttaagccgct aaaggcatta tccgccaagt    660 acaattttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg aagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aatttttgtt aaatcagctc attttttaac caataggccg aaatcggcaa atcccttat   1440 aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttgggt cgaggtgccg taaagcacta   1620
aatcggaacc ctaaagggag ccccgattt agagcttgac ggggaaagcc ggcgaacgtg   1680
gcgagaaagg aagggaagaa agcgaaagga gcggggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctgggta attaatcagc   2280 gaagcgatga ttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tcccatctat ttcactgct gttttgttcg   2520 ctgcttcttc tgctttggct gctccagttg cttcaagttc acattaccac gaaatcaaca   2580
atttcattaa caacaaaccc attaaattta gttatttctc ttcaaggttg tattgcagtg   2640
ccaagccaat agtacacaga gaaaacaagt tcacaaaatc attctcacta tcacacttac   2700
aacgtaaatc ttctatcaag gcccatggag agatagaggc tgatggaagt aacgggactt   2760
```

```
ctgagttcaa cgtaatgaag tccggaaatg ctatctggag atttgtgagg ccgtatgccg   2820
ctaaaggtgt cctgtttaac tccgcggcaa tgttcgctaa ggaacttgtt ggaaatctga   2880
acttatttag ctggccgttg atgttcaaga tcctttcatt tactcttgtc attctgtgta   2940
tctttgtatc tacatcaggc ataaatcaga tatatgatct agacatcgat agactgaaca   3000
aaccgaactt gcccgtggca agcggggaaa ttagcgtaga attggcatgg ttacttacta   3060
tagtatgtac gattagtgga cttaccttaa ccattataac taatagtggc ccctttttc    3120 cgttccttta ctcagcctcc atattctttg gtttcctata ctccgccccc ccgttccgtt   3180
ggaagaaaaa cccctttacc gcctgctttt gcaatgtgat gttatacgtg gaaccagtg    3240 ttggggttta ttatgcctgc aaagccagtt tgggccttcc tgccaattgg tctccagcat   3300
tctgcctttt attttggttt attagtctgc tttccatacc tatcagcata gctaaggatt   3360
tatctgatat tgaaggtgat aggaagtttg gaatcattac tttctctact aagttcgggg   3420
caaaaccgat cgcgtacata tgtcacgggc ttatgctttt gaattacgtg agtgttatgg   3480
ccgcggccat aatatggcct caattcttca actcctcagt aatactgtta tcacatgcct   3540
tcatggcgat ctgggttttg taccaagcgt ggatactgga gaaaagtaac tatgcaacgg   3600
aaacttgcca gaaatattac atcttcttat ggataatatt ctcccttgag cacgcttttt   3660
acctattcat gtaggatggg ctgcaggaat tcgatatcaa gcttatcgat accgtcgacc   3720
tcgagtcatg taattagtta tgtcacgctt acattcacgc cctcccccca catccgctct   3780
aaccgaaaag gaaggagtta gacaacctga agtctaggtc cctatttatt tttttatagt   3840
tatgttagta ttaagaacgt tatttatatt tcaaattttt cttttttttc tgtacagacg   3900
cgtgtacgca tgtaacatta tactgaaaac cttgcttgag aaggtttggg gacgctcgaa   3960
ggctttaatt tgcggccggt acccagcttt tgttcccttt agtgagggtt aattccgagc   4020
ttggcgtaat catggtcata gctgtttcct gtgtgaaatt gttatccgct cacaattcca   4080
cacaacatag gagccggaag cataaagtgt aaagcctggg gtgcctaatg agtgaggtaa   4140
ctcacattaa ttgcgttgcg ctcactgccc gctttccagt cgggaaacct gtcgtgccag   4200
ctgcattaat gaatcggcca acgcgcgggg agaggcggtt tgcgtattgg gcgctcttcc   4260
gcttcctcgc tcactgactc gctgcgctcg gtcgttcggc tgcggcgagc ggtatcagct   4320
cactcaaagg cggtaatacg gttatccaca gaatcagggg ataacgcagg aaagaacatg   4380
tgagcaaaag gccagcaaaa ggccaggaac cgtaaaaagg ccgcgttgct ggcgtttttc   4440
cataggctcg gcccccctga cgagcatcac aaaaatcgac gctcaagtca gaggtggcga   4500
aacccgacag gactataaag ataccaggcg ttccccctg gaagctccct cgtgcgctct   4560
cctgttccga ccctgccgct taccggatac ctgtccgcct ttctcccttc gggaagcgtg   4620
gcgctttctc aatgctcacg ctgtaggtat ctcagttcgg tgtaggtcgt tcgctccaag   4680
ctgggctgtg tgcacgaacc ccccgttcag cccgaccgct gcgccttatc cggtaactat   4740
cgtcttgagt ccaacccggt aagacacgac ttatcgccac tggcagcagc cactggtaac   4800
aggattagca gagcgaggta tgtaggcggt gctacagagt tcttgaagtg gtggcctaac   4860
tacggctaca ctagaaggac agtatttggt atctgcgctc tgctgaagcc agttaccttc   4920
ggaaaaagag ttggtagctc ttgatccggc aaacaaacca ccgctggtag cggtggtttt   4980
tttgtttgca agcagcagat tacgcgcaga aaaaaaggat ctcaagaaga tcctttgatc   5040
ttttctacgg ggtctgacgc tcagtggaac gaaaactcac gttaagggat tttggtcatg   5100
agattatcaa aaaggatctt cacctagatc cttttaaatt aaaaatgaag ttttaaatca   5160
```

```
atctaaagta tatatgagta aacttggtct gacagttacc aatgcttaat cagtgaggca    5220
cctatctcag cgatctgtct atttcgttca tccatagttg cctgactgcc cgtcgtgtag    5280
ataactacga tacgggaggg cttaccatct ggccccagtg ctgcaatgat accgcgagac    5340
ccacgctcac cggctccaga tttatcagca ataaaccagc cagccggaag ggccgagcgc    5400
agaagtggtc ctgcaacttt atccgcctcc atccagtcta ttaattgttg ccgggaagct    5460
agagtaagta gttcgccagt taatagtttg cgcaacgttg ttgccattgc tacaggcatc    5520
gtggtgtcac gctcgtcgtt tggtatggct tcattcagct ccggttccca acgatcaagg    5580
cgagttacat gatcccccat gttgtgaaaa aaagcggtta gctccttcgg tcctccgatc    5640
gttgtcagaa gtaagttggc cgcagtgtta tcactcatgg ttatggcagc actgcataat    5700
tctcttactg tcatgccatc cgtaagatgc ttttctgtga ctggtgagta ctcaaccaag    5760
tcattctgag aatagtgtat gcggcgaccg agttgctctt gcccggcgtc aatacgggat    5820
aataccgcgc cacatagcag aactttaaaa gtgctcatca ttggaaaacg ttcttcgggg    5880
cgaaaactct caaggatctt accgctgttg agatccagtt cgatgtaacc cactcgtgca    5940
cccaactgat cttcagcatc ttttactttc accagcgttt ctgggtgagc aaaaacagga    6000
aggcaaaatg ccgcaaaaaa gggaataagg gcgacacgga aatgttgaat actcatactc    6060
ttcctttttc aatattattg aagcatttat cagggttatt gtctcatgag cggatacata    6120
tttgaatgta tttagaaaaa taaacaaata ggggttccgc gcacatttcc ccgaaaagtg    6180
ccacctgacg tctaagaaac cattattatc atgacattaa cctataaaaa taggcgtatc    6240
acgaggccct ttcgtc                                                    6256
```

<210> SEQ ID NO 48
<211> LENGTH: 648
<212> TYPE: DNA
<213> ORGANISM: Artificial Sequence
<220> FEATURE:
<223> OTHER INFORMATION: Codon Optimized

<400> SEQUENCE: 48

```
atgagcatcg aaatggcctg ggtcctgacc atattctgtg ctatcagtgg gttaatactt     60
acaatcacta tgaacagcgg ccctctattt ccattcttgt actgtggatc tatatttgtt    120
gctggctttc tatatagtgc tccgcccttc agatttaaga ataaccactt cactgccctg    180
ctgtgtaatt acgtaatgtt tgtcagcaca acccttcaga tatactgcgc atacaaggcg    240
ggccttggcc ttccactgaa ttggagcccc gcgttctgcc tattagtgtg gttcttgtca    300
ttaatcgctg tcactatatg tattggcaaa gatttgtcag acattgaagg cgatagaaag    360
ttcggcgtaa caaccttccc gacagaatac ggggcaaagc cctagcgct aatttgccac    420 ggcctgattc tattagacta cgtgggtctg atggcagccg ccataatctg gccgcagtta    480
ttcaactcta agctaatcct actgtctcat gcgtttatgg ccgtgtgggt cgtttatcag    540
gcttggattt tggaaaagag caattatacg accgaggcat gtcaaaagta ctatatgtac    600
ttatggacga tctattctgt cgagcacatc ttatatctgt tcatgtag                 648
```

<210> SEQ ID NO 49
<211> LENGTH: 423
<212> TYPE: DNA
<213> ORGANISM: Artificial Sequence
<220> FEATURE:
<223> OTHER INFORMATION: Codon Optimized

```
<400> SEQUENCE: 49
atggcataca aggcgggcct tggccttcca ctgaattgga gccccgcgtt ctgcctatta      60
gtgtggttct tgtcattaat cgctgtcact atatgtattg caaagatttt gtcagacatt     120
gaaggcgata gaaagttcgg cgtaacaacc ttcccgacag aatacggggc aaagcccata     180
gcgctaattt gccacggcct gattctatta gactacgtgg gtctgatggc agccgccata     240
atctggccgc agttattcaa ctctaagcta atcctactgt ctcatgcgtt tatggccgtg     300
tgggtcgttt atcaggcttg gattttggaa aagagcaatt atacgaccga ggcatgtcaa     360
aagtactata tgtacttatg gacgatctat tctgtcgagc acatcttata tctgttcatg     420
tag                                                                   423

<210> SEQ ID NO 50
<211> LENGTH: 485
<212> TYPE: DNA
<213> ORGANISM: Artificial Sequence
<220> FEATURE:
<223> OTHER INFORMATION: Codon Optimized

<400> SEQUENCE: 50
atgagattcc catctatttt cactgctgtt tgttcgctg cttcttctgc tttggctgct       60
ccagttcata caaggcgggc cttggccttc cactgaattg agccccgcg ttctgcctat      120 tagtgtggtt cttgtcatta atcgctgtca ctatatgtat tggcaaagat tgtcagaca     180 ttgaaggcga tagaaagttc ggcgtaacaa ccttcccgac agaatacggg gcaaagccca     240
tagcgctaat ttgccacggc ctgattctat tagactacgt gggtctgatg gcagccgcca     300
taatctggcc gcagttattc aactctaagc taatcctact gtctcatgcg tttatggccg     360
tgtgggtcgt ttatcaggct tggattttgg aaaagagcaa ttatacgacc gaggcatgtc     420
aaaagtacta tatgtactta tggacgatct attctgtcga gcacatctta tatctgttca     480
tgtag                                                                 485

<210> SEQ ID NO 51
<211> LENGTH: 5713
<212> TYPE: DNA
<213> ORGANISM: Artificial Sequence
<220> FEATURE:
<223> OTHER INFORMATION: Codon Optimized

<400> SEQUENCE: 51
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc tttttttga tttcggtttc     240 tttgaaattt ttttgattcg gtaatctccg aacagaagga agaacgaagg aaggagcaca     300
gacttagatt ggtatatata cgcatatgta gtgttgaaga acatgaaat tgcccagtat     360 tcttaaccca actgcacaga caaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aatttgttt actaaaaaca catgtggata     600
tcttgactga ttttccatg gagggcacag ttaagccgct aaaggcatta tccgccaagt     660
acaatttttt actcttcgaa gacagaaaat ttgctgacat tggtaataca gtcaaattgc     720
```

```
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aattttttgtt aaatcagctc attttttaac caataggccg aaatcggcaa aatcccttat   1440
aaatcaaaag aatagaccga tagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttgggt cgaggtgccg taaagcacta   1620
aatcggaacc ctaaagggag ccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttgatct attaacagat atataaatgg aaaagctgca taaccacttt   2340
aactaatact ttcaacattt tcagtttgta ttacttctta ttcaaatgtc ataaagtat   2400
caacaaaaaa ttgttaatat acctctatac tttaacgtca aggagaaaaa accccggatt   2460
ctagaactag tggatccccc atcatgagca tcgaaatggc ctgggtcctg accatattct   2520
gtgctatcag tgggttaata cttacaatca ctatgaacag cggccctcta tttccattct   2580
tgtactgtgg atctatattt gttgctggct ttctatatag tgctccgccc ttcagattta   2640
agaataacca cttcactgcc ctgctgtgta attacgtaat gtttgtcagc caacccttc    2700
agatatactg cgcatacaag gcgggccttg gccttccact gaattggagc cccgcgttct   2760
gcctattagt gtggttcttg tcattaatcg ctgtcactat atgtattggc aaagatttgt   2820
cagacattga aggcgataga aagttcggcg taacaacctt cccgacagaa tacgggggcaa   2880
agcccatagc gctaatttgc cacggcctga ttctattaga ctacgtgggt ctgatggcag   2940
ccgccataat ctgccgcag ttattcaact ctaagctaat cctactgtct catgcgttta   3000
tggccgtgtg ggtcgtttat caggcttgga ttttggaaaa gagcaattat acgaccgagg   3060
```

```
catgtcaaaa gtactatatg tacttatgga cgatctattc tgtcgagcac atcttatatc    3120
tgttcatgta ggatgggctg caggaattcg atatcaagct tatcgatacc gtcgacctcg    3180
agtcatgtaa ttagttatgt cacgcttaca ttcacgccct ccccccacat ccgctctaac    3240
cgaaaaggaa ggagttagac aacctgaagt ctaggtccct atttattttt ttatagttat    3300
gttagtatta agaacgttat ttatatttca aattttcctt tttttttctgt acagacgcgt    3360
gtacgcatgt aacattatac tgaaaacctt gcttgagaag gttttgggac gctcgaaggc    3420
tttaatttgc ggccggtacc cagcttttgt tcccttttagt gagggttaat tccgagcttg    3480
gcgtaatcat ggtcatagct gtttcctgtg tgaaattgtt atccgctcac aattccacac    3540
aacataggag ccggaagcat aaagtgtaaa gcctggggtg cctaatgagt gaggtaactc    3600
acattaattg cgttgcgctc actgcccgct ttccagtcgg gaaacctgtc gtgccagctg    3660
cattaatgaa tcggccaacg cgcggggaga ggcggtttgc gtattgggcg ctcttccgct    3720
tcctcgctca ctgactcgct gcgctcggtc gttcggctgc ggcgagcggt atcagctcac    3780
tcaaaggcgg taatacggtt atccacagaa tcagggggata cgcaggaaa gaacatgtga    3840
gcaaaaggcc agcaaaaggc caggaaccgt aaaaaggccg cgttgctggc gtttttccat    3900
aggctcggcc cccctgacga gcatcacaaa aatcgacgct caagtcagag gtggcgaaac    3960
ccgacaggac tataaagata ccaggcgttc cccctggaa gctccctcgt gcgctctcct    4020
gttccgaccc tgccgcttac cggatacctg tccgcctttc tcccttcggg aagcgtggcg    4080
ctttctcaat gctcacgctg taggtatctc agttcggtgt aggtcgttcg ctccaagctg    4140
ggctgtgtgc acgaaccccc cgttcagccc gaccgctgcg ccttatccgg taactatcgt    4200
cttgagtcca acccggtaag acacgactta tcgccactgg cagcagccac tggtaacagg    4260
attagcagag cgaggtatgt aggcggtgct acagagttct tgaagtggtg gcctaactac    4320
ggctacacta aaggacagt atttggtatc tgcgctctgc tgaagccagt taccttcgga    4380
aaaagagttg gtagctcttg atccggcaaa caaaccaccg ctggtagcgg tggtttttttt   4440
gtttgcaagc agcagattac gcgcagaaaa aaaggatctc aagaagatcc tttgatcttt    4500
tctacggggt ctgacgctca gtggaacgaa aactcacgtt aagggatttt ggtcatgaga    4560
ttatcaaaaa ggatcttcac ctagatcctt ttaaattaaa aatgaagttt taaatcaatc    4620
taaagtatat atgagtaaac ttggtctgac agttaccaat gcttaatcag tgaggcacct    4680
atctcagcga tctgtctatt tcgttcatcc atagttgcct gactgcccgt cgtgtagata    4740
actacgatac gggagggctt accatctggc cccagtgctg caatgatacc gcgagaccca    4800
cgctcaccgg ctccagattt atcagcaata aaccagccag ccggaagggc cgagcgcaga    4860
agtggtcctg caactttatc cgcctccatc cagtctatta attgttgccg gaagctaga    4920
gtaagtagtt cgccagttaa tagtttgcgc aacgttgttg ccattgctac aggcatcgtg    4980
gtgtcacgct cgtcgtttgg tatggcttca ttcagctccg gttcccaacg atcaaggcga    5040
gttacatgat cccccatgtt gtgaaaaaaa gcggttagct ccttcggtcc tccgatcgtt    5100
gtcagaagta agttggccgc agtgttatca ctcatggtta tggcagcact gcataattct    5160
cttactgtca tgccatccgt aagatgcttt tctgtgactg gtgagtactc aaccaagtca    5220
ttctgagaat agtgtatgcg gcgaccgagt tgctcttgcc cggcgtcaat acgggataat    5280
accgcgccac atagcagaac tttaaaagtg ctcatcattg gaaaacgttc ttcggggcga    5340
aaactctcaa ggatcttacc gctgttgaga tccagttcga tgtaacccac tcgtgcaccc    5400
aactgatctt cagcatcttt tactttcacc agcgtttctg ggtgagcaaa aacaggaagg    5460
```

-continued

| | |
|---|---|
| caaaatgccg caaaaaggg aataagggcg acacggaaat gttgaatact catactcttc | 5520 |
| cttttcaat attattgaag catttatcag ggttattgtc tcatgagcgg atacatattt | 5580 |
| gaatgtattt agaaaaataa acaaataggg gttccgcgca catttccccg aaaagtgcca | 5640 |
| cctgacgtct aagaaaccat tattatcatg acattaacct ataaaaatag gcgtatcacg | 5700 |
| aggccctttc gtc | 5713 |

<210> SEQ ID NO 52
<211> LENGTH: 5488
<212> TYPE: DNA
<213> ORGANISM: Artificial Sequence
<220> FEATURE:
<223> OTHER INFORMATION: Codon Optimized

<400> SEQUENCE: 52

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accacgcttt tcaattcaat tcatcatttt ttttttattc ttttttttga tttcggtttc | 240 |
| tttgaaattt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |
| tactggagtt agttgaagca ttaggtccca aaatttgttt actaaaaaca catgtggata | 600 |
| tcttgactga tttttccatg gagggcacag ttaagccgct aaaggcatta tccgccaagt | 660 |
| acaattttt actcttcgaa gacagaaaat ttgctgacat tggtaataca gtcaaattgc | 720 |
| agtactctgc gggtgtatac agaatagcag aatgggcaga cattacgaat gcacgcggtg | 780 |
| tggtgggccc aggtattgtt agcggtttga agcaggcggc agaagaagta acaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag ttacgattg gttgattatg acacccggtg | 1020 |
| tgggtttaga tgacaaggga gacgcattgg gtcaacagta tagaaccgtg atgatgtgg | 1080 |
| tctctacagg atctgacatt attattgttg gaagaggact atttgcaaag gaagggatg | 1140 |
| ctaaggtaga gggtgaacgt tacagaaaag caggctggga agcatatttg agaagatgcg | 1200 |
| gccagcaaaa ctaaaaaact gtattataag taaatgcatg tatactaaac tcacaaatta | 1260 |
| gagcttcaat ttaattatat cagttattac cctgcggtgt gaaataccgc acagatgcgt | 1320 |
| aaggagaaaa taccgcatca ggaaattgta acgttaata ttttgttaaa attcgcgtta | 1380 |
| aatttttgtt aaatcagctc atttttaac caataggccg aaatcggcaa atcccttat | 1440 |
| aaatcaaaag aatagaccga gatagggttg agtgttgttc cagtttggaa caagagtcca | 1500 |
| ctattaaaga acgtggactc caacgtcaaa gggcgaaaaa ccgtctatca gggcgatggc | 1560 |
| ccactacgtg aaccatcacc ctaatcaagt ttttgggt cgaggtgccg taaagcacta | 1620 |
| aatcggaacc ctaaagggag ccccccgattt agagcttgac ggggaaagcc ggcgaacgtg | 1680 |
| gcgagaaagg aagggaagaa agcgaaagga gcgggcgcta gggcgctggc aagtgtagcg | 1740 |

```
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta aagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga tttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggcat acaaggcggg ccttggcctt ccactgaatt    2520
ggagccccgc gttctgccta ttagtgtggt tcttgtcatt aatcgctgtc actatatgta    2580
ttggcaaaga tttgtcagac attgaaggcg atagaaagtt cggcgtaaca accttcccga    2640
cagaatacgg ggcaaagccc atagcgctaa tttgccacgg cctgattcta ttagactacg    2700
tgggtctgat ggcagccgcc ataatctggc cgcagttatt caactctaag ctaatcctac    2760
tgtctcatgc gtttatggcc gtgtgggtcg tttatcaggc ttggattttg gaaagagca    2820
attatacgac cgaggcatgt caaaagtact atatgtactt atggacgatc tattctgtcg    2880
agcacatctt atatctgttc atgtaggatg ggctgcagga attcgatatc aagcttatcg    2940
ataccgtcga cctcgagtca tgtaattagt tatgtcacgc ttacattcac gccctccccc    3000
cacatccgct ctaaccgaaa aggaaggagt tagacaacct gaagtctagg tccctattta    3060
ttttttata gttatgttag tattaagaac gttatttata tttcaaattt ttcttttttt    3120
tctgtacaga cgcgtgtacg catgtaacat tatactgaaa accttgcttg agaaggtttt    3180
gggacgctcg aaggctttaa tttgcggccg gtacccagct tttgttccct ttagtgaggg    3240
ttaattccga gcttggcgta atcatggtca tagctgtttc ctgtgtgaaa ttgttatccg    3300
ctcacaattc cacacaacat aggagccgga agcataaagt gtaaagcctg gggtgcctaa    3360
tgagtgaggt aactcacatt aattgcgttg cgctcactgc ccgctttcca gtcgggaaac    3420
ctgtcgtgcc agctgcatta tgaatcggc caacgcgcgg ggagaggcgg tttgcgtatt    3480
gggcgctctt ccgcttcctc gctcactgac tcgctgcgct cggtcgttcg gctgcggcga    3540
gcggtatcag ctcactcaaa ggcggtaata cggttatcca cagaatcagg gataacgca    3600
ggaaagaaca tgtgagcaaa aggccagcaa aaggccagga accgtaaaaa ggccgcgttg    3660
ctggcgtttt tccataggct cggcccccct gacgagcatc acaaaaatcg acgctcaagt    3720
cagaggtggc gaaacccgac aggactataa agataccagg cgttccccc tggaagctcc    3780
ctcgtgcgct ctcctgttcc gaccctgccg cttaccggat acctgtccgc ctttctccct    3840
tcgggaagcg tggcgctttc tcaatgctca cgctgtaggt atctcagttc ggtgtaggtc    3900
gttcgctcca agctgggctg tgtgcacgaa ccccccgttc agcccgaccg ctgcgcctta    3960
tccggtaact atcgtcttga gtccaaccg gtaagacacg acttatcgcc actggcagca    4020
gccactggta acaggattag cagagcgagg tatgtaggcg gtgctacaga gttcttgaag    4080
tggtggccta actacggcta cactagaagg acagtatttg gtatctgcgc tctgctgaag    4140
```

```
ccagttacct tcggaaaaag agttggtagc tcttgatccg gcaaacaaac caccgctggt    4200
agcggtggtt ttttttgtttg caagcagcag attacgcgca gaaaaaaagg atctcaagaa   4260
gatcctttga tcttttctac ggggtctgac gctcagtgga acgaaaactc acgttaaggg   4320
attttggtca tgagattatc aaaaaggatc ttcacctaga tccttttaaa ttaaaaatga   4380
agttttaaat caatctaaag tatatatgag taaacttggt ctgacagtta ccaatgctta   4440
atcagtgagg cacctatctc agcgatctgt ctatttcgtt catccatagt tgcctgactg   4500
cccgtcgtgt agataactac gatacgggag ggcttaccat ctggccccag tgctgcaatg   4560
ataccgcgag acccacgctc accggctcca gatttatcag caataaacca gccagccgga   4620
agggccgagc gcagaagtgg tcctgcaact ttatccgcct ccatccagtc tattaattgt   4680
tgccgggaag ctagagtaag tagttcgcca gttaatagtt tgcgcaacgt tgttgccatt   4740
gctacaggca tcgtggtgtc acgctcgtcg tttggtatgg cttcattcag ctccggttcc   4800
caacgatcaa ggcgagttac atgatccccc atgttgtgaa aaaagcggt tagctccttc    4860 ggtcctccga tcgttgtcag aagtaagttg gccgcagtgt tatcactcat ggttatggca   4920
gcactgcata attctcttac tgtcatgcca tccgtaagat gcttttctgt gactggtgag   4980
tactcaacca agtcattctg agaatagtgt atgcggcgac cgagttgctc ttgcccggcg   5040
tcaatacggg ataataccgc gccacatagc agaactttaa aagtgctcat cattggaaaa   5100
cgttcttcgg ggcgaaaact ctcaaggatc ttaccgctgt tgagatccag ttcgatgtaa   5160
cccactcgtg cacccaactg atcttcagca tcttttactt tcaccagcgt ttctgggtga   5220
gcaaaaacag gaaggcaaaa tgccgcaaaa aagggaataa gggcgacacg aaatgttga    5280 atactcatac tcttcctttt tcaatattat tgaagcattt atcagggtta ttgtctcatg   5340
agcggataca tatttgaatg tatttagaaa aataaacaaa tagggggttcc gcgcacattt    5400 ccccgaaaag tgccacctga cgtctaagaa accattatta tcatgacatt aacctataaa   5460
aataggcgta tcacgaggcc ctttcgtc                                        5488

<210> SEQ ID NO 53
<211> LENGTH: 5550
<212> TYPE: DNA
<213> ORGANISM: Artificial Sequence
<220> FEATURE:
<223> OTHER INFORMATION: Codon Optimized

<400> SEQUENCE: 53
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accacgcttt tcaattcaat tcatcatttt ttttttattc tttttttttga tttcggtttc    240 tttgaaattt ttttgattcg gtaatctccg aacagaagga agaacgaagg aaggagcaca    300
gacttagatt ggtatatata cgcatatgta gtgttgaaga acatgaaat tgcccagtat    360 tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660
```

-continued

```
acaattttt  actcttcgaa  gacagaaaat  ttgctgacat  tggtaataca  gtcaaattgc   720
agtactctgc  gggtgtatac  agaatagcag  aatgggcaga  cattacgaat  gcacacggtg   780
tggtgggccc  aggtattgtt  agcggtttga  agcaggcggc  agaagaagta  acaaaggaac   840
ctagaggcct  tttgatgtta  gcagaattgt  catgcaaggg  ctccctatct  actggagaat   900
atactaaggg  tactgttgac  attgcgaaga  gcgacaaaga  ttttgttatc  ggctttattg   960
ctcaaagaga  catgggtgga  agagatgaag  gttacgattg  gttgattatg  acacccggtg  1020
tgggtttaga  tgacaaggga  gacgcattgg  gtcaacagta  tagaaccgtg  gatgatgtgg  1080
tctctacagg  atctgacatt  attattgttg  gaagaggact  atttgcaaag  ggaagggatg  1140
ctaaggtaga  gggtgaacgt  tacagaaaag  caggctggga  agcatatttg  agaagatgcg  1200
gccagcaaaa  ctaaaaaact  gtattataag  taaatgcatg  tatactaaac  tcacaaatta  1260
gagcttcaat  ttaattatat  cagttattac  cctgcggtgt  gaaataccgc  acagatgcgt  1320
aaggagaaaa  taccgcatca  ggaaattgta  aacgttaata  ttttgttaaa  attcgcgtta  1380
aatttttgtt  aaatcagctc  attttttaac  caataggccg  aaatcggcaa  aatcccttat  1440
aaatcaaaag  aatagaccga  gatagggttg  agtgttgttc  cagtttggaa  caagagtcca  1500
ctattaaaga  acgtggactc  caacgtcaaa  gggcgaaaaa  ccgtctatca  gggcgatggc  1560
ccactacgtg  aaccatcacc  ctaatcaagt  tttttggggt  cgaggtgccg  taaagcacta  1620
aatcggaacc  ctaaagggag  cccccgattt  agagcttgac  ggggaaagcc  ggcgaacgtg  1680
gcgagaaagg  aagggaagaa  agcgaaagga  gcgggcgcta  gggcgctggc  aagtgtagcg  1740
gtcacgctgc  gcgtaaccac  cacacccgcc  gcgcttaatg  cgccgctaca  gggcgcgtcg  1800
cgccattcgc  cattcaggct  gcgcaactgt  tgggaagggc  gatcggtgcg  ggcctcttcg  1860
ctattacgcc  agctggcgaa  gggggatgt  gctgcaaggc  gattaagttg  ggtaacgcca  1920
gggttttccc  agtcacgacg  ttgtaaaacg  acggccagtg  aattgtaata  cgactcacta  1980
tagggcgaat  tggagctcta  gtacggatta  gaagccgccg  agcgggcgac  agccctccga  2040
cggaagactc  tcctccgtgc  gtcctcgtct  tcaccggtcg  cgttcctgaa  acgcagatgt  2100
gcctcgcgcc  gcactgctcc  gaacaataaa  gattctacaa  tactagcttt  tatggttatg  2160
aagaggaaaa  attggcagta  acctggcccc  acaaaccttc  aaattaacga  atcaaattaa  2220
caaccatagg  atgataatgc  gattagtttt  ttagccttat  ttctggggta  attaatcagc  2280
gaagcgatga  ttttgatct  attaacagat  atataaatgg  aaaagctgca  taaccacttt  2340
aactaatact  ttcaacattt  tcagtttgta  ttacttctta  ttcaaatgtc  ataaaagtat  2400
caacaaaaaa  ttgttaatat  acctctatac  tttaacgtca  aggagaaaaa  accccggatt  2460
ctagaactag  tggatccccc  atcatgagat  tcccatctat  tttcactgct  gttttgttcg  2520
ctgcttcttc  tgctttggct  gctccagttc  atacaaggcg  ggccttggcc  ttccactgaa  2580
ttggagcccc  gcgttctgcc  tattagtgtg  gttcttgtca  ttaatcgctg  tcactatatg  2640
tattggcaaa  gatttgtcag  acattgaagg  cgatagaaag  ttcggcgtaa  caaccttccc  2700
gacagaatac  ggggcaaagc  ccatagcgct  aatttgccac  ggcctgattc  tattagacta  2760
cgtgggtctg  atggcagccg  ccataatctg  gccgcagtta  ttcaactcta  agctaatcct  2820
actgtctcat  gcgtttatgg  ccgtgtgggt  cgtttatcag  gcttggattt  tggaaaagag  2880
caattatacg  accgaggcat  gtcaaaagta  ctatatgtac  ttatggacga  tctattctgt  2940
cgagcacatc  ttatatctgt  tcatgtagga  tgggctgcag  gaattcgata  tcaagcttat  3000
cgataccgtc  gacctcgagt  catgtaatta  gttatgtcac  gcttacattc  acgccctccc  3060
```

```
cccacatccg ctctaaccga aaaggaagga gttagacaac ctgaagtcta ggtccctatt    3120
tattttttta tagttatgtt agtattaaga acgttattta tatttcaaat ttttcttttt    3180
tttctgtaca gacgcgtgta cgcatgtaac attatactga aaaccttgct tgagaaggtt    3240
ttgggacgct cgaaggcttt aatttgcggc cggtacccag cttttgttcc ctttagtgag    3300
ggttaattcc gagcttggcg taatcatggt catagctgtt tcctgtgtga aattgttatc    3360
cgctcacaat tccacacaac ataggagccg aagcataaa  gtgtaaagcc tggggtgcct    3420
aatgagtgag gtaactcaca ttaattgcgt tgcgctcact gcccgctttc cagtcgggaa    3480
acctgtcgtg ccagctgcat taatgaatcg gccaacgcgc ggggagaggc ggtttgcgta    3540
ttgggcgctc ttccgcttcc tcgctcactg actcgctgcg ctcggtcgtt cggctgcggc    3600
gagcggtatc agctcactca aaggcggtaa tacggttatc cacagaatca ggggataacg    3660
caggaaagaa catgtgagca aaaggccagc aaaaggccag gaaccgtaaa aaggccgcgt    3720
tgctggcgtt tttccatagg ctcggccccc ctgacgagca tcacaaaaat cgacgctcaa    3780
gtcagaggtg gcgaaacccg acaggactat aaagatacca ggcgttcccc cctggaagct    3840
ccctcgtgcg ctctcctgtt ccgaccctgc cgcttaccgg atacctgtcc gcctttctcc    3900
cttcgggaag cgtggcgctt tctcaatgct cacgctgtag gtatctcagt tcggtgtagg    3960
tcgttcgctc caagctgggc tgtgtgcacg aaccccccgt tcagcccgac cgctgcgcct    4020
tatccggtaa ctatcgtctt gagtccaacc cggtaagaca cgacttatcg ccactggcag    4080
cagccactgg taacaggatt agcagagcga ggtatgtagg cggtgctaca gagttcttga    4140
agtggtggcc taactacggc tacactagaa ggacagtatt tggtatctgc gctctgctga    4200
agccagttac cttcggaaaa agagttggta gctcttgatc cggcaaacaa accaccgctg    4260
gtagcggtgg tttttttgtt tgcaagcagc agattacgcg cagaaaaaaa ggatctcaag    4320
aagatccttt gatcttttct acggggtctg acgctcagtg gaacgaaaac tcacgttaag    4380
ggattttggt catgagatta tcaaaaagga tcttcaccta gatcctttta aattaaaaat    4440
gaagttttaa atcaatctaa agtatatatg agtaaacttg gtctgacagt taccaatgct    4500
taatcagtga ggcacctatc tcagcgatct gtctatttcg ttcatccata gttgcctgac    4560
tgcccgtcgt gtagataact acgatacggg agggcttacc atctggcccc agtgctgcaa    4620
tgataccgcg agacccacgc tcaccggctc cagatttatc agcaataaac cagccagccg    4680
gaagggccga gcgcagaagt ggtcctgcaa ctttatccgc ctccatccag tctattaatt    4740
gttgccggga agctagagta agtagttcgc cagttaatag tttgcgcaac gttgttgcca    4800
ttgctacagg catcgtggtg tcacgctcgt cgtttggtat ggcttcattc agctccggtt    4860
cccaacgatc aaggcgagtt acatgatccc ccatgttgtg aaaaaaagcg gttagctcct    4920
tcggtcctcc gatcgttgtc agaagtaagt tggccgcagt gttatcactc atggttatgg    4980
cagcactgca taattctctt actgtcatgc catccgtaag atgcttttct gtgactggtg    5040
agtactcaac caagtcattc tgagaatagt gtatgcggcg accgagttgc tcttgcccgg    5100
cgtcaatacg ggataatacc gcgccacata gcagaacttt aaaagtgctc atcattggaa    5160
aacgttcttc ggggcgaaaa ctctcaagga tcttaccgct gttgagatcc agttcgatgt    5220
aacccactcg tgcacccaac tgatcttcag catcttttac tttcaccagc gtttctgggt    5280
gagcaaaaac aggaaggcaa aatgccgcaa aaaagggaat aagggcgaca cggaaatgtt    5340
gaatactcat actcttcctt tttcaatatt attgaagcat ttatcagggt tattgtctca    5400
```

| | |
|---|---|
| tgagcggata catatttgaa tgtatttaga aaaataaaca aataggggtt ccgcgcacat | 5460 |
| ttccccgaaa agtgccacct gacgtctaag aaaccattat tatcatgaca ttaacctata | 5520 |
| aaaataggcg tatcacgagg ccctttcgtc | 5550 |

<210> SEQ ID NO 54
<211> LENGTH: 1155
<212> TYPE: DNA
<213> ORGANISM: Artificial Sequence
<220> FEATURE:
<223> OTHER INFORMATION: Codon Optimized

<400> SEQUENCE: 54

| | |
|---|---|
| atggaattat cattatctct gggcgggccg acgatattcc ccagatatag agcaagctat | 60 |
| acttccacta aactgaccac tcatttctct aattttccgt ccaaattcag cacaaaaaat | 120 |
| ttccaccaga cgctatcttt ctacggacca acgagaggca gcaaatcatt gttgaatacc | 180 |
| catcagtgga ggaactccat aagagcctgc gccgaggcgg gggctgccgg gtcaaacccg | 240 |
| gtgctaaaca aggtctctga cttagggac gcatgctggc gtttcttaag gccgcatact | 300 |
| ataaggggga ccaccctggg tagtatagcc ctagtagcaa gggcgcttat agaaaatccc | 360 |
| aacttaatca agtggagtct tttactgaag gctttctctg gcttactagc cttaatttgc | 420 |
| gggaacggct acattgtagg aatcaaccaa atctatgaca taggtattga taaggtcaac | 480 |
| aaaccgtacc ttcccatagc cgcgggtgat tgtcagtcc agagtgcttg gtaccttgta | 540 |
| atattgtttg ccgttgcggg tctactaact gttggcttca attttgggcc gttcattacg | 600 |
| tctctatact gcttaggact tgttctgggg acaatatata gcgttccacc ctttaggatg | 660 |
| aaagatttc cggttgcagc attcttaatc attgcgaccg tgaggggttt tctattaaac | 720 |
| tttggtgtat actacgccac aagagctgca ttgggcttaa cctttgaatg gagtagtgcg | 780 |
| gttgcgttca ttacgacctt cgttacatta ttcgctttgg tgatagctat aacgaaagat | 840 |
| ctgccagacg tggagggaga ccgtaaattt cagatcagca cattcgcaac aaagcttggt | 900 |
| gtgagaaaca tcgcgtatct tggatctgga ctattattat taaactacat tggggcaatt | 960 |
| gcggcggcca tttatatgcc tcaggctttt aagagaaatt taatgcttcc tatccacacc | 1020 |
| atcttggcgt tgagccttgt cttccaggcc tgggtcttgg aacaagcgaa ttacaccaag | 1080 |
| gaggctattg ctgggttcta tagattcatt tggaatttgt tctatgtaga atacattata | 1140 |
| ttccccttta tatag | 1155 |

<210> SEQ ID NO 55
<211> LENGTH: 933
<212> TYPE: DNA
<213> ORGANISM: Artificial Sequence
<220> FEATURE:
<223> OTHER INFORMATION: Codon Optimized

<400> SEQUENCE: 55

| | |
|---|---|
| atggccgggt caaacccggt gctaaacaag gtctctgact ttagggacgc atgctggcgt | 60 |
| ttcttaaggc cgcatactat aaggggggacc accctgggta gtatagccct agtagcaagg | 120 |
| gcgcttatag aaaatcccaa cttaatcaag tggagtcttt tactgaaggc tttctctggc | 180 |
| ttactagcct taatttgcgg gaacggctac attgtaggaa tcaaccaaat ctatgacata | 240 |
| ggtattgata aggtcaacaa accgtacctt cccatagccg cgggtgattt gtcagtccag | 300 |
| agtgcttggt accttgtaat attgtttgcc gttgcgggtc tactaactgt tggcttcaat | 360 |
| tttgggccgt tcattacgtc tctatactgc ttaggacttg ttctggggac aatatatagc | 420 |

```
gttccaccct ttaggatgaa aagatttccg gttgcagcat tcttaatcat tgcgaccgtg    480 agggqttttc tattaaactt tggtgtatac tacgccacaa gagctgcatt gggcttaacc    540
tttgaatgga gtagtgcggt tgcgttcatt acgaccttcg ttacattatt cgctttggtg    600
atagctataa cgaaagatct gccagacgtg gagggagacc gtaaatttca gatcagcaca    660
ttcgcaacaa agcttggtgt gagaaacatc gcgtatcttg atctggact attattatta    720 aactacattg gggcaattgc ggcggccatt tatatgcctc aggcttttaa gagaaattta    780
atgcttccta tccacaccat cttggcgttg agccttgtct tccaggcctg gtcttggaa    840 caagcgaatt acaccaagga ggctattgct gggttctata gattcatttg gaatttgttc    900
tatgtagaat acattatatt cccctttata tag                                 933

<210> SEQ ID NO 56
<211> LENGTH: 996
<212> TYPE: DNA
<213> ORGANISM: Artificial Sequence
<220> FEATURE:
<223> OTHER INFORMATION: Codon Optimized

<400> SEQUENCE: 56
atgagattcc catctatttt cactgctgtt ttgttcgctg cttcttctgc tttggctgct    60
ccagttgccg ggtcaaaccc ggtgctaaac aaggtctctg actttaggga cgcatgctgg    120
cgtttcttaa ggccgcatac tataaggggg accaccctgg gtagtatagc cctagtagca    180
agggcgctta tagaaaatcc caacttaatc aagtggagtc ttttactgaa ggctttctct    240
ggcttactag ccttaatttg cgggaacggc tacattgtag gaatcaacca aatctatgac    300
ataggtattg ataaggtcaa caaaccgtac cttcccatag ccgcgggtga tttgtcagtc    360
cagagtgctt ggtaccttgt aatattgttt gccgttgcgg gtctactaac tgttggcttc    420
aattttgggc cgttcattac gtctctatac tgcttaggac ttgttctggg gacaatatat    480
agcgttccac cctttaggat gaaaagattt ccggttgcag cattcttaat cattgcgacc    540
gtgaggggtt ttctattaaa ctttggtgta tactacgcca caagagctgc attgggctta    600
acctttgaat ggagtagtgc ggttgcgttc attacgacct tcgttacatt attcgctttg    660
gtgatagcta taacgaaaga tctgccagac gtggagggag accgtaaatt tcagatcagc    720
acattcgcaa caaagcttgg tgtgagaaac atcgcgtatc ttggatctgg actattatta    780
ttaaactaca ttggggcaat tgcggcggcc atttatatgc ctcaggcttt taagagaaat    840
ttaatgcttc ctatccacac catcttggcg ttgagccttg tcttccaggc ctgggtcttg    900
gaacaagcga attacaccaa ggaggctatt gctgggttct atagattcat ttggaatttg    960
ttctatgtag aatacattat attccccttt atatag                              996

<210> SEQ ID NO 57
<211> LENGTH: 6220
<212> TYPE: DNA
<213> ORGANISM: Artificial Sequence
<220> FEATURE:
<223> OTHER INFORMATION: Codon Optimized

<400> SEQUENCE: 57
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120 ttggcgggtg tcggqctgg cttaactatg cggcatcaga gcagattgta ctgagagtgc    180
```

```
accacgcttt tcaattcaat tcatcatttt tttttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat     360 tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttccatg gagggcacag ttaagccgct aaaggcatta tccgccaagt     660 acaattttt actcttcgaa gacagaaaat ttgctgacat tggtaataca gtcaaattgc     720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa atcccttat   1440 aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg gtaacgcca    1920 gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttgatct attaacagat atataaatgg aaaagctgca taaccacttt    2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggaat tatcattatc tctgggcggg ccgacgatat   2520
tccccagata tagagcaagc tatacttcca ctaaactgac cactcatttc tctaattttc   2580
```

```
cgtccaaatt cagcacaaaa aatttccacc agacgctatc tttctacgga ccaacgagag    2640
gcagcaaatc attgttgaat acccatcagt ggaggaactc cataagagcc tgcgccgagg    2700
cgggggctgc cggtcaaac ccggtgctaa acaaggtctc tgactttagg gacgcatgct    2760
ggcgtttctt aaggccgcat actataaggg ggaccaccct gggtagtata gccctagtag    2820
caagggcgct tatagaaaat cccaacttaa tcaagtggag tcttttactg aaggctttct    2880
ctggcttact agccttaatt tgcgggaacg gctacattgt aggaatcaac caaatctatg    2940
acataggtat tgataaggtc aacaaaccgt accttcccat agccgcgggt gatttgtcag    3000
tccagagtgc ttggtacctt gtaatattgt ttgccgttgc gggtctacta actgttggct    3060
tcaattttgg gccgttcatt acgtctctat actgcttagg acttgttctg gggacaatat    3120
atagcgttcc acccttaagg atgaaaagat ttccggttgc agcattctta atcattgcga    3180
ccgtgagggg ttttctatta aactttggtg tatactacgc cacaagagct gcattgggct    3240 taaccctttga atggagtagt gcggttgcgt tcattacgac cttcgttaca ttattcgctt    3300
tggtgatagc tataacgaaa gatctgccag acgtggaggg agaccgtaaa tttcagatca    3360
gcacattcgc aacaaagctt ggtgtgagaa acatcgcgta tcttggatct ggactattat    3420
tattaaacta cattggggca attgcggcgg ccatttatat gcctcaggct tttaagagaa    3480
atttaatgct tcctatccac accatcttgg cgttgagcct tgtcttccag gcctgggtct    3540
tggaacaagc gaattacacc aaggaggcta ttgctgggtt ctatagattc atttggaatt    3600
tgttctatgt agaatacatt atattcccct ttatatagga tgggctgcag gaattcgata    3660
tcaagcttat cgataccgtc gacctcgagt catgtaatta gttatgtcac gcttacattc    3720
acgccctccc cccacatccg ctctaaccga aaaggaagga gttagacaac ctgaagtcta    3780
ggtccctatt tatttttttta tagttatgtt agtattaaga acgttattta tatttcaaat    3840 tttttcttttt tttctgtaca gacgcgtgta cgcatgtaac attatactga aaaccttgct    3900
tgagaaggtt ttgggacgct cgaaggcttt aatttgcggc cggtacccag cttttgttcc    3960
ctttagtgag ggttaattcc gagcttggcg taatcatggt catagctgtt tcctgtgtga    4020
aattgttatc cgctcacaat tccacacaac ataggagccg gaagcataaa gtgtaaagcc    4080
tggggtgcct aatgagtgag gtaactcaca ttaattgcgt tgcgctcact gcccgctttc    4140
cagtcgggaa acctgtcgtg ccagctgcat taatgaatcg gccaacgcgc ggggagaggc    4200
ggtttgcgta ttgggcgctc ttccgcttcc tcgctcactg actcgctgcg ctcggtcgtt    4260
cggctgcggc gagcggtatc agctcactca aaggcggtaa tacggttatc cacagaatca    4320
ggggataacg caggaaagaa catgtgagca aaaggccagc aaaaggccag gaaccgtaaa    4380
aaggccgcgt tgctggcgtt tttccatagg ctccgccccc ctgacgagca tcacaaaaat    4440
cgacgctcaa gtcagaggtg gcgaaacccg acaggactat aaagatacca ggcgttcccc    4500
cctggaagct ccctcgtgcg ctctcctgtt ccgaccctgc cgcttaccgg atacctgtcc    4560
gcctttctcc cttcgggaag cgtggcgctt tctcaatgct cacgctgtag gtatctcagt    4620
tcggtgtagg tcgttcgctc caagctgggc tgtgtgcacg aacccccgt tcagcccgac    4680 cgctgcgcct tatccggtaa ctatcgtctt gagtccaacc cggtaagaca cgacttatcg    4740
ccactggcag cagccactgg taacaggatt agcagagcga ggtatgtagg cggtgctaca    4800
gagttcttga agtggtggcc taactacggc tacactagaa ggacagtatt tggtatctgc    4860
gctctgctga agccagttac cttcggaaaa agagttggta gctcttgatc cggcaaacaa    4920
```

```
accaccgctg gtagcggtgg ttttttttgtt tgcaagcagc agattacgcg cagaaaaaaa   4980
ggatctcaag aagatccttt gatcttttct acggggtctg acgctcagtg aacgaaaac    5040
tcacgttaag ggattttggt catgagatta tcaaaaagga tcttcaccta gatccttta    5100
aattaaaaat gaagttttaa atcaatctaa agtatatatg agtaaacttg gtctgacagt    5160
taccaatgct taatcagtga ggcacctatc tcagcgatct gtctatttcg ttcatccata    5220
gttgcctgac tgcccgtcgt gtagataact acgatacggg agggcttacc atctggcccc    5280
agtgctgcaa tgataccgcg agacccacgc tcaccggctc cagatttatc agcaataaac    5340
cagccagccg aagggccga gcgcagaagt ggtcctgcaa ctttatccgc ctccatccag    5400
tctattaatt gttgccggga agctagagta agtagttcgc cagttaatag tttgcgcaac    5460
gttgttgcca ttgctacagg catcgtggtg tcacgctcgt cgtttggtat ggcttcattc    5520
agctccggtt cccaacgatc aaggcgagtt acatgatccc ccatgttgtg aaaaaaagcg    5580
gttagctcct tcggtcctcc gatcgttgtc agaagtaagt tggccgcagt gttatcactc    5640
atggttatgg cagcactgca taattctctt actgtcatgc catccgtaag atgcttttct    5700
gtgactggtg agtactcaac caagtcattc tgagaatagt gtatgcggcg accgagttgc    5760
tcttgcccgg cgtcaatacg ggataatacc gcgccacata gcagaacttt aaaagtgctc    5820
atcattggaa aacgttcttc ggggcgaaaa ctctcaagga tcttaccgct gttgagatcc    5880
agttcgatgt aacccactcg tgcacccaac tgatcttcag catcttttac tttcaccagc    5940
gtttctgggt gagcaaaaac aggaaggcaa aatgccgcaa aaaagggaat aagggcgaca    6000
cggaaatgtt gaatactcat actcttcctt tttcaatatt attgaagcat ttatcagggt    6060
tattgtctca tgagcggata catatttgaa tgtatttaga aaaataaaca aataggggtt    6120
ccgcgcacat ttccccgaaa agtgccacct gacgtctaag aaaccattat tatcatgaca    6180
ttaacctata aaaataggcg tatcacgagg ccctttcgtc                          6220
```

<210> SEQ ID NO 58
<211> LENGTH: 6220
<212> TYPE: DNA
<213> ORGANISM: Artificial Sequence
<220> FEATURE:
<223> OTHER INFORMATION: Codon Optimized

<400> SEQUENCE: 58

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accacgcttt tcaattcaat tcatcatttt tttttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
```

```
tggtgggccc aggtattgtt agcggtttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg aagaggact atttgcaaag ggaagggatg      1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta aacgttaata ttttgttaaa attcgcgtta     1380
aatttttgtt aaatcagctc attttttaac caataggccg aaatcggcaa atcccttat      1440
aaatcaaaag aatagaccga gatagggttg agtgttgttc cagtttggaa caagagtcca     1500
ctattaaaga acgtggactc caacgtcaaa gggcgaaaaa ccgtctatca gggcgatggc     1560
ccactacgtg aaccatcacc ctaatcaagt tttttgggt cgaggtgccg taaagcacta      1620
aatcggaacc ctaaagggag ccccgattt agagcttgac ggggaaagcc ggcgaacgtg      1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa gggggatgt gctgcaaggc gattaagttg ggtaacgcca      1920
gggttttccc agtcacgacg ttgtaaaacg acggccagtg aattgtaata cgactcacta     1980
tagggcgaat tggagctcta gtacggatta gaagccgccg agcgggcgac agccctccga     2040
cggaagactc tcctccgtgc gtcctcgtct tcaccggtcg cgttcctgaa acgcagatgt     2100
gcctcgcgcc gcactgctcc gaacaataaa gattctacaa tactagcttt tatggttatg     2160
aagaggaaaa attggcagta acctggcccc acaaaccttc aaattaacga atcaaattaa     2220
caaccatagg atgataatgc gattagtttt ttagccttat ttctggggta attaatcagc     2280
gaagcgatga tttttgatct attaacagat atataaatgg aaaagctgca taaccacttt     2340
aactaatact ttcaacattt tcagtttgta ttacttctta ttcaaatgtc ataaaagtat     2400
caacaaaaaa ttgttaatat acctctatac tttaacgtca aggagaaaaa accccggatt     2460
ctagaactag tggatccccc atcatggaat tatcattatc tctgggcggg ccgacgatat     2520
tccccagata tagagcaagc tatacttcca ctaaactgac cactcatttc tctaattttc     2580
cgtccaaatt cagcacaaaa aatttccacc agacgctatc tttctacgga ccaacgagag     2640
gcagcaaatc attgttgaat acccatcagt ggaggaactc cataagagcc tgcgccgagg     2700
cggggctgc cgggtcaaac ccggtgctaa acaaggtctc tgactttagg gacgcatgct      2760
ggcgtttctt aaggccgcat actataaggg ggaccaccct gggtagtata gccctagtag     2820
caagggcgct tatagaaaat cccaacttaa tcaagtggag tcttttactg aaggctttct     2880
ctggcttact agccttaatt tgcgggaacg gctacattgt aggaatcaac caaatctatg     2940
acataggtat tgataaggtc aacaaaccgt accttcccat agccgcgggt gatttgtcag     3000
tccagagtgc ttggtacctt gtaatattgt ttgccgttgc gggtctacta actgttggct     3060
tcaatttttgg gccgttcatt acgtctctat actgcttagg acttgttctg gggacaatat     3120
```

```
atagcgttcc acccttttagg atgaaaagat ttccggttgc agcattctta atcattgcga    3180
ccgtgagggg ttttctatta aactttggtg tatactacgc cacaagagct gcattgggct    3240
taacctttga atggagtagt gcggttgcgt tcattacgac cttcgttaca ttattcgctt    3300
tggtgatagc tataacgaaa gatctgccag acgtggaggg agaccgtaaa tttcagatca    3360
gcacattcgc aacaaagctt ggtgtgagaa acatcgcgta tcttggatct ggactattat    3420
tattaaacta cattggggca attgcggcgg ccatttatat gcctcaggct tttaagagaa    3480
atttaatgct tcctatccac accatcttgg cgttgagcct tgtcttccag gcctgggtct    3540
tggaacaagc gaattacacc aaggaggcta ttgctgggtt ctatagattc atttggaatt    3600
tgttctatgt agaatacatt atattcccct ttatatagga tgggctgcag gaattcgata    3660
tcaagcttat cgataccgtc gacctcgagt catgtaatta gttatgtcac gcttacattc    3720
acgccctccc cccacatccg ctctaaccga aaggaagga gttagacaac ctgaagtcta    3780
ggtccctatt tattttttta tagttatgtt agtattaaga acgttattta tatttcaaat    3840
tttctttttt tttctgtaca gacgcgtgta cgcatgtaac attatactga aaaccttgct    3900
tgagaaggtt ttgggacgct cgaaggcttt aatttgcggc cggtacccag cttttgttcc    3960
ctttagtgag ggttaattcc gagcttggcg taatcatggt catagctgtt tcctgtgtga    4020
aattgttatc cgctcacaat tccacacaac ataggagccg gaagcataaa gtgtaaagcc    4080
tggggtgcct aatgagtgag gtaactcaca ttaattgcgt tgcgctcact gcccgctttc    4140
cagtcgggaa acctgtcgtg ccagctgcat taatgaatcg gccaacgcgc ggggagaggc    4200
ggtttgcgta ttgggcgctc ttccgcttcc tcgctcactg actcgctgcg ctcggtcgtt    4260
cggctgcggc gagcggtatc agctcactca aaggcggtaa tacggttatc cacagaatca    4320
ggggataacg caggaaagaa catgtgagca aaaggccagc aaaaggccag gaaccgtaaa    4380
aaggccgcgt tgctggcgtt tttccatagg ctccgccccc ctgacgagca tcacaaaaat    4440
cgacgctcaa gtcagaggtg gcgaaacccg acaggactat aaagatacca ggcgttcccc    4500
cctggaagct ccctcgtgcg ctctcctgtt ccgaccctgc cgcttaccgg atacctgtcc    4560
gcctttctcc cttcgggaag cgtggcgctt tctcaatgct cacgctgtag gtatctcagt    4620
tcggtgtagg tcgttcgctc caagctgggc tgtgtgcacg aaccccccgt tcagcccgac    4680
cgctgcgcct tatccggtaa ctatcgtctt gagtccaacc cggtaagaca cgacttatcg    4740
ccactggcag cagccactgg taacaggatt agcagagcga ggtatgtagg cggtgctaca    4800
gagttcttga agtggtggcc taactacggc tacactagaa ggacagtatt tggtatctgc    4860
gctctgctga agccagttac cttcggaaaa agagttggta gctcttgatc cggcaaacaa    4920
accaccgctg gtagcggtgg tttttttgtt tgcaagcagc agattacgcg cagaaaaaaa    4980
ggatctcaag aagatccttt gatcttttct acggggtctg acgctcagtg gaacgaaaac    5040
tcacgttaag ggattttggt catgagatta tcaaaaagga tcttcaccta gatccttta    5100
aattaaaaat gaagttttaa atcaatctaa agtatatatg agtaaacttg gtctgacagt    5160
taccaatgct taatcagtga ggcacctatc tcagcgatct gtctatttcg ttcatccata    5220
gttgcctgac tgcccgtcgt gtagataact acgatacggg agggcttacc atctggcccc    5280
agtgctgcaa tgataccgcg agacccacgc tcaccggctc cagatttatc agcaataaac    5340
cagccagccg aagggccga gcgcagaagt ggtcctgcaa ctttatccgc ctccatccag    5400
tctattaatt gttgccggga agctagagta agtagttcgc cagttaatag tttgcgcaac    5460
gttgttgcca ttgctacagg catcgtggtg tcacgctcgt cgtttggtat ggcttcattc    5520
```

-continued

```
agctccggtt cccaacgatc aaggcgagtt acatgatccc ccatgttgtg aaaaaaagcg    5580
gttagctcct tcggtcctcc gatcgttgtc agaagtaagt tggccgcagt gttatcactc    5640
atggttatgg cagcactgca taattctctt actgtcatgc catccgtaag atgcttttct    5700
gtgactggtg agtactcaac caagtcattc tgagaatagt gtatgcggcg accgagttgc    5760
tcttgcccgg cgtcaatacg ggataatacc gcgccacata gcagaacttt aaaagtgctc    5820
atcattggaa aacgttcttc ggggcgaaaa ctctcaagga tcttaccgct gttgagatcc    5880
agttcgatgt aacccactcg tgcacccaac tgatcttcag catcttttac tttcaccagc    5940
gtttctgggt gagcaaaaac aggaaggcaa aatgccgcaa aaaagggaat aagggcgaca    6000
cggaaatgtt gaatactcat actcttcctt tttcaatatt attgaagcat ttatcagggt    6060
tattgtctca tgagcggata catatttgaa tgtatttaga aaaataaaca aatagggggtt    6120 ccgcgcacat ttccccgaaa agtgccacct gacgtctaag aaaccattat tatcatgaca    6180
ttaacctata aaaataggcg tatcacgagg cccttttcgtc                         6220
```

```
<210> SEQ ID NO 59
<211> LENGTH: 6061
<212> TYPE: DNA
<213> ORGANISM: Artificial Sequence
<220> FEATURE:
<223> OTHER INFORMATION: Codon Optimized

<400> SEQUENCE: 59
```

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt tttttattc ttttttttga tttcggtttc      240
tttgaaattt ttttgattcg gtaatctccg aacagaagga agaacgaagg aaggagcaca     300
gacttagatt ggtatatata cgcatatgta gtgttgaaga acatgaaat tgcccagtat      360 tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga ttttccatg gagggcacag ttaagccgct aaaggcatta tccgccaagt      660 acaattttt actcttcgaa gacagaaaat ttgctgacat tggtaataca gtcaaattgc     720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg    1080
tctctacagg atctgacatt attattgttg gaagaggact atttgcaaag gaagggatg    1140 ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
```

```
aaggagaaaa taccgcatca ggaaattgta aacgttaata ttttgttaaa attcgcgtta    1380
aatttttgtt aaatcagctc atttttttaac caataggccg aaatcggcaa aatcccttat    1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttggggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta aagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatgagat tccatctat tttcactgct gttttgttcg    2520
ctgcttcttc tgctttggct gctccagttg ccgggtcaaa cccggtgcta acaaggtct    2580 ctgactttag ggacgcatgc tggcgtttct taaggccgca tactataagg gggaccaccc    2640
tgggtagtat agccctagta gcaagggcgc ttatagaaaa tcccaactta atcaagtgga    2700
gtcttttact gaaggctttc tctggcttac tagccttaat ttgcgggaac ggctacattg    2760
taggaatcaa ccaaatctat gacataggta ttgataaggt caacaaaccg taccttccca    2820
tagccgcggg tgatttgtca gtccagagtg cttggtacct tgtaatattg tttgccgttg    2880
cgggtctact aactgttggc ttcaattttg ggccgttcat tacgtctcta tactgcttag    2940
gacttgttct ggggacaata tatagcgttc cacccttag gatgaaaaga tttccggttg    3000
cagcattctt aatcattgcg accgtgaggg gttttctatt aaactttggt gtatactacg    3060
ccacaagagc tgcattgggc ttaacctttg aatggagtag tgcggttgcg ttcattacga    3120
ccttcgttac attattcgct ttggtgatag ctataacgaa agatctgcca gacgtggagg    3180
gagaccgtaa atttcagatc agcacattcg caacaaagct tggtgtgaga acatcgcgt    3240 atcttggatc tggactatta ttattaaact acattgggc aattgcggcg gccatttata    3300
tgcctcaggc ttttaagaga aatttaatgc ttcctatcca caccatcttg gcgttgagcc    3360
ttgtcttcca ggcctgggtc ttggaacaag cgaattacac caaggaggct attgctgggt    3420
tctatagatt catttggaat ttgttctatg tagaatacat tatattcccc tttatatagg    3480
atgggctgca ggaattcgat atcaagctta tcgataccgt cgacctcgag tcatgtaatt    3540
agttatgtca cgcttacatt cacgccctcc ccccacatcc gctctaaccg aaaaggaagg    3600
agttagacaa cctgaagtct aggtccctat ttattttttt atagtatgt tagtattaag    3660 aacgttattt atatttcaaa ttttttctttt ttttctgtac agacgcgtgt acgcatgtaa    3720
```

```
cattatactg aaaaccttgc ttgagaaggt tttgggacgc tcgaaggctt taatttgcgg    3780
ccggtaccca gcttttgttc cctttagtga gggttaattc cgagcttggc gtaatcatgg    3840
tcatagctgt ttcctgtgtg aaattgttat ccgctcacaa ttccacacaa cataggagcc    3900
ggaagcataa agtgtaaagc ctggggtgcc taatgagtga gtaactcac attaattgcg     3960
ttgcgctcac tgcccgcttt ccagtcggga aacctgtcgt gccagctgca ttaatgaatc    4020
ggccaacgcg cggggagagg cggtttgcgt attgggcgct cttccgcttc ctcgctcact    4080
gactcgctgc gctcggtcgt tcggctgcgg cgagcggtat cagctcactc aaaggcggta    4140
atacggttat ccacagaatc aggggataac gcaggaaaga acatgtgagc aaaaggccag    4200
caaaaggcca ggaaccgtaa aaaggccgcg ttgctggcgt ttttccatag gctcggcccc    4260
cctgacgagc atcacaaaaa tcgacgctca agtcagaggt ggcgaaaccc gacaggacta    4320
taaagatacc aggcgttccc ccctggaagc tccctcgtgc gctctcctgt tccgaccctg    4380
ccgcttaccg gatacctgtc cgcctttctc ccttcgggaa gcgtggcgct ttctcaatgc    4440
tcacgctgta ggtatctcag ttcggtgtag gtcgttcgct ccaagctggg ctgtgtgcac    4500
gaaccccccg ttcagcccga ccgctgcgcc ttatccggta actatcgtct tgagtccaac    4560
ccggtaagac acgacttatc gccactggca gcagccactg gtaacaggat tagcagagcg    4620
aggtatgtag gcggtgctac agagttcttg aagtggtggc ctaactacgg ctacactaga    4680
aggacagtat ttggtatctg cgctctgctg aagccagtta ccttcggaaa aagagttggt    4740
agctcttgat ccggcaaaca aaccaccgct ggtagcggtg gtttttttgt ttgcaagcag    4800
cagattacgc gcagaaaaaa aggatctcaa gaagatcctt tgatcttttc tacggggtct    4860
gacgctcagt ggaacgaaaa ctcacgttaa gggattttgg tcatgagatt atcaaaaagg    4920
atcttcacct agatcctttt aaattaaaaa tgaagtttta atcaatcta aagtatatat     4980
gagtaaactt ggtctgacag ttaccaatgc ttaatcagtg aggcacctat ctcagcgatc    5040
tgtctatttc gttcatccat agttgcctga ctgcccgtcg tgtagataac tacgatacgg    5100
gagggcttac catctggccc cagtgctgca atgataccgc gagacccacg ctcaccggct    5160
ccagatttat cagcaataaa ccagccagcc ggaagggccg agcgcagaag tggtcctgca    5220
actttatccg cctccatcca gtctattaat tgttgccggg aagctagagt aagtagttcg    5280
ccagttaata gtttgcgcaa cgttgttgcc attgctacag gcatcgtggt gtcacgctcg    5340
tcgtttggta tggcttcatt cagctccggt tcccaacgat caaggcgagt tacatgatcc    5400
cccatgttgt gaaaaaaagc ggttagctcc ttcggtcctc cgatcgttgt cagaagtaag    5460
ttggccgcag tgttatcact catggttatg gcagcactgc ataattctct tactgtcatg    5520
ccatccgtaa gatgcttttc tgtgactggt gagtactcaa ccaagtcatt ctgagaatag    5580
tgtatgcggc gaccgagttg ctcttgcccg gcgtcaatac gggataatac cgcgccacat    5640
agcagaactt taaaagtgct catcattgga aaacgttctt cggggcgaaa actctcaagg    5700
atcttaccgc tgttgagatc cagttcgatg taacccactc gtgcacccaa ctgatcttca    5760
gcatctttta ctttcaccag cgtttctggg tgagcaaaaa caggaaggca aaatgccgca    5820
aaaaagggaa taagggcgac acggaaatgt tgaatactca tactcttcct ttttcaatat    5880
tattgaagca tttatcaggg ttattgtctc atgagcggat acatatttga atgtatttag    5940
aaaaataaac aaataggggt tccgcgcaca tttccccgaa aagtgccacc tgacgtctaa    6000
gaaaccatta ttatcatgac attaacctat aaaaataggc gtatcacgag gccctttcgt    6060
```

|   |   |
|---|---|
| c | 6061 |

<210> SEQ ID NO 60
<211> LENGTH: 1161
<212> TYPE: DNA
<213> ORGANISM: Artificial Sequence
<220> FEATURE:
<223> OTHER INFORMATION: Codon Optimized

<400> SEQUENCE: 60

|   |   |
|---|---|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt tggatgctag acaagatatg ttggttgttg aagttccaaa attgggtaaa | 300 |
| gatgcttgtg ctaaagctat taagaatgg ggtcaaccaa atctaaaat tactcatttg | 360 |
| atttttactt ctgcttctac tactgatatg ccaggtgctg attatcattg tgctaaattg | 420 |
| ttgggtttgt ctccatctgt taaaagagtt atgatgtatc aattgggttg ttatggtggt | 480 |
| ggtactgttt tgagaattgc taaagatatt gctgaaaata taaaggtgc tagagttttg | 540 |
| gctgtttgtt gtgatattat ggcttgtttg tttagaggtc catctgattc tgatttggaa | 600 |
| gcttcttttgt tggttggtca agctattttt ggtgatggtc tgctgctgt tattgttggt | 660 |
| gctgaaccag atgaatctgt tggtgaaaga ccaattttg aattggtttc tactggtcaa | 720 |
| actatttttgc caaattctga aggtactatt ggtggtcata ttagagaagc tggtttgatt | 780 |
| tttgatttgc ataaagatgt tccaatgttg atttctaata atattgaaaa atgtttgatt | 840 |
| gaagcttta ctccaattgg tatttctgat tggaattcta ttttttggat tactcatcca | 900 |
| ggtggtaaag ctattttgga taaagttgaa gaaaaattgg atttgaaaaa agaaaaattt | 960 |
| gttgattcta gacatgtttt gtctgaacat ggtaatatgt cttcttctac tgttttgttt | 1020 |
| gttatggatg aattgagaaa aagatctttg gaagaaggta atctactac tggtgatggt | 1080 |
| tttgatgggg gtgttttgtt tggttttggt ccaggttga ctgttgaaag agttgttgtt | 1140 |
| agatctgttc caattaaata t | 1161 |

<210> SEQ ID NO 61
<211> LENGTH: 1155
<212> TYPE: DNA
<213> ORGANISM: Artificial Sequence
<220> FEATURE:
<223> OTHER INFORMATION: Codon Optimized

<400> SEQUENCE: 61

|   |   |
|---|---|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt tggatgctag acaagatatg ttggttgttg aagttccaaa attgggtaaa | 300 |
| gatgcttgtg ctaaagctat taagaatgg ggtcaaccaa atctaaaat tactcatttg | 360 |
| attttttactt ctgcttctac tactgatatg ccaggtgctg attatcattg tgctaaattg | 420 |
| ttgggtttgt ctccatctgt taaaagagtt atgatgtatc aattgggttg ttatggtggt | 480 |
| ggtactgttt tgagaattgc taaagatatt gctgaaaata taaaggtgc tagagttttg | 540 |

```
gctgtttgtt gtgatattat ggcttgtttg tttagaggtc catctgattc tgatttggaa    600
ttgttggttg gtcaagctat ttttggtgat ggtgctgctg ctgttattgt tggtgctgaa    660
ccagatgaat ctgttggtga agaccaatt tttgaattgg tttctactgg tcaaactatt     720
ttgccaaatt ctgaaggtac tattggtggt catattagag aagctggttt gattttttgat   780 ttgcataaag atgttccaat gttgatttct aataatattg aaaaatgttt gattgaagct    840
tttactccaa ttggtatttc tgattggaat tctattttt ggattactca tccaggtggt     900
aaagctattt tggataaagt tgaagaaaaa ttgcatttga atctgataa atttgttgat     960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaagagttgt tgttagatct   1140
gttccaatta aatat                                                    1155
```

<210> SEQ ID NO 62
<211> LENGTH: 1155
<212> TYPE: DNA
<213> ORGANISM: Artificial Sequence
<220> FEATURE:
<223> OTHER INFORMATION: Codon Optimized

<400> SEQUENCE: 62

```
atgaatcatt tgagagctga aggtccagct tctgttttgg ctattggtac tgctaatcca     60
gaaaatattt tgattcaaga tgaatttcca gattattatt ttagagttac taaatctgaa    120
catatgactc aattgaaaga aaaatttaga aaaatttgtg ataaatctat gattagaaaa    180
agaaattgtt ttttgaatga gaacatttg aaacaaaatc caagattggt tgaacatgaa     240
atgcaaactt ggatgctag acaagatatg ttggttgttg aagttccaaa attgggtaaa    300
gatgcttgtg ctaaagctat taagaatgg ggtcaaccaa aatctaaaat tactcatttg    360 attttttactt ctgcttctac tactgatatg ccaggtgctg attatcattg tgctaaattg   420
ttgggtttgt ctccatctgt taaagagtt atgatgtatc aattgggttg ttatggtggt    480
ggtactgttt tgagaattgc taaagatatt gctgaaaata taaaggtgc tagagttttg    540 gctgtttgtt gtgatattat ggcttgtttg tttagaggtc catctgattc tgatttggaa    600
ttgttggttg gtcaagctat ttttggtgat ggtgctgctg ctgttattgt tggtgctgaa    660
ccagatgaat ctgttggtga agaccaatt tttgaattgg tttctactgg tcaaactatt     720
ttgccaaatt ctgaaggtac tattggtggt catattagag aagctggttt gattttttgat   780 ttgcataaag atgttccaat gttgatttct aataatattg aaaaatgttt gattgaagct    840
tttactccaa ttggtatttc tgattggaat tctattttt ggattactca tccaggtggt     900
aaagctattt tggataaagt tgaagaaaaa ttgcatttga aaaagaaaa atttgttgat     960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaactgttgt tttgagatct   1140
gttccaatta attat                                                    1155
```

<210> SEQ ID NO 63
<211> LENGTH: 1155
<212> TYPE: DNA
<213> ORGANISM: Artificial Sequence
<220> FEATURE:

<223> OTHER INFORMATION: Codon Optimized

<400> SEQUENCE: 63

| | |
|---|---:|
| atgaatcatt tgagagctga aggtccagct tctgttttgg ctattggtac tgctaatcca | 60 |
| gaaaatattt tgttgcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt tggatgctag acaagatatg ttggttgttg aagttccaaa attgggtaaa | 300 |
| gatgcttgtg ctaaagctat taagaatgg ggtcaaccaa atctaaaat tactcatttg | 360 |
| atttttactt ctgcttctac tactgatatg ccaggtgctg attatcattg tgctaaattg | 420 |
| ttgggtttgt ctccatctgt taaaagagtt atgatgtatc aattgggttg ttatggtggt | 480 |
| ggtactgttt tgagaattgc taaagatatt gctgaaaata taaaggtgc tagagttttg | 540 |
| gctgtttgtt gtgatattat ggcttgtttg tttagaggtc catctgaatc tgatttggaa | 600 |
| ttgttggttg gtcaagctat ttttggtgat ggtgctgctg ctgttattgt tggtgctgaa | 660 |
| ccagatgaat ctgttggtga agaccaatt tttgaattgg tttctactgg tcaaactatt | 720 |
| ttgccaaatt ctgaaggtac tattggtggt catattagag aagctggttt gattttgat | 780 |
| ttgcataaag atgttccaat gttgatttct aataatattg aaaaatgttt gattgaagct | 840 |
| tttactccaa ttggtatttc tgattggaat tctattttt ggattactca tccaggtggt | 900 |
| aaagctattt tggataaagt tgaagaaaaa ttgcatttga atctgataa atttgttgat | 960 |
| tctagacatg ttttgtctga acatggtaat atgtcttctt ctactgtttt gtttgttatg | 1020 |
| gatgaattga aaaaagatc tttggaagaa ggtaaatcta ctactggtga tggttttgaa | 1080 |
| tggggtgttt tgtttggttt tggtccaggt ttgactgttg aaagagttgt tgttagatct | 1140 |
| gttccaatta aatat | 1155 |

<210> SEQ ID NO 64
<211> LENGTH: 1155
<212> TYPE: DNA
<213> ORGANISM: Artificial Sequence
<220> FEATURE:
<223> OTHER INFORMATION: Codon Optimized

<400> SEQUENCE: 64

| | |
|---|---:|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaatattt ttttgaatga agaacatttg aaacaaaatc caaaattggt tgaacatgat | 240 |
| gttcaaactt tggatgctag acaagatatg ttggttgttg aagttccaaa attgggtaaa | 300 |
| gatgcttgtg ctaaagctat taagaatgg ggtcaaccaa atctaaaat tactcatttg | 360 |
| atttttactt ctgcttctac tactgatatg ccaggtgctg attatcattg tgctaaattg | 420 |
| ttgggtttgt ctccatctgt taaaagagtt atgatgtatc aattgggttg ttatggtggt | 480 |
| ggtactgttt tgagaattgc taaagatatt gctgaaaata taaaggtgc tagagttttg | 540 |
| gctgtttgtt gtgatattat ggcttgtttg tttagaggtc catctgattc tgatttggaa | 600 |
| ttgttggttg gtcaagctat ttttggtgat ggtgctgctg ctgttattgt tggtgctgaa | 660 |
| ccagatgaat ctgttggtga agaccaatt tttgaattgg tttctactgg tcaaactatt | 720 |
| ttgccaaatt ctgaaggtac tattggtggt catattagag aagctggttt gattttgat | 780 |

```
ttgcataaag atgttccaat gttgatttct aataatattg aaaaatgttt gattgaagct      840
tttactccaa ttggtatttc tgattggaat tctattttt ggattactca tccaggtggt        900
aaagctattt tggataaagt tgaagaaaaa ttgcatttga atctgataa atttgttgat       960 tctagacatg ttttgtctga acatggtaat atgtcttctt ctactgtttt gtttgttatg      1020
gatgaattga aaaaagatc tttggaagaa ggtaaatcta ctactggtga tggttttgaa      1080
tggggtgttt tgtttggttt tggtccaggt ttgactgttg aaagagttgt tgttagatct     1140
gttccaatta aatat                                                       1155
```

<210> SEQ ID NO 65
<211> LENGTH: 1155
<212> TYPE: DNA
<213> ORGANISM: Artificial Sequence
<220> FEATURE:
<223> OTHER INFORMATION: Codon Optimized

<400> SEQUENCE: 65

```
atgaatcatt tgagagctga aggtccagct tctgttttgg ctattggtac tgctaatcca       60
gaaaatattt tgattcaaga tgaatttcca gattattatt ttagagttac taaatctgaa      120
catatgactc aattgaaaga aaaatttaga aaaatttgtg ataaatctat gattagaaaa     180
agaaattgtt ttttgaatga agaacatttg aaacaaaatc caagattggt tgaacatgaa      240
atgcaaactt tggatgctag acaagatatg ttggttgttg aagttccaaa attgggtaaa      300
gatgcttgtg ctaaagctat taagaatgg ggtcaaccaa atctaaaat tactcatttg       360 atttttactt ctgcttctac tactgatatg ccaggtgctg attatcattg tgctaaattg      420 ttgggttttgt ctccatctgt taaaagagtt atgatgtatc aattgggttg ttatggtggt    480
ggtactgttt tgagaattgc taaagatatt gctgaaaata taaaggtgc tagagttttg     540 gctgtttgtt gtgatatgac tgcttgtttg tttagaggtc catctgattc taatttggaa      600
ttgttggttg gtcaagctat ttttggtgat ggtgctgctg ctgttattgt tggtgctgaa     660
ccagatgaat ctgttggtga agaccaattt tttgaattgg tttctactgg tcaaactttt       720
ttgccaaatt ctgaaggtac tattggtggt catattgaga aagctggttt gatgtttgat      780
ttgcataaag atgttccaat gttgatttct aataatattg aaaaatgttt gattgaagct       840
tttactccaa ttggtatttc tgattggaat tctattttt ggattactca tccaggtggt        900
aaagctattt tggataaagt tgaagaaaaa ttgcatttga atctgataa atttgttgat       960 tctagacatg ttttgtctga acatggtaat atgtcttctt ctactgtttt gtttgttatg      1020
gatgaattga aaaaagatc tttggaagaa ggtaaatcta ctactggtga tggttttgaa      1080
tggggtgttt tgtttggttt tggtccaggt ttgactgttg aaagagttgt tttgagatct     1140
gttccaatta attat                                                       1155
```

<210> SEQ ID NO 66
<211> LENGTH: 1173
<212> TYPE: DNA
<213> ORGANISM: Artificial Sequence
<220> FEATURE:
<223> OTHER INFORMATION: Codon Optimized

<400> SEQUENCE: 66

```
atggaagaaa ttaaaggtgt tttgaaagct aaagatgttg ttgtgttgc tactattttg        60 gctattggta ctgctaatcc attgaattgt gttaatcaag atgaattttt gcattcttat       120
```

| | | |
|---|---|---|
| tttaaattga ctaataatca taataatact tcttttaaag aattgtttac tagaatttgt | 180 | |
| aataattcta tgattaaaaa tagatatatg catttgactg aagatatttt gaaagaaaat | 240 | |
| ccaaatttgt gtgattatgc tgctcaatct ttgaatacta gacaagatat aaaattaaa | 300 | |
| gaaattccaa aattggctga aagagctgct atggttgcta ttaaagaatg ggtaaaacca | 360 | |
| atttctaatt tgactcatat tatttttcat tcttctactg gtgctgctga tatgccaggt | 420 | |
| gctgattatc aattggttaa atctttgggt ttgaatagat ctattaaaag aattatgttg | 480 | |
| tataatttgg gttgttttgc tggtggtact gttttgagag ttgctaaaga tttggttgaa | 540 | |
| aataatttgg gtgcttctgt tttggctgtt tgtgctgaaa ttacttctgc tgatgctact | 600 | |
| tttggtagat tgtctgaaga tgataaaggt agattggttg gtcatgctat ttttggtgat | 660 | |
| ggtgctgctg ctttggttat tggtaatgct gatgatccag aaaataaagg tttgttttcaa | 720 | |
| attgtttcta cttctcaaac tattttgcca aattctgaag gttgtattga aggtcatatt | 780 | |
| agagaagatg gtgttacttt tactttgtct ccaagagttc aaaaattgat tggtgataat | 840 | |
| attgaaactt gttgatgga agcttttact ccatttaaaa tttctgattg gaattctttg | 900 | |
| ttttgggttg ttcatccagg tggtgctgct attttgagag aagttgaatc tagagttggt | 960 | |
| ttggaacaag aaaaattgag agcttcttgg catgttttga gagaatatgg taatatttct | 1020 | |
| tctgcttctg ttttgtttat tttggatgaa atgagaaata aatctttgga agaaggtaga | 1080 | |
| aaaactactg tgaaggtaa aaattggggt gttttgtttg gttttggtcc aggtttgact | 1140 | |
| gttgaaactg ttgttttgca ttctattcca att | 1173 | |

<210> SEQ ID NO 67
<211> LENGTH: 1155
<212> TYPE: DNA
<213> ORGANISM: Artificial Sequence
<220> FEATURE:
<223> OTHER INFORMATION: Codon Optimized

<400> SEQUENCE: 67

| | | |
|---|---|---|
| atgaatcatt tgagagctga aggtccagct tctgttttgg ctattggtac tgctaatcca | 60 | |
| gaaaatattt tgattcaaga tgaatttcca gattattatt ttagagttac taaatctgaa | 120 | |
| catatgactc aattgaaaga aaatttaga aaaatttgtg ataaatctat gattagaaaa | 180 | |
| agaaattgtt ttttgaatga agaacatttg aaacaaaatc caagattggt tgaacatgaa | 240 | |
| atgcaaactt tggatgctag acaagatatg ttggttgttg aagttccaaa attgggtaaa | 300 | |
| gatgcttgtg ctaaagctat taagaatgg ggtcaaccaa aatctaaaat tactcatttg | 360 | |
| attttttactt ctgcttctac tactgatatg ccaggtgctg attatcattg tgctaaattg | 420 | |
| ttgggttttgt ctccatctgt taaaagagtt atgatgtatc aattgggttg ttatggtggt | 480 | |
| ggtactgttt tgagaattgc taaagatatt gctgaaaata taaaggtgc tagagttttg | 540 | |
| gctgtttgtt gtgatattat ggcttgtttg tttagaggtc catctgattc tgatttggaa | 600 | |
| tgttggttg gtcaagctat ttttggtgat ggtgctgctg ctgttattgt tggtgctgaa | 660 | |
| ccagatgaat ctgttggtga agaccaatt tttgaattgg tttctactgg tcaaactatt | 720 | |
| ttgccaaatt ctgaaggtac tattggtggt catattagag aagctggttt gattttttgat | 780 | |
| ttgcataaag atgttccaat gttgatttct aataatattg aaaaatgttt gattgaagct | 840 | |
| tttactccaa ttggtatttc tgattggaat ctatttttt ggattactca tccaggtggt | 900 | |
| aaagctattt ggataaaagt tgaagaaaaa ttgcatttga atctgataa atttgttgat | 960 | |
| tctagacatg ttttgtctga acatggtaat atgtcttctt ctactgtttt gtttgttatg | 1020 | |

```
gatgaattga gaaaaagatc tttggaagaa ggtaaatcta ctactggtga tggttttgaa    1080
tggggtgttt tgtttggttt tggtccaggt ttgactgttg aaagagttgt tgttagatct    1140
gttccaatta aatat                                                     1155
```

<210> SEQ ID NO 68
<211> LENGTH: 1200
<212> TYPE: DNA
<213> ORGANISM: Artificial Sequence
<220> FEATURE:
<223> OTHER INFORMATION: Codon Optimized

<400> SEQUENCE: 68

```
atgaatcatt tgagagctga aggtccagct tctgttttgg ctattggtac tgctaatcca     60
gaaaatattt tgattcaaga tgaatttcca gattattatt ttagagttac taaatctgaa    120
catatgactc aattgaaaga aaaatttaga aaaatttgtg ataaatctat gattagaaaa    180
agaaattgtt ttttgaatga gaacatttg aaacaaaatc caagattggt tgaacatgaa     240
atgcaaactt tggatgctag acaagatatg ttggttgttg aagttccaaa attgggtaaa    300
gatgcttgtg ctaaagctat taagaatgg ggtcaaccaa atctaaaat tactcatttg      360 atttttactt ctgcttctac tactgatatg ccaggtgctg attatcattg tgctaaattg    420 ttgggttttgt ctccatctgt taaaagagtt atgatgtatc aattgggttg ttatggtggt   480
ggtactgttt tgagaattgc taaagatatt gctgaaaata taaaggtgc tagagttttg    540 gctgtttgtt gtgatattat ggcttgtttg tttagaggtc catctgattc tgatttggaa   600
ttgttggttg gtcaagctat ttttggtgat ggtgctgctg ctgttattgt tggtgctgaa    660
ccagatgaat ctgttggtga agaccaatt tttgaattgg tttctactgg tcaaactatt     720
ttgccaaatt ctgaaggtac tattggtggt catattgag aagctggttt gattttgat     780 ttgcataaag atgttccaat gttgatttct aataatatg aaaaatgttt gattgaagct    840
tttactccaa ttggtatttc tgattggaat tctatttttt ggattactca tccaggtggt    900
aaagctattt tggataaagt tgaagaaaaa ttgcatttga atctgataaa atttgttgat    960
tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaagaggtag atggagaaaa   1140
ggtaatttgc cattggaaat ggatttgtct ggtgtttttt ttttgggttt ggatcaagtt   1200
```

<210> SEQ ID NO 69
<211> LENGTH: 1167
<212> TYPE: DNA
<213> ORGANISM: Artificial Sequence
<220> FEATURE:
<223> OTHER INFORMATION: Codon Optimized

<400> SEQUENCE: 69

```
atggttactg ttgaagaatt tagaaaagct caaagagctg aaggtccagc tactattatg      60
gctattggta ctgctactcc agctaattgt gttttgcaat ctgaatatcc agattattat    120
tttagaatta ctaattctga acataaaact gaattgaaag aaaaatttaa agaatgtgt      180 gataaatcta tgattagaaa aagatatatg catttgactg aagaaatttt gaaagaaaat    240
ccaaatttgt gtgcttatga agctccatct ttggatgcta gacaagatat ggttgttgtt    300
gaagttccaa aattgggtaa agaagctgct actaaagcta ttaaagaatg gggtcaacca    360
```

```
aaatctaaaa ttactcattt ggttttttgt actacttctg gtgttgatat gccaggtgct    420
gattatcaat tgactaaatt gttgggtttg agaccatctg ttaaaagatt gatgatgtat    480
caacaaggtt gttttgctgg tggtactgtt ttgagattgg ctaaagattt ggctgaaaat    540
aataaaggtg ctagagtttt ggttgttgt tctgaaatta ctgctgttac ttttagaggt    600
ccaaatgata ctcatttgga ttctttggtt ggtcaagctt gtttggtga tggttctgct    660 gctttgattg ttggttctga tccaattcca gaagttgaaa aaccaatttt tgaattggtt    720
tctgctgctc aaactatttt gccagattct gatggtgcta ttgatggtca tttgagagaa    780
gttggtttga cttttcattt gttgaaagat gttccaggtt tgatttctaa aaatattgaa    840
aaatctttga atgaagcttt taaaccattg ggtatttctg attggaattc tttgttttgg    900
attgctcatc caggtggtcc agctattttg gatcaagttg aatctaaatt ggctttgaaa    960
actgaaaaat tgagagctac tagacatgtt ttgtctgaat atggtaatat gtcttctgct   1020
tgtgttttgt ttattttgga tgaaatgaga agaaaatgtg ttgaagatgg tttgaatact   1080
actggtgaag gtttggaatg gggtgttttg tttggttttg gtccaggttt gactgttgaa   1140
actgttgttt tgcattctgt tgctatt                                       1167

<210> SEQ ID NO 70
<211> LENGTH: 573
<212> TYPE: DNA
<213> ORGANISM: Artificial Sequence
<220> FEATURE:
<223> OTHER INFORMATION: Codon Optimized

<400> SEQUENCE: 70
atgaatcatt tgagagctga aggtccagct tctgttttgg ctattggtac tgctaatcca     60
gaaaatattt tgattcaaga tgaatttcca gattattatt ttagagttac taaatctgaa    120
catatgactc aattgaaaga aaaatttaga aaaatttgtg ataaatctat gattagaaaa    180
agaaattgtt ttttgaatga agaacatttg aaacaaaatc caagattggc tgaacatgaa    240
atgcaaactt tggatgctag acaagatatg ttggttgttg aagttccaaa attgggtaaa    300
gatgcttgtg ctaaagctat taagaatggg ggtcaaccaa atctaaaat tactcatttg    360 atttttactt ctgcttctac tactgatatg ccaggtgctg attatcattg tgctaaattg    420 ttgggttttgt ctccatctgt taaaagagtt atgatgtatc aattgggttg ttatggtggt    480
ggtactgttt tgagaattgc taaagatatt gctgaaaata ataaaggtgc tagagttttg    540
gctgtttgtt gtgatattat ggctttttt ttt                                  573

<210> SEQ ID NO 71
<211> LENGTH: 597
<212> TYPE: DNA
<213> ORGANISM: Artificial Sequence
<220> FEATURE:
<223> OTHER INFORMATION: Codon Optimized

<400> SEQUENCE: 71
atggcttgtt tgtttagagg tccatctgaa tctgatttgg aattgttggt tggtcaagct     60 attttggtg atggtgctgc tgctgttatt gttggtgcta aaccagatga atctgttggt    120
gaaagaccaa ttttgaatt ggtttctact ggtcaaacta ttttgccaaa ttctgaaggt    180
actattggtg gtcatattag agaagctggt ttgattttg atttgcataa agatgttcca    240
atgttgattt ctaataatat tgaaaaatgt ttgattgaag cttttactcc aattggtatt    300
tctgattgga attctatttt ttggattact catccaggtg gtaaagctat tttggataaa    360
```

| | |
|---|---|
| gttgaagaaa aattgcattt gaaatctgat aaatttgttg attctagaca tgttttgtct | 420 |
| gaacatggta atatgtcttc ttctactgtt ttgtttgtta tggatgaatt gagaaaaaga | 480 |
| tctttggaag aaggtaaatc tactactggt gatggttttg aatggggtgt tttgtttggt | 540 |
| tttggtccag gtttgactgt tgaaagagtt gttgttagat ctgttccaat taaatat | 597 |

<210> SEQ ID NO 72
<211> LENGTH: 936
<212> TYPE: DNA
<213> ORGANISM: Artificial Sequence
<220> FEATURE:
<223> OTHER INFORMATION: Codon Optimized

<400> SEQUENCE: 72

| | |
|---|---|
| atgaatttgg aaatattga taaagttaat tctccaggta ctgaagataa agattttgat | 60 |
| tctagagctt ctggttctaa aactaatggt tgtgaatctt ctgataatga agttgaatct | 120 |
| tctattaatg ctaatccaaa ttctatttct ggttcttctt ctggttttgg taatggtaaa | 180 |
| agagaaggtg ttaaaagagc tgctccaggt gatattgctc aacttctag acattataga | 240 |
| tcttttgtcta tggattctta tatgggttct ttgcaatttg atgatgaatc tttgaaattg | 300 |
| ttgccattgg gtactggtgt tggtttgcaa tctccaaatt cttggctga tggtaattct | 360 |
| actaaatttg gtatggaatt tccaaatggt gaatttaatg ctgttgaatt gaaaaaaatt | 420 |
| atggaatctg aaaaattgac tgaaattgct ttgtctgatc caaaaagagc taaaagaatt | 480 |
| ttggctaata gacaatctgc tgctagatct aaagaaagaa gatctagata tatttctgaa | 540 |
| ttggaacata agttcaaac tttgcaaact gaagctacta ctttgtctgc tcaagttact | 600 |
| aaattgcaaa gagattctgt tggttttgact tctcaaaatt ctgaattgaa atttagagtt | 660 |
| caagctatgg aacaacaagc tcaattgaaa gatgctttga tgatgctttt gagagctgaa | 720 |
| gttcaaagat tgaaattgac tgctgctgaa ttgtctggtg aagctcattt gtctaattgt | 780 |
| atggctcaac aattgtctat taatcaacaa atgtatcaaa tgcaacatag acaaactgtt | 840 |
| caattgaatt tgtatcaaat gcaacaacaa caacaacata tgaaatgtc ttctcaacca | 900 |
| tgttctggtg aagttactga acatgaatct tctaaa | 936 |

<210> SEQ ID NO 73
<211> LENGTH: 10349
<212> TYPE: DNA
<213> ORGANISM: Artificial Sequence
<220> FEATURE:
<223> OTHER INFORMATION: Codon Optimized

<400> SEQUENCE: 73

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aaacaggaag gcaaaatgcc gcaaaaaagg gaataagggc | 480 |
| gacacggaaa tgttgaatac tcatactctt ccttttttcaa tattattgaa gcatttatca | 540 |

```
gggttattgt ctcatgagcg atacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttttatt   1020 tgttgtattt tttttttttt agagaaaatc ctccaatatc aaattaggaa tcgtagtttc   1080
atgattttct gttacaccta acttttgtg tggtgccctc ctccttgtca atattaatgt   1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gttatgtac aaatatcata aaaaagaga atcttttaa gcaaggattt   1380 tcttaacttc ttcggcgaca gcatcaccga cttcggtggt actgttggaa ccacctaaat   1440
caccagttct gataccgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaaatac   2040
ctcccactaa ttctctgaca caacgaagt cagtaccttt agcaaattgt ggcttgattg   2100
gagataagtc taaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaata   2820 atggttgcta agagattcga actcttgcat cttacgatac ctgagtattc ccacagttaa   2880
ctgcggtcaa gatatttctt gaatcaggcg ccttagaccg ctcggccaaa caaccaatta   2940
```

```
cttgttgaga aatagagtat aattatccta taaatataac gttttttgaac acacatgaac    3000 aaggaagtac aggacaattg attttgaaga gaatgtggat tttgatgtaa ttgttgggat    3060
tccattttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacct tgaaatagac atcgtgatga ttaccgttta acaatgtttt    4560
tgaggcacca acataacag gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc caagatatgt caccatctct    5280
```

```
caattctgca ccaatgttag aaccactaca agggataact attgccattg gggatttagc    5340
ttcaactact cttgaataca atggtattct cttttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg ccaaatata taacaacagc    5520 atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttttcag ggtctggaat    6000 ccaagcaggt ggggctggac cgaaatcctt gtagcaacca taaaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt acttttttt tggatggacg    6300 caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480 tacgattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatcgtta aaagagttat gatgtatcaa ttgggttgtt atggtggtgg    7440
tactgttttg agaattgcta agatattgc tgaaaataat aaaggtgcta gagttttggc    7500 tgttgttgt gatattatgg cttgtttgt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
```

-continued

```
gccaaattct gaaggtacta ttggtggtca tattagagaa gctggtttga tttttgattt    7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg gttttgaatg    8040
gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttca agacctacgt taatttggtc aacattatac ctgctatgaa    8280
agatgtatac tggggtaaag acgttacaca aaagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaggaa ggagttagac aacctgaagt ctaggtccct atttatttt ttatagttat    8640
gttagtatta agaacgttat ttatatttca aattttcttt ttttctgt acagacgcgt    8700
gtacgcatgt aacattatac tgaaaaccttt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcaggggata acgcaggaaa gaacatgtga    9180
gcaaaaggcc agcaaaaggc caggaaccgt aaaaaggccg cgttgctggc gtttttccat    9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg cctaactac    9660
ggctacacta gaaggacagt atttggtatc tgcgctctgc tgaagccagt taccttcgga    9720
aaaagagttg gtagctcttg atccggcaaa caaaccaccg ctggtagcgg tggtttttt    9780
gtttgcaagc agcagattac gcgcagaaaa aaaggatctc aagaagatcc tttgatcttt    9840
tctacggggt ctgacgctca gtggaacgaa aactcacgtt aagggatttt ggtcatgaga    9900
ttatcaaaaa ggatcttcac ctagatcctt taaattaaa aatgaagttt taaatcaatc    9960
taaagtatat atgagtaaac ttggtctgac agttaccaat gcttaatcag tgaggcacct   10020
```

```
atctcagcga tctgtctatt tcgttcatcc atagttgcct gactgcccgt cgtgtagata   10080
actacgatac gggagggctt accatctggc cccagtgctg caatgatacc gcgagaccca   10140
cgctcaccgg ctccagattt atcagcaata aaccagccag ccggaagggc cgagcgcaga   10200
agtggtcctg caactttatc cgcctccatc cagtctatta attgttgccg ggaagctaga   10260
gtaagtagtt cgccagttaa tagtttgcgc aacgttgttg ccattgctac aggcatcgtg   10320
gtgtcacgct cgtcgtttgg tatggcttc                                    10349

<210> SEQ ID NO 74
<211> LENGTH: 10349
<212> TYPE: DNA
<213> ORGANISM: Artificial Sequence
<220> FEATURE:
<223> OTHER INFORMATION: Codon Optimized

<400> SEQUENCE: 74
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcgggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020 tgttgtatt ttttttttt agagaaaatc ctccaatatc aaattaggaa tcgtagtttc   1080
atgattttct gttacaccta acttttttgtg tggtgccctc ctccttgtca atattaatgt   1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaatttt   1320 catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
```

```
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg cgtacaatt    2160
gaagttcttt acggattttt agtaaaacct tgttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccttat atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttct cccaattttt    2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg cctagaccg ctcggccaaa caaccaatta    2940
cttgttgaga aatagagtat aattatccta taaatataac gttttgaac acacatgaac    3000
aaggaagtac aggacaattg atttttgaaga gaatgtggat tttgatgtaa ttgttgggat   3060
tccatttta ataaggcaat aatattaggt atgtggatat actagaagtt ctcctcgagg    3120
gtcgatatgc ggtgtgaaat accgcacaga tgcgtaagga gaaataccg catcaggaaa    3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga agccggcga acgtggcgag aaaggaaggg aagaaagcga    3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
cctttttcggt tagagcggat gtgggggag ggcgtgaatg taagcgtgac ataactaatt   4080
```

```
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgtttt    4560
tgaggcacca acataacag gacctaatgc caattcaccg atacctggct tattttttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctcттттcтaa aaagtaatcc caagatatgt caccatctct    5280
caattctgca ccaatgttag aaccactaca agggataact attgccattg gggatttagc    5340
ttcaactact cttgaataca atggtattct ctttttacct ctgatgatgt gatcttgtgt    5400
gaaaattgcc ttagctttgg ataatctcaa tctagttgag atttcaggg cggaaaatga    5460 atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820 aатттттcaтт tcatccatca atactgttct ccaatagact tcagggtttc taacagaaaa    5880

ttcttggaag tgagaaaaag aagaaattgg atctttgtac tttacaccca aaaattcttt    5940

acctctcttt tccaacaaag cacccaaatt agttgacttg actttttcag ggtctggaat    6000
ccaagcaggt ggggctggac cgaaatcctt gtagcaacca taaacaaca tttggtgtaa    6060 ggagaaaggc aaatctggtg acaagatatg gttagcgatg ttgatccaag tttgaggggt    6120

tgcagcacca taattacaaa cgatttctgc caatctacca tgtaatgttt ctgctacttc    6180

tgaggtgata cccaatgcga tgaaatctga ggcaacgact gaatccaagg acttatagtt    6240

тттассссатт cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa cttcagtaa tacgcttaac tgctcattgc tatattgaag    6480
```

```
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga ttttgatttt    7740
gcataaagat gttccaatgt tgatttctaa taatattgaa aaatgtttga ttgaagcttt    7800
tactccaatt ggtatttctg attggaattc tattttttgg attactcatc aggtggtaa    7860 agctatttg gataaagttg aagaaaaatt gcatttgaaa aaagaaaaat tgttgattc    7920 tagacatgtt ttgtctgaac atggtaatat gtcttcttct actgttttgt tgttatgga    7980 tgaattgaga aaaagatctt tggaagaagg taaatctact actggtgatg gttttgaatg    8040
gggtgttttg tttggttttg gtccaggttt gactgttgaa actgttgttt gagatctgt    8100 tccaattaat tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttca agacctacgt taatttggtc aacattatac ctgctatgaa    8280
agatgtatac tgggggtaaag acgttacaca aagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct cccccacat ccgctctaac    8580 cgaaaaggaa ggagttagac aacctgaagt ctaggtccct atttatttttt ttatagttat    8640 gttagtatta agaacgttat ttatatttca aatttttctt ttttttctgt acagacgcgt    8700
gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
```

```
gcgtaatcat ggtcatagct gtttcctgtg tgaaattgtt atccgctcac aattccacac      8880
aacataggag ccggaagcat aaagtgtaaa gcctggggtg cctaatgagt gaggtaactc      8940
acattaattg cgttgcgctc actgcccgct ttccagtcgg gaaacctgtc gtgccagctg      9000
cattaatgaa tcggccaacg cgcgggaga ggcggtttgc gtattgggcg ctcttccgct      9060
tcctcgctca ctgactcgct gcgctcggtc gttcggctgc ggcgagcggt atcagctcac      9120
tcaaaggcgg taatacggtt atccacagaa tcaggggata acgcaggaaa gaacatgtga      9180
gcaaaaggcc agcaaaaggc caggaaccgt aaaaaggccg cgttgctggc gtttttccat      9240
aggctcggcc cccctgacga gcatcacaaa aatcgacgct caagtcagag gtggcgaaac      9300
ccgacaggac tataaagata ccaggcgttc ccccctggaa gctccctcgt gcgctctcct      9360
gttccgaccc tgccgcttac cggatacctg tccgcctttc tcccttcggg aagcgtggcg      9420
ctttctcaat gctcacgctg taggtatctc agttcggtgt aggtcgttcg ctccaagctg      9480
ggctgtgtgc acgaaccccc cgttcagccc gaccgctgcg ccttatccgg taactatcgt      9540
cttgagtcca acccggtaag acacgactta tcgccactgg cagcagccac tggtaacagg      9600
attagcagag cgaggtatgt aggcggtgct acagagttct tgaagtggtg cctaactac      9660 ggctacacta agaggacagt attggtatc tgcgctctgc tgaagccagt taccttcgga      9720
aaaagagttg gtagctcttg atccggcaaa caaaccaccg ctggtagcgg tggtttttt      9780 gtttgcaagc agcagattac gcgcagaaaa aaaggatctc aagaagatcc tttgatcttt      9840
tctacggggt ctgacgctca gtggaacgaa aactcacgtt aagggatttt ggtcatgaga      9900
ttatcaaaaa ggatcttcac ctagatcctt ttaaattaaa aatgaagttt taaatcaatc      9960
taaagtatat atgagtaaac ttggtctgac agttaccaat gcttaatcag tgaggcacct     10020
atctcagcga tctgtctatt tcgttcatcc atagttgcct gactgcccgt cgtgtagata     10080
actacgatac gggagggctt accatctggc cccagtgctg caatgatacc gcgagaccca     10140
cgctcaccgg ctccagattt atcagcaata aaccagccag ccggaagggc cgagcgcaga     10200
agtggtcctg caactttatc cgcctccatc cagtctatta attgttgccg ggaagctaga     10260
gtaagtagtt cgccagttaa tagtttgcgc aacgttgttg ccattgctac aggcatcgtg     10320
gtgtcacgct cgtcgtttgg tatggcttc                                       10349
```

<210> SEQ ID NO 75
<211> LENGTH: 10349
<212> TYPE: DNA
<213> ORGANISM: Artificial Sequence
<220> FEATURE:
<223> OTHER INFORMATION: Codon Optimized

<400> SEQUENCE: 75

```
attcagctcc ggttcccaac gatcaaggcg agttacatga tccccatgt tgtgaaaaaa        60 agcggttagc tccttcggtc ctccgatcgt tgtcagaagt aagttggccg cagtgttatc       120
actcatggtt atggcagcac tgcataattc tcttactgtc atgccatccg taagatgctt       180
ttctgtgact ggtgagtact caaccaagtc attctgagaa tagtgtatgc ggcgaccgag       240
ttgctcttgc ccggcgtcaa tacgggataa taccgcgcca catagcagaa ctttaaaagt       300
gctcatcatt ggaaaacgtt cttcggggcg aaaactctca aggatcttac cgctgttgag       360
atccagttcg atgtaaccca ctcgtgcacc caactgatct tcagcatctt ttactttcac       420
cagcgtttct gggtgagcaa aaacaggaag gcaaaatgcc gcaaaaaagg gaataagggc       480
gacacggaaa tgttgaatac tcatactctt ccttttcaa tattattgaa gcatttatca       540
```

```
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020
tgttgtattt ttttttttt agagaaaatc ctccaatatc aaattaggaa tcgtagtttc   1080
atgattttct gttacaccta acttttgtg tggtgccctc ctccttgtca atattaatgt   1140
taaagtgcaa ttcttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680 ctggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaatac    2040 ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccta atggcttcgg    2400 ctgtgatttc ttgaccaacg tggtcacctg gcaaaacgac gatcttctta ggggcagaca   2460
taggggcaga cattagaatg gtatatcctt gaaatatata tatattgc tgaaatgtaa    2520 aaggtaagaa aagttagaaa gtaagacgat tgctaaccac ctattggaaa aacaatagg    2580 tccttaaata atattgtcaa cttcaagtat tgtgatgcaa gcatttagtc atgaacgctt   2640
ctctattcta tatgaaaagc cggttccggc ctctcacctt tccttttct cccaattttt    2700 cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaata    2820 atggttgcta agagattcga actcttgcat cttacgatac ctgagtattc ccacagttaa   2880
```

```
ctgcggtcaa gatatttctt gaatcaggcg ccttagaccg ctcggccaaa caaccaatta    2940
cttgttgaga aatagagtat aattatccta taaatataac gttttttgaac acacatgaac   3000 aaggaagtac aggacaattg attttgaaga gaatgtggat tttgatgtaa ttgttgggat    3060 tccatttta ataaggcaat aatattaggt atgtggatat actagaagtt ctcctcgagg     3120
gtcgatatgc ggtgtgaaat accgcacaga tgcgtaagga gaaataccg catcaggaaa    3180 ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcaccctaat     3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccaggggtt ttcccagtca cgacgttgta   3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020 cctttcggt tagagcggat gtgggggag ggcgtgaatg taagcgtgac ataactaatt      4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa tctcaattgg ttcaaatcaa tggttgtgtc     4260
gtttgaatcc ttcaatacga aaaatatgac caattgttct ggaccaccac ccaaaggtgg    4320
aacaccaata gcagtggttt caaaaactct gtcatctact tcattacaga ctcttttcgat   4380 ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta acaatgtttt    4560
tgaggcacca acataacag gacctaatgc caattcaccg atacctggct tattttttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920 gaccttgca tcttgaacaa atttagcgaa accagagact aaaggactac cgttgtacaa     4980
ggcaatagat gcaccattta acaaactagc ataaccaaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc caagatatgt caccatctct    5280
```

```
caattctgca ccaatgttag aaccactaca agggataact attgccattg gggatttagc    5340
ttcaactact cttgaataca atggtattct cttttttacct ctgatgatgt gatcttgtgt   5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttttcag gtctggaat    6000 ccaagcaggt ggggctggac cgaaatcctt gtagcaacca taaacaaca tttggtgtaa     6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt acttttttttt tggatggacg    6300 caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa cttttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020 aaatatttg ttgcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta aagaatgggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta aagatattgc tgaaaataat aaaggtgcta gagttttggc    7500
tgtttgttgt gatattatgg cttgtttgtt tagaggtcca tctgaatctg atttggaatt    7560
gttggttggt caagctattt ttggtgatgg tgctgctgct gttattgttg gtgctgaacc    7620
```

```
agatgaatct gttggtgaaa gaccaatttt tgaattggtt tctactggtc aaactatttt    7680
gccaaattct gaaggtacta ttggtggtca tattagagaa gctggtttga tttttgattt    7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg ttttgaatg     8040
gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttttca agacctacgt taatttggtc aacattatac ctgctatgaa    8280
agatgtatac tggggtaaag acgttacaca aagaaagaa gaaggttata cacacattgt     8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct cccccccacat ccgctctaac    8580
cgaaaaggaa ggagttagac aacctgaagt ctaggtccct atttattttt ttatagttat    8640
gttagtatta agaacgttat ttatatttca aattttctt ttttttctgt acagacgcgt     8700
gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcaggggata acgcaggaaa gaacatgtga    9180
gcaaaaggcc agcaaaaggc caggaaccgt aaaaaggccg cgttgctggc gttttttccat   9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg cctaactac     9660
ggctacacta aaggacagt atttggtatc tgcgctctgc tgaagccagt taccttcgga     9720
aaaagagttg gtagctcttg atccggcaaa caaaccaccg ctggtagcgg tggtttttt    9780
gtttgcaagc agcagattac gcgcagaaaa aaaggatctc aagaagatcc tttgatcttt    9840
tctacggggt ctgacgctca gtggaacgaa aactcacgtt aagggatttt ggtcatgaga    9900
ttatcaaaaa ggatcttcac ctagatcctt ttaaattaaa aatgaagttt taaatcaatc    9960
taaagtatat atgagtaaac ttggtctgac agttaccaat gcttaatcag tgaggcacct   10020
```

```
atctcagcga tctgtctatt tcgttcatcc atagttgcct gactgcccgt cgtgtagata   10080
actacgatac gggagggctt accatctggc cccagtgctg caatgatacc gcagacccca   10140
cgctcaccgg ctccagattt atcagcaata aaccagccag ccggaagggc cgagcgcaga   10200
agtggtcctg caactttatc cgcctccatc cagtctatta attgttgccg ggaagctaga   10260
gtaagtagtt cgccagttaa tagtttgcgc aacgttgttg ccattgctac aggcatcgtg   10320
gtgtcacgct cgtcgtttgg tatggcttc                                    10349

<210> SEQ ID NO 76
<211> LENGTH: 10349
<212> TYPE: DNA
<213> ORGANISM: Artificial Sequence
<220> FEATURE:
<223> OTHER INFORMATION: Codon Optimized

<400> SEQUENCE: 76
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt ccttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020
tgttgtattt tttttttttt agagaaaatc ctccaatatc aaattaggaa tcgtagtttc   1080
atgattttct gttacaccta acttttgtg tggtgccctc ctccttgtca atattaatgt   1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaagaga atcttttta gcaaggattt   1380 tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
```

```
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca ataggcaat ggtggctcat     1920
gttgtagggc catgaaagcg gccattcttg tgattctttg cacttctgga acggtgtatt    1980
gttcactatc ccaagcgaca ccatcaccat cgtcttcctt tctcttacca aagtaaatac    2040
ctcccactaa ttctctgaca acaacgaagt cagtaccttt agcaaattgt ggcttgattg    2100
gagataagtc taaaagagag tcggatgcaa agttacatgg tcttaagttg cgtacaatt    2160
gaagttcttt acggattttt agtaaaccct tgttcaggtct aacactaccg gtaccccatt   2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaacctta atggcttcgg    2400
ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttttct cccaattttt    2700
cagttgaaaa aggtatatgc gtcaggcgac ctctgaaatt aacaaaaaat ttccagtcat    2760
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg attttgaaga gaatgtggat tttgatgtaa ttgttgggat    3060
tccatttta ataaggcaat aatattaggt atgtggatat actagaagtt ctcctcgagg     3120
gtcgatatgc ggtgtgaaat accgcacaga tgcgtaagga gaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg aaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacaggcg cgtcgcgcca ttcgccattc aggctgcgca    3660
actgttggga agggcgatcg gtgcgggcct ttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
cctttttcggt tagagcggat gtgggggagg ggcgtgaatg taagcgtgac ataactaatt    4080
```

```
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccT tgaaatagac atcgtgatga ttaccgttta acaatgtttt    4560
tgaggcacca acataacag gacctaatgc caattcaccg atacctggct tattttTagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctcttttctaa aaagtaatcc caagatatgt caccatctct    5280
caattctgca ccaatgttag aaccactaca agggataact attgccattg gggatttagc    5340
ttcaactact cttgaataca atggtattct ctttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg ccaaatata taacaacagc    5520 atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat    6000 ccaagcaggt ggggctggac cgaaatcctt gtagcaacca taaacaaca tttggtgtaa    6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
```

```
aaaaaaccett ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaactgcat  aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140 aaatatttttt ttgaatgaag aacatttgaa acaaaatcca aaattggttg aacatgatgt    7200
tcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc  tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga tttttgattt    7740
gcataaagat gttccaatgt tgatttctaa taatattgaa aaatgtttga ttgaagcttt    7800
tactccaatt ggtatttctg attggaattc tattttttgg attactcatc aggtggtaa    7860 agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg gttttgaatg    8040
gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaatttttca agacctacgt taatttggtc aacattatac ctgctatgaa    8280
agatgtatac tggggtaaag acgttacaca aaagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct cccccacat  ccgctctaac    8580 cgaaaaggaa ggagttagac aacctgaagt ctaggtccct atttattttt ttatagttat    8640
gttagtatta agaacgttat ttatatttca aattttctct tttttctgt  acagacgcgt    8700 gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
```

| | |
|---|---|
| gcgtaatcat ggtcatagct gtttcctgtg tgaaattgtt atccgctcac aattccacac | 8880 |
| aacataggag ccggaagcat aaagtgtaaa gcctggggtg cctaatgagt gaggtaactc | 8940 |
| acattaattg cgttgcgctc actgcccgct ttccagtcgg gaaacctgtc gtgccagctg | 9000 |
| cattaatgaa tcggccaacg cgcggggaga ggcggtttgc gtattgggcg ctcttccgct | 9060 |
| tcctcgctca ctgactcgct gcgctcggtc gttcggctgc ggcgagcggt atcagctcac | 9120 |
| tcaaaggcgg taatacggtt atccacagaa tcaggggata acgcaggaaa gaacatgtga | 9180 |
| gcaaaaggcc agcaaaaggc caggaaccgt aaaaaggccg cgttgctggc gttttttccat | 9240 |
| aggctcggcc cccctgacga gcatcacaaa aatcgacgct caagtcagag gtggcgaaac | 9300 |
| ccgacaggac tataaagata ccaggcgttc cccctggaa gctccctcgt gcgctctcct | 9360 |
| gttccgaccc tgccgcttac cggatacctg tccgcctttc tcccttcggg aagcgtggcg | 9420 |
| ctttctcaat gctcacgctg taggtatctc agttcggtgt aggtcgttcg ctccaagctg | 9480 |
| ggctgtgtgc acgaaccccc cgttcagccc gaccgctgcg ccttatccgg taactatcgt | 9540 |
| cttgagtcca acccggtaag acacgactta tcgccactgg cagcagccac tggtaacagg | 9600 |
| attagcagag cgaggtatgt aggcggtgct acagagttct tgaagtggtg cctaactac | 9660 |
| ggctacacta aaggacagt atttggtatc tgcgctctgc tgaagccagt taccttcgga | 9720 |
| aaaagagttg gtagctcttg atccggcaaa caaaccaccg ctggtagcgg tggtttttt | 9780 |
| gtttgcaagc agcagattac gcgcagaaaa aaaggatctc aagaagatcc tttgatcttt | 9840 |
| tctacggggt ctgacgctca gtggaacgaa aactcacgtt aagggatttt ggtcatgaga | 9900 |
| ttatcaaaaa ggatcttcac ctagatcctt ttaaattaaa aatgaagttt taaatcaatc | 9960 |
| taaagtatat atgagtaaac ttggtctgac agttaccaat gcttaatcag tgaggcacct | 10020 |
| atctcagcga tctgtctatt tcgttcatcc atagttgcct gactgcccgt cgtgtagata | 10080 |
| actacgatac gggagggctt accatctggc cccagtgctg caatgatacc gcgagaccca | 10140 |
| cgctcaccgg ctccagattt atcagcaata aaccagccag ccggaagggc cgagcgcaga | 10200 |
| agtggtcctg caactttatc cgcctccatc cagtctatta attgttgccg gaagctaga | 10260 |
| gtaagtagtt cgccagttaa tagtttgcgc aacgttgttg ccattgctac aggcatcgtg | 10320 |
| gtgtcacgct cgtcgtttgg tatggcttc | 10349 |

<210> SEQ ID NO 77
<211> LENGTH: 10349
<212> TYPE: DNA
<213> ORGANISM: Artificial Sequence
<220> FEATURE:
<223> OTHER INFORMATION: Codon Optimized

<400> SEQUENCE: 77

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aaacaggaag gcaaaatgcc gcaaaaaagg gaataagggc | 480 |

```
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaaattc ttgagggaac tttcaccatt atgggaaatg    960
gttcaagaag gtattgactt aaactccatc aaatggtcag gtcattgagt gttttttatt   1020
tgttgtattt ttttttttt agagaaaatc ctccaatatc aaattaggaa tcgtagtttc   1080
atgattttct gttacaccta acttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca ataggcaat ggtggctcat    1920
gttgtagggc catgaaagcg gccattcttg tgattcttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccta atggcttcgg    2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aacaatagg    2580
tccttaaata atattgtcaa cttcaagtat tgtgatgcaa gcatttagtc atgaacgctt   2640
ctctattcta tatgaaaagc cggttccggc ctctcacctt tccttttct cccaattttt    2700
cagttgaaaa aggtatatgc gtcaggcgac tctgaaatt aacaaaaaat ttccagtcat    2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
```

```
ctgcggtcaa gatatttctt gaatcaggcg ccttagaccg ctcggccaaa caaccaatta    2940
cttgttgaga aatagagtat aattatccta taaatataac gttttttgaac acacatgaac   3000 aaggaagtac aggacaattg attttgaaga gaatgtggat tttgatgtaa ttgttgggat    3060
tccattttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatatttg ttaaaattcg cgttaaattt ttgttaaatc agctcatttt     3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420 caagttttt ggggtcgagg tgccgtaaag cactaaatcg gaaccctaaa gggagccccc     3480
gatttagagc ttgacgggga agccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggag ggcgtgaatg taagcgtgac ataactaatt     4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa tctcaattgg ttcaaatcaa tggttgtgtc     4260
gtttgaatcc ttcaatacga aaatatgac caattgttct ggaccaccac ccaaaggtgg     4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacct tgaaatagac atcgtgatga ttaccgttta acaatgtttt     4560
tgaggcacca aacataacag gacctaatgc caattcaccg atacctggct tattttttagg   4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc     5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
```

```
gcagttttta aactccttgg ctctttctaa aaagtaatcc caagatatgt caccatctct    5280
caattctgca ccaatgttag aaccactaca agggataact attgccattg gggatttagc    5340
ttcaactact cttgaataca atggtattct cttttacct ctgatgatgt gatcttgtgt     5400
gaaaattgcc ttagctttgg ataatctcaa tctagttgag atttcagggg cggaaaatga    5460
atctgctata gagacaacta cgtaaccagc caatactatg ccaaatata taacaacagc     5520 atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat     6000 ccaagcaggt ggggctggac cgaaatcctt gtagcaacca taaacaaca tttggtgtaa     6060 ggagaaaggc aaatctggtg acaagatatg gttagcgatg ttgatccaag tttgagggt     6120 tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt ctttaatcg tggatccttc aaaaattctt actttttt tggatggacg       6300 caaagaagtt aataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccactta actaatactt tcaacatttt     6840
cggtttgtat tacttcttat tcaaatgtaa taaaagtatc aacaaaaat tgttaatata     6900 cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta atctgaaca     7080 tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta aagatattgc tgaaaataat aaaggtgcta gagttttggc    7500
tgtttgttgt gatatgactg cttgtttgtt tagaggtcca tctgattcta atttggaatt    7560
gttggttggt caagctattt ttggtgatgg tgctgctgct gttattgttg gtgctgaacc    7620
```

```
agatgaatct gttggtgaaa gaccaatttt tgaattggtt tctactggtc aaactttttt    7680
gccaaattct gaaggtacta ttggtggtca tattagagaa gctggtttga tgtttgattt    7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt tgttatggaa    7980
tgaattgaga aaaagatctt tggaagaagg taaatctact actggtgatg ttttgaatg    8040 gggtgttttg tttggttttg gtccaggttt gactgttgaa agagttgttt tgagatctgt    8100
tccaattaat tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaatttttca agacctacgt taatttggtc aacattatac ctgctatgaa    8280
agatgtatac tggggtaaag acgttacaca aagaaagaa gaaggttata cacacattgt     8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaaggaa ggagttagac aacctgaagt ctaggtccct atttattttt ttatagttat    8640
gttagtatta agaacgttat ttatatttca aattttctt tttttctgt acagacgcgt       8700 gtacgcatgt aacattatac tgaaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcagggggata acgcaggaaa gaacatgtga    9180
gcaaaaggcc agcaaaaggc caggaaccgt aaaaaggccg cgttgctggc gttttttccat    9240 aggctcggcc ccctgacga gcatcacaaa aatcgacgct caagtcagag gtggcgaaac      9300
ccgacaggac tataaagata ccaggcgttc cccctggaa gctccctcgt gcgctctcct     9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg gcctaactac    9660
ggctacacta aaggacagt atttggtatc tgcgctctgc tgaagccagt taccttcgga    9720
aaaagagttg gtagctcttg atccggcaaa caaaccaccg ctggtagcgg tggtttttt    9780 gtttgcaagc agcagattac gcgcagaaaa aaaggatctc aagaagatcc tttgatcttt    9840
tctacggggt ctgacgctca gtggaacgaa aactcacgtt aagggatttt ggtcatgaga    9900
ttatcaaaaa ggatcttcac ctagatcctt ttaaattaaa aatgaagttt taaatcaatc    9960
```

| | | | | |
|---|---|---|---|---|
| taaagtatat | atgagtaaac | ttggtctgac | agttaccaat gcttaatcag | tgaggcacct | 10020 |
| atctcagcga | tctgtctatt | tcgttcatcc | atagttgcct gactgcccgt | cgtgtagata | 10080 |
| actacgatac | gggagggctt | accatctggc | cccagtgctg caatgatacc | gcgagaccca | 10140 |
| cgctcaccgg | ctccagattt | atcagcaata | aaccagccag ccggaagggc | cgagcgcaga | 10200 |
| agtggtcctg | caactttatc | cgcctccatc | cagtctatta attgttgccg | ggaagctaga | 10260 |
| gtaagtagtt | cgccagttaa | tagtttgcgc | aacgttgttg ccattgctac | aggcatcgtg | 10320 |
| gtgtcacgct | cgtcgtttgg | tatggcttc | | | 10349 |

<210> SEQ ID NO 78
<211> LENGTH: 10367
<212> TYPE: DNA
<213> ORGANISM: Artificial Sequence
<220> FEATURE:
<223> OTHER INFORMATION: Codon Optimized

<400> SEQUENCE: 78

| | | | | | |
|---|---|---|---|---|---|
| attcagctcc | ggttcccaac | gatcaaggcg | agttacatga tcccccatgt | tgtgaaaaaa | 60 |
| agcggttagc | tccttcggtc | ctccgatcgt | tgtcagaagt aagttggccg | cagtgttatc | 120 |
| actcatggtt | atggcagcac | tgcataattc | tcttactgtc atgccatccg | taagatgctt | 180 |
| ttctgtgact | ggtgagtact | caaccaagtc | attctgagaa tagtgtatgc | ggcgaccgag | 240 |
| ttgctcttgc | ccggcgtcaa | tacgggataa | taccgcgcca catagcagaa | ctttaaaagt | 300 |
| gctcatcatt | ggaaaacgtt | cttcggggcg | aaaactctca aggatcttac | cgctgttgag | 360 |
| atccagttcg | atgtaaccca | ctcgtgcacc | caactgatct tcagcatctt | ttactttcac | 420 |
| cagcgtttct | gggtgagcaa | aaacaggaag | gcaaaatgcc gcaaaaaagg | gaataagggc | 480 |
| gacacggaaa | tgttgaatac | tcatactctt | cctttttcaa tattattgaa | gcatttatca | 540 |
| gggttattgt | ctcatgagcg | gatacatatt | tgaatgtatt tagaaaaata | aacaaatagg | 600 |
| ggttccgcgc | acatttcccc | gaaaagtgcc | acctgacgtc taagaaacca | ttattatcat | 660 |
| gacattaacc | tataaaaata | ggcgtatcac | gaggcccttt cgtctcgcgc | gtttcggtga | 720 |
| tgacggtgaa | aacctctgac | acatgcagct | cccggagacg gtcacagctt | gtctgtaagc | 780 |
| ggatgccggg | agcagacaag | cccgtcaggg | cgcgtcagcg ggtgttggcg | ggtgtcgggg | 840 |
| ctggcttaac | tatgcggcat | cagagcagat | tgtactgaga gtgcaccata | tcgactacgt | 900 |
| cgtaaggccg | tttctgacag | agtaaaattc | ttgagggaac tttcaccatt | atgggaaatg | 960 |
| gttcaagaag | gtattgactt | aaactccatc | aaatggtcag gtcattgagt | gttttttatt | 1020 |
| tgttgtattt | ttttttttt | agagaaaatc | ctccaatatc aaattaggaa | tcgtagtttc | 1080 |
| atgattttct | gttacaccta | acttttgtg | tggtgccctc ctccttgtca | atattaatgt | 1140 |
| taaagtgcaa | ttctttttcc | ttatcacgtt | gagccattag tatcaatttg | cttacctgta | 1200 |
| ttcctttact | atcctccttt | ttctccttct | tgataaatgt atgtagattg | cgtatatagt | 1260 |
| ttcgtctacc | ctatgaacat | attccatttt | gtaatttcgt gtcgtttcta | ttatgaattt | 1320 |
| catttataaa | gtttatgtac | aaatatcata | aaaaagaga tcttttttaa | gcaaggattt | 1380 |
| tcttaacttc | ttcggcgaca | gcatcaccga | cttcggtggt actgttggaa | ccacctaaat | 1440 |
| caccagttct | gatacctgca | tccaaaacct | ttttaactgc atcttcaatg | gccttacctt | 1500 |
| cttcaggcaa | gttcaatgac | aatttcaaca | tcattgcagc agacaagata | gtggcgatag | 1560 |
| ggtcaacctt | attctttggc | aaatctggag | cagaaccgtg gcatggttcg | tacaaaccaa | 1620 |
| atgcggtgtt | cttgtctggc | aaagaggcca | aggacgcaga tggcaacaaa | cccaaggaac | 1680 |

```
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaatac   2040 ctcccactaa ttctctgaca caacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtacccatt   2220 taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccta atggcttcgg   2400 ctgtgatttc ttgaccaacg tggtcacctg gcaaaacgac gatcttctta ggggcagaca   2460 tagggggcaga cattgaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac tctgaaatt aacaaaaat ttccagtcat   2760 cgaatttgat tctgtgcgat agcgccctg tgtgttctcg ttatgttgag gaaaaaata   2820 atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gttttgaac acacatgaac   3000 aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420 caagttttt ggggtcgagg tgccgtaaag cactaaatcg aaccctaaa gggagccccc   3480 gatttagagc ttgacgggga agccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacaggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
```

```
ccttttcggt tagagcggat gtgggggagg ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctcttttcgat   4380 ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta acaatgtttt   4560
tgaggcacca acataacag gacctaatgc caattcaccg atacctggct tattttagg      4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc caagatatgt caccatctct    5280
caattctgca ccaatgttag aaccactaca agggataact attgccattg gggatttagc    5340
ttcaactact cttgaataca atggtattct ctttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg ccaaatata taacaacagc    5520 atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttacccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttttcag ggtctggaat    6000 ccaagcaggt ggggctggac cgaaatcctt gtagcaacca taaaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
```

```
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
ggaagaaatt aaaggtgttt tgaaagctaa agatgttggt tgtgttgcta ctattttggc    7020
tattggtact gctaatccat tgaattgtgt taatcaagat gaattttttgc attcttattt    7080 taaattgact aataatcata ataatacttc ttttaaagaa ttgtttacta gaatttgtaa    7140
taattctatg attaaaaata gatatatgca tttgactgaa gatattttga aagaaaatcc    7200
aaatttgtgt gattatgctg ctcaatcttt gaatactaga caagatatta aaattaaaga    7260
aattccaaaa ttggctgaaa gagctgctat ggttgctatt aaagaatggg gtaaaccaat    7320
ttctaatttg actcatatta tttttcattc ttctactggt gctgctgata tgccaggtgc    7380
tgattatcaa ttggttaaat ctttgggttt gaatagatct attaaaagaa ttatgttgta    7440
taatttgggt tgttttgctg gtggtactgt tttgagagtt gctaaagatt tggttgaaaa    7500
taatttgggt gcttctgttt tggctgtttg tgctgaaatt acttctgctg atgctacttt    7560
tggtagattg tctgaagatg ataaaggtag attggttggt catgctattt ttggtgatgg    7620
tgctgctgct ttggttattg gtaatgctga tgatccagaa aataaaggtt tgtttcaaat    7680
tgtttctact tctcaaacta ttttgccaaa ttctgaaggt tgtattgaag gtcatattag    7740
agaagatggt gttacttttta ctttgtctcc aagagttcca aaattgattg gtgataatat    7800
tgaaacttgt ttgatggaag cttttactcc atttaaaatt tctgattgga attctttgtt    7860
ttgggttgtt catccaggtg gtgctgctat tttgagagaa gttgaatcta gagttggttt    7920
ggaacaagaa aaattgagag cttcttggca tgttttgaga gaatatggta atatttcttc    7980
tgcttctgtt ttgtttatt tggatgaaat gagaaataaa tctttggaag aaggtagaaa    8040
aactactggt gaaggtaaaa attggggtgt tttgtttggt tttggtccag gtttgactgt    8100
tgaaactgtt gttttgcatt ctattccaat gaaggtaga ggttccttgt taacttgtgg    8160
tgacgttgaa gaaacccag gtcctatggc cgtcaagcat tgatagtat tgaagtttaa    8220 agatgaaatc acagaagctc aaaaggaaga attttttcaag acctacgtta atttggtcaa    8280
cattatacct gctatgaaag atgtatactg gggtaaagac gttacacaaa agaaagaaga    8340
aggttataca cacattgtcg aagtaaccctt cgaatcagtt gaaactatcc aagattacat    8400
cattcatcca gctcacgttg gttttggtga cgtttacaga tccttctggg aaaaattgtt    8460
gatcttcgat tacaccccaa gaaagtgatg atgggctgca ggaattcgat atcaagctta    8520
tcgataccgt cgacctcgag tcatgtaatt agttatgtca cgcttacatt cacgccctcc    8580
ccccacatcc gctctaaccg aaaaggaagg agttagacaa cctgaagtct aggtccctat    8640
ttattttttt atagttatgt tagtattaag aacgttattt atatttcaaa ttttttctttt    8700 ttttctgtac agacgcgtgt acgcatgtaa cattatactg aaaaccttgc ttgagaaggt    8760
```

| | |
|---|---|
| tttgggacgc tcgaaggctt taatttgcgg ccggtaccca gcttttgttc cctttagtga | 8820 |
| gggttaattc cgagcttggc gtaatcatgg tcatagctgt ttcctgtgtg aaattgttat | 8880 |
| ccgctcacaa ttccacacaa cataggagcc ggaagcataa agtgtaaagc ctggggtgcc | 8940 |
| taatgagtga gtaactcac attaattgcg ttgcgctcac tgcccgcttt ccagtcggga | 9000 |
| aacctgtcgt gccagctgca ttaatgaatc ggccaacgcg cggggagagg cggtttgcgt | 9060 |
| attgggcgct cttccgcttc ctcgctcact gactcgctgc gctcggtcgt tcggctgcgg | 9120 |
| cgagcggtat cagctcactc aaaggcggta atacggttat ccacagaatc aggggataac | 9180 |
| gcaggaaaga acatgtgagc aaaaggccag caaaaggcca ggaaccgtaa aaaggccgcg | 9240 |
| ttgctggcgt ttttccatag gctcggcccc cctgacgagc atcacaaaaa tcgacgctca | 9300 |
| agtcagaggt ggcgaaaccc gacaggacta taaagatacc aggcgttccc cctggaagc | 9360 |
| tccctcgtgc gctctcctgt tccgaccctg ccgcttaccg gatacctgtc cgcctttctc | 9420 |
| ccttcgggaa gcgtggcgct ttctcaatgc tcacgctgta ggtatctcag ttcggtgtag | 9480 |
| gtcgttcgct ccaagctggg ctgtgtgcac gaaccccccg ttcagcccga ccgctgcgcc | 9540 |
| ttatccggta actatcgtct tgagtccaac ccggtaagac acgacttatc gccactggca | 9600 |
| gcagccactg gtaacaggat tagcagagcg aggtatgtag cggtgctac agagttcttg | 9660 |
| aagtggtggc ctaactacgg ctacactaga aggacagtat ttggtatctg cgctctgctg | 9720 |
| aagccagtta ccttcggaaa aagagttggt agctcttgat ccggcaaaca aaccaccgct | 9780 |
| ggtagcggtg gttttttgt ttgcaagcag cagattacgc gcagaaaaaa aggatctcaa | 9840 |
| gaagatcctt tgatcttttc tacggggtct gacgctcagt ggaacgaaaa ctcacgttaa | 9900 |
| gggattttgg tcatgagatt atcaaaaagg atcttcacct agatcctttt aaattaaaaa | 9960 |
| tgaagtttta aatcaatcta agtatatat gagtaaactt ggtctgacag ttaccaatgc | 10020 |
| ttaatcagtg aggcacctat ctcagcgatc tgtctatttc gttcatccat agttgcctga | 10080 |
| ctgcccgtcg tgtagataac tacgatacgg gagggcttac catctggccc cagtgctgca | 10140 |
| atgataccgc gagacccacg ctcaccggct ccagatttat cagcaataaa ccagccagcc | 10200 |
| ggaagggccg agcgcagaag tggtcctgca actttatccg cctccatcca gtctattaat | 10260 |
| tgttgccggg aagctagagt aagtagttcg ccagttaata gtttgcgcaa cgttgttgcc | 10320 |
| attgctacag gcatcgtggt gtcacgctcg tcgtttggta tggcttc | 10367 |

<210> SEQ ID NO 79
<211> LENGTH: 10349
<212> TYPE: DNA
<213> ORGANISM: Artificial Sequence
<220> FEATURE:
<223> OTHER INFORMATION: Codon Optimized

<400> SEQUENCE: 79

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aacaggaag gcaaaatgcc gcaaaaaagg gaataagggc | 480 |

```
gacacggaaa tgttgaatac tcatactctt cctttttcaa tattattgaa gcatttatca    540 ggggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggccctttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaaattc ttgagggaac tttcaccatt atgggaaatg    960
gttcaagaag gtattgactt aaactccatc aaatggtcag gtcattgagt gttttttatt   1020
tgttgtattt ttttttttttt agagaaaatc ctccaatatc aaattaggaa tcgtagtttc   1080
atgattttct gttcacccta actttttgtg tggtgccctc ctccttgtca atattaatgt   1140
taaagtgcaa ttcttttttcc ttatcacgtt gagccattag tatcaattttg cttacctgta   1200 ttcctttact atcctccttt ttctccttct tgataaatgt atgtagattg cgtatatagt   1260
ttcgtctacc ctatgaacat attccattttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgtggaa ccacctaaat   1440 caccagttct gataacctgca tccaaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaagagag tcggatgcaa agttacatgg tcttaagttg cgtacaatt   2160 gaagttcttt acggattttt agtaaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccttta atggcttcgg   2400 ctgtgatttc ttgaccaacg tggtcacctg gcaaaacgac gatcttctta ggggcagaca   2460 tagggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttct cccaattttt   2700 cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
```

```
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg attttgaaga gaatgtggat tttgatgtaa ttgttgggat    3060
tccattttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatatttg ttaaaattcg cgttaaattt ttgttaaatc agctcatttt     3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcacctaat     3420
caagtttttt ggggtcgagg tgccgtaaag cactaaatcg aaccctaaa gggagccccc     3480
gatttagagc ttgacgggga agccggcga acgtggcgag aaggaaggg aagaaagcga      3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaatttg aaatataaat aacgttctta     3960
atactaacat aactataaaa aaataaatag ggacctagac ttcaggttgt ctaactcctt    4020
cctttcggt tagagcggat gtgggggag ggcgtgaatg taagcgtgac ataactaatt      4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttctttgc aaacccaagt taaggataa tctcaattgg ttcaaatcaa tggttgtgtc      4260
gtttgaatcc ttcaatacga aaatatgac caattgttct ggaccaccac ccaaaggtgg     4320
aacaccaata gcagtggttt caaaaactct gtcatctact tcattacaga ctcttcgat     4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgtttt    4560
tgaggcacca acataacag gacctaatgc caattcaccg atacctggct tattttagg      4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc     5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
```

-continued

```
gcagttttta aactccttgg ctctttctaa aaagtaatcc caagatatgt caccatctct    5280
caattctgca ccaatgttag aaccactaca agggataact attgccattg gggatttagc    5340
ttcaactact cttgaataca atggtattct cttttacct ctgatgatgt gatcttgtgt     5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag gtctggaat      6000 ccaagcaggt ggggctggac cgaaatcctt gtagcaacca taaacaaca tttggtgtaa    6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt ctgggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020 aaatatttg attcaagatg aatttccaga ttattatttt agagttacta atctgaaca     7080 tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
tgtttgttgt gatattatgg cttgtttgtt tagaggtcca tctgattctg atttggaatt    7560
```

```
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga ttttttgattt   7740 gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt tgttatgga    7980 tgaattgaga aaaagatctt tggaagaagg taaatctact actggtgatg gttttgaatg    8040
gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaatttttca agacctacgt taatttggtc aacattatac ctgctatgaa    8280
agatgtatac tggggtaaag acgttacaca aagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaaggaa ggagttagac aacctgaagt ctaggtccct attatatttttt ttatagttat   8640 gttagtatta agaacgttat ttatatttca aatttttctt tttttttctgt acagacgcgt   8700 gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcagggggata acgcaggaaa gaacatgtga    9180
gcaaaaggcc agcaaaaggc caggaaccgt aaaaaggccg cgttgctggc gtttttccat    9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg gcctaactac    9660
ggctacacta aaggacagt atttggtatc tgcgctctgc tgaagccagt taccttcgga    9720
aaaagagttg gtagctcttg atccggcaaa caaaccaccg ctggtagcgg tggttttttt    9780
gtttgcaagc agcagattac gcgcagaaaa aaggatctc aagaagatcc tttgatcttt    9840
tctacggggt ctgacgctca gtggaacgaa aactcacgtt aagggatttt ggtcatgaga    9900
ttatcaaaaa ggatcttcac ctagatcctt ttaaattaaa aatgaagttt taaatcaatc    9960
```

-continued

| | |
|---|---|
| taaagtatat atgagtaaac ttggtctgac agttaccaat gcttaatcag tgaggcacct | 10020 |
| atctcagcga tctgtctatt tcgttcatcc atagttgcct gactgcccgt cgtgtagata | 10080 |
| actacgatac gggagggctt accatctggc cccagtgctg caatgatacc gcgagaccca | 10140 |
| cgctcaccgg ctccagattt atcagcaata aaccagccag ccggaagggc cgagcgcaga | 10200 |
| agtggtcctg caactttatc cgcctccatc cagtctatta attgttgccg ggaagctaga | 10260 |
| gtaagtagtt cgccagttaa tagtttgcgc aacgttgttg ccattgctac aggcatcgtg | 10320 |
| gtgtcacgct cgtcgtttgg tatggcttc | 10349 |

<210> SEQ ID NO 80
<211> LENGTH: 10394
<212> TYPE: DNA
<213> ORGANISM: Artificial Sequence
<220> FEATURE:
<223> OTHER INFORMATION: Codon Optimized

<400> SEQUENCE: 80

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aaacaggaag gcaaaatgcc gcaaaaaagg gaataagggc | 480 |
| gacacggaaa tgttgaatac tcatactctt cctttttcaa tattattgaa gcatttatca | 540 |
| gggttattgt ctcatgagcg gatacatatt tgaatgtatt tagaaaaata aacaaatagg | 600 |
| ggttccgcgc acatttcccc gaaaagtgcc acctgacgtc taagaaacca ttattatcat | 660 |
| gacattaacc tataaaaata ggcgtatcac gaggcccttt cgtctcgcgc gtttcggtga | 720 |
| tgacggtgaa aacctctgac acatgcagct cccggagacg gtcacagctt gtctgtaagc | 780 |
| ggatgccggg agcagacaag cccgtcaggg cgcgtcagcg ggtgttggcg ggtgtcgggg | 840 |
| ctggcttaac tatgcggcat cagagcagat tgtactgaga gtgcaccata tcgactacgt | 900 |
| cgtaaggccg tttctgacag agtaaaattc ttgagggaac tttcaccatt atgggaaatg | 960 |
| gttcaagaag gtattgactt aaactccatc aaatggtcag gtcattgagt gttttttatt | 1020 |
| tgttgtattt ttttttttt agagaaaatc ctccaatatc aaattaggaa tcgtagtttc | 1080 |
| atgattttct gttacaccta actttttgtg tggtgccctc ctccttgtca atattaatgt | 1140 |
| taaagtgcaa ttctttttcc ttatcacgtt gagccattag tatcaatttg cttacctgta | 1200 |
| ttcctttact atcctccttt ttctccttct tgataaatgt atgtagattg cgtatatagt | 1260 |
| ttcgtctacc ctatgaacat attccatttt gtaatttcgt gtcgtttcta ttatgaattt | 1320 |
| catttataaa gttatgtgac aaatatcata aaaaaagaga atcttttttaa gcaaggattt | 1380 |
| tcttaacttc ttcggcgaca gcatcaccga cttcggtggt actgttggaa ccacctaaat | 1440 |
| caccagttct gatacctgca tccaaaacct tttaactgc atcttcaatg gccttacctt | 1500 |
| cttcaggcaa gttcaatgac aatttcaaca tcattgcagc agacaagata gtggcgatag | 1560 |
| ggtcaacctt attctttggc aaatctggag cagaaccgtg gcatggttcg tacaaaccaa | 1620 |

```
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca agtaaatac     2040 ctcccactaa ttctctgaca caacgaagt cagtaccttt agcaaattgt ggcttgattg     2100
gagataagtc taaaagagag tcggatgcaa agttacatgg tcttaagttg gcgtacaatt    2160
gaagttcttt acggattttt agtaaacctt gttcaggtct aacactaccg gtaccccatt    2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaacctta atggcttcgg    2400
ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttttct cccaattttt    2700 cagttgaaaa aggtatatgc gtcaggcgac tctgaaatt aacaaaaaat ttccagtcat    2760
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttttgaac acacatgaac    3000 aaggaagtac aggacaattg atttttgaaga gaatgtggat tttgatgtaa ttgttgggat    3060 tccatttttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatatttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaagggg     3720 gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
```

```
cctttcggt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta caatgttttt    4560
tgaggcacca acataacag gacctaatgc caattcaccg atacctggct tattttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctcttttctaa aaagtaatcc caagatatgt caccatctct    5280
caattctgca ccaatgttag aaccactaca agggataact attgccattg gggatttagc    5340
ttcaactact cttgaataca atggtattct cttttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct tttctaaac ccatttcttc    5580 caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820 aatttttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg actttttcag ggtctggaat    6000
ccaagcaggt ggggctggac cgaaatcctt gtagcaacca taaacaaca tttggtgtaa    6060 ggagaaaggc aaatctggtg acaagatatg gttagcgatg ttgatccaag tttgaggggt    6120
tgcagcacca taattacaaa cgattctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
```

```
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatgggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga ttttgattt    7740
gcataaagat gttccaatgt tgatttctaa taatattgaa aaatgtttga ttgaagcttt    7800
tactccaatt ggtatttctg attggaattc tatttttttgg attactcatc caggtggtaa    7860
agctattttg gataaagttg aagaaaaatt gcatttgaaa tctgataaat tgttgattc    7920
tagacatgtt ttgtctgaac atggtaatat gtcttcttct actgtttttgt ttgttatgga    7980
tgaattgaga aaaagatctt tggaagaagg taaatctact actggtgatg gtttttgaatg    8040
gggtgttttg tttggttttg gtccaggttt gactgttgaa agaggtagat ggagaaaagg    8100
taatttgcca ttggaaatgg atttgtctgg tgttttttt ttgggtttgg atcaagttga    8160
aggtagaggt tccttgttaa cttgtggtga cgttgaagaa aacccaggtc ctatggccgt    8220
caagcatttg atagtattga agtttaaaga tgaaatcaca gaagctcaaa aggaagaatt    8280
tttcaagacc tacgttaatt tggtcaacat tatacctgct atgaaagatg tatactgggg    8340
taaagacgtt acacaaaaga aagaagaagg ttatacacac attgtcgaag taaccttcga    8400
atcagttgaa actatccaag attacatcat tcatccagct cacgttggtt ttggtgacgt    8460
ttacagatcc ttctgggaaa aattgttgat cttcgattac accccaagaa agtgatgatg    8520
ggctgcagga attcgatatc aagcttatcg ataccgtcga cctcgagtca tgtaattagt    8580
tatgtcacgc ttacattcac gccctccccc cacatccgct ctaaccgaaa aggaaggagt    8640
tagacaacct gaagtctagg tccctattta ttttttttata gttatgttag tattaagaac    8700
gttatttata tttcaaattt ttcttttttt tctgtacaga cgcgtgtacg catgtaacat    8760
```

```
tatactgaaa accttgcttg agaaggtttt gggacgctcg aaggctttaa tttgcggccg      8820
gtacccagct tttgttccct ttagtgaggg ttaattccga gcttggcgta atcatggtca      8880
tagctgtttc ctgtgtgaaa ttgttatccg ctcacaattc cacacaacat aggagccgga      8940
agcataaagt gtaaagcctg gggtgcctaa tgagtgaggt aactcacatt aattgcgttg      9000
cgctcactgc ccgctttcca gtcgggaaac ctgtcgtgcc agctgcatta atgaatcggc      9060
caacgcgcgg ggagaggcgg tttgcgtatt gggcgctctt ccgcttcctc gctcactgac      9120
tcgctgcgct cggtcgttcg gctgcggcga gcggtatcag ctcactcaaa ggcggtaata      9180
cggttatcca cagaatcagg ggataacgca ggaaagaaca tgtgagcaaa aggccagcaa      9240
aaggccagga accgtaaaaa ggccgcgttg ctggcgtttt tccataggct ccgcccccct      9300
gacgagcatc acaaaaatcg acgctcaagt cagaggtggc gaaacccgac aggactataa      9360
agataccagg cgttccccc  tggaagctcc ctcgtgcgct ctcctgttcc gaccctgccg      9420
cttaccggat acctgtccgc ctttctccct tcgggaagcg tggcgctttc tcaatgctca      9480
cgctgtaggt atctcagttc ggtgtaggtc gttcgctcca agctgggctg tgtgcacgaa      9540
ccccccgttc agcccgaccg ctgcgcctta tccggtaact atcgtcttga gtccaacccg      9600
gtaagacacg acttatcgcc actggcagca gccactggta acaggattag cagagcgagg      9660
tatgtaggcg gtgctacaga gttcttgaag tggtggccta actacggcta cactagaagg      9720
acagtatttg gtatctgcgc tctgctgaag ccagttacct tcggaaaaag agttggtagc      9780
tcttgatccg gcaaacaaac caccgctggt agcggtggtt ttttgtttg  caagcagcag      9840 attacgcgca gaaaaaagg  atctcaagaa gatcctttga tcttttctac ggggtctgac      9900
gctcagtgga acgaaaactc acgttaaggg attttggtca tgagattatc aaaaaggatc      9960
ttcacctaga tccttttaaa ttaaaaatga agttttaaat caatctaaag tatatatgag     10020
taaacttggt ctgacagtta ccaatgctta atcagtgagg cacctatctc agcgatctgt     10080
ctatttcgtt catccatagt tgcctgactg cccgtcgtgt agataactac gatacgggag     10140
ggcttaccat ctggccccag tgctgcaatg ataccgcgag acccacgctc accggctcca     10200
gatttatcag caataaacca gccagccgga agggccgagc gcagaagtgg tcctgcaact     10260
ttatccgcct ccatccagtc tattaattgt tgccgggaag ctagagtaag tagttcgcca     10320
gttaatagtt tgcgcaacgt tgttgccatt gctacaggca tcgtggtgtc acgctcgtcg     10380
tttggtatgg cttc                                                      10394
```

<210> SEQ ID NO 81
<211> LENGTH: 10361
<212> TYPE: DNA
<213> ORGANISM: Artificial Sequence
<220> FEATURE:
<223> OTHER INFORMATION: Codon Optimized

<400> SEQUENCE: 81

```
attcagctcc ggttcccaac gatcaaggcg agttacatga tccccatgt  tgtgaaaaaa        60 agcggttagc tccttcggtc ctccgatcgt tgtcagaagt aagttggccg cagtgttatc       120
actcatggtt atggcagcac tgcataattc tcttactgtc atgccatccg taagatgctt       180
ttctgtgact ggtgagtact caaccaagtc attctgagaa tagtgtatgc ggcgaccgag       240
ttgctcttgc ccggcgtcaa tacgggataa taccgcgcca catagcagaa ctttaaaagt       300
gctcatcatt ggaaaacgtt cttcggggcg aaaactctca aggatcttac cgctgttgag       360
```

```
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaaatt ctgagggaac tttcaccatt atgggaaatg    960
gttcaagaag gtattgactt aaactccatc aaatggtcag gtcattgagt gttttttatt    1020
tgttgtattt tttttttttt agagaaaatc ctccaatatc aaattaggaa tcgtagtttc    1080
atgattttct gttacaccta acttttttgtg tggtgccctc ctccttgtca atattaatgt    1140
taaagtgcaa ttctttttcc ttatcacgtt gagccattag tatcaatttg cttacctgta    1200
ttcctttact atcctccttt ttctccttct tgataaatgt atgtagattg cgtatatagt    1260
ttcgtctacc ctatgaacat attccatttt gtaatttcgt gtcgtttcta ttatgaattt    1320
catttataaa gtttatgtac aaatatcata aaaaagaga tcttttttaa gcaaggattt    1380
tcttaacttc ttcggcgaca gcatcaccga cttcggtggt actgttggaa ccacctaaat    1440
caccagttct gatacctgca tccaaaacct ttttaactgc atcttcaatg gccttacctt    1500
cttcaggcaa gttcaatgac aatttcaaca tcattgcagc agacaagata gtggcgatag    1560
ggtcaacctt attctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca aagtaaatac    2040
ctcccactaa ttctctgaca acaacgaagt cagtaccttt agcaaattgt ggcttgattg    2100
gagataagtc taaaagagag tcggatgcaa agttacatgg tcttaagttg gcgtacaatt    2160
gaagttcttt acggattttt agtaaacctt gttcaggtct aacactaccg gtaccccatt    2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaacctta atggcttcgg    2400
ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttctc cccaattttt    2700
cagttgaaaa aggtatatgc gtcaggcgac ctctgaaatt aacaaaaaat ttccagtcat    2760
```

```
cgaatttgat tctgtgcgat agcgccctg  tgtgttctcg ttatgttgag gaaaaaata   2820
atggttgcta agagattcga actcttgcat cttacgatac ctgagtattc ccacagttaa  2880
ctgcggtcaa gatatttctt gaatcaggcg ccttagaccg ctcggccaaa caaccaatta  2940
cttgttgaga aatagagtat aattatccta taaatataac gttttgaac  acacatgaac  3000
aaggaagtac aggacaattg attttgaaga gaatgtggat tttgatgtaa ttgttgggat  3060
tccatttta  ataaggcaat aatattaggt atgtggatat actagaagtt ctcctcgagg  3120
gtcgatatgc ggtgtgaaat accgcacaga tgcgtaagga gaaaataccg catcaggaaa  3180
ttgtaaacgt taatattttg ttaaaattcg cgttaaattt ttgttaaatc agctcatttt  3240
ttaaccaata ggccgaaatc ggcaaaatcc cttataaatc aaaagaatag accgagatag  3300
ggttgagtgt tgttccagtt tggaacaaga gtccactatt aaagaacgtg gactccaacg  3360
tcaaagggcg aaaaaccgtc tatcagggcg atggcccact acgtgaacca tcaccctaat  3420
caagtttttt ggggtcgagg tgccgtaaag cactaaatcg gaaccctaaa gggagccccc  3480
gatttagagc ttgacgggga agccggcga  acgtggcgag aaaggaaggg aagaaagcga  3540
aaggagcggg cgctagggcg ctggcaagtg tagcggtcac gctgcgcgta accaccacac  3600
ccgccgcgct taatgcgccg ctacagggcg cgtcgcgcca ttcgccattc aggctgcgca  3660
actgttggga agggcgatcg gtgcgggcct cttcgctatt acgccagctg gcgaaggggg  3720
gatgtgctgc aaggcgatta agttgggtaa cgccagggtt ttcccagtca cgacgttgta  3780
aaacgacggc cagtgaattg taatacgact cactataggg cgaattggag ctctagtcgc  3840
aaattaaagc cttcgagcgt cccaaaacct tctcaagcaa ggttttcagt ataatgttac  3900
atgcgtacac gcgtctgtac agaaaaaaaa gaaaatttg  aaatataaat aacgttctta  3960
atactaacat aactataaaa aaataaatag ggacctagac ttcaggttgt ctaactcctt  4020
ccttttcggt tagagcggat gtgggggag  ggcgtgaatg taagcgtgac ataactaatt  4080
acatgatcat tcgaaatgac tgaattgttg tctcaaaact cttctcatga tcttgtttgt  4140
tgcagttcta ggtaaggatg acaatgggac aactctagta actttgaata atgggttcaa  4200
tttctttttgc aaacccaagt taaaggataa tctcaattgg ttcaaatcaa tggttgtgtc  4260
gtttgaatcc ttcaatacga aaatatgac  caattgttct ggaccaccac ccaaaggtgg  4320
aacaccaata gcagtggttt caaaaactct gtcatctact tcattacaga ctctttcgat  4380
ttcgatagaa ctaattttga taccaccgat gttcatagtg tcatcggctc taccgtgtgc  4440
atggtagtaa ccgttagagg tcaattcgaa aatgtcacca tgtcttctca atacttcacc  4500
attcaaggtt ggcatacct  tgaaatagac atcgtgatga ttaccgttta acaatgtttt  4560
tgaggcacca aacataacag gacctaatgc caattcaccg atacctggct tattttagg   4620
cattgggtaa ccgttcttat ctaatatgta caaggtgcaa cccatacatt gggatgaaaa  4680
agaacttaaa gattgagctt gcaaaaatga accagcagaa aaagcaccac cgatttctgt  4740
accaccacac atttctataa ctggcttgta gttagctcta cccattaacc acaaatattc  4800
gtctacatta gaggcttcac cggatgaaga aaagcatctt atggtggacc aatcgtaacc  4860
tgaaacacaa tttgtggatt tccatgatct tacaatagat ggtacgacac ccaacattgt  4920
gacctttgca tcttgaacaa atttagcgaa accagagact aaaggactac cgttgtacaa  4980
ggcaatagat gcaccattta acaaactagc ataaccaaac caaggaccca tcatccaacc  5040
caaattagtt ggccatacta taacgtcacc ttttctaata tccaaatgag accaaccatc  5100
```

```
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc aagatatgt caccatctct     5280 caattctgca ccaatgttag aaccactaca agggataact attgccattg gggatttagc    5340
ttcaactact cttgaataca atggtattct cttttacct ctgatgatgt gatcttgtgt     5400
gaaaattgcc ttagctttgg ataatctcaa tctagttgag atttcagggg cggaaaatga    5460
atctgctata gagacaacta cgtaaccagc caatactatg ccaaatata taacaacagc     5520 atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat     6000 ccaagcaggt ggggctggac cgaaatcctt gtagcaacca taaacaaca tttggtgtaa     6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt ctttaatcg tggatccttc aaaaattctt actttttttt tggatggacg     6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaccttca atgaacgaa tcaaattaac aaccatagga tgataatgcg      6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
ggttactgtt gaagaattta gaaaagctca agagctgaa ggtccagcta ctattatggc     7020
tattggtact gctactccag ctaattgtgt tttgcaatct gaatatccag attattattt    7080
tagaattact aattctgaac ataaaactga attgaaagaa aaatttaaaa gaatgtgtga    7140
taaatctatg attagaaaaa gatatatgca tttgactgaa gaaattttga aagaaaatcc    7200
aaatttgtgt gctatgaag ctccatcttt ggatgctaga caagatatgg ttgttgttga     7260
agttccaaaa ttgggtaaag aagctgctac taaagctatt aaagaatggg gtcaaccaaa    7320
atctaaaatt actcatttgg tttttgtac tacttctggt gttgatatgc caggtgctga     7380
ttatcaattg actaaattgt tgggtttgag accatcgtt aaaagattga tgatgtatca     7440
acaaggttgt tttgctggtg gtactgtttt gagattggct aaagatttgg ctgaaaataa    7500
```

```
taaaggtgct agagttttgg ttgtttgttc tgaaattact gctgttactt ttagaggtcc    7560
aaatgatact catttggatt ctttggttgg tcaagctttg tttggtgatg gttctgctgc    7620
tttgattgtt ggttctgatc caattccaga agttgaaaaa ccaattttg aattggtttc    7680 tgctgctcaa actattttgc cagattctga tggtgctatt gatggtcatt tgagagaagt    7740
tggtttgact tttcatttgt tgaaagatgt tccaggtttg atttctaaaa atattgaaaa    7800
atctttgaat gaagctttta aaccattggg tatttctgat tggaattctt tgttttggat    7860
tgctcatcca ggtggtccag ctattttgga tcaagttgaa tctaaattgg ctttgaaaac    7920
tgaaaaattg agagctacta gacatgtttt gtctgaatat ggtaatatgt cttctgcttg    7980
tgttttgttt attttggatg aaatgagaag aaaatgtgtt gaagatggtt tgaatactac    8040
tggtgaaggt ttggaatggg gtgttttgtt tggttttggt ccaggtttga ctgttgaaac    8100
tgttgttttg cattctgttg ctattgaagg tagaggttcc ttgttaactt gtggtgacgt    8160
tgaagaaaac ccaggtccta tggccgtcaa gcatttgata gtattgaagt ttaaagatga    8220
aatcacagaa gctcaaaagg aagaattttt caagacctac gttaatttgg tcaacattat    8280
acctgctatg aaagatgtat actggggtaa agacgttaca caaagaaag aagaaggtta    8340 tacacacatt gtcgaagtaa ccttcgaatc agttgaaact atccaagatt acatcattca    8400
tccagctcac gttggttttg gtgacgttta cagatccttc tgggaaaaat tgttgatctt    8460
cgattacacc ccaagaaagt gatgatgggc tgcaggaatt cgatatcaag cttatcgata    8520
ccgtcgacct cgagtcatgt aattagttat gtcacgctta cattcacgcc ctccccccac    8580
atccgctcta accgaaaagg aaggagttag acaacctgaa gtctaggtcc ctatttattt    8640
ttttatagtt atgttagtat taagaacgtt atttatattt caaattttc ttttttttct    8700 gtacagacgc gtgtacgcat gtaacattat actgaaaacc ttgcttgaga aggttttggg    8760
acgctcgaag gctttaattt gcggccggta cccagctttt gttcccttta gtgagggtta    8820
attccgagct tggcgtaatc atggtcatag ctgtttcctg tgtgaaattg ttatccgctc    8880
acaattccac acaacatagg agccggaagc ataaagtgta aagcctgggg tgcctaatga    8940
gtgaggtaac tcacattaat tgcgttgcgc tcactgcccg ctttccagtc gggaaacctg    9000
tcgtgccagc tgcattaatg aatcggccaa cgcgcgggga gaggcggttt gcgtattggg    9060
cgctcttccg cttcctcgct cactgactcg ctgcgctcgg tcgttcggct gcggcgagcg    9120
gtatcagctc actcaaaggc ggtaatacgg ttatccacag aatcagggga taacgcagga    9180
aagaacatgt gagcaaaagg ccagcaaaag gccaggaacc gtaaaaaggc cgcgttgctg    9240
gcgtttttcc ataggctcgg cccccctgac gagcatcaca aaaatcgacg ctcaagtcag    9300
aggtggcgaa acccgacagg actataaaga taccaggcgt tccccctgg aagctccctc    9360 gtgcgctctc ctgttccgac cctgccgctt accggatacc tgtccgcctt tctcccttcg    9420
ggaagcgtgg cgctttctca atgctcacgc tgtaggtatc tcagttcggt gtaggtcgtt    9480
cgctccaagc tgggctgtgt gcacgaaccc cccgttcagc ccgaccgctg cgccttatcc    9540
ggtaactatc gtcttgagtc aacccggta agacacgact tatcgccact ggcagcagcc    9600
actggtaaca ggattagcag agcgaggtat gtaggcggtg ctacagagtt cttgaagtgg    9660
tggcctaact acggctacac tagaaggaca gtatttggta tctgcgctct gctgaagcca    9720
gttaccttcg gaaaaagagt tggtagctct tgatccggca aacaaaccac cgctggtagc    9780
ggtggttttt ttgtttgcaa gcagcagatt acgcgcagaa aaaaaggatc tcaagaagat    9840
```

| | |
|---|---|
| cctttgatct tttctacggg gtctgacgct cagtggaacg aaaactcacg ttaagggatt | 9900 |
| ttggtcatga gattatcaaa aaggatcttc acctagatcc tttaaatta aaaatgaagt | 9960 |
| tttaaatcaa tctaaagtat atatgagtaa acttggtctg acagttacca atgcttaatc | 10020 |
| agtgaggcac ctatctcagc gatctgtcta tttcgttcat ccatagttgc ctgactgccc | 10080 |
| gtcgtgtaga taactacgat acgggagggc ttaccatctg gccccagtgc tgcaatgata | 10140 |
| ccgcgagacc cacgctcacc ggctccagat ttatcagcaa taaaccagcc agccggaagg | 10200 |
| gccgagcgca gaagtggtcc tgcaacttta tccgcctcca tccagtctat taattgttgc | 10260 |
| cgggaagcta gagtaagtag ttcgccagtt aatagtttgc gcaacgttgt tgccattgct | 10320 |
| acaggcatcg tggtgtcacg ctcgtcgttt ggtatggctt c | 10361 |

<210> SEQ ID NO 82
<211> LENGTH: 9767
<212> TYPE: DNA
<213> ORGANISM: Artificial Sequence
<220> FEATURE:
<223> OTHER INFORMATION: Codon Optimized

<400> SEQUENCE: 82

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccgcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aacaggaag gcaaaatgcc gcaaaaaagg gaataagggc | 480 |
| gacacggaaa tgttgaatac tcatactctt cctttttcaa tattattgaa gcatttatca | 540 |
| gggttattgt ctcatgagcg gatacatatt tgaatgtatt tagaaaaata aacaaatagg | 600 |
| ggttccgcgc acatttcccc gaaaagtgcc acctgacgtc taagaaacca ttattatcat | 660 |
| gacattaacc tataaaaata ggcgtatcac gaggcccttt cgtctcgcgc gtttcggtga | 720 |
| tgacggtgaa aacctctgac acatgcagct cccggagacg gtcacagctt gtctgtaagc | 780 |
| ggatgccggg agcagacaag cccgtcaggg cgcgtcagcg ggtgttggcg ggtgtcgggg | 840 |
| ctggcttaac tatgcggcat cagagcagat tgtactgaga gtgcaccata tcgactacgt | 900 |
| cgtaaggccg tttctgacag agtaaaattc ttgagggaac tttcaccatt atgggaaatg | 960 |
| gttcaagaag gtattgactt aaactccatc aaatggtcag gtcattgagt gttttttatt | 1020 |
| tgttgtattt ttttttttt agagaaaatc ctccaatatc aaattaggaa tcgtagtttc | 1080 |
| atgattttct gttacaccta acttttgtg tggtgccctc ctccttgtca atattaatgt | 1140 |
| taaagtgcaa ttctttttcc ttatcacgtt gagccattag tatcaatttg cttacctgta | 1200 |
| ttcctttact atcctccttt ttctccttct tgataaatgt atgtagattg cgtatatagt | 1260 |
| ttcgtctacc ctatgaacat attccatttt gtaattcgt gtcgtttcta ttatgaattt | 1320 |
| catttataaa gtttatgtac aaatatcata aaaaagaga atcttttaa gcaaggattt | 1380 |
| tcttaacttc ttcggcgaca gcatcaccga cttcggtggt actgttggaa ccacctaaat | 1440 |
| caccagttct gatacctgca tccaaaacct tttaactgc atcttcaatg gccttacctt | 1500 |
| cttcaggcaa gttcaatgac aatttcaaca tcattgcagc agacaagata gtggcgatag | 1560 |

```
ggtcaacctt attctttggc aaatctggag cagaaccgtg gcatggttcg tacaaaccaa      1620
atgcggtgtt cttgtctggc aaagaggcca aggacgcaga tggcaacaaa cccaaggaac      1680
ctgggataac ggaggcttca tcggagatga tatcaccaaa catgttgctg gtgattataa      1740
taccatttag gtgggttggg ttcttaacta ggatcatggc ggcagaatca atcaattgat      1800
gttgaacctt caatgtaggg aattcgttct tgatggtttc ctccacagtt tttctccata      1860
atcttgaaga ggccaaaaca ttagctttat ccaaggacca aataggcaat ggtggctcat      1920
gttgtagggc catgaaagcg gccattcttg tgattctttg cacttctgga acggtgtatt      1980
gttcactatc ccaagcgaca ccatcaccat cgtcttcctt tctcttacca aagtaaatac      2040
ctcccactaa ttctctgaca acaacgaagt cagtaccttt agcaaattgt ggcttgattg      2100
gagataagtc taaagagag tcggatgcaa agttacatgg tcttaagttg gcgtacaatt      2160
gaagttcttt acggattttt agtaaaacctt gttcaggtct aacactaccg gtaccccatt      2220
taggaccacc cacagcacct aacaaaacgg catcaacctt cttggaggct tccagcgcct      2280
catctggaag tgggacacct gtagcatcga tagcagcacc accaattaaa tgattttcga      2340
aatcgaactt gacattggaa cgaacatcag aaatagcttt aagaaccttt atggcttcgg      2400
ctgtgatttc ttgaccaacg tggtcacctg gcaaaacgac gatcttctta ggggcagaca      2460
taggggcaga cattgaatg gtatatcctt gaaatatata tatatattgc tgaaatgtaa      2520
aaggtaagaa aagttagaaa gtaagacgat tgctaaccac ctattggaaa aaacaatagg      2580
tccttaaata atattgtcaa cttcaagtat tgtgatgcaa gcatttagtc atgaacgctt      2640
ctctattcta tatgaaaagc cggttccggc ctctcacctt tccttttct cccaattttt      2700 cagttgaaaa aggtatatgc gtcaggcgac tctgaaatt aacaaaaaat ttccagtcat      2760
cgaatttgat tctgtgcgat agcgcccctg tgtgttctcg ttatgttgag gaaaaaaata      2820
atggttgcta agagattcga actcttgcat cttacgatac ctgagtattc ccacagttaa      2880
ctgcggtcaa gatatttctt gaatcaggcg ccttagaccg ctcggccaaa caaccaatta      2940
cttgttgaga aatagagtat aattatccta taaatataac gttttgaac acacatgaac      3000 aaggaagtac aggacaattg attttgaaga gaatgtggat tttgatgtaa ttgttgggat      3060 tccatttta ataaggcaat aatattaggt atgtggatat actagaagtt ctcctcgagg      3120
gtcgatatgc ggtgtgaaat accgcacaga tgcgtaagga gaaataccg catcaggaaa      3180 ttgtaaacgt taatattttg ttaaaattcg cgttaaattt tgttaaatc agctcatttt      3240 ttaaccaata ggccgaaatc ggcaaaatcc cttataaatc aaaagaatag accgagatag      3300
ggttgagtgt tgttccagtt tggaacaaga gtccactatt aaagaacgtg gactccaacg      3360
tcaaagggcg aaaaccgtc tatcaggcg atggcccact acgtgaacca tcacctaat      3420 caagtttttt ggggtcgagg tgccgtaaag cactaaatcg aaccctaaa gggagccccc      3480 gatttagagc ttgacgggga agccggcga acgtggcgag aaaggaaggg aagaaagcga      3540
aaggagcggg cgctagggcg ctggcaagtg tagcggtcac gctgcgcgta accaccacac      3600
ccgccgcgct taatgcgccg ctacagggcg cgtcgcgcca ttcgccattc aggctgcgca      3660
actgttggga agggcgatcg gtgcgggcct ttcgctatt acgccagctg gcgaaggggg      3720
gatgtgctgc aaggcgatta agttgggtaa cgccagggtt ttcccagtca cgacgttgta      3780
aaacgacggc cagtgaattg taatacgact cactataggg cgaattggag ctctagtcgc      3840
aaattaaagc cttcgagcgt cccaaaacct tctcaagcaa ggttttcagt ataatgttac      3900
```

```
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggggag ggcgtgaatg taagcgtgac ataactaatt   4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctcttttcgat   4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta acaatgtttt   4560
tgaggcacca acataacag gacctaatgc caattcaccg atacctggct tattttaggg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagtttta aactccttgg ctcttttctaa aaagtaatcc caagatatgt caccatctct   5280
caattctgca ccaatgttag aaccactaca agggataact attgccattg gggatttagc    5340
ttcaactact cttgaataca atggtattct ctttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat     6000
ccaagcaggt ggggctggac cgaaatcctt gtagcaacca taaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaaattctt acttttttt tggatggacg    6300
```

```
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020 aaatatttg attcaagatg aatttccaga ttattatttt agagttacta aatctgaaca     7080
tatgactcaa ttgaaagaaa aatttagaaa aatttgtgat aaatctatga ttagaaaaag    7140
aaattgtttt ttgaatgaag aacatttgaa acaaaatcca agattggctg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta aagatattgc tgaaaataat aaaggtgcta gagttttggc    7500
tgtttgttgt gatattatgg cttttttttt tgaaggtaga ggttccttgt taacttgtgg    7560
tgacgttgaa gaaacccag gtcctatggc cgtcaagcat ttgatagtat tgaagtttaa    7620
agatgaaatc acagaagctc aaaaggaaga atttttcaag acctacgtta atttggtcaa    7680
cattatacct gctatgaaag atgtatactg gggtaaagac gttacacaaa agaaagaaga    7740
aggttataca cacattgtcg aagtaacctt cgaatcagtt gaaactatcc aagattacat    7800
cattcatcca gctcacgttg gttttggtga cgtttacaga tccttctggg aaaaattgtt    7860
gatcttcgat tacaccccaa gaaagtgatg atgggctgca ggaattcgat atcaagctta    7920
tcgataccgt cgacctcgag tcatgtaatt agttatgtca cgcttacatt cacgccctcc    7980
ccccacatcc gctctaaccg aaaaggaagg agttagacaa cctgaagtct aggtccctat    8040 ttatttttt atagttatgt tagtattaag aacgttattt atatttcaaa ttttctttt      8100 ttttctgtac agacgcgtgt acgcatgtaa cattatactg aaaaccttgc ttgagaaggt    8160
tttgggacgc tcgaaggctt taatttgcgg ccggtaccca gcttttgttc cctttagtga    8220
gggtaaattc cgagcttggc gtaatcatgg tcatagctgt ttcctgtgtg aaattgttat    8280
ccgctcacaa ttccacacaa cataggagcc ggaagcataa agtgtaaagc ctggggtgcc    8340
taatgagtga ggtaactcac attaattgcg ttgcgctcac tgcccgcttt ccagtcggga    8400
aacctgtcgt gccagctgca ttaatgaatc ggccaacgcg cggggagagg cggtttgcgt    8460
attgggcgct cttccgcttc ctcgctcact gactcgctgc gctcggtcgt tcggctgcgg    8520
cgagcggtat cagctcactc aaaggcggta atacggttat ccacagaatc aggggataac    8580
gcaggaaaga acatgtgagc aaaaggccag caaaaggcca ggaaccgtaa aaaggccgcg    8640
```

```
ttgctggcgt ttttccatag gctcggcccc cctgacgagc atcacaaaaa tcgacgctca    8700
agtcagaggt ggcgaaaccc gacaggacta taaagatacc aggcgttccc ccctggaagc    8760
tccctcgtgc gctctcctgt tccgaccctg ccgcttaccg gatacctgtc cgcctttctc    8820
ccttcgggaa gcgtggcgct ttctcaatgc tcacgctgta ggtatctcag ttcggtgtag    8880
gtcgttcgct ccaagctggg ctgtgtgcac gaaccccccg ttcagcccga ccgctgcgcc    8940
ttatccggta actatcgtct tgagtccaac ccggtaagac acgacttatc gccactggca    9000
gcagccactg gtaacaggat tagcagagcg aggtatgtag gcggtgctac agagttcttg    9060
aagtggtggc ctaactacgg ctacactaga aggacagtat ttggtatctg cgctctgctg    9120
aagccagtta ccttcggaaa aagagttggt agctcttgat ccggcaaaca aaccaccgct    9180
ggtagcggtg ttttttttgt ttgcaagcag cagattacgc gcagaaaaaa aggatctcaa    9240
gaagatcctt tgatcttttc tacggggtct gacgctcagt ggaacgaaaa ctcacgttaa    9300
gggattttgg tcatgagatt atcaaaaagg atcttcacct agatcctttt aaattaaaaa    9360
tgaagtttta aatcaatcta agtatatat gagtaaactt ggtctgacag ttaccaatgc    9420
ttaatcagtg aggcacctat ctcagcgatc tgtctatttc gttcatccat agttgcctga    9480
ctgcccgtcg tgtagataac tacgatacgg agggcttac catctggccc cagtgctgca    9540
atgataccgc gagacccacg ctcaccggct ccagatttat cagcaataaa ccagccagcc    9600
ggaagggccg agcgcagaag tggtcctgca actttatccg cctccatcca gtctattaat    9660
tgttgccggg aagctagagt aagtagttcg ccagttaata gtttgcgcaa cgttgttgcc    9720
attgctacag gcatcgtggt gtcacgctcg tcgtttggta tggcttc               9767
```

<210> SEQ ID NO 83
<211> LENGTH: 9791
<212> TYPE: DNA
<213> ORGANISM: Artificial Sequence
<220> FEATURE:
<223> OTHER INFORMATION: Codon Optimized

<400> SEQUENCE: 83

```
attcagctcc ggttcccaac gatcaaggcg agttacatga tcccccatgt tgtgaaaaaa      60
agcggttagc tccttcggtc ctccgatcgt tgtcagaagt aagttggccg cagtgttatc     120
actcatggtt atggcagcac tgcataattc tcttactgtc atgccatccg taagatgctt     180
ttctgtgact ggtgagtact caaccaagtc attctgagaa tagtgtatgc ggcgaccgag     240
ttgctcttgc ccggcgtcaa tacgggataa taccgcgcca catagcagaa ctttaaaagt     300
gctcatcatt ggaaaacgtt cttcggggcg aaaactctca aggatcttac cgctgttgag     360
atccagttcg atgtaaccca ctcgtgcacc caactgatct tcagcatctt ttactttcac     420
cagcgtttct gggtgagcaa aaacaggaag gcaaaatgcc gcaaaaaagg gaataagggc     480
gacacggaaa tgttgaatac tcatactctt ccttttcaa tattattgaa gcatttatca     540
gggttattgt ctcatgagcg gatacatatt tgaatgtatt tagaaaaata aacaaatagg     600
ggttccgcgc acatttcccc gaaaagtgcc acctgacgtc taagaaacca ttattatcat     660
gacattaacc tataaaaata ggcgtatcac gaggcccttt cgtctcgcgc gtttcggtga     720
tgacggtgaa aacctctgac acatgcagct cccggagacg gtcacagctt gtctgtaagc     780
ggatgccggg agcagacaag cccgtcaggg cgcgtcagcg ggtgttggcg ggtgtcgggg     840
ctggcttaac tatgcggcat cagagcagat tgtactgaga gtgcaccata tcgactacgt     900
cgtaaggccg tttctgacag agtaaaattc ttgagggaac tttcaccatt atgggaaatg     960
```

```
gttcaagaag gtattgactt aaactccatc aaatggtcag gtcattgagt gttttttatt    1020
tgttgtattt ttttttttt agagaaaatc ctccaatatc aaattaggaa tcgtagtttc    1080 atgatttct gttacaccta acttttgtg tggtgccctc ctccttgtca atattaatgt    1140
taaagtgcaa ttcttttcc ttatcacgtt gagccattag tatcaatttg cttacctgta    1200
ttcctttact atcctccttt ttctccttct tgataaatgt atgtagattg cgtatatagt    1260
ttcgtctacc ctatgaacat attccatttt gtaatttcgt gtcgtttcta ttatgaattt    1320 cattttataaa gtttatgtac aaatatcata aaaaagaga atctttttaa gcaaggattt    1380
tcttaacttc ttcggcgaca gcatcaccga cttcggtggt actgttggaa ccacctaaat    1440
caccagttct gatacctgca tccaaaacct ttttaactgc atcttcaatg ccttaccttt    1500
cttcaggcaa gttcaatgac aatttcaaca tcattgcagc agacaagata gtggcgatag    1560
ggtcaacctt attctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca aagtaaatac    2040
ctcccactaa ttctctgaca caacgaagt cagtacctt agcaaattgt ggcttgattg    2100
gagataagtc taaagagag tcggatgcaa agttacatgg tcttaagttg gcgtacaatt    2160
gaagttcttt acggattttt agtaaacctt gttcaggtct aacactaccg gtaccccatt    2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaaccta atggcttcgg    2400 ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580 tccttaaaata atattgtcaa cttcaagtat tgtgatgcaa gcatttagtc atgaacgctt    2640
ctctattcta tatgaaaagc cggttccggc ctctcaccct tccttttct cccaattttt    2700 cagttgaaaa aggtatatgc gtcaggcgac ctctgaaatt aacaaaaaat ttccagtcat    2760
cgaatttgat tctgtgcgat agcgccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac    3000 aaggaagtac aggacaattg attttgaaga gaatgtggat tttgatgtaa ttgttgggat    3060 tccatttta ataaggcaat aatattaggt atgtggatat actagaagtt ctcctcgagg    3120
gtcgatatgc ggtgtgaaat accgcacaga tgcgtaagga gaaataccg catcaggaaa    3180 ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
```

-continued

```
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga agccggcgaa cgtggcgaga aaggaaggg  aagaaagcga   3540 aaggagcggg cgctagggcg ctggcaagtg tagcggtcac gctgcgcgta accaccacac   3600
ccgccgcgct taatgcgccg ctacaggcg  cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtgggggag  ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200 ttttcttttgc aaacccaagt taaaggataa tctcaattgg ttcaaatcaa tggttgtgtc   4260
gtttgaatcc ttcaatacga aaatatgac  caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca acataacag  gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta aacgtcacc  ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct cttttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
```

```
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag gtctggaat    6000 ccaagcaggt ggggctggac cgaaatcctt gtagcaacca taaacaaca tttggtgtaa    6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt acttttttt tggatggacg    6300 caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt ctgggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaat tgttaatata    6900 cctctatact ttaacgtcaa ggagaaaaaa ccccggatcc gtaatacgac tcactataat    6960
ggcttgtttg tttagaggtc catctgaatc tgatttggaa ttgttggttg gtcaagctat    7020
ttttggtgat ggtgctgctg ctgttattgt tggtgctgaa ccagatgaat ctgttggtga    7080
aagaccaatt tttgaattgg tttctactgg tcaaactatt ttgccaaatt ctgaaggtac    7140
tattggtggt catattagag aagctggttt gattttgat ttgcataaag atgttccaat    7200
gttgatttct aataatattg aaaaatgttt gattgaagct tttactccaa ttggtatttc    7260
tgattggaat tctatttttt ggattactca tccaggtgg aaagctattt tggataaagt    7320
tgaagaaaaa ttgcatttga atctgataa atttgttgat tctagacatg ttttgtctga    7380
acatggtaat atgtcttctt ctactgtttt gtttgttatg gatgaattga gaaaaagatc    7440
tttggaagaa ggtaaatcta ctactggtga tggttttgaa tggggtgttt tgtttggttt    7500
tggtccaggt ttgactgttg aaagagttgt tgttagatct gttccaatta aatatgaagg    7560
tagaggttcc ttgttaactt gtggtgacgt tgaagaaaac ccaggtccta tggccgtcaa    7620
gcatttgata gtattgaagt ttaaagatga aatcacagaa gctcaaaagg aagaattttt    7680
caagacctac gttaatttgg tcaacattat acctgctatg aaagatgtat actgggtaa    7740 agacgttaca caaagaaag aagaaggtta tacacacatt gtcgaagtaa ccttcgaatc    7800
agttgaaact atccaagatt acatcattca tccagctcac gttggttttg gtgacgttta    7860
cagatccttc tgggaaaaat tgttgatctt cgattacacc ccaagaaagt gatgatgggc    7920
tgcaggaatt cgatatcaag cttatcgata ccgtcgacct cgagtcatgt aattagttat    7980
gtcacgctta cattcacgcc ctcccccac atccgctcta accgaaaagg aaggagttag    8040
```

```
acaacctgaa gtctaggtcc ctatttattt ttttatagtt atgttagtat taagaacgtt      8100
atttatattt caaattttc ttttttttct gtacagacgc gtgtacgcat gtaacattat       8160
actgaaaacc ttgcttgaga aggttttggg acgctcgaag gctttaattt gcggccggta      8220
cccagctttt gttcccttta gtgagggtta attccgagct tggcgtaatc atggtcatag      8280
ctgtttcctg tgtgaaattg ttatccgctc acaattccac acaacatagg agccggaagc      8340
ataaagtgta aagcctgggg tgcctaatga gtgaggtaac tcacattaat tgcgttgcgc      8400
tcactgcccg ctttccagtc gggaaacctg tcgtgccagc tgcattaatg aatcggccaa      8460
cgcgcgggga gaggcggttt gcgtattggg cgctcttccg cttcctcgct cactgactcg      8520
ctgcgctcgg tcgttcggct gcggcgagcg gtatcagctc actcaaaggc ggtaatacgg      8580
ttatccacag aatcagggga taacgcagga aagaacatgt gagcaaaagg ccagcaaaag      8640
gccaggaacc gtaaaaaggc cgcgttgctg gcgtttttcc ataggctcgg ccccctgac       8700 gagcatcaca aaaatcgacg ctcaagtcag aggtggcgaa acccgacagg actataaaga      8760
taccaggcgt tcccccctgg aagctccctc gtgcgctctc ctgttccgac cctgccgctt      8820
accggatacc tgtccgcctt tctcccttcg ggaagcgtgg cgctttctca atgctcacgc      8880
tgtaggtatc tcagttcggt gtaggtcgtt cgctccaagc tgggctgtgt gcacgaaccc      8940
cccgttcagc ccgaccgctg cgccttatcc ggtaactatc gtcttgagtc caacccggta      9000
agacacgact tatcgccact ggcagcagcc actggtaaca ggattagcag agcgaggtat      9060
gtaggcggtg ctacagagtt cttgaagtgg tggcctaact acggctacac tagaaggaca      9120
gtatttggta tctgcgctct gctgaagcca gttaccttcg gaaaaagagt tggtagctct      9180
tgatccggca aacaaaccac cgctggtagc ggtggttttt ttgtttgcaa gcagcagatt      9240
acgcgcagaa aaaaggatc tcaagaagat cctttgatct tttctacggg gtctgacgct      9300
cagtggaacg aaaactcacg ttaagggatt ttggtcatga gattatcaaa aaggatcttc      9360
acctagatcc ttttaaatta aaaatgaagt tttaaatcaa tctaaagtat atatgagtaa      9420
acttggtctg acagttacca atgcttaatc agtgaggcac ctatctcagc gatctgtcta      9480
tttcgttcat ccatagttgc ctgactgccc gtcgtgtaga taactacgat acgggagggc      9540
ttaccatctg gccccagtgc tgcaatgata ccgcgagacc cacgctcacc ggctccagat      9600
ttatcagcaa taaccagcc agccggaagg gccgagcgca gaagtggtcc tgcaacttta      9660
tccgcctcca tccagtctat taattgttgc cgggaagcta gagtaagtag ttcgccagtt      9720
aatagtttgc gcaacgttgt tgccattgct acaggcatcg tggtgtcacg ctcgtcgttt      9780
ggtatggctt c                                                          9791

<210> SEQ ID NO 84
<211> LENGTH: 10130
<212> TYPE: DNA
<213> ORGANISM: Artificial Sequence
<220> FEATURE:
<223> OTHER INFORMATION: Codon Optimized

<400> SEQUENCE: 84
attcagctcc ggttcccaac gatcaaggcg agttacatga tcccccatgt tgtgaaaaaa        60
agcggttagc tccttcggtc ctccgatcgt tgtcagaagt aagttggccg cagtgttatc       120
actcatggtt atggcagcac tgcataattc tcttactgtc atgccatccg taagatgctt       180
ttctgtgact ggtgagtact caaccaagtc attctgagaa tagtgtatgc ggcgaccgag       240
ttgctcttgc ccggcgtcaa tacgggataa taccgcgcca catagcagaa ctttaaaagt       300
```

```
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggccottt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020
tgttgtattt ttttttttt agagaaaatc ctccaatatc aaattaggaa tcgtagtttc    1080
atgattttct gttacaccta acttttttgtg tggtgccctc ctccttgtca atattaatgt   1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gttatgtac aaatatcata aaaaagaga atctttttaa gcaaggattt    1380
tcttaacttc ttcggcgaca gcatcaccga cttcggtggt actgttggaa ccacctaaat   1440
caccagttct gataccctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagcttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaaatac   2040
ctcccactaa ttctctgaca acaacgaagt cagtaccttt agcaaattgt ggcttgattg   2100
gagataagtc taaagagag tcggatgcaa agttacatgg tcttaagttg gcgtacaatt   2160
gaagttcttt acggattttt agtaaacctt gttcaggtct aacactaccg gtacccoatt   2220 taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccttta atggcttcgg   2400 ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
```

```
ctctattcta tatgaaaagc cggttccggc ctctcacctt tccttttttct cccaattttt    2700
cagttgaaaa aggtatatgc gtcaggcgac ctctgaaatt aacaaaaaat ttccagtcat    2760
cgaatttgat tctgtgcgat agcgccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg attttgaaga gaatgtggat tttgatgtaa ttgttgggat    3060
tccatttta ataaggcaat aatattaggt atgtggatat actagaagtt ctcctcgagg     3120
gtcgatatgc ggtgtgaaat accgcacaga tgcgtaagga gaaataccg catcaggaaa     3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga agccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggag ggcgtgaatg taagcgtgac ataactaatt     4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa tctcaattgg ttcaaatcaa tggttgtgtc     4260
gtttgaatcc ttcaatacga aaaatatgac caattgttct ggaccaccac ccaaaggtgg    4320
aacaccaata gcagtggttt caaaaactct gtcatctact tcattacaga ctcttttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacct tgaaatagac atcgtgatga ttaccgttta acaatgtttt     4560
tgaggcacca acataacag gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaaccaac caaggaccca tcatccaacc    5040
```

```
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc aagatatgt caccatctct     5280 caattctgca ccaatgttag aaccactaca agggataact attgccattg gggatttagc    5340
ttcaactact cttgaataca atggtattct cttttttacct ctgatgatgt gatcttgtgt   5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat     6000 ccaagcaggt ggggctggac cgaaatcctt gtagcaacca taaaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatttggaa aatattgata aagttaattc tccaggtact gaagataaag attttgattc    7020
tagagcttct ggttctaaaa ctaatggttg tgaatcttct gataatgaag ttgaatcttc    7080
tattaatgct aatccaaatt ctatttctgg ttcttcttct ggttttggta atggtaaaag    7140
agaaggtgtt aaaagagctg ctccaggtga tattgctcca acttctagac attatagatc    7200
tttgtctatg gattcttata tgggttcttt gcaatttgat gatgaatctt tgaaattgtt    7260
gccattgggg actggtgttg gtttgcaatc tccaaattct ttggctgatg gtaattctac    7320
taaatttggt atggaatttc caaatggtga atttaatgct gttgaattga aaaaaattat    7380
```

```
ggaatctgaa aaattgactg aaattgcttt gtctgatcca aaaagagcta aaagaatttt      7440
ggctaataga caatctgctg ctagatctaa agaaagaaga tctagatata tttctgaatt      7500
ggaacataaa gttcaaactt tgcaaactga agctactact ttgtctgctc aagttactaa      7560
attgcaaaga gattctgttg gtttgacttc tcaaaattct gaattgaaat ttagagttca      7620
agctatggaa caacaagctc aattgaaaga tgctttgaat gatgctttga gagctgaagt      7680
tcaaagattg aaattgactg ctgctgaatt gtctggtgaa gctcatttgt ctaattgtat      7740
ggctcaacaa ttgtctatta atcaacaaat gtatcaaatg caacatagac aaactgttca      7800
attgaatttg tatcaaatgc aacaacaaca acaacataat gaaatgtctt ctcaaccatg      7860
ttctggtgaa gttactgaac atgaatcttc taaagaaggt agaggttcct tgttaacttg      7920
tggtgacgtt gaagaaaacc caggtcctat ggccgtcaag catttgatag tattgaagtt      7980
taaagatgaa atcacagaag ctcaaaagga agaattttc aagacctacg ttaatttggt      8040
caacattata cctgctatga agatgtata ctggggtaaa gacgttacac aaaagaaaga      8100
agaaggttat acacacattg tcgaagtaac cttcgaatca gttgaaacta ccaagattaa      8160
catcattcat ccagctcacg ttggttttgg tgacgtttac agatccttct gggaaaaatt      8220
gttgatcttc gattacaccc caagaaagtg atgatgggct gcaggaattc gatatcaagc      8280
ttatcgatac cgtcgacctc gagtcatgta attagttatg tcacgcttac attcacgccc      8340
tccccccaca tccgctctaa ccgaaaagga aggagttaga caacctgaag tctaggtccc      8400
tatttatttt tttatagtta tgttagtatt aagaacgtta tttatatttc aaatttttct      8460
tttttttctg tacagacgcg tgtacgcatg taacattata ctgaaaacct tgcttgagaa      8520
ggttttggga cgctcgaagg ctttaatttg cggccggtac ccagcttttg ttccctttag      8580
tgagggttaa ttccgagctt ggcgtaatca tggtcatagc tgtttcctgt gtgaaattgt      8640
tatccgctca caattccaca acatagga gccggaagca taaagtgtaa agcctggggt      8700
gcctaatgag tgaggtaact cacattaatt gcgttgcgct cactgcccgc tttccagtcg      8760
ggaaacctgt cgtgccagct gcattaatga atcggccaac gcgcggggag aggcggtttg      8820
cgtattgggc gctcttccgc ttcctcgctc actgactcgc tgcgctcggt cgttcggctg      8880
cggcgagcgg tatcagctca ctcaaaggcg gtaatacggt tatccacaga atcaggggat      8940
aacgcaggaa agaacatgtg agcaaaaggc cagcaaaagg ccaggaaccg taaaaaggcc      9000
gcgttgctgg cgtttttcca taggctcggc cccctgacg agcatcacaa aaatcgacgc      9060
tcaagtcaga ggtggcgaaa cccgacagga ctataaagat accaggcgtt cccccctgga      9120
agctccctcg tgcgctctcc tgttccgacc ctgccgctta ccggatacct gtccgccttt      9180
ctcccttcgg gaagcgtggc gctttctcaa tgctcacgct gtaggtatct cagttcggtg      9240
taggtcgttc gctccaagct gggctgtgtg cacgaacccc ccgttcagcc cgaccgctgc      9300
gccttatccg gtaactatcg tcttgagtcc aacccggtaa gacacgactt atcgccactg      9360
gcagcagcca ctggtaacag gattagcaga gcgaggtatg taggcggtgc tacagagttc      9420
ttgaagtggt ggcctaacta cggctacact agaaggacag tatttggtat ctgcgctctg      9480
ctgaagccag ttaccttcgg aaaaagagtt ggtagctctt gatccggcaa acaaaccacc      9540
gctggtagcg gtggtttttt tgtttgcaag cagcagatta cgcgcagaaa aaaggatct      9600 caagaagatc ctttgatctt ttctacgggg tctgacgctc agtggaacga aaactcacgt      9660
taagggattt tggtcatgag attatcaaaa aggatcttca cctagatcct ttaaattaa      9720 aaatgaagtt ttaaatcaat ctaaagtata tatgagtaaa cttggtctga cagttaccaa      9780
```

| | | | | |
|---|---|---|---|---|
| tgcttaatca | gtgaggcacc | tatctcagcg | atctgtctat | ttcgttcatc catagttgcc | 9840 |
| tgactgcccg | tcgtgtagat | aactacgata | cgggagggct | taccatctgg ccccagtgct | 9900 |
| gcaatgatac | cgcgagaccc | acgctcaccg | gctccagatt | tatcagcaat aaaccagcca | 9960 |
| gccggaaggg | ccgagcgcag | aagtggtcct | gcaactttat | ccgcctccat ccagtctatt | 10020 |
| aattgttgcc | gggaagctag | agtaagtagt | tcgccagtta | atagtttgcg caacgttgtt | 10080 |
| gccattgcta | caggcatcgt | ggtgtcacgc | tcgtcgtttg | gtatggcttc | 10130 |

```
<210> SEQ ID NO 85
<211> LENGTH: 2274
<212> TYPE: DNA
<213> ORGANISM: Artificial Sequence
<220> FEATURE:
<223> OTHER INFORMATION: Codon Optimized

<400> SEQUENCE: 85
```

| | | | | | |
|---|---|---|---|---|---|
| atgtatatgt | atcaagaagt | ttatttggtt | ccaactttgt | cttatttgta tttggttgtt | 60 |
| gttttgttgc | catctatttt | tttttctttt | agaagaatgg | cttttaaatc tttggattct | 120 |
| gttacttctt | ctgatattgc | tgctttgggt | attgaaccac | aattggctca ttctttgcat | 180 |
| ggtagattgg | ctgaaattgt | ttctaatcat | ggttctgcta | ctccacatac ttggagatgt | 240 |
| atttcttctc | atttgttgtc | tccagatttg | ccatttttctt | tgcatcaaat gttgtattat | 300 |
| ggttgttata | agattttggg | tccagatcca | ccagcttgga | ttccagatgc tgaaaatgct | 360 |
| atttctacta | atgttggtaa | attgttggaa | aaaagaggta | agaatttttt gggtgttaaa | 420 |
| tataaagatc | caatttctaa | ttttttctgat | tttcaagaat | tttctgttac taatccagaa | 480 |
| gtttattgga | gaactatttt | ggatgaaatg | aatatttctt | tttctaaacc accagaatgt | 540 |
| attttgagag | aaaattttc | tagagatggt | caaatttga | atccaggtgg tgaatggttg | 600 |
| ccaggtgctt | ttattaatcc | agctaaaaat | tgtttggatt | tgaattgtaa atctttggat | 660 |
| gatactatga | ttttgtggag | agatgaaggt | aaagatgatt | tgccagttaa taaaatgact | 720 |
| ttgaaagaat | tgagatctga | agtttggttg | gttgcttatg | ctttgaaaga attggaattg | 780 |
| gaaggtggtt | ctgctattgc | tattgatatg | ccaatgaatg | ttcattctgt tgttatttat | 840 |
| ttggctattg | ttttggctgg | ttatgttgtt | gtttctattg | ctgattcttt tgctgctcca | 900 |
| gaaatttcta | ctagattgaa | aattctaaa | gctaaagcta | tttttactca agatttgatt | 960 |
| gttagaggtg | aaaaaactat | tccattgtat | tctagaattg | ttgaagctca atctccattg | 1020 |
| gctattgtta | ttccatctaa | aggtttttct | gtttctgctc | aattgagaca tggtgatgtt | 1080 |
| tcttggcatg | attttttgaa | tagagctaat | aaatttaaaa | attatgaatt tgctgctgtt | 1140 |
| gaacaaccaa | ttgatgctta | tactaatatt | ttgtttttctt | ctggtactac tggtgaacca | 1200 |
| aaagctattc | catggactca | agctactcca | tttaaagctg | ctgctgatgc ttggtgtcat | 1260 |
| atggatattc | aaaaaggtga | tgttgttgct | tggccaacta | atttgggttg gatgatgggt | 1320 |
| ccatggttgg | tttatgcttc | tttgttgaat | ggtgcttcta | ttgctttgta taatggttct | 1380 |
| ccattgggtt | ctggttttgc | taaatttgtt | caagatgcta | agttactat gttgggtgtt | 1440 |
| attccatcta | ttgttagaac | ttggaaatct | actaattgtg | ttgctggtta tgattggtct | 1500 |
| actattagat | gttttcttc | tactggtgaa | gcttctaata | ttgatgaata tttgtggttg | 1560 |
| atgggtagag | cttattataa | accagttatt | gaatattgtg | gtggtactga aattggtggt | 1620 |
| ggttttgtta | ctggttcttt | gttgcaagct | caatctttgg | ctgctttttc tactccagct | 1680 |

| | |
|---|---:|
| atgggttgtt ctttgtttat tttgggttct gatggttatc caattccaaa acataaacca | 1740 |
| ggtattggtg aattggcttt gggtccattg atgtttggtg cttctaaaac tttgttgaat | 1800 |
| gctgatcatt atgatgttta ttttaaaaga atgccatctt gaatggtaa agttttgaga | 1860 |
| agacatggtg atatgtttga attgacttct aaaggttatt atcatgctca tggtagagct | 1920 |
| gatgatacta tgaatttggg tggtattaaa gtttcttctg ttgaaattga agaatttgt | 1980 |
| aatgaagctg atgaaaaagt tttggaaact gctgctattg gtgttccacc attggctggt | 2040 |
| ggtccagaac aattggttat tgctgttgtt ttgaaaaatt ctgatagaac tactgttgat | 2100 |
| ttgaatcaat tgagattgtc ttttaattct gctgttcaaa aaaaattgaa tccattgttt | 2160 |
| agagtttcta gagttgttcc attgtcttct tgccaagaa ctgctactaa taaagttatg | 2220 |
| agaagaattt tgagacaaca atttactcaa ttggataaat cttctaaaat ttaa | 2274 |

<210> SEQ ID NO 86
<211> LENGTH: 2331
<212> TYPE: DNA
<213> ORGANISM: Artificial Sequence
<220> FEATURE:
<223> OTHER INFORMATION: Codon Optimized

<400> SEQUENCE: 86

| | |
|---|---:|
| atggctttgg aattgccaca tttgttgcca tataaattgg ttaaaggtca aactttggtt | 60 |
| gctcaagctg ctagagctga attggcttct tcttcttctt cttctgttat ttgaaatct | 120 |
| aattttatta ataataatta tattaattat tgtaataata ataataataa tgaaagaaga | 180 |
| ttggttgtta gaagagattg ggaaactatg gcttcttctc catctcattc tagaaataat | 240 |
| aatgatatta gaactattaa tcatttgaga catgttgatt ctatggctac tatgccatct | 300 |
| ggtgctggta aaattccaag attgaatgct gttattttgg gtgaagcttt ggctactgaa | 360 |
| gaaaatgatt tggtttttcc aactgatgaa ttttctcaac aagctcatgt tccatctcca | 420 |
| caaaaatatt tggaaatgta taaagatctc attgaagatc cagctggttt ttggtctgaa | 480 |
| attgcttctc aatttattg gaaacaaaaa tgggatgatt ctgtttattc tgaaaatttg | 540 |
| gatgttctta aaggtagagt taatattgaa tggtttaaag gtgtattac taatatttgt | 600 |
| tataattgtt tggataaaaa tgttgaagct ggtttgggtg ataaaattgc tttgtattgg | 660 |
| gaaggtaatg atactggttt tgatgattct ttgacttatt ctcaattgtt gcataaagtt | 720 |
| tgtcaattgg ctaattattt gaaagatatg ggtgttcaaa aaggtgatgc tgttgttatt | 780 |
| tatttgccaa tgttgttgga attgccaatt actatgttgg cttgtgctag aattggtgct | 840 |
| gttcattctg ttgttttgc tggttttttct gctgaatctt tgtctcaaag aattattgat | 900 |
| tgtaaaccaa aagttgttat tacttgtaat gctgttaaaa gaggtccaaa aattattcat | 960 |
| ttgaaagata ttgttgatgc tgctttggtt gaatctgcta aaactggtgt tccaattgat | 1020 |
| acttgtttgg tttatgaaaa tcaattggct atgaaaagag atattactaa atggcaagat | 1080 |
| ggtagagata tttggtggca agatgttatt ccaaaatatc aactgaatg tgctgttgaa | 1140 |
| tgggttgatg ctgaagatcc attgttttg ttgtatactt ctggttctac tggtaaacca | 1200 |
| aaaggtgttt tgcatactac tggtggttat atggtttata ctgctactac ttttaaatat | 1260 |
| gcttttgatt ataaaccatc tgatgtttat tggtgtactg ctgattgtgg ttggattact | 1320 |
| ggtcattctt atgttactta tggtccattg ttgaatggtg cttcttgtat tgttttgaa | 1380 |
| ggtgctccaa attatccaga ttctggtaga tgttgggata ttgttgataa atataaagtt | 1440 |
| actattttt atactgctcc aacttggtt agatctttga tgagagatgg tgatgaatat | 1500 |

```
gttactagat attctagaaa atctttgaga attttgggtt ctgttggtga accaattaat    1560
ccatctgctt ggagatggtt ttataatgtt gttggtgatt ctagatgtcc aatttctgat    1620
acttggtggc aaactgaaac tggtggtttt atgattactc cattgccagg tgcttggcca    1680
caaaaaccag gttctgctac ttttccattt tttggtgtta aaccagttat tgttgatgaa    1740
aaaggtgttg aaattgaagg tgaatgttct ggttatttgt gtgttaaagg ttcttggcca    1800
ggtgctttta gaactttgta tggtgattat gaaagatatg aaactactta ttttaaacca    1860
tttactggtt attattttac tggtgatggt tgttctagag ataaagatgg ttatcattgg    1920
ttgactggta gagttgatga tgttattaat gtttctggtc atagaattgg tactgctgaa    1980
gttgaatctg ctttggtttc tcatccaaaa tgtgctgaag ctgctgttgt tggtattgaa    2040
catgaagtta aaggtcaagc tatttatgct tttgttactt tggttgaagg tgaaccatat    2100
tctgaagaat tgagaaaatc tttgattttg tctgttagaa acaaattggg tgcttttgct    2160
gctccagaaa gaattcattg ggctccaggt ttgccaaaaa ctagatctgg taaaattatg    2220
agaagaattt tgagaaaaat tgcttctggt caattggatg aattgggtga tacttctact    2280
ttggctgatc aaaatgttgt tgaacaattg atttctttgt ctaattgtta g             2331
```

<210> SEQ ID NO 87
<211> LENGTH: 1662
<212> TYPE: DNA
<213> ORGANISM: Artificial Sequence
<220> FEATURE:
<223> OTHER INFORMATION: Codon Optimized

<400> SEQUENCE: 87

```
atggaaaaaa aacaagataa tcataataat aataataata atggtgatga acaagaagaa      60
tttattttta gatctaaatt gccagatatt tatattccaa atcatccacc attgcattct     120
tattgttttg aaaatatttc tcaatttaaa gatagaccat gtttgattaa tggtgctact     180
ggtgaaacta ttacttatgc tgatgttgat ttgacttcta gaaagttgc tgctggtttg     240 gataaaattg gtattaaaca aggtgatgtt attatgttgt tgttgagaaa ttgtccagaa     300
tttgtttatt cttttttggc tgcttctcat attggtgctg ttgttactac tgctaatcca     360
ttttatactg ctgctgaagt tgctaaacaa gctgctgctt ctaatactaa attggttatt     420
actttgtctg gttttattga taagttaga gattttactg gtgatggtat taagttgtt     480 tgtgttgatg ctccaccaga tgaatctgaa tatttgcatt tttctgtttt gactcaagct     540
gatgaatctg aaattccaga tgttgaaatt aaaccagatg atgttgttgc tttgccatat     600
tcttctggta ctactggttt gccaaaaggt gttatgttga ctcatagagt tatggttact     660
ggtgttgctc aacaagttga tggtgataat ccaaattggc atttcatca aaatgatgtt     720 attttgtgtg ttttgccagt tttcatatt tattgtttga tgctattt gttgtgtggt     780 ttgagagttg gtgcttctat tttgattatg aaaaatttg aaatgaaaaa atggttgaa     840 ttgattgaaa aatttaaagt tactattgct ccagttgttc accaattgt tttgtctgtt     900 gttaaatttc agatttgca tagatatgat ttgtcttcta tagaactat tatgtctggt     960 ggtgctccaa tgggtaaaga tttggaagaa gctgttaaag aaaaatttcc acatgttact    1020
ttgggtcaag ttatggtat gactgaagct gaatgtttgt cttgtgtttt gggttttgct    1080
aaagaaccat ttccaactaa atttggtact gtggtactg ttgttagaaa tgctgaaatg    1140
aaaattgttg atccaaatac tggtgcttct ttgccaagaa atcaatctgg tgaaatttgt    1200
```

```
attagaggta acaaattat gaaaggttat attaatgatt ttgaagctac taaaggtact   1260
attgatgaag ctggttggtt gcatactggt gatattggtt ttgttgatga tgatgatgaa   1320
ttgtttattg ttgatagatt gaaagaattg attaaatata aaggttttca agttgctcca   1380
gctgaattgg aatctttgtt gattgctcat ccaaatattt ctgatgctgc tgttgttcca   1440
atgaaagatg aagctgctgg tgaagttcca gttgcttttg ttgttagatc taatggttct   1500
aaaatttctg aagaagatat taaacaatat atttctaaac aagttgtttt ttataaaaga   1560
attgctaaag tttttttat tgaagaaatt ccaaaatctc cagctggtaa aattttgaga   1620
aaatctttga gagctagatt ggttactgaa caagctattt aa                     1662

<210> SEQ ID NO 88
<211> LENGTH: 1719
<212> TYPE: DNA
<213> ORGANISM: Artificial Sequence
<220> FEATURE:
<223> OTHER INFORMATION: Codon Optimized

<400> SEQUENCE: 88
atgatttcta ttgctccacc attgaaaact caaaataaac aagaaatttc tactattgat     60
cataatgatc ataatcaaga acatattttt aaatctaaat tgccagaaat tccaatttct    120
aataatattc cattgcattc ttatattttt caaaatttgc cagaaaaatc taatagacca    180
tgtttgatta ctggtactac tactcaaact acttattctt attctcaaac tcatcatatt    240
gctaaaaaaa ttgctaaagg tttgtctaaa ttgaatatta taaaaatga tgttattatg    300 attttgttgc caaattgtcc agaatttatt ttttcttttt ttggtgcttc tatgattggt    360
gctgctatta ctactgctaa tccatttttat acttctccag aaatttttaa acaattgcaa    420
atttctaaag ctaaattggt tattactcaa actcaatttg tttctaaatt gattgatttt    480
ccagaaaaag ttattggtag agattttact gttgttactg ttgatggtga tgaaaatcca    540
tctccagaaa attgtttgcc attttctatt ttgactggtg aagatgaaac tgaagaaatt    600
tctattgatc caaatgatcc aattgctatt ccatttttctt ctggtactac tggtttgcca    660
aaaggtgttt ttttgactca taaaaatttg attacttctg ttgctcaaca agttgatggt    720
gataatccaa atatgtattt gagatctgat gatgttgttt tgtgtgtttt gccattgttt    780
catatttatt ctttgaattc tgttttgttg tgtgctttga gagttggtgc ttctgttttg    840
ttggttccaa aatttgaaat tggtactttg ttggaattga ttcaaaaaca tagagttact    900
gttgctccag ttgttccacc attggttttg ggtttggcta aaaatccagt tgtttctgaa    960
tttgatttgt cttctattag aatggttttg tctggtgctg ctccattggg tatggaattg   1020
gaagatgctt tgagaagaag agttccacaa gctgttattg gtcaaggtta tggtatgact   1080
gaagctggtc cagttttgtc tatgtgtttg gcttttgcta acaaccatt tccaactaaa   1140 tctggttctt gtggtactgt tgttagaaat gctcaattga agttattga tccagaaact   1200 ggtgcttctt tgtcttataa tcaaccaggt gaaatttgta ttagaggtca tcaaattatg   1260
aaaggttatt tggataattc tgatgctact gctaatacta ttgatgttga tggttggttg   1320
catactggtg atattggtta tgttgatgat gatgatgaaa tttttattgt tgatagagtt   1380
aaagaaatta ttaaatttaa aggttttca agttccaccag ctgaattgga agctttgttg   1440
atttctcatc catcattgc tgatgctgct gttgttccac aaaaagatga agttgctggt   1500
gaagttccag ttgcttttgt tgttaaatct aataataaag attttgattt gtctgaagat   1560
gctgttaaag aatttattgc taaacaagtt gttttttata aaaaattgca taaagtttat   1620
```

```
tttgttcatt ctattccaaa atctccatct ggtaaaattt tgagaaaaga tttggttgct   1680
aaattggctt tggcttctac tttgattatt tcttcttaa                         1719

<210> SEQ ID NO 89
<211> LENGTH: 2184
<212> TYPE: DNA
<213> ORGANISM: Artificial Sequence
<220> FEATURE:
<223> OTHER INFORMATION: Condon Optimized

<400> SEQUENCE: 89
atgggtagaa aatctatttc tgaagttggt gttgaagatt tggttcaagc tggtttgact     60
actgaagaag ctactggttt tcaaagagtt ttgaaagatt ctttgtcttg tactaaaggt    120
tctgatccat ctgaagtttg agacatttg gttgctagaa gagttttgaa accatggcat     180
ccacatggtt tgcatcaatt ggtttattat tctgtttatg ctcattggga tgtttcttct    240
aaaggtccac caccatattg gtttccatct ttgtatgaat ctaaacatac taatatgggt    300
ggtattatgg aaaaacatgg ttcttctttg ttgggtccat tgtataaaga tccaattact    360
tcttattctt tgtttcaaaa attttctgct caacatccag aagcttattg gtctattgtt    420
ttgaaagaat tgtctgtttc ttttcaagaa gaaccaaaat gtattttgga tagatctgat    480
ttgaaatcta acatggtgg ttcttggttg ccaggttctg ttttgaatat tgctgaatgt    540
tgtttgttgc caactgctta tccaagaaaa gatgatgatt ctttggctat tgtttggaga    600
gatgaaggtt gtgatgattc tggtattaat attattactt tgaaacaatt gagagaacaa    660
gttatttctg ttgctaaagc tttggatgct atgttttcta aaggtgatgc tattgctatt    720
gatatgccaa tgactgctaa tgctgttatt atttatttgg ctattatttt gtctggtttg    780
gttgttgttt ctattgctga ttcttttgct ccaaaagaaa tttctattag attgagagtt    840
tctcaagcta aagctatttt tactcaagat tttattttga gaggttctag aaaatttcca    900
ttgtattcta gagttgttga agctgctcca gataaagtta ttgttttgcc agctattggt    960
tctaatgttg gtattcaatt gagagaacaa gatatgtctt ggggtgattt tttgtcttct   1020
gttggtacta gatctagaaa ttattctcca tgttatcaac cagttgatac tttgattaat   1080
attttgtttt cttctggtac tactggtgaa ccaaaagcta ttccatggac tcaattgtct   1140
ccaattagat gtgctgctga atcttgggct catatggata tgcaagttgg tgatgttttt   1200
tgttggccaa ctaatttggg ttgggttatg ggtccaattt tgattttttc ttcttttttg   1260
tctggtgcta ctttggcttt gatcatggt tctccattgg ttatggttt tggtaaattt   1320 gttcaagatg ctggtgttac taaattgggt actgttccat ctttggttaa agcttggaaa   1380
aatactcaat gtatgaatgg tttggattgg actaaaatta atgtttttgc ttctactggt   1440
gaaacttcta atgttgatga tgatttgtgg ttgtcttcta gagcttatta taaaccagtt   1500
attgaatgtt gtggtggtac tgaattgtct tcttcttata ttcaaggttc tttgttgcaa   1560
ccacaagctt ttggtgcttt ttctactact tctatgacta cttctttggt tattttggat   1620
gaacatggta atccatttcc agatgatcaa gcttgtattg gtgaagttgg tttgtttcca   1680
ttgtatttgg gtgctactga tagattgttg aatgctgatc atgaagaagt ttatttttaaa  1740 ggtatgccat tgtataaagg tatgagattg agaagacatg gtgatattat taaaagaact   1800
gttggtggta ttttattgt tcaaggtaga gctgatgata ctatgaattt gggtggtatt   1860
aaaacttctt ctgttgaaat tgaaagagtt tgtgatagag ctgatgaatc tattgttgaa   1920
```

| | |
|---|---|
| actgctgctg tttctgtttc tccagttgat ggtggtccag aacaattggt tatgtttgtt | 1980 |
| gttttgaaaa atggttataa ttctgaagct gaaaatttga aactaaaatt ttctaaagct | 2040 |
| attcaatcta atttgaatcc attgtttaaa gttagatttg ttaaaattgt tccagaattt | 2100 |
| ccaagaactg cttctaataa attgttgaga agagtttttga gagatcaaat taaacatgaa | 2160 |
| ttgtctgctc attctagaat ttaa | 2184 |

<210> SEQ ID NO 90
<211> LENGTH: 2172
<212> TYPE: DNA
<213> ORGANISM: Artificial Sequence
<220> FEATURE:
<223> OTHER INFORMATION: Codon Optimized

<400> SEQUENCE: 90

| | |
|---|---|
| atgtctattt ctgaagttgg tgttgaagat ttggttcaag ctggtttgac tactgaagaa | 60 |
| gctactggtt ttcaaagagt tttgaaagat tctttgtctt gtactaaagg ttctgatcca | 120 |
| tctgaagttt ggagacattt ggttgctaga agagctttga aaccatggca tccacatggt | 180 |
| ttgcatcaat tggtttatta ttctgtttat gctcattggg atgtttcttc taaaggtcca | 240 |
| ccaccatatt ggtttccatc tttgtatgaa tctaaacata ctaatatggg tggtattatg | 300 |
| gaaaaacatg gttcttcttt gttgggtcca ttgtataaag atccaattac ttcttattct | 360 |
| ttgtttcaaa attttctgc tcaacatcca gaagcttatt ggtctattgt tttgaaagaa | 420 |
| ttgtctgttt cttttcaaga agaaccaaaa tgtattttgg atagatctga tttgaaatct | 480 |
| aaacatggtg gttcttggtt gccaggttct gttttgaatg ttgctgaatg ttgtttgttg | 540 |
| ccaactgctt atccaagaaa agatgatgat tctttggcta ttgtttggag agatgaaggt | 600 |
| tgtgatgatt ctggtattaa tattattact ttgaaacaat tgagagaaca agttatttct | 660 |
| gttgctaaag ctttggatgc tatgtttttct aaaggtgatg ctattgctat tgatatgcca | 720 |
| atgactgcta atgctgttat tatttatttg gctattattt tgtctggttt ggttgttgtt | 780 |
| tctattgctg attcttttgc tccaaaagaa atttctatta gattgagagt ttctcaagct | 840 |
| aaagctattt ttactcaaga ttttattttg agaggttcta gaaaatttcc attgtattct | 900 |
| agagttgttg aagctgctcc agataaagtt attgttttgc cagctattgg ttctaatgtt | 960 |
| ggtattcaat tgagagaaca agatatgtct tggggtgatt ttttgtcttc tgttggtact | 1020 |
| agatctagaa attattctcc atgttatcaa ccagttgata ctttgattaa tattttgttt | 1080 |
| tcttctggta ctactggtga accaaaaagct attccatgga ctcaattgtc tccaattaga | 1140 |
| tgtgctgctg aatcttgggc tcatatggat atgcaagttg gtgatgtttt tgttggcca | 1200 |
| actaatttgg gttgggttat gggtccaatt ttgattttt cttctttttt gtctggtgct | 1260 |
| actttggctt tgtatcatgg ttctccattg ggttatggtt tggtaaatt tgttcaagat | 1320 |
| gctggtgtta ctaaattggg tactgttcca tctttggtta agcttggaa aaatactcaa | 1380 |
| tgtatgaatg gttggattg gactaaaatt aaatgttttg cttctactgg tgaaacttct | 1440 |
| aatgttgatg atgatttgtg gttgtcttct agagcttatt ataaaccagt tattgaatgt | 1500 |
| tgtggtggta ctgaattgtc ttcttcttat attcaaggtt ctttgttgca accacaagct | 1560 |
| tttggtgctt tttctactac ttctatgact acttcttttgg ttattttgga tgaacatggt | 1620 |
| aatccatttc cagatgatca agcttgtatt ggtgaagttg gtttgttcc attgtatttg | 1680 |
| ggtgctactg atagattgtt gaatgctgat catgaagaag tttattttaa agaatgtcat | 1740 |
| tatactaaag aatgtgcttc tgaaacttgg agatattatc aaagaactgt tggtggttat | 1800 |

```
tttattgttc aaggtagagc tgatgatact atgaatttgg gtggtattaa aacttcttct   1860
gttgaaattg aaagagtttg tgatagagct gatgaatcta ttgttgaaac tgctgctgtt   1920
tctgtttctc cagttgatgg tggtccagaa caattggtta tgtttgttgt tttgaaaaat   1980
ggttataatt ctgaagctga aaatttgaga actaaatttt ctaaagctat tcaatctaat   2040
ttgaatccat tgtttaaagt tagatttgtt aaaattgttc cagaatttcc aagaactgct   2100
tctaataaat tgttgagaag agttttgaga gatcaaatta acatgaatt gtctgctcat    2160 tctagaattt aa                                                      2172
```

<210> SEQ ID NO 91
<211> LENGTH: 2148
<212> TYPE: DNA
<213> ORGANISM: Artificial Sequence
<220> FEATURE:
<223> OTHER INFORMATION: Codon Optimized

<400> SEQUENCE: 91

```
atgggttcta aatctatttc tgaagttggt gttgatgatt tggttcaagc tggtttgact   60
actgaagaag ctactggttt tcaaagagtt ttgaaagatt ctttgtcttg tactaaaggt   120
tctgatccat ctgaagtttg agacatttg gttgctagaa gagttttgaa accatggtct    180
gtttatgctc attgggatgt ttcttctaaa ggtccaccac atattggtt tccatctttg    240 tatcattcta agatactaa tttgggtaga ttgatggaaa acatggtcc atctttgttg     300 ggtccattgt ataaagatcc aattacttct tattctttgt ttcaaaaatt ttctgttgaa   360
catccagaag tttattggtc tattgctttg aaagaattgt ctgtttcttt tcaagaagaa   420
ccaaaatgta ttttggataa atctgataaa tctaaacatg gtggttcttg gttgccaggt   480
gctgttttga atattgctga atgttgtttg ttgccaactt cttatccaag aaaagatgat   540 gattcttttgg ctattgtttg gagagatgaa ggttctgatg attcttctgt taatttgatt   600
actttgaaac aattgagaga acaagttatt tctgttgcta atctttggaa tgctatgttt   660
tctaaaggtg atgctattgc tatggatatg ccaatgactg ctaatgctgt tattatttat   720
ttggctatta ttttgtctgg tttggttgtt gtttctattg ctgattcttt tgctccaaaa   780
gaaattgctt ctagattgca tgtttctcaa gctaaagcta ttttttactca agatttatt    840 ttgagaggtg gtagaaaatt tccattgtat tctagagttg ttgaagctgc tccagataga   900
gttattgttt tgccagctac tggttctaat attggtattc aattgagaga acaagatatg   960
tcttggggtg atttttgtc ttctgttggt actagatcta gaaaatattc tccatgttat   1020
caaccagttg attctttgat taatatttg ttttcttctg gtactactgg tgaaccaaaa   1080
gctattccat ggactcattt gtctccaatt agatgttctt ctgatttttg ggcttatatg   1140
gatattaaag ttggtgatgt tgtttgttgg ccaactaatt tgggttgggc tttgggtcca   1200
tttattttgt ttacttgttt tttgtctggt gctgttttgg ctttgtatca tggttctcca   1260
ttgggtagag ttttggtaa atttgttcaa gatgcttctg ttactaaatt gggtactgtt   1320
ccatctttgg ttaaaacttg gaaaaatact caatgtatga aaggtttgga ttggactaaa   1380
attaaatctt tgcttctac tggtgaaact tctaatgttg atgatgattt gtggttgtct   1440
tctcaagctt attataaacc agttattgaa tgttgtggtg gtactgaatt ggcttcttct   1500
tatattcaag ttctttgtt gcaaccacaa gcttttggtg cttttaatac tgctactatg   1560
actacttctt ttgttattat tgatgaacat ggtaatccat atccagatga tcaagcttgt   1620
```

```
actggtgaag ttggtttgat tccattgtat ttgggtgctt ctgatagatt gttgaatgct      1680
gatcatgaag aagtttattt taaaggtatg ccattgtata aaggtatgag attgagaaga      1740
catggtgata ttattaatag aactgttggt ggttatttta ttgttcaagg tagagctgat      1800
gatactatga atttgggtgg tattaaaact tcttcttttg aaattgaaca tgtttgtgat      1860
agagctgatg attctatttt ggaaactgct gctgtttctg tttctccaat tggtggtggt      1920
ccagaacaat tggttatgtt tgttgttttg aaaaatggtt atgatgctga agctgaaaat      1980
ttgagaacta aattttctaa agctattcaa tctaatttga atccattgtt taaagttact      2040
gctgttaaaa ttgttcatga atttccaaga actatgtcta ataaattgtt gagaagagtt      2100
ttgagagatc aattgaatag agaattttct attcaatcta aaatttag                  2148
```

<210> SEQ ID NO 92
<211> LENGTH: 303
<212> TYPE: DNA
<213> ORGANISM: Artificial Sequence
<220> FEATURE:
<223> OTHER INFORMATION: Codon Optimized

<400> SEQUENCE: 92

```
atggctgtta acatttgat tattttgaaa tttaagatg aaattactga agctcaaaaa       60
gaagaatttt ttaaaactta tgttaatttg gttaatatta ttccagctat gaaagatgtt     120
tattggggta agatgttac tcaaaaaaat aagaagaag ttatactca tattgttgaa        180 gttacttttg aatctgttga aactattcaa gattatatta ttcatccagc tcatgttggt     240
tttggtgatg tttatagatg ttttttggaa aaattgttga ttttttgatta tactccaaga    300 aaa                                                                   303
```

<210> SEQ ID NO 93
<211> LENGTH: 330
<212> TYPE: DNA
<213> ORGANISM: Artificial Sequence
<220> FEATURE:
<223> OTHER INFORMATION: Codon Optimized

<400> SEQUENCE: 93

```
atggaagaag ctaaaggtgt tgttaaacat gttttgttgg ctaaatttaa agaaggtact      60
tctgatgatc aaattcaaca attgattaaa ggttatgcta atttgttgaa tttgattcca     120
tctatgaaat cttttcattg gggtaaagat gtttctttg aaaatttgca tcaaggtttt      180
actcatattt ttgaatctac ttttgaaaat actgaaggtg ttgctgaata tgttgctcat     240
ccagctcatg ttgaatttgc taatgttttt ttgtctaatt tggataaagt tgttgttttt     300
gattataaac caactactgt tttgttgcca                                      330
```

<210> SEQ ID NO 94
<211> LENGTH: 42
<212> TYPE: DNA
<213> ORGANISM: Artificial Sequence
<220> FEATURE:
<223> OTHER INFORMATION: Primer

<400> SEQUENCE: 94

```
aggaaacgaa gataaatctc gagtttatca ttatcaatac tg                        42
```

<210> SEQ ID NO 95
<211> LENGTH: 37
<212> TYPE: DNA
<213> ORGANISM: Artificial Sequence

```
<220> FEATURE:
<223> OTHER INFORMATION: Primer

<400> SEQUENCE: 95
ggaaaaatca gtcaaggcaa attaaagcct tcgagcg                              37

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
gatgggggat ccactagttc tagaatc                                        27

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
tgatgggctg caggaattcg atatc                                          25

<210> SEQ ID NO 98
<211> LENGTH: 38
<212> TYPE: DNA
<213> ORGANISM: Artificial Sequence
<220> FEATURE:
<223> OTHER INFORMATION: Primer

<400> SEQUENCE: 98
gaactagtgg atcccccatc atgaaccatt tgagagcc                            38

<210> SEQ ID NO 99
<211> LENGTH: 32
<212> TYPE: DNA
<213> ORGANISM: Artificial Sequence
<220> FEATURE:
<223> OTHER INFORMATION: Primer

<400> SEQUENCE: 99
tattttggct ttaactttct tggggtgtaa tc                                  32

<210> SEQ ID NO 100
<211> LENGTH: 43
<212> TYPE: DNA
<213> ORGANISM: Artificial Sequence
<220> FEATURE:
<223> OTHER INFORMATION: Primer

<400> SEQUENCE: 100
agaaagttaa agccaaaata atgataacga gaataatatc aag                      43

<210> SEQ ID NO 101
<211> LENGTH: 28
<212> TYPE: DNA
<213> ORGANISM: Artificial Sequence
<220> FEATURE:
<223> OTHER INFORMATION: Primer

<400> SEQUENCE: 101
ataaacccat ggcgcagacc tgtgagag                                       28
```

<210> SEQ ID NO 102
<211> LENGTH: 28
<212> TYPE: DNA
<213> ORGANISM: Artificial Sequence
<220> FEATURE:
<223> OTHER INFORMATION: Primer

<400> SEQUENCE: 102
ggtctgcgcc atgggtttat catccgtc                                28

<210> SEQ ID NO 103
<211> LENGTH: 41
<212> TYPE: DNA
<213> ORGANISM: Artificial Sequence
<220> FEATURE:
<223> OTHER INFORMATION: Primer

<400> SEQUENCE: 103
cgaattcctg cagcccatca gtgtctatgt ctaggtaaag g                 41

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
tgatgggctg caggaattcg atatc                                   25

<210> SEQ ID NO 105
<211> LENGTH: 27
<212> TYPE: DNA
<213> ORGANISM: Artificial Sequence
<220> FEATURE:
<223> OTHER INFORMATION: Primer

<400> SEQUENCE: 105
gatgggggat ccactagttc tagaatc                                 27

<210> SEQ ID NO 106
<211> LENGTH: 33
<212> TYPE: DNA
<213> ORGANISM: Artificial Sequence
<220> FEATURE:
<223> OTHER INFORMATION: Primer

<400> SEQUENCE: 106
caccagaacc gaaggtagag gttctttgtt aac                          33

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107
cgaattcctg cagcccatca ctttgatctc ttgtagacct tattc             45

<210> SEQ ID NO 108
<211> LENGTH: 42
<212> TYPE: DNA
<213> ORGANISM: Artificial Sequence
<220> FEATURE:
<223> OTHER INFORMATION: Primer

<400> SEQUENCE: 108
gaactagtgg atcccccatc atggtttcca atcacttgtt tg    42

<210> SEQ ID NO 109
<211> LENGTH: 29
<212> TYPE: DNA
<213> ORGANISM: Artificial Sequence
<220> FEATURE:
<223> OTHER INFORMATION: Primer

<400> SEQUENCE: 109
ctctaccttc ggttctggtg tataagtcg    29

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
gatccactag ttctagaatc cg    22

<210> SEQ ID NO 111
<211> LENGTH: 35
<212> TYPE: DNA
<213> ORGANISM: Artificial Sequence
<220> FEATURE:
<223> OTHER INFORMATION: Primer

<400> SEQUENCE: 111
tctagaacta gtggatcatg aaccatttga gagcc    35

<210> SEQ ID NO 112
<211> LENGTH: 28
<212> TYPE: DNA
<213> ORGANISM: Artificial Sequence
<220> FEATURE:
<223> OTHER INFORMATION: Primer

<400> SEQUENCE: 112
tcgttatcac tttcttgggg tgtaatcg    28

<210> SEQ ID NO 113
<211> LENGTH: 36
<212> TYPE: DNA
<213> ORGANISM: Artificial Sequence
<220> FEATURE:
<223> OTHER INFORMATION: Primer

<400> SEQUENCE: 113
ccaagaaagt gataacgaga ataatatcaa gaatac    36

<210> SEQ ID NO 114
<211> LENGTH: 44
<212> TYPE: DNA
<213> ORGANISM: Artificial Sequence
<220> FEATURE:
<223> OTHER INFORMATION: Primer

<400> SEQUENCE: 114
aggtcgacgg tatcgttaaa taaaaacgta taccaaatat tcag    44

<210> SEQ ID NO 115
<211> LENGTH: 18

```
<212> TYPE: DNA
<213> ORGANISM: Artificial Sequence
<220> FEATURE:
<223> OTHER INFORMATION: Primer

<400> SEQUENCE: 115
cgataccgtc gacctcga                                              18

<210> SEQ ID NO 116
<211> LENGTH: 32
<212> TYPE: DNA
<213> ORGANISM: Artificial Sequence
<220> FEATURE:
<223> OTHER INFORMATION: Primer

<400> SEQUENCE: 116
ggttaaacta gtatgggtaa aaactataag tc                              32

<210> SEQ ID NO 117
<211> LENGTH: 33
<212> TYPE: DNA
<213> ORGANISM: Artificial Sequence
<220> FEATURE:
<223> OTHER INFORMATION: Primer

<400> SEQUENCE: 117
gtgcccgtcg actcattcga aatgactgaa ttg                             33
```